US008409856B2

(12) United States Patent
Dobie et al.

(10) Patent No.: US 8,409,856 B2
(45) Date of Patent: Apr. 2, 2013

(54) COMPOSITIONS AND THEIR USES DIRECTED TO GEMIN GENES

(75) Inventors: Kenneth W. Dobie, Del Mar, CA (US); Susan M. Freier, San Diego, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 12/787,764

(22) Filed: May 26, 2010

(65) Prior Publication Data

US 2011/0105586 A1 May 5, 2011

Related U.S. Application Data

(62) Division of application No. 11/226,884, filed on Sep. 13, 2005, now Pat. No. 7,759,479.

(60) Provisional application No. 60/609,711, filed on Sep. 13, 2004.

(51) Int. Cl.
*C12N 15/85* (2006.01)
*A61K 48/00* (2006.01)
*C07H 21/04* (2006.01)

(52) U.S. Cl. .................. 435/325; 536/24.31; 536/24.33; 536/24.5; 514/44

(58) Field of Classification Search ........................ None
See application file for complete search history.

(56) References Cited

U.S. PATENT DOCUMENTS

| | | | | |
|---|---|---|---|---|
| 5,700,920 | A | 12/1997 | Altmann et al. | |
| 5,801,154 | A | 9/1998 | Baracchini et al. | |
| 5,998,148 | A * | 12/1999 | Bennett et al. | 435/6.11 |
| 6,525,191 | B1 | 2/2003 | Ramasamy | |
| 6,582,908 | B2 | 6/2003 | Fodor et al. | |
| 6,936,467 | B2 | 8/2005 | Kmiec et al. | |
| 2001/0053519 | A1 | 12/2001 | Fodor et al. | |
| 2002/0156268 | A1 | 10/2002 | Krotz et al. | |
| 2003/0228597 | A1 | 12/2003 | Cowsert et al. | |

FOREIGN PATENT DOCUMENTS

| | | |
|---|---|---|
| WO | WO 01/77384 | 10/2001 |
| WO | WO 2005/001031 | 1/2005 |

OTHER PUBLICATIONS

Taylor et al. (DDT, vol. 4, No. 12, 1999, pp. 562-567).*
Aerbajinai et al., "Increased expression level of the splicing variant of SIP2 in motor neuron diseases" Int. J. Biochem. Cell Biol. (2002) 34:699-707.
Baccon et al., "Identification and Characterization of Gamin7, a Novel Component of the Survival of Motor Neuron Complex" J. Biol. Chem. (2002) 277(35):31957-31962.
Bachand et al., "The Product of the Survival of Motor Neuron (SMN) Gene is a Human Telomerase-associated Protein" Mol. Biol. Cell (2002) 13:3192-3202.
Barth et al., "Eptstein-Barr Virus Nuclear Antigen 2 Binds via It's Methylated Arginine-Glycine Repeat to the Survival Motorn Neuron Protein" J. Virol. (2003) 77(8):5008-5013.
Boisvert et al., "Symmetrical dimethylarginine methylation is required for the localization of SMN in Cajal bodies and pre-mRNA splicing" J. Cell Biol. (2002) 159(6):957-969.
Branch et al., "A good antisense milecule is hard to find" TIBS (1998) 23:45-50.
Brichta et al., "Valproic acid increases the SMN2 protein level: a well-known drug as a potential therapy for spinal muscular atrophy" Hum. Mol. Genet. (2003) 12(19):2481-2489.
Carnegie et al., "Protein phosphatase 4 interacts with the Survival of Motor Neurons complex and enhances the temporal localization of snRNPs" J. Cell Sci. (2003) 116:1905-1913.
Cartegni et al., "Disruption of an SF2/ASF-dependent exonic splicing enhancer in SMN2 causes spinal muscular atrophy in the absence of SMN1" Nature Genet. (2002) 30:377-384.
Charroux et al., "Gemin3: A Novel DEAD Box Protein that Interacts with SMN, the Spinal Muscular Atrophy Gene Product, and Is a Component of Gems" J. Cell Biol. (1999) 147(6):1181-1193.
Charroux et al., "Gemin4: A Novel Component of the SMN Complex that is Found in both Gems and Nucleoli" J. Cell. Biol. (2000) 148(6):1177-1186.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Claus et al., "Fibroblast growth factor-223 binds directly to the survival of motorneuron protein and is associated with small nuclear RNAs" Biochem. J. (2004) 384:559-565.
Clermont et al., "Molecular Analysis of SMA Patients without Homozygous SMN1 Deletions Using a New Strategy for Identification of SMN1 Subtle Mutations" Hum. Mutat. (2004) 24:417-427.
Comjin et al., "The Two-Handed E Box Binding Zinc Finger Protein SIP1 Downregulates E-Cadherin and Induces Invasion" Mol. Cell (2001) 7:1267-1278.
Crooke et al., "Basic Principles of Antisense Therapeutics" Antisense Research and Application (1998) Chapter 1:1-50.
Dostie et al., "Numerous microRNPs in neuronal cells containing novel microRNAs" RNA (2003) 9:180-186, Erratum in RNA (2003) 9(5):631-632.
Feldkotter et al., "Quantitative Analyses of SMN1 and SMN2 Based on Real-Time LightCycler PCR: Fast and Highly Reliable Carrier Testing and Prediction of Severity of Spinal Muscular Atrophy" Am. J. Hum. Genet. (2002) 70:358-368.
Ferrer et al., "Synthesis and Hybridization Properties of DNA-PNA Chimeras Carrying 5-Bromouracil and 5-Methylcytosine" Bioorganic & Medicinal Chemistry (2000) 8:291-297.
Friesen et al., "A Novel WE Repeat Protein Component of the Methylosome Binds SM Proteins" J. Biol. Chem. (2002) 277(10):8243-8247.
Fury et al., "Multiple Protein:Protein Interactions between the snRNP Common Core Proteins" Exp. Cell Res. (1997) 237:63-69.
Gubitz et al., "Gemin5, a Novel WD Repeat Protein Component of the SMN Complex That Binds SM Proteins" J. Biol. Chem. (2002) 277(7):5631-5636.
Helmken et al., "Evidence for a modifying pathway in SMA discordant families: reduced SMN level decreases the amount of its interacting partners and Htra2-beta1" Hum. Genet. (2003) 114:11-21.

(Continued)

*Primary Examiner* — Amy Bowman
(74) *Attorney, Agent, or Firm* — Isis Pharmaceuticals, Inc. Patent Dept.

(57) ABSTRACT

Disclosed herein are compounds, compositions and methods for modulating the expression of a Gemin Gene. Also provided are methods of target validation. Also provided are uses of disclosed compounds and compositions in the manufacture of a medicament for treatment of diseases and disorders.

16 Claims, No Drawings

OTHER PUBLICATIONS

Ilangovan eta 1., "Inhibition of Apoptosis by Z-VAD-fmk in SMN-depleted S2 Cells" J. Biol. Chem. (2003) 278(33):30993-30999.
Kashima et al., "A negative element in SMN2 exon 7 inhibits splicing in spinal muscular atrophy" Nature Genet. (2003) 34(4):460-463.
Kernochian et al., "The role of histone acetylation in SMN gene expression" Hum. Mol. Genet. (2005) 14(9):1171-1182.
Khanh et al., "Molecular Genetic Analyses of Five Vietnamese Patients with Spinal Muscular Atrophy" Kobe J. Med. Sci. (2002) 48(6):177-182.
Krauer et al., "The Epstein-Barr virus nuclear antigen-6 protein co-localizes with EBNA-3 and survival of motor neurons protein" Virol. (2004) 318:280-294.
Lai et al., "SMN1 Deletions Among Singaporean Patients with Spinal Muscular Atrophy" Ann. Acad. Med. Singapore (2005) 24:73-77.
Lehner et al., "A Protein Interaction Framework for Human mRNA Degradation" Genome Res. (2004) 14:1315-1323.
Lehner et al., "Analysis of a high-throughput yeast two-hybrid system and its use to predict the function of intracellular proteins encoded within the human MHC class III region" Genomics (2004) 83:153-167.
Liu, Q et al., "The Spinal Muscular Atrophy disease Gene Product, SMN, and Its Associated Protein SIP1 Are in a Complex with Spliceosomal snRNP Proteins" Cell (1997) 90:1013-1021.
Ma et al., "The Gemin6-Gemin7 Heterodimer from the Survival of Motor Neurons Complex Has an SM Protein-Like Structure" Structure (2005) 13:883-892.
Majumder et al., "Identification of a Novel Cyclic AMP-response Element (CRE-II) and the Role of CREB-1 in the cAMP-induced Expression of the Survival Motor Neuron (SMN) Gene" J. Biol. Chem. (2004) 279(15):14803-14811.
Malatesta et al., "Ultrastructural characterization of a nuclear domain highly enriched in survival of motor neuron (SMN) protein" Exp. Cell Res. (2004) 292:312-321.
Massenet et al., "The SMN Complex is Associated with snRNPs throughout their Cytoplasmic Assembly Pathway" Mol. Cell. Biol. (2002) 22(18):6533-6541.
McConnell et al., "Branchpoint selection in the splicing of U12-dependent introns in vitro" RNA (2002) 8:579-586.
Meister et al., "Characterization of a nuclear 20S compex containing the survival of motorn neurons (SMN) protein and a specific subset of spliceosomal SM Poriteins" Hum. Mol. Genet. (2000) 9(13):1977-1986.
Mourelatos et al., "miRNPs: a novel class of ribonucleoproteins containing numerous microRNAs" Genes Dev. (2002) 16:720-728.
Narayanan et al., "SMN, the spinal muscular atrophy protein, forms a pre-import snRNP complex with snurportin1 and importin Beta" Hum. Mol. Genet. (2002) 11(15):1785-1795.
Nelson et la., "miRNP:mRNA association in the polyribosomes in a human nueronal cell line" RNA (2004) 10:387-394.
New England Biolabs 1998/99 Catalog (cover page and pp. 121 and 284).
Ogino et al., "SMN Dosage Analysis and Risk Assessment for Spinal Muscular Atrophy" Am. J. Hum. Genet. (2002) 70:1596-1598; author reply 1598-1599.
Olie et al., "Analysis of ribosyl-modified, mixed backbone analogs of a bcl-2/bcl-xL antisense oligonucleotide" Biochimica et Biophysica Acta (2002) 1576:101-109.
Parl et al., "Association of galectin-1 and galectin-3 with Gemin4 in complexes containing the SMN protein" Nucleic Acids Res. (2001) 27(17):3595-3602.
Pellizzoni et al., "A Functional Interaction between the Survival Motorn Neuron Complex and RNA Polymerase II" J. Cell Biol. (2001) 152(1):75-85.
Pellizzoni et al., "Purification of Native Survival of Motorn Neurons Complexes and Identification of Gemin6 as a Novel Component" J. Biol. Chem. (2002) 277(9)7540-7545.
Pellizzoni et al., "Essential Role for the SMN Complex in the Specificity of snRNP Assembly" Science (2002) 298:1775-1779.
Prior et al., "Homozygous SMN1 Deletions in Unaffected Family Members and Modification of the Phenotype by SMN2" Am. J. Med. Genet. (2004) 130A:307-310.
Reynolds et al., "Rational siRNA design for RNA interference" Nature Biotechnology (2004) 22(3):326-330.
Sanghvi et al., "Heterocyclic Base Modifications in Nucleic Acids and their Applications in Antisense Oligonucleotides" Antisense Research and Applications (1993) pp. 273-288.
Singh et al., "In vivo selection reveals combinatorial controls that define a critical exon in the spinal muscular atrophy genes" RNA (2004) 10:1291-1305.
Singh et al., "An extended inhibitory context causes skipping of exon 7 of SMN2 in spinal muscular atrophy" Biochem. Biophys. Res. Commun. (2004) 315:381-388.
Skordis et al., "Bifunctional antisense oligonucleotides provide a trans-acting splicing enhancer that stimulates SMN2 gene expression in patient fibroblasts" PNAS (2003) 100(7):4114-4119.
Sleeman et al., "snRNP protein expression enhances the formation of Cajal bodies containing p80-coilin and SMN" J. Cell Sci. (2001) 114:4407-4419.
Sleeman et al., "Cajal body proteins SMN and Coilin show differential dynamic behavious in vivo" J. Cell Sci. (2003) 116:2039-2050.
Swoboda et al., "Natural History of Denervation in SMA:Relation to Age, SMN2 Copy Number, and Function" Ann. Neurol. (2005) 57:704-712.
Urlaub et al., "Sm Protein-Sm site RNA interactions within the inner ring of spliceosomal snRNP core structure" Embo. J. (2001) 20 (1&2):187-196.
Vyas et al., "Involvement of survival motorn neuron (SMN) protein in cell death" Hum. Mol. Genet. (2002) 11(2):2751-2764.
Wan et al., "The Survival of Motor Neurons Protein Determines the Capacity for snRNP Assembly: Biochemical Deficiency in Spinal Muscular Atrophy" Mol. Cell. Biol. (2005) 25(13):5543-5551.
Wolstencroft et al., "A non-sequence-specific requirement for SMN protein activity: the role of aminoglycosides in inducing elevated SMN protein levels" Hum. Mol. Genet. (2005) 14(9):1199-1210.
Young et al., "SRp30c-depdendent stimulation of survival motor neuron (SMN) exon 7 inclusion is facilitated by a direct interaction with hTra2B1" Hum. Mol. Genet. (2002) 11(5):577-587.
Young et al., "MinuteVirus of Mice NS1i Interacts with the SMN Protein, and They Colocalize in Novel Nuclear Bodies Induced by Parvovirus Infection" J. Virol. (2002) 76(8):3892-3904.
Young et al., "Minute Virus of Mice Small Nonstructural Protein NS2 Interacts and Colocalizes with Smn Protein" J. Virol. (2002) 76(12):6364-6369.
Zhang et al., "Sip 1, a Novel RS Domain-Containing Protein Essential for Pre-mRNA Splicing" Mol. Cell. Biol. (1998) 18(2):676-684.
Zhang et al., "Active Transport of the Survival Motor Neuron Protein and the Role of Exon-7 in Cytoplasmic Localization" J. Neurosci. (2003) 23(16):6627-6637.
Zou et al., "Survival Motor Neuron (SMN) Protein Interacts with Transcription Corepressor mSin3A" J. Biol. Chem. (2004) 279(15):14922-14928.

* cited by examiner

COMPOSITIONS AND THEIR USES DIRECTED TO GEMIN GENES

REFERENCE TO RELATED APPLICATIONS

This application is a divisional application under 35 U.S.C. §121 of U.S. application Ser. No. 11/226,884, filed Sep. 13, 2005, now U.S. Pat. No. 7,759,479, which claims benefit of U.S. provisional application 60/609,711, filed Sep. 13, 2004, the entire contents of each is being expressly incorporated herein by reference.

SEQUENCE LISTING

The present application is being filed along with a Sequence Listing in electronic format. The Sequence Listing is provided as a file entitled RTS0491USC1SEQ.txt, created on May 26, 2010 which is 261 Kb in size. The information in the electronic format of the sequence listing is incorporated herein by reference in its entirety.

FIELD OF THE INVENTION

Disclosed herein are compounds, compositions and methods for modulating the expression of a Gemin gene in a cell, tissue or animal.

BACKGROUND OF THE INVENTION

Targeting disease-causing gene sequences was first suggested more than thirty years ago (Belikova et al., Tet. Lett., 1967, 37, 3557-3562), and antisense activity was demonstrated in cell culture more than a decade later (Zamecnik et al., Proc. Natl. Acad. Sci. U.S.A., 1978, 75, 280-284). One advantage of antisense technology in the treatment of a disease or condition that stems from a disease-causing gene is that it is a direct genetic approach that has the ability to modulate (increase or decrease) the expression of specific disease-causing genes. Another advantage is that validation of a therapeutic target using antisense compounds results in direct and immediate discovery of the drug candidate; the antisense compound is the potential therapeutic agent.

Generally, the principle behind antisense technology is that an antisense compound hybridizes to a target nucleic acid and modulates gene expression activities or function, such as transcription or translation. The modulation of gene expression can be achieved by, for example, target degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi generally refers to antisense-mediated gene silencing involving the introduction of dsRNA leading to the sequence-specific reduction of targeted endogenous mRNA levels. Regardless of the specific mechanism, this sequence-specificity makes antisense compounds extremely attractive as tools for target validation and gene functionalization, as well as therapeutics to selectively modulate the expression of genes involved in the pathogenesis of malignancies and other diseases.

Antisense compounds have been employed as therapeutic agents in the treatment of disease states in animals, including humans. Antisense oligonucleotide drugs are being safely and effectively administered to humans in numerous clinical trials. In 1998, the antisense compound, Vitravene® (fomivirsen; developed by Isis Pharmaceuticals Inc., Carlsbad, Calif.) was the first antisense drug to achieve marketing clearance from the U.S. Food and Drug Administration (FDA), and is currently used in the treatment of cytomegalovirus (CMV)-induced retinitis in AIDS patients. A New Drug Application (NDA) for Genasense™ (oblimersen sodium; developed by Genta, Inc., Berkeley Heights, N.J.), an antisense compound which targets the Bcl-2 mRNA overexpressed in many cancers, was accepted by the FDA. Many other antisense compounds are in clinical trials, including those targeting c-myc (NeuGene® AVI-4126, AVI BioPharma, Ridgefield Park, N.J.), TNF-alpha (ISIS 104838, developed by Isis Pharmaceuticals, Inc.), VLA4 (ATL1102, Antisense Therapeutics Ltd., Toorak, Victoria, Australia) and DNA methyltransferase (MG98, developed by MGI Pharma, Bloomington, Minn.), to name a few.

New chemical modifications have improved the potency and efficacy of antisense compounds, uncovering the potential for oral delivery as well as enhancing subcutaneous administration, decreasing potential for side effects, and leading to improvements in patient convenience. Chemical modifications increasing potency of antisense compounds allow administration of lower doses, which reduces the potential for toxicity, as well as decreasing overall cost of therapy. Modifications increasing the resistance to degradation result in slower clearance from the body, allowing for less frequent dosing. Different types of chemical modifications can be combined in one compound to further optimize the compound's efficacy.

Much of the information regarding the biogenesis of the small nuclear ribonucleoproteins (snRNPs) came from studies of spinal muscular atrophy (SMA). SMA, a motor neuron degenerative disease that results from deletions or mutations in the Survival of Motor Neurons (SMN) gene, is an autosomal recessive disease that is the leading hereditary cause of infant mortality (Gubitz et al., Exp. Cell. Res., 2004, 296, 51-56). The SMN protein is present in the cytoplasm and nucleus, where it is enriched within discrete bodies called Gems (for "Gemini of Cajal bodies") which are related to and often associated with Cajal bodies (Gubitz et al., Exp. Cell. Res., 2004, 296, 51-56; Liu and Dreyfuss, Embo J., 1996, 15, 3555-3565; Yong et al., Trends Cell Biol., 2004, 14, 226-232). Cajal bodies are known to contain high levels of factors involved in the transcription and processing of many types of nuclear RNAs, including snRNPs, nucleolar ribonucleoproteins (snoRNPs), and the three eukaryotic RNA polymerases, and are most likely sites of assembly and modification of the nuclear transcription and RNA machinery (Gubitz et al., Exp. Cell. Res., 2004, 296, 51-56).

The snRNP particles are components of the spliceosome, the eukaryotic pre-mRNA splicing machinery. Each major snRNP contains a small nuclear RNA (snRNA) as well as a common set of Sm proteins and a set of proteins specific to the particular snRNA. The common Sm proteins are arranged into a core on a uridine-rich sequence in the cytoplasm after nuclear export of the nacent snRNAs. Proper assembly of the core is required for subsequent import of the snRNPs into the nucleus. As compared to other RNP complexes, such as the small nucleolar RNPs which are assembled in the nucleus where they function, the assembly of snRNPs appears to be strictly regulated and complex (Yong et al., Trends Cell Biol., 2004, 14, 226-232).

The SMN protein oligomerizes with a group of proteins named the Gemins. The Gemins include Gemin2, Gemin3, a DEAD/H box helicase, Gemin4, Gemin5, Gemin6, and Gemin7. The Gemins colocalize with SMN in gems and are present in the cytoplasm and nucleoplasm (Gubitz et al., Exp. Cell. Res., 2004, 296, 51-56). It appears that individual Gemins of the SMN complex interact with distinct sets of Sm proteins indicating that multiple contacts are likely to be important for the function of the SMN complex in snRNP core assembly (Baccon et al., J. Biol. Chem., 2002, 277, 31957-31962). The SMN complex was found to function as a specificity factor for the assembly of spliceosomal snRNP, ensuring that Sm cores are only formed on the correct RNA molecules (Pellizzoni et al., Science, 2002, 298, 1775-1779).

Gemin2 (also known as SIP1, SMP-interacting protein 1, and survival of motor neuron protein interacting protein 1) was isolated in a yeast two-hybrid screen of a HeLa cell library using SMN as bait. These proteins were tightly associated and colocalized to Gems, prompting a search for other protein components of the complex. The SMN/Gemin2 pair was found to interact directly with several of the snRNP Sm core proteins (Liu et al., Cell, 1997, 90, 1013-1021). Further implicating the pair in snRNP biogenesis, the SMN/Gemin2 complex associated with spliceosomal snRNAs U1 and U5 in the cytoplasm of *Xenopus oocytes*, and antibodies against Gemin2 inhibited Sm core assembly of the spliceosomal snRNPs U1, U2, U4, and U5 and their transport to the nucleus (Fischer et al., Cell, 1997, 90, 1023-1029).

Together with Gemin2, Gemin3 and Gemin4 (also known as GIP1 or gem-associated protein 4) were also found to complex with SMN and snRNP proteins (Charroux et al., J. Cell Biol., 1999, 147, 1181-1194; Charroux et al., J. Cell Biol., 2000, 148, 1177-1186). Gemin3 was the only protein of the SMN complex that bound specifically to GST-Gemin4, suggesting that the presence of Gemin4 in the complex is a result of its direct interaction with Gemin3, but not with SMN. The direct and avid interaction of Gemin4 with the DEAD/H box-containing helicase protein Gemin3 may indicate that they function together. Gemin4 also interacts with several of the core Sm proteins, and co-localizes with SMN to gems. Gemin4 localizes to the nucleolus, potentially indicating additional functions in ribosome biogenesis (Charroux et al., J. Cell Biol., 2000, 148, 1177-1186).

Gemin4 proteins are found predominantly in the SMN complex, however, a less abundant Gemin3-Gemin4 complex has also been found (Charroux et al., J. Cell Biol., 2000, 148, 1177-1186; Mourelatos et al., Genes & Development, 2002, 16, 720-728). Immunoprecipitation studies showed that Gemin3 and Gemin4 are associated in a complex with eIF2c2, a member of the large Argonaute family of proteins, members of which have been implicated in RNA interference (RNAi) mechanisms and developmental regulation by short temporal RNAs (stRNAs). The complex, a miRNP, also contained RNAs about 22 nucleotides in length, corresponding to microRNAs (miRNAs). 40 miRNAs were captured in these studies (Mourelatos et al., Genes & Development, 2002, 16, 720-728). Monoclonal antibodies to either Gemin3 or Gemin4 immunoprecipitated let-7-programmed RNA-induced silencing complex (RISC) activity, leading to the notion that the Gemin4-containing miRNP may be the human RISC which can carry out both target cleavage in the RNAi pathway and translational control in the miRNA pathway (Hutvagner and Zamore, Science, 2002, 297, 2056-2060).

In a yeast-two hybrid assay, Gemin4 was found to interact with galectin-1 and galectin-3, nuclear-localized proteins that were shown to be required factors for splicing in a cell-free assay. This interaction is thought to be functionally relevant in the splicing pathway (Park et al., Nucleic Acids Res., 2001, 29, 3595-3602).

Gemin5 (also known as DKFZP586M1824 protein; gem-associated protein 5) was found by coimmunoprecipitation of proteins that associate with SMN in vivo. Like SMN, Gemin5 is localized in the cytoplasm, nucleoplasm, and is highly enriched in the nuclear gems. It binds to SMN by direct protein-protein interaction in vitro and interacts with several of the snRNP core Sm proteins. The Gemin5 protein is predicted to contain up to 13 WD repeats in its amino-terminal half, and a coiled-coil near its carboxyl terminus. Because both WD repeats and coiled-coil motifs are protein-protein interaction domains, Gemin5 may serve as a structural platform for protein assembly (Gubitz et al., J. Biol. Chem., 2002, 277, 5631-5636).

Extracts from stable cell lines expressing epitope-tagged SMN or Gemin2 proteins were analyzed by immunoprecipitation with an antibody recognizing the epitope. Both tagged-proteins were isolated with the SMN complex which was found to contain additional previously unidentified proteins including Gemin6 (also known as GEM-associated protein 6 or hypothetical protein FLJ23459). Database searches revealed that Gemin6 is not significantly homologous to other proteins and contains no common motifs which may be indicative of function. Like the other members of the SMN complex, Gemin6 was shown to interact with several Sm proteins (Baccon et al., J. Biol. Chem., 2002, 277, 31957-31962). The Gemin6 localization is similar to the other components of the SMN complex, but direct interaction of Gemin6 with SMN, Gemin2, Gemin3, Gemin4 or Gemin5 was not detectable (Pellizzoni et al., J. Biol. Chem., 2002, 277, 7540-7545).

However, Gemin7 (also known as hypothetical protein FLJ13956), also identified using the epitope-tagged system to purify SMN complexes, was shown to bind directly to Gemin6 and SMN in vitro, therefore it likely mediates the association of Gemin6 with the SMN complex. Like Gemin6, Gemin7 does not contain any known motifs that may suggest possible functions, but it does interact with a subset of the Sm proteins. Like the other complex members, Gemin7 colocalizes with SMN in gems (Baccon et al., J. Biol. Chem., 2002, 277, 31957-31962).

Beyond interactions with Sm proteins and snRNAs, the SMN complex interacts directly with several protein targets that are components of RNPs which function in various aspects of RNA metabolism. Among these substrates are the Sm-like (Lsm) proteins of the snRNPs, also essential components of the splicing machinery (Friesen and Dreyfuss, J. Biol. Chem., 2000, 275, 26370-26375). Fibrillarin and GAR1, components of small nucleolar RNPs (snoRNPs), also interact with SMN. Fibrillarin is a marker for Box C/D snoRNPs, the class that is necessary for cleavage and site-specific methylation of rRNA. Box H/ACA snoRNPs contain GAR1 and guide the pseudouridylation of rRNA (Pellizzoni et al., Curr. Biol., 2001, 11, 1079-1088). Thus, the SMN complex also appears to be involved in snoRNP biogenesis (Jones et al., J Biol. Chem., 2001, 276, 38645-38651; Pellizzoni et al., Curr. Biol., 2001, 11, 1079-1088). Additional SMN complex substrates are hnRNP U and Q, RNA helicase A, and Epstein-Barr virus nuclear antigen 2 (EBNA2), coilin, and nucleolin (Barth et al., J. Virol., 2003, 77, 5008-5013; Gubitz et al., Exp. Cell. Res., 2004, 296, 51-56; Liu and Dreyfuss, Embo J., 1996, 15, 3555-3565; Mourelatos et al., Genes & Development, 2002, 16, 720-728; Yong et al., Trends Cell Biol., 2004, 14, 226-232). Because most SMN complex substrates are components of various RNP complexes involved in RNA processing, the SMN complex may take part in many aspects of cellular RNA metabolism (Gubitz et al., Exp. Cell. Res., 2004, 296, 51-56).

Disclosed in U.S. Pat. No. 6,646,113 is an antisense isolated nucleic acid complementary to the nucleic acid encoding a human Survival of Motor Neuron-Interacting Protein 1, wherein said nucleic acid encodes a protein that differs from the amino acid sequence disclosed by a mutation that inhibits binding of the Survival of Motor Neuron protein, and further wherein said mutation is selected from the group consisting of a deletion of the carboxyl terminal 89 amino acids relative to the amino acid sequence disclosed therein and a deletion of the carboxyl terminal 162 amino acids relative to the amino acid sequence disclosed therein. Also disclosed are antisense oligomers of between about 10 to about 30, and more preferably about 15 nucleotides (Dreyfuss et al., 2003).

U.S. pregrant publication 20030228617 discloses a kit comprising a plurality of oligonucleotide primers and instructions for employing the plurality of oligonucleotide primers to determine the expression level of at least one of the genes represented in a group of sequences, said group including a nucleic acid sequence of a partial cDNA and a full-length cDNA corresponding to the human survival of motor neuron protein interacting protein 1 (SIP1) gene (Aune and Olsen, 2003).

The role of Gemin2, Gemin4, Gemin5, Gemin6, and Gemin7 in RNA metabolism makes these attractive targets for therapeutic and investigative strategies aimed at antisense technology. Consequently, there remains a need for agents capable of effectively modulating Gemin2, Gemin4, Gemin5, Gemin6, and Gemin7 function.

Antisense technology is an effective means for reducing the expression of one or more specific gene products and can therefore prove to be uniquely useful in a number of therapeutic, diagnostic, and research applications.

Consequently, there remains a long-felt need for agents that specifically regulate gene expression via antisense mechanisms. Disclosed herein are antisense compounds useful for modulating gene expression pathways, including those relying on mechanisms of action such as RNaseH, RNAi and dsRNA enzymes, as well as other antisense mechanisms based on target degradation or target occupancy. One having skill in the art, once armed with this disclosure will be able, without undue experimentation, to identify, prepare and exploit antisense compounds for these uses.

SUMMARY OF THE INVENTION

Provided herein are oligomeric compounds, especially antisense nucleic acid and nucleic acid-like oligomers, e.g., antisense oligonucleotides, which are targeted to a nucleic acid encoding a Gemin Gene, and which modulate the expression of a Gemin Gene. Gemin Genes disclosed herein include Gemin2, Gemin4, Gemin5, Gemin6, Gemin7. Also disclosed are pharmaceutical compositions including said oligomeric compounds, and methods of using said oligomeric compounds to modulate expression of a Gemin Gene.

In one embodiment, the invention provides oligomeric compounds of from, e.g., 13 to 30 nucleobases in length targeted to a nucleic acid molecule encoding a Gemin Gene, e.g., Gemin2 (SEQ ID NO: 7), wherein said oligomeric compound specifically hybridizes with said nucleic acid molecule encoding the Gemin Gene and inhibits the expression of the Gemin Gene. In some embodiments, the oligomeric compound is 20 nucleobases in length. In further embodiments, the oligomeric compound is an antisense oligonucleotide.

The oligomeric compound can be chimeric and include at least one modified internucleoside linkage, e.g., a phosphorothioate internucleoside linkage; and/or at least one modified sugar moiety, e.g., a 2'-O-methoxyethyl sugar moiety, and/or at least one modified nucleobase, e.g., a 5-methylcytosine. In one embodiment, the oligomeric compound is an antisense, chimeric oligonucleotide 20 nucleobases in length and includes at least one phosphorothioate internucleoside linkage and at least one 2'-O-methoxyethyl sugar moiety and at least one 5-methylcytosine.

Pharmaceutical, therapeutic and other compositions comprising the oligomeric compounds of the present invention are also provided. In one embodiment, the invention provides a composition that includes an oligomeric compound of the invention and a pharmaceutically acceptable carrier, e.g., colloidal dispersion system, or diluent.

Further provided are methods of modulating the expression of a Gemin Gene, e.g., Gemin2, in cells, tissues or animals comprising contacting said cells, tissues or animals with one or more of the compounds or compositions of the present invention. In some embodiments, the methods are performed in vitro.

Methods of treating an animal, particularly a human, suspected of having or at risk for a disease or condition associated with expression of a Gemin Gene are also set forth herein. Such methods include administering a therapeutically or prophylactically effective amount of one or more of the oligomeric compounds or compositions of the present invention to an animal, particularly a human.

Further provided are methods of identifying the relationship between a Gemin Gene and a disease state, phenotype, or condition by detecting or modulating said Gemin Gene comprising contacting a sample, tissue, cell, or organism with one or more oligomeric compounds, measuring the nucleic acid or protein level of said Gemin Gene and/or a related phenotypic or chemical endpoint coincident with or at some time after treatment, and optionally comparing the measured value to a non-treated sample or sample treated with a further compound.

Further provided are methods of screening for modulators of a Gemin Gene expression by contacting a target segment of a nucleic acid molecule encoding said Gemin Gene with one or more candidate modulators, and selecting for one or more candidate modulators which decrease or increase the expression of a nucleic acid molecule encoding said Gemin Gene.

Also provided is the use of the compounds or compositions of the invention in the manufacture of a medicament for the treatment of one or more conditions associated with a target of the invention. Further contemplated are methods where cells or tissues are contacted in vivo with an effective amount of one or more of the disclosed compounds or compositions. Also provided are ex vivo methods of treatment that include contacting cells or tissues with an effective amount of one or more of the compounds or compositions of the invention and then introducing said cells or tissues into an animal.

DETAILED DESCRIPTION OF THE INVENTION

Overview

Disclosed herein are oligomeric compounds, including antisense oligonucleotides and other antisense compounds for use in modulating the expression of nucleic acid molecules encoding a Gemin Gene, e.g., Gemin2, Gemin4, Gemin5, Gemin6, Gemin7, and the like. This is accomplished by providing oligomeric compounds which hybridize with one or more target nucleic acid molecules encoding a Gemin Gene. As used herein, the terms “target nucleic acid” and “nucleic acid molecule encoding a Gemin Gene” have been used for convenience to encompass DNA encoding a Gemin Gene, RNA (including pre-mRNA and mRNA or portions thereof) transcribed from such DNA, and also cDNA derived from such RNA.

In one embodiment, the oligomeric compounds of the invention are antisense compounds, e.g., antisense oligonucleotides. The principle behind antisense technology is that an antisense compound, which hybridizes to a target nucleic acid, interferes with gene expression activities such as transcription or translation. This sequence specificity makes antisense compounds extremely attractive as tools for target validation and gene functionalization, as well as therapeutics to selectively modulate the expression of genes involved in disease.

The term "oligomeric compound" refers to a polymeric structure capable of hybridizing to a region of a nucleic acid molecule. This term includes oligonucleotides, oligonucleosides, oligonucleotide analogs, oligonucleotide mimetics and chimeric combinations of these. Oligomeric compounds are routinely prepared linearly but can be joined or otherwise prepared to be circular. Moreover, branched structures are known in the art. An "antisense compound" or "antisense oligomeric compound" or "antisense oligonucleotide" refers to an oligomeric compound that is at least partially complementary to the region of a nucleic acid molecule to which it hybridizes and modulates (increases or decreases) its expression. Consequently, while all antisense compounds can be said to be oligomeric compounds, not all oligomeric compounds are antisense compounds. Antisense oligonucleotides may be chemically modified or unmodified. Nonlimiting examples of oligomeric compounds include primers, probes, antisense compounds, antisense oligonucleotides, external guide sequence (EGS) oligonucleotides, alternate splicers, and siRNAs. As such, these compounds can be introduced in the form of single-stranded, double-stranded, circular, branched or hairpins and can contain structural elements such as internal or terminal bulges, loops or mismatches. Oligomeric double-stranded compounds can be two strands hybridized to form double-stranded compounds or a single strand with sufficient self complementarity to allow for hybridization and formation of a fully or partially double-stranded compound.

Antisense Mechanisms

Oligomeric compounds that modulate Gemin Gene expression via antisense mechanisms are one embodiment of the invention. While not wishing to be bound by theory, antisense mechanisms fall into two general non-exclusive categories. These categories are antisense mechanisms that (1) involve target degradation and (2) involve an occupancy-based mechanism wherein the cellular machinery is stalled and may or may not involve target degradation component.

A target degradation mechanism can include an RNase H mechanism. RNAse H is a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression.

A target degradation mechanism can include RNA interference (RNAi). RNAi is a form of posttranscriptional gene silencing that was initially defined in the nematode, *Caenorhabditis elegans*, resulting from exposure to double-stranded RNA (dsRNA). In many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing (Guo and Kempheus, *Cell,* 1995, 81, 611-620; Montgomery et al., *Proc. Natl. Acad. Sci. USA,* 1998, 95, 15502-15507). The RNAi compounds are often referred to as short interfering RNAs or siRNAs. Recently, it has been shown that it is, in fact, the single-stranded RNA oligomers of antisense polarity of the siRNAs which are the potent inducers of RNAi (Tijsterman et al., *Science,* 2002, 295, 694-697). Both RNAi compounds (i.e., single- or double-stranded RNA or RNA-like compounds) and single-stranded RNase H-dependent antisense compounds bind to their RNA target by base pairing (i.e., hybridization) and induce site-specific cleavage of the target RNA by specific RNAses; i.e., both work via an antisense mechanism (Vickers et al., 2003, *J. Biol. Chem.,* 278, 7108-7118). Double-stranded ribonucleases (dsRNases) such as those in the RNase III and ribonuclease L family of enzymes have been postulated to play a role in RNA target degradation. Double-stranded ribonucleases and oligomeric compounds that trigger them are further described in U.S. Pat. Nos. 5,898,031 and 6,107,094.

Nonlimiting examples of an occupancy based mechanism include inhibition of translation, modulation of splicing, modulation of poly(A) site selection and disruption of regulatory RNA structure. A method of controlling the behavior of a cell through modulation of the processing of an mRNA target by contacting the cell with an antisense compound acting via such a mechanism is disclosed in U.S. Pat. No. 6,210,892 and U.S. Pre-Grant Publication 20020049173.

Certain types of antisense compounds which specifically hybridize to the 5' cap region of their target mRNA interfere with translation of the target mRNA into protein. Such oligomers include peptide-nucleic acid (PNA) oligomers, morpholino oligomers snf oligonucleosides (such as those having an MMI or amide internucleoside linkage) and oligonucleotides having modifications at the 2' position of the sugar. This is believed to occur via interference with ribosome assembly on the target mRNA. Methods for inhibiting the translation of a selected capped target mRNA by contacting target mRNA with an antisense compound are disclosed in U.S. Pat. No. 5,789,573.

Antisense compounds targeted to specific splice variants of an RNA can be used to modulate the populations of alternatively spliced RNA products (see U.S. Patent Application entitled "Isoform-Specific Targeting of Splice Variants" filed Aug. 29, 2003, Ser. No. 10/651,772).

Antisense compounds targeted to a specific poly(A) site of mRNA can be used to modulate the populations of alternatively polyadenylated transcripts. In addition, antisense compounds can be used to disrupt RNA regulatory structure thereby affecting, for example, the stability of the targeted RNA and its subsequent expression. Methods directed to such modulation are disclosed in U.S. Pat. No. 6,210,892 and Pre-Grant Publication 20020049173.

siRNAs

In another embodiment of the invention, oligomeric compounds of the invention comprise double-stranded antisense compounds encompassing short interfering RNAs (siRNAs). As used herein, the term "siRNA" is defined as a double-stranded compound having a first and second strand and comprises a central complementary portion between said first and second strands and terminal portions that are optionally complementary between said first and second strands or with the target mRNA. The ends of the strands may be modified by the addition of one or more natural or modified nucleobases to form an overhang. In one nonlimiting example, the first strand of the siRNA is antisense to the target nucleic acid, while the second strand is complementary to the first strand. Once the antisense strand is designed to target a particular nucleic acid target, the sense strand of the dsRNA is then designed and synthesized as the complement of the antisense strand and either strand may contain modifications or additions to either terminus. For example, in one embodiment, both strands of the siRNA duplex would be complementary over the central nucleobases, each having overhangs at one or both termini. It is possible for one end of a duplex to be blunt and the other to have overhanging nucleobases. In one embodiment, the number of overhanging nucleobases is from 1 to 6 on the 3' end of each strand of the duplex. In another embodiment, the number of overhanging nucleobases is from 1 to 6 on the 3' end of only one strand of the duplex. In a further embodiment, the number of overhanging nucleobases is from 1 to 6 on one or both 5' ends of the duplexed strands. In another embodiment, the number of overhanging nucleobases is zero.

In one embodiment of the invention, double-stranded antisense compounds are canonical siRNAs. As used herein, the term "canonical siRNA" is defined as a double-stranded oligomeric compound having a first strand and a second strand each strand being 21 nucleobases in length with the strands being complementary over 19 nucleobases and having on each 3' termini of each strand a deoxy thymidine dimer (dTdT) which in the double-stranded compound acts as a 3' overhang.

Each strand of the siRNA duplex may be from about 8 to about 80 nucleobases, 10 to 50, 13 to 80, 13 to 50, 13 to 30, 13 to 24, 19 to 23, 20 to 80, 20 to 50, 20 to 30, or 20 to 24 nucleobases. The central complementary portion may be from about 8 to about 80 nucleobases in length, 10 to 50, 13 to 80, 13 to 50, 13 to 30, 13 to 24, 19 to 23, 20 to 80, 20 to 50, 20 to 30, or 20 to 24 nucleobases. The terminal portions can be from 1 to 6 nucleobases. The siRNAs may also have no terminal portions. The two strands of an siRNA can be linked internally leaving free 3' or 5' termini or can be linked to form a continuous hairpin structure or loop. The hairpin structure may contain an overhang on either the 5' or 3' terminus producing an extension of single-stranded character.

In another embodiment, the double-stranded antisense compounds are blunt-ended siRNAs. As used herein the term "blunt-ended siRNA" is defined as an siRNA having no terminal overhangs. That is, at least one end of the double-stranded compound is blunt. siRNAs whether canonical or blunt act to elicit dsRNAse enzymes and trigger the recruitment or activation of the RNAi antisense mechanism. In a further embodiment, single-stranded RNAi (ssRNAi) compounds that act via the RNAi antisense mechanism are contemplated.

Further modifications can be made to the double-stranded compounds and may include conjugate groups attached to one of the termini, selected nucleobase positions, sugar positions or to one of the internucleoside linkages. Alternatively, the two strands can be linked via a non-nucleic acid moiety or linker group. When formed from only one strand, the compounds can take the form of a self-complementary hairpin-type molecule that doubles back on itself to form a duplex. Thus, the compounds can be fully or partially double-stranded. When formed from two strands, or a single strand that takes the form of a self-complementary hairpin-type molecule doubled back on itself to form a duplex, the two strands (or duplex-forming regions of a single strand) are complementary when they base pair in Watson-Crick fashion.

Compounds

The oligomeric compounds in accordance with this invention may comprise a complementary oligomeric compound from about 8 to about 80 nucleobases (i.e. from about 8 to about 80 linked nucleosides). In other words, a single-stranded compound of the invention comprises from 8 to about 80 nucleobases, and a double-stranded antisense compound of the invention (such as a siRNA, for example) comprises two strands, each of which is from about 8 to about 80 nucleobases. In some embodiments, oligomeric compounds of the invention are 10 to 50, 13 to 80, 13 to 50, 13 to 30, 13 to 24, 19 to 23, 20 to 80, 20 to 50, 20 to 30, or 20 to 24 nucleobases in length. In one embodiment, the oligomeric compounds are 20 nucleobases in length.

Contained within the oligomeric compounds of the invention (whether single or double stranded and on at least one strand) are antisense portions. The "antisense portion" is that part of the oligomeric compound that is designed to confer antisense activity by one of the aforementioned potential antisense mechanisms. One of ordinary skill in the art will appreciate that this comprehends antisense portions of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases.

In one embodiment, the antisense compounds of the invention have antisense portions of 10 to 50 nucleobases. One having ordinary skill in the art will appreciate that this embodies antisense compounds having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases.

In one embodiment, the antisense compounds of the invention have antisense portions of 13 to 80 nucleobases. One having ordinary skill in the art will appreciate that this embodies antisense compounds having antisense portions of 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases.

In one embodiment, the antisense compounds of the invention have antisense portions of 13 to 50 nucleobases. One having ordinary skill in the art will appreciate that this embodies antisense compounds having antisense portions of 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, or 50 nucleobases.

In one embodiment, the antisense compounds of the invention have antisense portions of 13 to 30 nucleobases. One having ordinary skill in the art will appreciate that this embodies antisense compounds having antisense portions of 13, 14, 15, 16, 17, 18, 19, 20, 21, 22, 23, 24, 25, 26, 27, 28, 29 or 30 nucleobases.

In some embodiments, the antisense compounds of the invention have antisense portions of 13 to 24 nucleobases. One having ordinary skill in the art will appreciate that this embodies antisense compounds having antisense portions of 13, 14, 15, 16, 17, 18, 19, 20, 21, 22, 23 or 24 nucleobases.

In one embodiment, the antisense compounds of the invention have antisense portions of 19 to 23 nucleobases. One having ordinary skill in the art will appreciate that this embodies antisense compounds having antisense portions of 19, 20, 21, 22 or 23 nucleobases.

In one embodiment, the antisense compounds of the invention have antisense portions of 20 to 80 nucleobases. One having ordinary skill in the art will appreciate that this embodies antisense compounds having antisense portions of 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases.

In one embodiment, the antisense compounds of the invention have antisense portions of 20 to 50 nucleobases. One having ordinary skill in the art will appreciate that this embodies antisense compounds having antisense portions of 20, 21, 22, 23, 24, 25, 26, 27, 28, 29 30, 31, 32, 33, 34, 35, 36, 37, 38, 39, 40, 41, 42, 43, 44, 45, 46, 47, 48, 49, or 50 nucleobases.

In one embodiment, the antisense compounds of the invention have antisense portions of 20 to 30 nucleobases. One having ordinary skill in the art will appreciate that this embodies antisense compounds having antisense portions of 20, 21, 22, 23, 24, 25, 26, 27, 28, 29, or 30 nucleobases.

In one embodiment, the antisense compounds of the invention have antisense portions of 20 to 24 nucleobases. One having ordinary skill in the art will appreciate that this embodies antisense compounds having antisense portions of 20, 21, 22, 23, or 24 nucleobases.

Antisense compounds 8-80 nucleobases in length comprising a stretch of at least eight (8) consecutive nucleobases selected from within the illustrative antisense compounds are considered to be suitable antisense compounds as well.

Exemplary compounds include oligonucleotide sequences that comprise at least the 8 consecutive nucleobases from the 5'-terminus of one of the illustrative antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Other compounds are represented by oligonucleotide sequences that comprise at least the 8 consecutive nucleobases from the 3'-terminus of one of the illustrative antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). It is also understood that compounds may be represented by oligonucleotide sequences that comprise at least 8 consecutive nucleobases from an internal portion of the sequence of an illustrative compound, and may extend in either or both directions until the oligonucleotide contains about 8 about 80 nucleobases.

One having skill in the art armed with the antisense compounds illustrated herein will be able, without undue experimentation, to identify further antisense compounds.

Chemical Modifications

As is known in the art, a nucleoside is a base-sugar combination. The base portion of the nucleoside is normally a heterocyclic base (sometimes referred to as a "nucleobase" or simply a "base"). The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages

Specific examples of oligomeric compounds useful of the present invention include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

Oligomeric compounds can have one or more modified internucleoside linkages. Modified oligonucleotide backbones containing a phosphorus atom therein include, for example, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, phosphonoacetate and thiophosphonoacetate (see Sheehan et al., *Nucleic Acids Research,* 2003, 31(14), 4109-4118 and Dellinger et al., *J. Am. Chem. Soc.,* 2003, 125, 940-950), selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

N3'-P5'-phosphoramidates have been reported to exhibit both a high affinity towards a complementary RNA strand and nuclease resistance (Gryaznov et al., *J. Am. Chem. Soc.,* 1994, 116, 3143-3144). N3'-P5'-phosphoramidates have been studied with some success in vivo to specifically down regulate the expression of the c-myc gene (Skorski et al., *Proc. Natl. Acad. Sci.,* 1997, 94, 3966-3971; and Faira et al., *Nat. Biotechnol.,* 2001, 19, 40-44).

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050.

In some embodiments of the invention, oligomeric compounds may have one or more phosphorothioate and/or heteroatom internucleoside linkages, in particular —CH2-NH—O—CH2-, —CH2-N(CH3)-O—CH2- (known as a methylene (methylimino) or MMI backbone), —CH2-O—N(CH3)-CH2-, —CH2-N(CH3)-N(CH3)-CH2- and —O—N(CH3)-CH2-CH2- (wherein the native phosphodiester internucleotide linkage is represented as —O—P(═O)(OH)—O—CH2-). The MMI type intemucleoside linkages are disclosed in the above referenced U.S. Pat. No. 5,489,677. Amide internucleoside linkages are disclosed in the above referenced U.S. Pat. No. 5,602,240.

Some oligonucleotide backbones that do not include a phosphorus atom therein have backbones that are formed by short chain alkyl or cycloalkyl intemucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

Modified Sugars

Oligomeric compounds may also contain one or more substituted sugar moieties. Suitable compounds can comprise one of the following at the T position: OH; F; O—, S—, or N-alkyl; O—, S—, or N-alkenyl; O—, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Also suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78, 486-504) i.e., an alkoxyalkoxy group. A further modification includes 2'-dimethylaminooxyethoxy, i.e., a $O(CH_2)_2ON(CH_3)_2$ group, also known as 2'-DMAOE, as described in examples hereinbelow, and 2'-dimethylamino-ethoxyethoxy (also known in the art as 2'-O-dimethyl-amino-ethoxy-ethyl or 2'-DMAEOE), i.e., 2'-O—$CH_2$—O—$CH_2$—$N(CH_3)_2$, also described in examples hereinbelow.

Other modifications include 2'-methoxy (2'-O—$CH_3$), 2'-aminopropoxy (2'-$OCH_2CH_2CH_2NH_2$), 2'-allyl (2'-$CH_2$—CH═$CH_2$), 2'-O-allyl (2'-O—$CH_2$—CH═$CH_2$) and 2'-fluoro (2'-F). The 2'-modification may be in the arabino (up) position or ribo (down) position. One 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Antisense compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; and, 6,147,200.

In one aspect of the present invention oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. There is an apparent preference for an RNA type duplex (A form helix, predominantly 3'-endo) as a requirement (e.g. trigger) of RNA interference which is supported in part by the fact that duplexes composed of 2'-deoxy-2'-F-nucleosides appears efficient in triggering RNAi response in the *C. elegans* system. Properties that are enhanced by using more stable 3'-endo nucleosides include but are not limited to: modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. Also provided herein are oligomeric triggers of RNAi having one or more nucleosides modified in such a way as to favor a C3'-endo type conformation.

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2'deoxy-2'F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Along similar lines, triggers of RNAi response might be composed of one or more nucleosides modified in such a way that conformation is locked into a C3'-endo type conformation, i.e. Locked Nucleic Acid (LNA, Singh et al, Chem. Commun. (1998), 4, 455-456), and ethylene bridged Nucleic Acids (ENA™, Morita et al, Bioorganic & Medicinal Chemistry Letters (2002), 12, 73-76.)

One conformation of modified nucleosides and their oligomers can be estimated by various methods such as molecular dynamics calculations, nuclear magnetic resonance spectroscopy and CD measurements. Hence, modifications predicted to induce RNA-like conformations, A-form duplex geometry in an oligomeric context, are selected for use in the modified oligonucleotides of the present invention. The synthesis of numerous of the modified nucleosides amenable to the present invention are known in the art (see for example, Chemistry of Nucleosides and Nucleotides Vol 1-3, ed. Leroy B. Townsend, 1988, Plenum press., and the examples section below.)

Oligonucleotide Mimetics

Another group of oligomeric compounds includes oligonucleotide mimetics. The term “mimetic” as it is applied to oligonucleotides includes oligomeric compounds wherein the furanose ring or the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid.

One such oligomeric compound, an oligonucleotide mimetic that has been shown to have excellent hybridization properties, is referred to as a peptide nucleic acid (PNA) (Nielsen et al., *Science,* 1991, 254, 1497-1500). PNAs have favorable hybridization properties, high biological stability and are electrostatically neutral molecules. PNA compounds have been used to correct aberrant splicing in a transgenic mouse model (Sazani et al., *Nat. Biotechnol.,* 2002, 20, 1228-1233). In PNA oligomeric compounds, the sugar-backbone of an oligonucleotide is replaced with an amide containing backbone, in particular an aminoethylglycine backbone. The nucleobases are bound directly or indirectly (—C(=O)—$CH_2$— as shown below) to aza nitrogen atoms of the amide portion of the backbone. Representative United States patents that teach the preparation of PNA oligomeric compounds include, but are not limited to, U.S. Pat. Nos. 5,539,082; 5,714,331; and 5,719,262. PNA compounds can be obtained commercially from Applied Biosystems (Foster City, Calif., USA). Numerous modifications to the basic PNA backbone are known in the art; particularly useful are PNA compounds with one or more amino acids conjugated to one or both termini. For example, 1-8 lysine or arginine residues are useful when conjugated to the end of a PNA molecule.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups have been selected to give a non-ionic oligomeric compound. The non-ionic morpholino-based oligomeric compounds are less likely to have undesired interactions with cellular proteins. Morpholino-based oligomeric compounds are non-ionic mimetics of oligonucleotides which are less likely to form undesired interactions with cellular proteins (Dwaine A. Braasch and David R. Corey, *Biochemistry,* 2002, 41(14), 4503-4510). Morpholino-based oligomeric compounds have been studied in zebrafish embryos (see: *Genesis*, volume 30, issue 3, 2001 and Heasman, J., *Dev. Biol.,* 2002, 243, 209-214). Further studies of morpholino-based oligomeric compounds have also been reported (Nasevicius et al., *Nat. Genet.,* 2000, 26, 216-220; and Lacerra et al., *Proc. Natl. Acad. Sci.,* 2000, 97, 9591-9596). Morpholino-based oligomeric compounds are disclosed in U.S. Pat. No. 5,034,506. The morpholino class of oligomeric compounds have been prepared having a variety of different linking groups joining the monomeric subunits. Linking groups can be varied from chiral to achiral, and from charged to neutral. U.S. Pat. No. 5,166,315 discloses linkages including —O—P(=O)(N($CH_3$)$_2$)—O—; U.S. Pat. No. 5,034,506 discloses achiral intermorpholino linkages; and U.S. Pat. No. 5,185,444 discloses phosphorus containing chiral intermorpholino linkages.

A further class of oligonucleotide mimetic is referred to as cyclohexene nucleic acids (CeNA). The furanose ring normally present in a DNA or RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (Wang et al., *J. Am. Chem. Soc.,* 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate *E. coli* RNase H resulting in cleavage of the target RNA strand.

A further modification includes bicyclic sugar moieties such as “Locked Nucleic Acids” (LNAs) in which the 2'-hydroxyl group of the ribosyl sugar ring is linked to the 4' carbon atom of the sugar ring thereby forming a 2'-C,4'-C-oxymethylene linkage to form the bicyclic sugar moiety (reviewed in Elayadi et al., *Curr. Opinion Invens. Drugs,* 2001, 2, 558-561; Braasch et al., *Chem. Biol.,* 2001, 8 1-7; and Orum et al., *Curr. Opinion Mol. Ther.,* 2001, 3, 239-243; see also U.S. Pat. Nos. 6,268,490 and 6,670,461). The linkage can be a methylene (—$CH_2$—) group bridging the 2' oxygen atom and the 4' carbon atom, for which the term LNA is used for the bicyclic moiety; in the case of an ethylene group in this position, the term ENA™ is used (Singh et al., Chem. Commun., 1998, 4, 455-456; ENA™: Morita et al., *Bioorganic Medicinal Chemistry,* 2003, 11, 2211-2226). LNA and other bicyclic sugar analogs display very high duplex thermal stabilities with complementary DNA and RNA (Tm=+3 to +10 C), stability towards 3'-exonucleolytic degradation and good solubility properties. LNA's are commercially available from ProLigo (Paris, France and Boulder, Colo., USA).

An isomer of LNA that has also been studied is alpha-L-LNA which has been shown to have superior stability against a 3'-exonuclease (Frieden et al., *Nucleic Acids Research,* 2003, 21, 6365-6372). The alpha-L-LNA's were incorporated into antisense gapmers and chimeras that showed potent antisense activity.

Another similar bicyclic sugar moiety that has been prepared and studied has the bridge going from the 3'-hydroxyl group via a single methylene group to the 4' carbon atom of the sugar ring thereby forming a 3'-C,4'-C-oxymethylene linkage (see U.S. Pat. No. 6,043,060).

The conformations of LNAs determined by 2D NMR spectroscopy have shown that the locked orientation of the LNA nucleotides, both in single-stranded LNA and in duplexes, constrains the phosphate backbone in such a way as to introduce a higher population of the N-type conformation (Petersen et al., J. Mol. Recognit., 2000, 13, 44-53). These conformations are associated with improved stacking of the nucleobases (Wengel et al., Nucleosides Nucleotides, 1999, 18, 1365-1370).

LNA has been shown to form exceedingly stable LNA:LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands. DNA:LNA chimeras have been shown to efficiently inhibit gene expression when targeted to a variety of regions (5'-untranslated region, region of the start codon or coding region) within the luciferase mRNA (Braasch et al., *Nucleic Acids Research,* 2002, 30, 5160-5167).

Potent and nontoxic antisense oligonucleotides containing LNAs have been described (Wahlestedt et al., *Proc. Natl. Acad. Sci. U.S.A.,* 2000, 97, 5633-5638). The authors have demonstrated that LNAs confer several desired properties. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in *Escherichia coli*. Lipofectin-mediated efficient delivery of LNA into living human breast cancer cells has also been accomplished. Further successful in vivo studies involving LNA's have shown knock-down of the rat delta opioid receptor without toxicity (Wahlestedt et al., *Proc. Natl. Acad. Sci.,* 2000, 97, 5633-5638) and in another study showed a blockage of the translation of the large subunit of RNA polymerase II (Fluiter et al., *Nucleic Acids Res.,* 2003, 31, 953-962).

The synthesis and preparation of the LNA monomers adenine, cytosine, guanine, 5-methylcytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., WO 99/14226). Furthermore, synthesis of 2'-amino-LNA, a novel conformationally restricted high-affinity oligonucleotide analog has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Another oligonucleotide mimetic that has been prepared and studied is threose nucleic acid. This oligonucleotide mimetic is based on threose nucleosides instead of ribose nucleosides. Initial interest in (3',2')-alpha-L-threose nucleic acid (TNA) was directed to the question of whether a DNA polymerase existed that would copy the TNA. It was found that certain DNA polymerases are able to copy limited stretches of a TNA template (reported in *Chemical and Engineering News,* 2003, 81, 9). In another study it was determined that TNA is capable of antiparallel Watson-Crick base pairing with complementary DNA, RNA and TNA oligonucleotides (Chaput et al., *J. Am. Chem. Soc.,* 2003, 125, 856-857).

In one study (3',2')-alpha-L-threose nucleic acid was prepared and compared to the 2' and 3' amidate analogs (Wu et al., *Organic Letters,* 2002, 4(8), 1279-1282). The amidate analogs were shown to bind to RNA and DNA with comparable strength to that of RNA/DNA.

Further oligonucleotide mimetics have been prepared to include bicyclic and tricyclic nucleoside analogs (see Steffens et al., *Helv. Chim. Acta,* 1997, 80, 2426-2439; Steffens et al., *J. Am. Chem. Soc.,* 1999, 121, 3249-3255; Renneberg et al., *J. Am. Chem. Soc.,* 2002, 124, 5993-6002; and Renneberg et al., *Nucleic acids res.,* 2002, 30, 2751-2757). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids which incorporate a phosphorus group in the backbone. This class of olignucleotide mimetic is reported to have useful physical and biological and pharmacological properties in the areas of inhibiting gene expression (antisense oligonucleotides, sense oligonucleotides and triplex-forming oligonucleotides), as probes for the detection of nucleic acids and as auxiliaries for use in molecular biology. Further oligonucleotide mimetics amenable to the present invention have been prepared wherein a cyclobutyl ring replaces the naturally occurring furanosyl ring.

Modified and Alternate Nucleobases

Oligomeric compounds may also include nucleobase (often referred to in the art as heterocyclic base or simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C{\equiv}C-CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-b)(1,4)benzoxazin-2(3H)-one), carbazole cytidine(2H-pyrimido(4,5-b)indol-2-one), pyridoindole cytidine(H-pyrido(3',2':4,5)pyrrolo(2,3-d)pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are known to those skilled in ther art as suitable for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently suitable base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,681,941; and 5,750,692.

Oligomeric compounds of the present invention can also include polycyclic heterocyclic compounds in place of one or more of the naturally-occurring heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Representative cytosine analogs that make 3 hydrogen bonds with a guanosine in a second strand include 1,3-diazaphenoxazine-2-one ($R_{10}$=O, $R_{11}$—$R_{14}$=H) (Kurchavov, et al., *Nucleosides and Nucleotides,* 1997, 16, 1837-1846), 1,3-diazaphenothiazine-2-one ($R_{10}$=S, $R_{11}$—$R_{14}$=H), (Lin, K.-Y.; Jones, R. J.; Matteucci, M. J. Am. Chem. Soc. 1995, 117, 3873-3874) and 6,7,8,9-tetrafluoro-1,3-diazaphenoxazine-2-one ($R_{10}$=O, $R_{11}$—$R_{14}$=F) (Wang, J.; Lin, K.-Y., Matteucci, M. Tetrahedron Lett. 1998, 39, 8385-8388). Incorporated into oligonucleotides these base modifications were shown to hybridize with complementary guanine and the latter was also shown to hybridize with adenine and to enhance helical thermal stability by extended stacking interactions (also see U.S. Patent Application entitled "Modified Peptide Nucleic Acids" filed May 24, 2002, Ser. No. 10/155,920; and U.S. Patent Application entitled "Nuclease Resistant Chimeric Oligonucleotides" filed May 24, 2002, Ser. No. 10/013,295).

Further helix-stabilizing properties have been observed when a cytosine analog/substitute has an aminoethoxy moiety attached to the rigid 1,3-diazaphenoxazine-2-one scaffold ($R_{10}$=O, $R_{11}$=—O—$(CH_2)_2$—$NH_2$, $R_{12-14}$=H) (Lin, K.-Y.; Matteucci, M. J. Am. Chem. Soc. 1998, 120, 8531-8532). Binding studies demonstrated that a single incorporation could enhance the binding affinity of a model oligonucleotide to its complementary target DNA or RNA with a $\Delta T_m$ of up to 18° relative to 5-methyl cytosine ($dC5^{me}$), which is a high affinity enhancement for a single modification. On the other hand, the gain in helical stability does not compromise the specificity of the oligonucleotides.

Further tricyclic heterocyclic compounds and methods of using them that are amenable to use in the present invention are disclosed in U.S. Pat. Nos. 6,028,183, and 6,007,992.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNase H, enhance cellular uptake and exhibit an increased antisense activity (Lin, K-Y; Matteucci, M. J. Am. Chem. Soc. 1998, 120, 8531-8532). The activity enhancement was even more pronounced in case of G-clamp, as a single substitution was shown to significantly improve the in vitro potency of a 20 mer 2'-deoxyphosphorothioate oligonucleotides (Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518).

Further modified polycyclic heterocyclic compounds useful as heterocyclic bases are disclosed in but not limited to, the above noted U.S. Pat. No. 3,687,808, as well as U.S. Pat. No. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121, 5,596,091; 5,614,617; 5,645,985; 5,646,269; 5,750,692; 5,830,653; 5,763,588; 6,005,096; and 5,681,941, and Unites States Pre-Grant Publication 20030158403 filed Nov. 28, 2001.

Conjugates

Another modification of the oligomeric compounds of the invention involves chemically linking to the oligomeric compound one or more moieties or conjugates which enhance the properties of the oligomeric compound, such as to enhance the activity, cellular distribution or cellular uptake of the oligomeric compound. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. Nos. 6,287,860 and 6,762,169.

Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethyl-ammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligomeric compounds of the invention may also be conjugated to drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Oligomeric compounds can also be modified to have one or more stabilizing groups that are generally attached to one or both termini of an oligomeric compound to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., WO 97/26270). These terminal modifications protect the oligomeric compounds having terminal nucleic acid molecules from exonuclease degradation, and can improve delivery and/or localization within a cell. The cap can be present at either the 5'-terminus (5'-cap) or at the 3'-terminus (3'-cap) or can be present on both termini of a single strand, or one or more termini of both strands of a double-stranded compound. This cap structure is not to be confused with the inverted methylguanosine "5'cap" present at the 5' end of native mRNA molecules. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl riucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270). For siRNA constructs, the 5' end (5' cap) is commonly but not limited to 5'-hydroxyl or 5'-phosphate.

Particularly suitable 3'-cap structures include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925).

Further 3' and 5'-stabilizing groups that can be used to cap one or both ends of an oligomeric compound to impart nuclease stability include those disclosed in WO 03/004602 published on Jan. 16, 2003.

Chimeric Compounds

It is not necessary for all positions in a given oligomeric compound to be uniformly modified, and in fact more than one of the aforementioned modifications may be incorporated in a single compound or even within a single nucleoside within an oligomeric compound.

The present invention also includes oligomeric compounds which are chimeric compounds. "Chimeric" oligomeric compounds or "chimeras," in the context of this invention, are single- or double-stranded oligomeric compounds, such as oligonucleotides, which contain two or more chemically distinct regions, each comprising at least one monomer unit, i.e., a nucleotide in the case of an oligonucleotide compound. Chimeric antisense oligonucleotides are one form of oligomeric compound. These oligonucleotides typically contain at least one region which is modified so as to confer upon the oligonucleotide increased resistance to nuclease degradation, increased cellular uptake, alteration of charge, increased stability and/or increased binding affinity for the target nucleic acid. An additional region of the oligonucleotide may serve as a substrate for RNAses or other enzymes. By way of example, RNAse H is a cellular endonuclease which cleaves the RNA strand of an RNA:DNA duplex. Activation of RNase H, therefore, results in cleavage of the RNA target when bound by a DNA-like oligomeric compound, thereby greatly enhancing the efficiency of oligonucleotide-mediated inhibition of gene expression. The cleavage of RNA:RNA hybrids can, in like fashion, be accomplished through the actions of endoribonucleases, such as RNase III or RNAseL which cleaves both cellular and viral RNA. Cleavage products of the RNA target can be routinely detected by gel electrophoresis and, if necessary, associated nucleic acid hybridization techniques known in the art.

Chimeric oligomeric compounds of the invention can be formed as composite structures of two or more oligonucleotides, modified oligonucleotides, oligonucleosides, oligonucleotide mimetics, or regions or portions thereof. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922.

A "gapmer" is defined as an oligomeric compound, generally an oligonucleotide, having a 2'-deoxyoligonucleotide flanked by non-deoxyoligonucleotides. The central region is referred to as the "gap." The flanking regions are referred to as "wings." While not wishing to be bound by theory, the gap of the gapmer presents a substrate recognizable by RNase H when bound to the RNA target whereas the wings do not provide such a substrate but can confer other properties such as contributing to duplex stability or advantageous pharmacokinetic effects. Each wing can be one or more non-deoxyoligonucleotide monomers (if one of the wings has zero non-deoxyoligonucleotide monomers, a "hemimer" is described). In one embodiment, the gapmer is a ten deoxynucleotide gap flanked by five non-deoxynucleotide wings. This is refered to as a 5-10-5 gapmer. Other configurations are readily recognized by those skilled in the art. In one embodiment the wings comprise 2'-MOE modified nucleotides. In another embodiment the gapmer has a phosphorothioate backbone. In another embodiment the gapmer has 2'-MOE wings and a phosphorothioate backbone. Other suitable modifications are readily recognizable by those skilled in the art.

Oligomer Synthesis

Oligomerization of modified and unmodified nucleosides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Oligomeric compounds of the present invention can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Starting Materials and Intermediates

The following precursor compounds, including amidites and their intermediates can be prepared by methods routine to those skilled in the art; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, (5'-O-(4,4'-Dimethoxytriphenylmethyl)-2'-deoxy-$N^4$-benzoyl-5-methylcytidin-3'-O-yl)-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, (5'-O-(4,4'-Dimethoxytriphenylmethyl)-2'-O-(2-methoxyethyl)-5-methyluridin-3'-O-yl)-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-$N^4$-benzoyl-5-methylcytidine penultimate intermediate, (5'-O-(4,4'-Dimethoxytriphenylmethyl)-2'-O-(2-methoxyethyl)-$N^4$-benzoyl-5-methylcytidin-3'-O-yl)-2-cyanoethyl-N,N-diisopropylphosphoramidite (MOE 5-Me-C amidite), (5'-O-(4,4'-Dimethoxytriphenylmethyl)-2'-O-(2-methoxyethyl)-$N^6$-benzoyladenosin-3'-O-yl)-2-cyanoethyl-N,N-diisopropylphosphoramidite (MOE A amdite), (5'-O-(4,4'-Dimethoxytriphenylmethyl)-2'-O-(2-methoxyethyl)-$N^4$-isobutyrylguanosin-3'-O-yl)-2-cyanoethyl-N,N-diisopropylphosphoramidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-$O^2$-2'-anhydro-5-methyluridine, 5'-O-tert-Butyldiphenylsilyl-2'-O-(2-hydroxyethyl)-5-methyluridine, 2'-O-((2-phthalimidoxy)ethyl)-5'-t-butyldiphenylsilyl-5-methyluridine, 5'-O-tert-butyldiphenylsilyl-2'-O-((2-formadoximinooxy)ethyl)-5-methyluridine, 5'-O-tert-Butyldiphenylsilyl-2'-O—(N,N dimethylaminooxyethyl)-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-((2-cyanoethyl)-N,N-diisopropylphosphoramidite), 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-((2-cyanoethyl)-N,N-diisopropylphosphoramidite), 2'-dimethylaminoethoxyethoxy (2'-DMAEOE) nucleoside amidites, 2'-O-(2(2-N,N-dimethylaminoethoxy)ethyl)-5-methyl uridine, 5'-O-dimethoxytrityl-2'-O-(2(2-N,N-dimethylaminoethoxy)-ethyl))-5-methyl uridine and 5'-O-Dimethoxytrityl-2'-O-(2(2-N,N-dimethylaminoethoxy)-ethyl))-5-methyl uridine-3'-O-(cyanoethyl-N,N-diisopropyl) phosphoramidite.

The preparation of such precursor compounds for oligonucleotide synthesis are routine in the art and disclosed in U.S. Pat. No. 6,426,220 and published PCT WO 02/36743.

2'-Deoxy and 2'-methoxy beta-cyanoethyldiisopropyl phosphoramidites can be purchased from commercial sources (e.g. Chemgenes, Needham, Mass. or Glen Research, Inc. Sterling, Va.). Other 2'-O-alkoxy substituted nucleoside amidites can be prepared as described in U.S. Pat. No. 5,506,351.

Oligonucleotides containing 5-methyl-2'-deoxycytidine (5-Me-C) nucleotides can be synthesized routinely according to published methods (Sanghvi, et. al., *Nucleic Acids Research,* 1993, 21, 3197-3203) using commercially available phosphoramidites (Glen Research, Sterling Va. or ChemGenes, Needham, Mass.).

2'-fluoro oligonucleotides can be synthesized routinely as described (Kawasaki, et. al., *J. Med. Chem.,* 1993, 36, 831-841) and U.S. Pat. No. 5,670,633.

2'-O-Methoxyethyl-substituted nucleoside amidites can be prepared routinely as per the methods of Martin, P., *Helvetica Chimica Acta,* 1995, 78, 486-504.

Aminooxyethyl and dimethylaminooxyethyl amidites can be prepared routinely as per the methods of U.S. Pat. No. 6,127,533.

Oligonucleotide Synthesis

Phosphorothioate-containing oligonucleotides (P═S) can be synthesized by methods routine to those skilled in the art (see, for example, Protocols for Oligonucleotides and Analogs, Ed. Agrawal (1993), Humana Press). Phosphinate oligonucleotides can be prepared as described in U.S. Pat. No. 5,508,270.

Alkyl phosphonate oligonucleotides can be prepared as described in U.S. Pat. No. 4,469,863.

3'-Deoxy-3'-methylene phosphonate oligonucleotides can be prepared as described in U.S. Pat. Nos. 5,610,289 or 5,625,050.

Phosphoramidite oligonucleotides can be prepared as described in U.S. Pat. No. 5,256,775 or U.S. Pat. No. 5,366,878.

Alkylphosphonothioate oligonucleotides can be prepared as described in published PCT applications PCT/US94/00902 and PCT/US93/06976 (published as WO 94/17093 and WO 94/02499, respectively).

3'-Deoxy-3'-amino phosphoramidate oligonucleotides can be prepared as described in U.S. Pat. No. 5,476,925.

Phosphotriester oligonucleotides can be prepared as described in U.S. Pat. No. 5,023,243.

Borano phosphate oligonucleotides can be prepared as described in U.S. Pat. Nos. 5,130,302 and 5,177,198.

4'-thio-containing oligonucleotides can be synthesized as described in U.S. Pat. No. 5,639,873.

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P═O or P═S linkages can be prepared as described in U.S. Pat. Nos. 5,378,825, 5,386,023, 5,489,677, 5,602,240 and 5,610,289.

Formacetal and thioformacetal linked oligonucleosides can be prepared as described in U.S. Pat. Nos. 5,264,562 and 5,264,564.

Ethylene oxide linked oligonucleosides can be prepared as described in U.S. Pat. Nos. 5,223,618.

Peptide Nucleic Acid Synthesis

Peptide nucleic acids (PNAs) can be prepared in accordance with any of the various procedures referred to in Peptide Nucleic Acids (PNA): Synthesis, Properties and Potential Applications, *Bioorganic & Medicinal Chemistry,* 1996, 4, 5-23. They may also be prepared in accordance with U.S. Pat. Nos. 5,539,082, 5,700,922, 5,719,262, 6,559,279 and 6,762,281.

Synthesis of 2'-O-Protected Oligomers/RNA Synthesis

Oligomeric compounds incorporating at least one 2'-O-protected nucleoside by methods routine in the art. After incorporation and appropriate deprotection the 2'-O-protected nucleoside will be converted to a ribonucleoside at the position of incorporation. The number and position of the 2-ribonucleoside units in the final oligomeric compound can vary from one at any site or the strategy can be used to prepare up to a full 2'-OH modified oligomeric compound.

A large number of 2'-O-protecting groups have been used for the synthesis of oligoribo-nucleotides and any can be used. Some of the protecting groups used initially for oligoribonucleotide synthesis included tetrahydropyran-1-yl and 4-methoxytetrahydropyran-4-yl. These two groups are not compatible with all 5'-O-protecting groups so modified versions were used with 5'-DMT groups such as 1-(2-fluorophenyl)-4-methoxypiperidin-4-yl (Fpmp). Reese et al. have identified a number of piperidine derivatives (like Fpmp) that are useful in the synthesis of oligoribonucleotides including 1-[(chloro-4-methyl)phenyl]-4'-methoxypiperidin-4-yl (Reese et al., Tetrahedron Lett., 1986, (27), 2291). Another approach is to replace the standard 5'-DMT (dimethoxytrityl) group with protecting groups that were removed under non-acidic conditions such as levulinyl and 9-fluorenylmethoxycarbonyl. Such groups enable the use of acid labile 2'-protecting groups for oligoribonucleotide synthesis. Another more widely used protecting group, initially used for the synthesis of oligoribonucleotides, is the t-butyldimethylsilyl group (Ogilvie et al., Tetrahedron Lett., 1974, 2861; Hakimelahi et al., Tetrahedron Lett., 1981, (22), 2543; and Jones et al., J. Chem. Soc. Perkin I., 2762). The 2'-O-protecting groups can require special reagents for their removal. For example, the t-butyldimethylsilyl group is normally removed after all other cleaving/deprotecting steps by treatment of the oligomeric compound with tetrabutylammonium fluoride (TBAF).

One group of researchers examined a number of 2'-O-protecting groups (Pitsch, S., Chimia, 2001, (55), 320-324.) The group examined fluoride labile and photolabile protecting groups that are removed using moderate conditions. One photolabile group that was examined was the [2-(nitrobenzyl)oxy]methyl (nbm) protecting group (Schwartz et al., Bioorg. Med. Chem. Lett., 1992, (2), 1019.) Other groups examined included a number structurally related formaldehyde acetal-derived, 2'-O-protecting groups. Also prepared were a number of related protecting groups for preparing 2'-O-alkylated nucleoside phosphoramidites including 2'-O-[(triisopropylsilyl)oxy]methyl (2'-O—$CH_2$-O—Si(iPr)$_3$, TOM). One 2'-O-protecting group that was prepared to be used orthogonally to the TOM group was 2'-O—[(R)-1-(2-nitrophenyl)ethyloxy) methyl]((R)-mnbm).

Another strategy using a fluoride labile 5'-O-protecting group (non-acid labile) and an acid labile 2'-O-protecting group has been reported (Scaringe, Stephen A., Methods, 2001, (23) 206-217). A number of possible silyl ethers were examined for 5'-O-protection and a number of acetals and orthoesters were examined for 2'-O-protection. The protection scheme that gave the best results was 5'-O-silyl ether-2'-ACE (5'-O-bis(trimethylsiloxy)cyclododecyloxysilyl ether (DOD)-2'-O-bis(2-acetoxyethoxy)methyl (ACE). This approach uses a modified phosphoramidite synthesis approach in that some different reagents are required that are not routinely used for RNA/DNA synthesis.

The main RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilyl)oxy]methyl (2'-O—$CH_2$—O—Si(iPr)$_3$ (TOM), and the 5'-O-silyl ether-2'-ACE (5'-O-bis(trimethylsiloxy)cyclododecyloxysilyl ether (DOD)-2'-O-bis(2-acetoxyethoxy)methyl (ACE). Some companies currently offering RNA products include Pierce Nucleic Acid Technologies (Milwaukee, Wis.), Dharmacon Research Inc. (a subsidiary of Fisher Scientific, Lafayette, Colo.), and Integrated DNA Technologies, Inc. (Coralville, Iowa). One company, Princeton Separations, markets an RNA synthesis activator advertised to reduce coupling times especially with TOM and TBDMS chemistries. Such an activator would also be amenable to the oligomeric compounds of the present invention.

The primary groups being used for commercial RNA synthesis are:

TBDMS=5'-O-DMT-2'-O-t-butyldimethylsilyl;

TOM=2'-O-[(triisopropylsilyl)oxy]methyl;

DOD/ACE=(5'-O-bis(trimethylsiloxy)cyclododecyloxysilyl ether-2'-O-bis(2-acetoxyethoxy)methyl FPMP=5'-O-DMT-2'-O-[1(2-fluorophenyl)-4-methoxypiperidin-4-yl].

All of the aforementioned RNA synthesis strategies are amenable to the oligomeric compounds of the present invention. Strategies that would be a hybrid of the above e.g. using a 5'-protecting group from one strategy with a 2'-O-protecting from another strategy is also contemplated herein.

Synthesis of Chimeric Oligomeric Compounds (2'-O-Me)-(2'-deoxy)-(2'-O-Me) Chimeric Phosphorothioate Oligonucleotides Chimeric oligonucleotides having 2'-O-alkyl phosphorothioate and 2'-deoxy phosphorothioate oligonucleotide segments can be routinely synthesized by one skilled in the art, using, for example, an Applied Biosystems automated DNA synthesizer Model 394. Oligonucleotides can be synthesized using an automated synthesizer and 2'-deoxy-5'-dimethoxytrityl-3'-O-phosphoramidite for the DNA portion and 5'-dimethoxytrityl-2'-O-methyl-3'-O-phosphoramidite for the 2'-O-alkyl portion. In one nonlimiting example, the standard synthesis cycle is modified by incorporating coupling steps with increased reaction times for the 5'-dimethoxy-trityl-2'-O-methyl-3'-O-phosphoramidite. The fully protected oligonucleotide is cleaved from the support and deprotected in concentrated ammonia ($NH_4OH$) for 12-16 hr at 55° C. The deprotected oligonucleotide is then recovered by an appropriate method (precipitation, column chromatography, volume reduced in vacuo) and analyzed by methods routine in the art.

(2'-O-(2-Methoxyethyl))-(2'-deoxy)-(2'-O-(Methoxyethyl)) Chimeric Phosphorothioate Oligonucleotides (2'-O-(2-methoxyethyl))-(2'-deoxy)-(-2'-O-(methoxyethyl)) chimeric phosphorothioate oligonucleotides can be prepared as per the procedure above for the 2'-O-methyl chimeric oligonucleotide, with the substitution of 2'-O-(methoxyethyl) amidites for the 2'-O-methyl amidites.

(2'-O-(2-Methoxyethyl)Phosphodiester)-(2'-deoxy Phosphorothioate)-(2'-O-(2-Methoxyethyl)Phosphodiester) Chimeric Oligonucleotides (2'-O-(2-methoxyethyl phosphodiester)-(2'-deoxy phosphorothioate)-(2'-O-(methoxyethyl)phosphodiester) chimeric oligonucleotides can be prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides can be synthesized according to U.S. Pat. No. 5,623,065.

Oligomer Purification and Analysis

Methods of oligomeric compound purification and analysis are well known to those skilled in the art. Analysis methods include capillary electrophoresis (CE) and electrospray-mass spectroscopy. Such synthesis and analysis methods can be performed in multi-well plates.

Hybridization

"Hybridization" means the pairing of complementary strands of oligomeric compounds. While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An oligomeric compound is specifically hybridizable when there is a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays.

"Stringent hybridization conditions" or "stringent conditions" refers to conditions under which an oligomeric compound will hybridize to its target sequence, but to a minimal number of other sequences. Stringent conditions are sequence-dependent and will be different in different circumstances, and "stringent conditions" under which oligomeric compounds hybridize to a target sequence are determined by the nature and composition of the oligomeric compounds and the assays in which they are being investigated.

Complementarity

"Complementarity," as used herein, refers to the capacity for precise pairing between two nucleobases on one or two oligomeric compound strands. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be a complementary position. The oligomeric compound and the further DNA or RNA are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligomeric compound and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligomeric compounds of the present invention comprise at least 70%, or at least 75%, or at least 80%, or at least 85%, or at least 90%, or at least 95%, or at least 99% sequence complementarity to a target region within the target nucleic acid sequence to which they are targeted. For example, an oligomeric compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

The oligomeric compounds of the invention also include variants in which a different base is present at one or more of the nucleotide positions in the compound. For example, if the first nucleotide is an adenosine, variants may be produced which contain thymidine, guanosine or cytidine at this position. This may be done at any of the positions of the oligomeric compound. These compounds are then tested using the methods described herein to determine their ability to inhibit expression of a Gemin Gene mRNA.

In one embodiment, homology, sequence identity or complementarity, between the oligomeric compound and target nucleic acid is from about 50% to about 60%. In another embodiment, homology, sequence identity or complementarity, is from about 60% to about 70%. In another embodiment, homology, sequence identity or complementarity, is from about 70% to about 80%. In another embodiment, homology, sequence identity or complementarity, is from about 80% to about 90%. In still other embodiments, homology, sequence identity or complementarity, is about 90%, about 92%, about 94%, about 95%, about 96%, about 97%, about 98%, about 99% or about 100%.

Target Nucleic Acids

"Targeting" an oligomeric compound to a particular target nucleic acid molecule can be a multistep process. The process usually begins with the identification of a target nucleic acid whose expression is to be modulated. As used herein, the terms "target nucleic acid" and "nucleic acid encoding a Gemin Gene" encompass DNA encoding a Gemin Gene, RNA (including pre-mRNA and mRNA) transcribed from such DNA, and also cDNA derived from such RNA. For example, the target nucleic acid can be a cellular gene (or mRNA transcribed from the gene) whose expression is associated with a particular disorder or disease state, or a nucleic acid molecule from an infectious agent. As disclosed herein, the target nucleic acid encodes a Gemin Gene.

Target Regions, Segments, and Sites

The targeting process usually also includes determination of at least one target region, segment, or site within the target nucleic acid for the antisense interaction to occur such that the desired effect, e.g., modulation of expression, will result. "Region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Start Codons

Since, as is known in the art, the translation initiation codon is typically 5' AUG (in transcribed mRNA molecules; 5' ATG in the corresponding DNA molecule), the translation initiation codon is also referred to as the "AUG codon," the "start codon" or the "AUG start codon." A minority of genes have a translation initiation codon having the RNA sequence 5' GUG, 5' UUG or 5' CUG, and 5' AUA, 5' ACG and 5' CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. "Start codon" and "translation initiation codon" refer to the codon or codons that are used in vivo to initiate translation of an mRNA transcribed from a gene encoding a protein, regardless of the sequence(s) of such codons. It is also known in the art that a translation termination codon (or "stop codon") of a gene may have one of three sequences, i.e., 5' UAA, 5' UAG and 5' UGA (the corresponding DNA sequences are 5' TAA, 5' TAG and 5' TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with oligomeric compounds of the invention.

Coding Regions

The open reading frame (ORF) or "coding region," which is known in the art to refer to the region between the translation initiation codon and the translation termination codon, is also a region which may be targeted effectively. Within the context of the present invention, one region is the intragenic region encompassing the translation initiation or termination codon of the open reading frame (ORF) of a gene.

Untranslated Regions

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. The 5' cap region is also a target.

Introns and Exons

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence, resulting in exon-exon junctions at the site where exons are joined. Targeting exon-exon junctions can be useful in situations where aberrant levels of a normal splice product is implicated in disease, or where aberrant levels of an aberrant splice product is implicated in disease. Targeting splice sites, i.e., intron-exon junctions or exon-intron junctions can also be particularly useful in situations where aberrant splicing is implicated in disease, or where an overproduction of a particular splice product is implicated in disease. Aberrant fusion junctions due to rearrangements or deletions are also suitable targets. mRNA transcripts produced via the process of splicing of two (or more) mRNAs from different gene sources are known as "fusion transcripts" and are also suitable targets. It is also known that introns can be effectively targeted using antisense compounds targeted to, for example, DNA or pre-mRNA. Single-stranded antisense compounds such as oligonucleotide compounds that work via an RNase H mechanism are effective for targeting pre-mRNA. Antisense compounds that function via an occupancy-based mechanism are effective for redirecting splicing as they do not, for example, elicit RNase H cleavage of the mRNA, but rather leave the mRNA intact and promote the yield of desired splice product(s).

Variants

It is also known in the art that alternative RNA transcripts can be produced from the same genomic region of DNA. These alternative transcripts are generally known as "variants." More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants." Consequently, mRNA variants are processed pre-mRNA variants and each unique pre-mRNA variant must always produce a unique mRNA variant as a result of splicing. These mRNA variants are also known as "alternative splice variants." If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Consequently, the types of variants described herein are also suitable target nucleic acids.

Target Names, Synonyms, Features

In accordance with the present invention are compositions and methods for modulating the expression of genes which are presented in Table 1. Table 1 lists the gene target names and their respective synonyms, as well as GenBank accession numbers used to design oligomeric compounds targeted to each gene. Table 1 also describes features contained within the gene target nucleic acid sequences of the invention. Representative features include 5'UTR, start codon, coding sequence (coding), stop codon, 3'UTR, exon, intron, exon: exon junction, intron:exon junction and exon:intron junction. "Feature start site" and "feature end site" refer to the first (5'-most) and last (3'-most) nucleotide numbers, respectively, of the described feature with respect to the designated sequence. For example, for a sequence containing a start codon comprising the first three nucleotides, "feature start site" is "1" and "feature end site" is "3".

TABLE 1

Gene Targets, Synonyms and Features

| Target Name | Synonyms | Species | Genbank # | Feature | Feature Start Site | Feature Stop Site | SEQ ID NO |
|---|---|---|---|---|---|---|---|
| Gemin2 | SIP1; SMP-interacting protein 1; survival of motor neuron protein interacting protein 1 | Human | AB037701.1 | start codon | 1 | 3 | 1 |
| Gemin2 | Same as above | Human | AB037701.1 | start codon | 1 | 3 | 1 |
| Gemin2 | Same as above | Human | AB037701.1 | CDS | 1 | 798 | 1 |
| Gemin2 | Same as above | Human | AB037701.1 | exon:exon junction | 170 | 171 | 1 |
| Gemin2 | Same as above | Human | AB037701.1 | exon | 171 | 255 | 1 |
| Gemin2 | Same as above | Human | AB037701.1 | stop codon | 213 | 215 | 1 |
| Gemin2 | Same as above | Human | AB037701.1 | exon:exon junction | 255 | 256 | 1 |
| Gemin2 | Same as above | Human | AB037701.1 | exon | 256 | 345 | 1 |
| Gemin2 | Same as above | Human | AB037701.1 | exon:exon junction | 345 | 346 | 1 |
| Gemin2 | Same as above | Human | AB037701.1 | exon | 346 | 405 | 1 |
| Gemin2 | Same as above | Human | AB037701.1 | exon:exon junction | 405 | 406 | 1 |
| Gemin2 | Same as above | Human | AB037701.1 | exon | 406 | 519 | 1 |
| Gemin2 | Same as above | Human | AB037701.1 | exon:exon junction | 519 | 520 | 1 |
| Gemin2 | Same as above | Human | AB037701.1 | exon | 520 | 588 | 1 |
| Gemin2 | Same as above | Human | AB037701.1 | exon:exon junction | 588 | 589 | 1 |
| Gemin2 | Same as above | Human | AB037701.1 | exon | 589 | 699 | 1 |
| Gemin2 | Same as above | Human | AB037701.1 | exon:exon junction | 699 | 700 | 1 |
| Gemin2 | Same as above | Human | AB037701.1 | exon | 700 | 758 | 1 |
| Gemin2 | Same as above | Human | AB037701.1 | exon:exon junction | 758 | 759 | 1 |
| Gemin2 | Same as above | Human | AB037701.1 | 3'UTR | 768 | 815 | 1 |
| Gemin2 | Same as above | Human | AB037701.1 | stop codon | 796 | 798 | 1 |
| Gemin2 | Same as above | Human | AB037701.1 | stop codon | 796 | 798 | 1 |
| Gemin2 | Same as above | Human | AB037701.1 | 3'UTR | 799 | 815 | 1 |
| Gemin2 | Same as above | Human | AB037702.1 | start codon | 1 | 3 | 2 |
| Gemin2 | Same as above | Human | AB037702.1 | start codon | 1 | 3 | 2 |
| Gemin2 | Same as above | Human | AB037702.1 | CDS | 1 | 753 | 2 |
| Gemin2 | Same as above | Human | AB037702.1 | exon:exon junction | 170 | 171 | 2 |

TABLE 1-continued

Gene Targets, Synonyms and Features

| Target Name | Synonyms | Species | Genbank # | Feature | Feature Start Site | Feature Stop Site | SEQ ID NO |
|---|---|---|---|---|---|---|---|
| Gemin2 | Same as above | Human | AB037702.1 | exon | 171 | 255 | 2 |
| Gemin2 | Same as above | Human | AB037702.1 | stop codon | 213 | 215 | 2 |
| Gemin2 | Same as above | Human | AB037702.1 | exon:exon junction | 255 | 256 | 2 |
| Gemin2 | Same as above | Human | AB037702.1 | exon | 256 | 345 | 2 |
| Gemin2 | Same as above | Human | AB037702.1 | exon:exon junction | 345 | 346 | 2 |
| Gemin2 | Same as above | Human | AB037702.1 | exon | 346 | 405 | 2 |
| Gemin2 | Same as above | Human | AB037702.1 | exon:exon junction | 405 | 406 | 2 |
| Gemin2 | Same as above | Human | AB037702.1 | exon | 406 | 519 | 2 |
| Gemin2 | Same as above | Human | AB037702.1 | exon:exon junction | 519 | 520 | 2 |
| Gemin2 | Same as above | Human | AB037702.1 | exon | 520 | 564 | 2 |
| Gemin2 | Same as above | Human | AB037702.1 | exon:exon junction | 564 | 565 | 2 |
| Gemin2 | Same as above | Human | AB037702.1 | exon | 565 | 633 | 2 |
| Gemin2 | Same as above | Human | AB037702.1 | exon:exon junction | 633 | 634 | 2 |
| Gemin2 | Same as above | Human | AB037702.1 | exon | 634 | 744 | 2 |
| Gemin2 | Same as above | Human | AB037702.1 | exon:exon junction | 744 | 745 | 2 |
| Gemin2 | Same as above | Human | AB037702.1 | stop codon | 751 | 753 | 2 |
| Gemin2 | Same as above | Human | AB037702.1 | 3'UTR | 754 | 801 | 2 |
| Gemin2 | Same as above | Human | AB037702.1 | stop codon | 782 | 784 | 2 |
| Gemin2 | Same as above | Human | AB037703.1 | start codon | 1 | 3 | 3 |
| Gemin2 | Same as above | Human | AB037703.1 | start codon | 1 | 3 | 3 |
| Gemin2 | Same as above | Human | AB037703.1 | CDS | 1 | 135 | 3 |
| Gemin2 | Same as above | Human | AB037703.1 | exon:exon junction | 90 | 91 | 3 |
| Gemin2 | Same as above | Human | AB037703.1 | exon | 91 | 175 | 3 |
| Gemin2 | Same as above | Human | AB037703.1 | stop codon | 133 | 135 | 3 |
| Gemin2 | Same as above | Human | AB037703.1 | 3'UTR | 136 | 825 | 3 |
| Gemin2 | Same as above | Human | AB037703.1 | exon:exon junction | 175 | 176 | 3 |
| Gemin2 | Same as above | Human | AB037703.1 | exon | 176 | 265 | 3 |
| Gemin2 | Same as above | Human | AB037703.1 | exon:exon junction | 265 | 266 | 3 |
| Gemin2 | Same as above | Human | AB037703.1 | exon | 266 | 325 | 3 |
| Gemin2 | Same as above | Human | AB037703.1 | exon:exon junction | 325 | 326 | 3 |
| Gemin2 | Same as above | Human | AB037703.1 | exon | 326 | 439 | 3 |
| Gemin2 | Same as above | Human | AB037703.1 | exon:exon junction | 439 | 440 | 3 |
| Gemin2 | Same as above | Human | AB037703.1 | exon | 440 | 484 | 3 |
| Gemin2 | Same as above | Human | AB037703.1 | exon:exon junction | 484 | 485 | 3 |
| Gemin2 | Same as above | Human | AB037703.1 | exon | 485 | 553 | 3 |
| Gemin2 | Same as above | Human | AB037703.1 | exon:exon junction | 553 | 554 | 3 |
| Gemin2 | Same as above | Human | AB037703.1 | exon | 554 | 664 | 3 |
| Gemin2 | Same as above | Human | AB037703.1 | exon:exon junction | 664 | 665 | 3 |
| Gemin2 | Same as above | Human | AB037703.1 | exon | 665 | 723 | 3 |
| Gemin2 | Same as above | Human | AB037703.1 | exon:exon junction | 723 | 724 | 3 |
| Gemin2 | Same as above | Human | AB037703.1 | stop codon | 761 | 763 | 3 |
| Gemin2 | Same as above | Human | BC028095.1 | start codon | 22 | 24 | 4 |
| Gemin2 | Same as above | Human | BC028095.1 | exon:exon junction | 191 | 192 | 4 |
| Gemin2 | Same as above | Human | BC028095.1 | exon | 192 | 276 | 4 |
| Gemin2 | Same as above | Human | BC028095.1 | stop codon | 234 | 236 | 4 |
| Gemin2 | Same as above | Human | BC028095.1 | exon:exon junction | 276 | 277 | 4 |
| Gemin2 | Same as above | Human | BC028095.1 | exon | 277 | 366 | 4 |
| Gemin2 | Same as above | Human | BC028095.1 | exon:exon junction | 366 | 367 | 4 |
| Gemin2 | Same as above | Human | BC028095.1 | exon | 367 | 426 | 4 |
| Gemin2 | Same as above | Human | BC028095.1 | exon:exon junction | 426 | 427 | 4 |
| Gemin2 | Same as above | Human | BC028095.1 | exon | 427 | 544 | 4 |
| Gemin2 | Same as above | Human | BC028095.1 | exon:exon junction | 544 | 545 | 4 |

TABLE 1-continued

| Gene Targets, Synonyms and Features | | | | | | | |
|---|---|---|---|---|---|---|---|
| Target Name | Synonyms | Species | Genbank # | Feature | Feature Start Site | Feature Stop Site | SEQ ID NO |
| Gemin2 | Same as above | Human | BC028095.1 | exon | 545 | 658 | 4 |
| Gemin2 | Same as above | Human | BC028095.1 | exon:exon junction | 658 | 659 | 4 |
| Gemin2 | Same as above | Human | BC028095.1 | exon | 659 | 703 | 4 |
| Gemin2 | Same as above | Human | BC028095.1 | exon:exon junction | 703 | 704 | 4 |
| Gemin2 | Same as above | Human | BC028095.1 | exon | 704 | 772 | 4 |
| Gemin2 | Same as above | Human | BC028095.1 | exon:exon junction | 772 | 773 | 4 |
| Gemin2 | Same as above | Human | BC028095.1 | exon | 773 | 883 | 4 |
| Gemin2 | Same as above | Human | BC028095.1 | exon:exon junction | 883 | 884 | 4 |
| Gemin2 | Same as above | Human | BC028095.1 | exon | 884 | 942 | 4 |
| Gemin2 | Same as above | Human | BC028095.1 | exon:exon junction | 942 | 943 | 4 |
| Gemin2 | Same as above | Human | BC028095.1 | exon | 943 | 1476 | 4 |
| Gemin2 | Same as above | Human | BC028095.1 | 3'UTR | 952 | 999 | 4 |
| Gemin2 | Same as above | Human | BC028095.1 | stop codon | 980 | 982 | 4 |
| Gemin2 | Same as above | Human | BC028095.1 | 3'UTR | 983 | 1341 | 4 |
| Gemin2 | Same as above | Human | BG779734.1 | exon:exon junction | 154 | 155 | 5 |
| Gemin2 | Same as above | Human | BG779734.1 | exon | 155 | 239 | 5 |
| Gemin2 | Same as above | Human | BG779734.1 | stop codon | 197 | 199 | 5 |
| Gemin2 | Same as above | Human | BG779734.1 | exon:exon junction | 239 | 240 | 5 |
| Gemin2 | Same as above | Human | BG779734.1 | exon | 240 | 329 | 5 |
| Gemin2 | Same as above | Human | BG779734.1 | exon:exon junction | 329 | 330 | 5 |
| Gemin2 | Same as above | Human | BG779734.1 | exon | 330 | 389 | 5 |
| Gemin2 | Same as above | Human | BG779734.1 | exon:exon junction | 389 | 390 | 5 |
| Gemin2 | Same as above | Human | BG779734.1 | exon | 390 | 503 | 5 |
| Gemin2 | Same as above | Human | BG779734.1 | exon:exon junction | 503 | 504 | 5 |
| Gemin2 | Same as above | Human | BG779734.1 | exon | 504 | 548 | 5 |
| Gemin2 | Same as above | Human | BG779734.1 | exon:exon junction | 548 | 549 | 5 |
| Gemin2 | Same as above | Human | BG779734.1 | exon | 549 | 659 | 5 |
| Gemin2 | Same as above | Human | BG779734.1 | exon:exon junction | 659 | 660 | 5 |
| Gemin2 | Same as above | Human | BI602162.1 | exon:exon junction | 173 | 174 | 6 |
| Gemin2 | Same as above | Human | BI602162.1 | exon | 174 | 258 | 6 |
| Gemin2 | Same as above | Human | BI602162.1 | stop codon | 216 | 218 | 6 |
| Gemin2 | Same as above | Human | BI602162.1 | exon:exon junction | 258 | 259 | 6 |
| Gemin2 | Same as above | Human | BI602162.1 | exon | 259 | 348 | 6 |
| Gemin2 | Same as above | Human | BI602162.1 | exon:exon junction | 348 | 349 | 6 |
| Gemin2 | Same as above | Human | BI602162.1 | exon | 349 | 408 | 6 |
| Gemin2 | Same as above | Human | BI602162.1 | exon:exon junction | 408 | 409 | 6 |
| Gemin2 | Same as above | Human | BI602162.1 | exon | 409 | 453 | 6 |
| Gemin2 | Same as above | Human | BI602162.1 | exon:exon junction | 453 | 454 | 6 |
| Gemin2 | Same as above | Human | BI602162.1 | exon | 454 | 564 | 6 |
| Gemin2 | Same as above | Human | BI602162.1 | exon:exon junction | 564 | 565 | 6 |
| Gemin2 | Same as above | Human | BI602162.1 | exon | 565 | 623 | 6 |
| Gemin2 | Same as above | Human | BI602162.1 | exon:exon junction | 623 | 624 | 6 |
| Gemin2 | Same as above | Human | BI602162.1 | 3'UTR | 633 | 680 | 6 |
| Gemin2 | Same as above | Human | BI602162.1 | stop codon | 661 | 663 | 6 |
| Gemin2 | Same as above | Human | BI602162.1 | 3'UTR | 664 | 680 | 6 |
| Gemin2 | Same as above | Human | NM_003616.1 | 5'UTR | 1 | 83 | 7 |
| Gemin2 | Same as above | Human | NM_003616.1 | exon | 1 | 253 | 7 |
| Gemin2 | Same as above | Human | NM_003616.1 | start codon | 84 | 86 | 7 |
| Gemin2 | Same as above | Human | NM_003616.1 | CDS | 84 | 926 | 7 |
| Gemin2 | Same as above | Human | NM_003616.1 | exon:exon junction | 253 | 254 | 7 |
| Gemin2 | Same as above | Human | NM_003616.1 | exon | 254 | 338 | 7 |
| Gemin2 | Same as above | Human | NM_003616.1 | stop codon | 296 | 298 | 7 |
| Gemin2 | Same as above | Human | NM_003616.1 | 3'UTR | 299 | 988 | 7 |

TABLE 1-continued

| Gene Targets, Synonyms and Features | | | | | | | |
|---|---|---|---|---|---|---|---|
| Target Name | Synonyms | Species | Genbank # | Feature | Feature Start Site | Feature Stop Site | SEQ ID NO |
| Gemin2 | Same as above | Human | NM_003616.1 | exon:exon junction | 338 | 339 | 7 |
| Gemin2 | Same as above | Human | NM_003616.1 | exon | 339 | 428 | 7 |
| Gemin2 | Same as above | Human | NM_003616.1 | exon:exon junction | 428 | 429 | 7 |
| Gemin2 | Same as above | Human | NM_003616.1 | exon | 429 | 488 | 7 |
| Gemin2 | Same as above | Human | NM_003616.1 | exon:exon junction | 488 | 489 | 7 |
| Gemin2 | Same as above | Human | NM_003616.1 | exon | 489 | 602 | 7 |
| Gemin2 | Same as above | Human | NM_003616.1 | exon:exon junction | 602 | 603 | 7 |
| Gemin2 | Same as above | Human | NM_003616.1 | exon | 603 | 647 | 7 |
| Gemin2 | Same as above | Human | NM_003616.1 | exon:exon junction | 647 | 648 | 7 |
| Gemin2 | Same as above | Human | NM_003616.1 | exon | 648 | 716 | 7 |
| Gemin2 | Same as above | Human | NM_003616.1 | exon:exon junction | 716 | 717 | 7 |
| Gemin2 | Same as above | Human | NM_003616.1 | exon | 717 | 827 | 7 |
| Gemin2 | Same as above | Human | NM_003616.1 | exon:exon junction | 827 | 828 | 7 |
| Gemin2 | Same as above | Human | NM_003616.1 | exon | 828 | 886 | 7 |
| Gemin2 | Same as above | Human | NM_003616.1 | exon:exon junction | 886 | 887 | 7 |
| Gemin2 | Same as above | Human | NM_003616.1 | 3'UTR | 896 | 943 | 7 |
| Gemin2 | Same as above | Human | NM_003616.1 | stop codon | 924 | 926 | 7 |
| Gemin2 | Same as above | Human | NM_003616.1 | 3'UTR | 927 | 1285 | 7 |
| Gemin2 | Same as above | Human | nucleotides 19913000 to 19938000 of NT_025892.9 | 5'UTR | 1037 | 1119 | 8 |
| Gemin2 | Same as above | Human | nucleotides 19913000 to 19938000 of NT_025892.9 | exon | 1037 | 1289 | 8 |
| Gemin2 | Same as above | Human | nucleotides 19913000 to 19938000 of NT_025892.9 | start codon | 1120 | 1122 | 8 |
| Gemin2 | Same as above | Human | nucleotides 19913000 to 19938000 of NT_025892.9 | intron:exon junction | 1289 | 1290 | 8 |
| Gemin2 | Same as above | Human | nucleotides 19913000 to 19938000 of NT_025892.9 | intron | 1290 | 1642 | 8 |
| Gemin2 | Same as above | Human | nucleotides 19913000 to 19938000 of NT_025892.9 | intron:exon junction | 1642 | 1643 | 8 |
| Gemin2 | Same as above | Human | nucleotides 19913000 to 19938000 of NT_025892.9 | exon | 1643 | 1727 | 8 |
| Gemin2 | Same as above | Human | nucleotides 19913000 to 19938000 of NT_025892.9 | stop codon | 1685 | 1687 | 8 |
| Gemin2 | Same as above | Human | nucleotides 19913000 to 19938000 of NT_025892.9 | intron:exon junction | 1727 | 1728 | 8 |
| Gemin2 | Same as above | Human | nucleotides 19913000 to 19938000 of NT_025892.9 | intron | 1728 | 4812 | 8 |
| Gemin2 | Same as above | Human | nucleotides 19913000 to 19938000 of NT_025892.9 | intron:exon junction | 4812 | 4813 | 8 |
| Gemin2 | Same as above | Human | nucleotides 19913000 to 19938000 of NT_025892.9 | exon | 4813 | 4902 | 8 |
| Gemin2 | Same as above | Human | nucleotides 19913000 to 19938000 of NT_025892.9 | intron:exon junction | 4902 | 4903 | 8 |
| Gemin2 | Same as above | Human | nucleotides 19913000 to 19938000 of NT_025892.9 | intron | 4903 | 5353 | 8 |
| Gemin2 | Same as above | Human | nucleotides 19913000 to 19938000 of NT_025892.9 | intron:exon junction | 5353 | 5354 | 8 |
| Gemin2 | Same as above | Human | nucleotides 19913000 to 19938000 of NT_025892.9 | exon | 5354 | 5413 | 8 |
| Gemin2 | Same as above | Human | nucleotides 19913000 to 19938000 of NT_025892.9 | intron:exon junction | 5413 | 5414 | 8 |
| Gemin2 | Same as above | Human | nucleotides 19913000 to 19938000 of NT_025892.9 | intron | 5414 | 8720 | 8 |
| Gemin2 | Same as above | Human | nucleotides 19913000 to 19938000 of NT_025892.9 | intron | 5414 | 9243 | 8 |
| Gemin2 | Same as above | Human | nucleotides 19913000 to 19938000 of NT_025892.9 | intron:exon junction | 8720 | 8721 | 8 |
| Gemin2 | Same as above | Human | nucleotides 19913000 to 19938000 of NT_025892.9 | exon | 8721 | 8838 | 8 |
| Gemin2 | Same as above | Human | nucleotides 19913000 to 19938000 of NT_025892.9 | intron:exon junction | 8838 | 8839 | 8 |
| Gemin2 | Same as above | Human | nucleotides 19913000 to 19938000 of NT_025892.9 | intron | 8839 | 9243 | 8 |
| Gemin2 | Same as above | Human | nucleotides 19913000 to 19938000 of NT_025892.9 | intron:exon junction | 9243 | 9244 | 8 |

TABLE 1-continued

| Gene Targets, Synonyms and Features | | | | | | | |
|---|---|---|---|---|---|---|---|
| Target Name | Synonyms | Species | Genbank # | Feature | Feature Start Site | Feature Stop Site | SEQ ID NO |
| Gemin2 | Same as above | Human | nucleotides 19913000 to 19938000 of NT_025892.9 | exon | 9244 | 9357 | 8 |
| Gemin2 | Same as above | Human | nucleotides 19913000 to 19938000 of NT_025892.9 | intron:exon junction | 9357 | 9358 | 8 |
| Gemin2 | Same as above | Human | nucleotides 19913000 to 19938000 of NT_025892.9 | intron | 9358 | 11805 | 8 |
| Gemin2 | Same as above | Human | nucleotides 19913000 to 19938000 of NT_025892.9 | intron:exon junction | 11805 | 11806 | 8 |
| Gemin2 | Same as above | Human | nucleotides 19913000 to 19938000 of NT_025892.9 | exon | 11806 | 11850 | 8 |
| Gemin2 | Same as above | Human | nucleotides 19913000 to 19938000 of NT_025892.9 | intron:exon junction | 11850 | 11851 | 8 |
| Gemin2 | Same as above | Human | nucleotides 19913000 to 19938000 of NT_025892.9 | intron | 11851 | 15093 | 8 |
| Gemin2 | Same as above | Human | nucleotides 19913000 to 19938000 of NT_025892.9 | intron:exon junction | 15093 | 15094 | 8 |
| Gemin2 | Same as above | Human | nucleotides 19913000 to 19938000 of NT_025892.9 | exon | 15094 | 15162 | 8 |
| Gemin2 | Same as above | Human | nucleotides 19913000 to 19938000 of NT_025892.9 | intron:exon junction | 15162 | 15163 | 8 |
| Gemin2 | Same as above | Human | nucleotides 19913000 to 19938000 of NT_025892.9 | intron | 15163 | 18771 | 8 |
| Gemin2 | Same as above | Human | nucleotides 19913000 to 19938000 of NT_025892.9 | intron:exon junction | 18771 | 18772 | 8 |
| Gemin2 | Same as above | Human | nucleotides 19913000 to 19938000 of NT_025892.9 | exon | 18772 | 18882 | 8 |
| Gemin2 | Same as above | Human | nucleotides 19913000 to 19938000 of NT_025892.9 | intron:exon junction | 18882 | 18883 | 8 |
| Gemin2 | Same as above | Human | nucleotides 19913000 to 19938000 of NT_025892.9 | intron | 18883 | 20474 | 8 |
| Gemin2 | Same as above | Human | nucleotides 19913000 to 19938000 of NT_025892.9 | intron:exon junction | 20474 | 20475 | 8 |
| Gemin2 | Same as above | Human | nucleotides 19913000 to 19938000 of NT_025892.9 | exon | 20475 | 20533 | 8 |
| Gemin2 | Same as above | Human | nucleotides 19913000 to 19938000 of NT_025892.9 | intron:exon junction | 20533 | 20534 | 8 |
| Gemin2 | Same as above | Human | nucleotides 19913000 to 19938000 of NT_025892.9 | intron | 20534 | 23253 | 8 |
| Gemin2 | Same as above | Human | nucleotides 19913000 to 19938000 of NT_025892.9 | intron:exon junction | 23253 | 23254 | 8 |
| Gemin2 | Same as above | Human | nucleotides 19913000 to 19938000 of NT_025892.9 | exon | 23254 | 23787 | 8 |
| Gemin2 | Same as above | Human | nucleotides 19913000 to 19938000 of NT_025892.9 | 3'UTR | 23263 | 23310 | 8 |
| Gemin2 | Same as above | Human | nucleotides 19913000 to 19938000 of NT_025892.9 | stop codon | 23291 | 23293 | 8 |
| Gemin2 | Same as above | Human | nucleotides 19913000 to 19938000 of NT_025892.9 | 3'UTR | 23294 | 23652 | 8 |
| Gemin4 | GIP1; gem-associated protein 4 | Human | AF177341.2 | CDS | 1310 | 4486 | 9 |
| Gemin4 | Same as above | Human | AF177341.2 | intron:exon junction | 1319 | 1320 | 9 |
| Gemin4 | Same as above | Human | AF177341.2 | CDS | 1343 | 4486 | 9 |
| Gemin4 | Same as above | Human | AF177341.2 | stop codon | 4484 | 4486 | 9 |
| Gemin4 | Same as above | Human | BG702457.1 | exon | 5 | 146 | 10 |
| Gemin4 | Same as above | Human | BG702457.1 | exon:exon junction | 146 | 147 | 10 |
| Gemin4 | Same as above | Human | BI458671.1 | exon:exon junction | 44 | 45 | 11 |
| Gemin4 | Same as above | Human | BI458671.1 | exon | 45 | 140 | 11 |
| Gemin4 | Same as above | Human | BI458671.1 | exon:exon junction | 140 | 141 | 11 |
| Gemin4 | Same as above | Human | NM_015721.1 | 5'UTR | 1 | 23 | 12 |
| Gemin4 | Same as above | Human | NM_015721.1 | start codon | 24 | 26 | 12 |
| Gemin4 | Same as above | Human | NM_015721.1 | CDS | 24 | 3200 | 12 |
| Gemin4 | Same as above | Human | NM_015721.1 | exon:exon junction | 33 | 34 | 12 |
| Gemin4 | Same as above | Human | NM_015721.1 | stop codon | 3198 | 3200 | 12 |
| Gemin4 | Same as above | Human | NM_015721.1 | 3'UTR | 3201 | 3472 | 12 |
| Gemin4 | Same as above | Human | the complement of nucleotides 144000 to 155000 of NT_035414.1 | exon | 1686 | 1827 | 13 |

TABLE 1-continued

| Gene Targets, Synonyms and Features | | | | | | | |
|---|---|---|---|---|---|---|---|
| Target Name | Synonyms | Species | Genbank # | Feature | Feature Start Site | Feature Stop Site | SEQ ID NO |
| Gemin4 | Same as above | Human | the complement of nucleotides 144000 to 155000 of NT_035414.1 | intron:exon junction | 1827 | 1828 | 13 |
| Gemin4 | Same as above | Human | the complement of nucleotides 144000 to 155000 of NT_035414.1 | intron | 1828 | 4050 | 13 |
| Gemin4 | Same as above | Human | the complement of nucleotides 144000 to 155000 of NT_035414.1 | intron:exon junction | 4050 | 4051 | 13 |
| Gemin4 | Same as above | Human | the complement of nucleotides 144000 to 155000 of NT_035414.1 | exon | 4051 | 4146 | 13 |
| Gemin4 | Same as above | Human | the complement of nucleotides 144000 to 155000 of NT_035414.1 | intron:exon junction | 4146 | 4147 | 13 |
| Gemin4 | Same as above | Human | the complement of nucleotides 144000 to 155000 of NT_035414.1 | intron | 4147 | 5927 | 13 |
| Gemin4 | Same as above | Human | the complement of nucleotides 144000 to 155000 of NT_035414.1 | intron:exon junction | 5927 | 5928 | 13 |
| Gemin4 | Same as above | Human | the complement of nucleotides 144000 to 155000 of NT_035414.1 | exon | 5928 | 9616 | 13 |
| Gemin4 | Same as above | Human | the complement of nucleotides 144000 to 155000 of NT_035414.1 | stop codon | 9097 | 9099 | 13 |
| Gemin5 | DKFZP586M1 824 protein; gem-associated protein 5 | Human | AL117665.1 | CDS | 1 | 3672 | 14 |
| Gemin5 | Same as above | Human | AL117665.1 | exon:exon junction | 59 | 60 | 14 |
| Gemin5 | Same as above | Human | AL117665.1 | exon | 60 | 225 | 14 |
| Gemin5 | Same as above | Human | AL117665.1 | exon:exon junction | 225 | 226 | 14 |
| Gemin5 | Same as above | Human | AL117665.1 | exon | 226 | 438 | 14 |
| Gemin5 | Same as above | Human | AL117665.1 | exon:exon junction | 438 | 439 | 14 |
| Gemin5 | Same as above | Human | AL117665.1 | exon | 439 | 524 | 14 |
| Gemin5 | Same as above | Human | AL117665.1 | exon:exon junction | 524 | 525 | 14 |
| Gemin5 | Same as above | Human | AL117665.1 | exon | 525 | 607 | 14 |
| Gemin5 | Same as above | Human | AL117665.1 | exon:exon junction | 607 | 608 | 14 |
| Gemin5 | Same as above | Human | AL117665.1 | exon | 608 | 744 | 14 |
| Gemin5 | Same as above | Human | AL117665.1 | exon:exon junction | 744 | 745 | 14 |
| Gemin5 | Same as above | Human | AL117665.1 | exon | 745 | 818 | 14 |
| Gemin5 | Same as above | Human | AL117665.1 | exon:exon junction | 818 | 819 | 14 |
| Gemin5 | Same as above | Human | AL117665.1 | exon | 819 | 1000 | 14 |
| Gemin5 | Same as above | Human | AL117665.1 | exon:exon junction | 1000 | 1001 | 14 |
| Gemin5 | Same as above | Human | AL117665.1 | exon | 1001 | 1140 | 14 |
| Gemin5 | Same as above | Human | AL117665.1 | exon:exon junction | 1140 | 1141 | 14 |
| Gemin5 | Same as above | Human | AL117665.1 | exon | 1141 | 1312 | 14 |
| Gemin5 | Same as above | Human | AL117665.1 | exon:exon junction | 1312 | 1313 | 14 |
| Gemin5 | Same as above | Human | AL117665.1 | exon | 1313 | 1540 | 14 |
| Gemin5 | Same as above | Human | AL117665.1 | exon:exon junction | 1540 | 1541 | 14 |
| Gemin5 | Same as above | Human | AL117665.1 | exon | 1541 | 1654 | 14 |
| Gemin5 | Same as above | Human | AL117665.1 | exon:exon junction | 1654 | 1655 | 14 |
| Gemin5 | Same as above | Human | AL117665.1 | exon | 1655 | 1777 | 14 |
| Gemin5 | Same as above | Human | AL117665.1 | exon:exon junction | 1777 | 1778 | 14 |
| Gemin5 | Same as above | Human | AL117665.1 | exon | 1778 | 1873 | 14 |
| Gemin5 | Same as above | Human | AL117665.1 | exon:exon junction | 1873 | 1874 | 14 |

TABLE 1-continued

| Target Name | Synonyms | Species | Genbank # | Feature | Feature Start Site | Feature Stop Site | SEQ ID NO |
|---|---|---|---|---|---|---|---|
| Gemin5 | Same as above | Human | AL117665.1 | exon | 1874 | 2011 | 14 |
| Gemin5 | Same as above | Human | AL117665.1 | exon:exon junction | 2011 | 2012 | 14 |
| Gemin5 | Same as above | Human | AL117665.1 | exon | 2012 | 2159 | 14 |
| Gemin5 | Same as above | Human | AL117665.1 | exon:exon junction | 2159 | 2160 | 14 |
| Gemin5 | Same as above | Human | AL117665.1 | exon | 2160 | 2279 | 14 |
| Gemin5 | Same as above | Human | AL117665.1 | exon:exon junction | 2279 | 2280 | 14 |
| Gemin5 | Same as above | Human | AL117665.1 | exon | 2280 | 2490 | 14 |
| Gemin5 | Same as above | Human | AL117665.1 | exon:exon junction | 2490 | 2491 | 14 |
| Gemin5 | Same as above | Human | AL117665.1 | exon | 2491 | 2742 | 14 |
| Gemin5 | Same as above | Human | AL117665.1 | exon:exon junction | 2742 | 2743 | 14 |
| Gemin5 | Same as above | Human | AL117665.1 | exon | 2743 | 2905 | 14 |
| Gemin5 | Same as above | Human | AL117665.1 | exon:exon junction | 2905 | 2906 | 14 |
| Gemin5 | Same as above | Human | AL117665.1 | exon | 2906 | 3407 | 14 |
| Gemin5 | Same as above | Human | AL117665.1 | exon:exon junction | 3407 | 3408 | 14 |
| Gemin5 | Same as above | Human | AL117665.1 | exon | 3408 | 3504 | 14 |
| Gemin5 | Same as above | Human | AL117665.1 | exon:exon junction | 3504 | 3505 | 14 |
| Gemin5 | Same as above | Human | AL117665.1 | exon | 3505 | 4569 | 14 |
| Gemin5 | Same as above | Human | AL117665.1 | stop codon | 3670 | 3672 | 14 |
| Gemin5 | Same as above | Human | AL117665.1 | 3'UTR | 3673 | 4586 | 14 |
| Gemin5 | Same as above | Human | BC036894.1 | 5'UTR | 1 | 63 | 15 |
| Gemin5 | Same as above | Human | BC036894.1 | exon | 11 | 229 | 15 |
| Gemin5 | Same as above | Human | BC036894.1 | start codon | 64 | 66 | 15 |
| Gemin5 | Same as above | Human | BC036894.1 | CDS | 64 | 2301 | 15 |
| Gemin5 | Same as above | Human | BC036894.1 | exon:exon junction | 229 | 230 | 15 |
| Gemin5 | Same as above | Human | BC036894.1 | exon | 230 | 390 | 15 |
| Gemin5 | Same as above | Human | BC036894.1 | exon:exon junction | 390 | 391 | 15 |
| Gemin5 | Same as above | Human | BC036894.1 | exon | 391 | 572 | 15 |
| Gemin5 | Same as above | Human | BC036894.1 | exon:exon junction | 572 | 573 | 15 |
| Gemin5 | Same as above | Human | BC036894.1 | exon | 573 | 724 | 15 |
| Gemin5 | Same as above | Human | BC036894.1 | exon:exon junction | 724 | 725 | 15 |
| Gemin5 | Same as above | Human | BC036894.1 | exon | 725 | 844 | 15 |
| Gemin5 | Same as above | Human | BC036894.1 | exon:exon junction | 844 | 845 | 15 |
| Gemin5 | Same as above | Human | BC036894.1 | exon | 845 | 977 | 15 |
| Gemin5 | Same as above | Human | BC036894.1 | exon:exon junction | 977 | 978 | 15 |
| Gemin5 | Same as above | Human | BC036894.1 | exon | 978 | 1143 | 15 |
| Gemin5 | Same as above | Human | BC036894.1 | exon:exon junction | 1143 | 1144 | 15 |
| Gemin5 | Same as above | Human | BC036894.1 | exon | 1144 | 1356 | 15 |
| Gemin5 | Same as above | Human | BC036894.1 | exon:exon junction | 1356 | 1357 | 15 |
| Gemin5 | Same as above | Human | BC036894.1 | exon | 1357 | 1442 | 15 |
| Gemin5 | Same as above | Human | BC036894.1 | exon:exon junction | 1442 | 1443 | 15 |
| Gemin5 | Same as above | Human | BC036894.1 | exon | 1443 | 1525 | 15 |
| Gemin5 | Same as above | Human | BC036894.1 | exon:exon junction | 1525 | 1526 | 15 |
| Gemin5 | Same as above | Human | BC036894.1 | exon | 1526 | 1662 | 15 |
| Gemin5 | Same as above | Human | BC036894.1 | exon:exon junction | 1662 | 1663 | 15 |
| Gemin5 | Same as above | Human | BC036894.1 | exon | 1663 | 1736 | 15 |
| Gemin5 | Same as above | Human | BC036894.1 | exon:exon junction | 1736 | 1737 | 15 |
| Gemin5 | Same as above | Human | BC036894.1 | exon | 1737 | 1918 | 15 |
| Gemin5 | Same as above | Human | BC036894.1 | exon:exon junction | 1918 | 1919 | 15 |
| Gemin5 | Same as above | Human | BC036894.1 | exon | 1919 | 2058 | 15 |
| Gemin5 | Same as above | Human | BC036894.1 | exon:exon junction | 2058 | 2059 | 15 |

TABLE 1-continued

| Gene Targets, Synonyms and Features | | | | | | | |
|---|---|---|---|---|---|---|---|
| Target Name | Synonyms | Species | Genbank # | Feature | Feature Start Site | Feature Stop Site | SEQ ID NO |
| Gemin5 | Same as above | Human | BC036894.1 | exon | 2059 | 2230 | 15 |
| Gemin5 | Same as above | Human | BC036894.1 | exon:exon junction | 2230 | 2231 | 15 |
| Gemin5 | Same as above | Human | the complement of nucleotides 2065000 to 2118000 of NT_034779.1 | exon | 839 | 1057 | 16 |
| Gemin5 | Same as above | Human | the complement of nucleotides 2065000 to 2118000 of NT_034779.1 | start codon | 892 | 894 | 16 |
| Gemin5 | Same as above | Human | the complement of nucleotides 2065000 to 2118000 of NT_034779.1 | intron:exon junction | 1057 | 1058 | 16 |
| Gemin5 | Same as above | Human | the complement of nucleotides 2065000 to 2118000 of NT_034779.1 | intron | 1058 | 1839 | 16 |
| Gemin5 | Same as above | Human | the complement of nucleotides 2065000 to 2118000 of NT_034779.1 | intron:exon junction | 1839 | 1840 | 16 |
| Gemin5 | Same as above | Human | the complement of nucleotides 2065000 to 2118000 of NT_034779.1 | exon | 1840 | 2000 | 16 |
| Gemin5 | Same as above | Human | the complement of nucleotides 2065000 to 2118000 of NT_034779.1 | intron:exon junction | 2000 | 2001 | 16 |
| Gemin5 | Same as above | Human | the complement of nucleotides 2065000 to 2118000 of NT_034779.1 | intron | 2001 | 3002 | 16 |
| Gemin5 | Same as above | Human | the complement of nucleotides 2065000 to 2118000 of NT_034779.1 | intron:exon junction | 3002 | 3003 | 16 |
| Gemin5 | Same as above | Human | the complement of nucleotides 2065000 to 2118000 of NT_034779.1 | exon | 3003 | 3184 | 16 |
| Gemin5 | Same as above | Human | the complement of nucleotides 2065000 to 2118000 of NT_034779.1 | intron:exon junction | 3184 | 3185 | 16 |
| Gemin5 | Same as above | Human | the complement of nucleotides 2065000 to 2118000 of NT_034779.1 | intron | 3185 | 6774 | 16 |
| Gemin5 | Same as above | Human | the complement of nucleotides 2065000 to 2118000 of NT_034779.1 | intron:exon junction | 6774 | 6775 | 16 |
| Gemin5 | Same as above | Human | the complement of nucleotides 2065000 to 2118000 of NT_034779.1 | exon | 6775 | 6926 | 16 |
| Gemin5 | Same as above | Human | the complement of nucleotides 2065000 to 2118000 of NT_034779.1 | intron:exon junction | 6926 | 6927 | 16 |
| Gemin5 | Same as above | Human | the complement of nucleotides 2065000 to 2118000 of NT_034779.1 | intron | 6927 | 7447 | 16 |
| Gemin5 | Same as above | Human | the complement of nucleotides 2065000 to 2118000 of NT_034779.1 | intron:exon junction | 7447 | 7448 | 16 |
| Gemin5 | Same as above | Human | the complement of nucleotides 2065000 to 2118000 of NT_034779.1 | exon | 7448 | 7567 | 16 |
| Gemin5 | Same as above | Human | the complement of nucleotides 2065000 to 2118000 of NT_034779.1 | intron:exon junction | 7567 | 7568 | 16 |
| Gemin5 | Same as above | Human | the complement of nucleotides 2065000 to 2118000 of NT_034779.1 | intron | 7568 | 10365 | 16 |
| Gemin5 | Same as above | Human | the complement of nucleotides 2065000 to 2118000 of NT_034779.1 | intron:exon junction | 10365 | 10366 | 16 |
| Gemin5 | Same as above | Human | the complement of nucleotides 2065000 to 2118000 of NT_034779.1 | exon | 10366 | 10498 | 16 |
| Gemin5 | Same as above | Human | the complement of nucleotides 2065000 to 2118000 of NT_034779.1 | intron:exon junction | 10498 | 10499 | 16 |

TABLE 1-continued

| Gene Targets, Synonyms and Features | | | | | | | |
|---|---|---|---|---|---|---|---|
| Target Name | Synonyms | Species | Genbank # | Feature | Feature Start Site | Feature Stop Site | SEQ ID NO |
| Gemin5 | Same as above | Human | the complement of nucleotides 2065000 to 2118000 of NT_034779.1 | intron | 10499 | 11474 | 16 |
| Gemin5 | Same as above | Human | the complement of nucleotides 2065000 to 2118000 of NT_034779.1 | intron:exon junction | 11474 | 11475 | 16 |
| Gemin5 | Same as above | Human | the complement of nucleotides 2065000 to 2118000 of NT_034779.1 | exon | 11475 | 11640 | 16 |
| Gemin5 | Same as above | Human | the complement of nucleotides 2065000 to 2118000 of NT_034779.1 | intron:exon junction | 11640 | 11641 | 16 |
| Gemin5 | Same as above | Human | the complement of nucleotides 2065000 to 2118000 of NT_034779.1 | intron | 11641 | 12950 | 16 |
| Gemin5 | Same as above | Human | the complement of nucleotides 2065000 to 2118000 of NT_034779.1 | intron:exon junction | 12950 | 12951 | 16 |
| Gemin5 | Same as above | Human | the complement of nucleotides 2065000 to 2118000 of NT_034779.1 | exon | 12951 | 13163 | 16 |
| Gemin5 | Same as above | Human | the complement of nucleotides 2065000 to 2118000 of NT_034779.1 | intron:exon junction | 13163 | 13164 | 16 |
| Gemin5 | Same as above | Human | the complement of nucleotides 2065000 to 2118000 of NT_034779.1 | intron | 13164 | 14470 | 16 |
| Gemin5 | Same as above | Human | the complement of nucleotides 2065000 to 2118000 of NT_034779.1 | intron:exon junction | 14470 | 14471 | 16 |
| Gemin5 | Same as above | Human | the complement of nucleotides 2065000 to 2118000 of NT_034779.1 | exon | 14471 | 14556 | 16 |
| Gemin5 | Same as above | Human | the complement of nucleotides 2065000 to 2118000 of NT_034779.1 | intron:exon junction | 14556 | 14557 | 16 |
| Gemin5 | Same as above | Human | the complement of nucleotides 2065000 to 2118000 of NT_034779.1 | intron | 14557 | 17599 | 16 |
| Gemin5 | Same as above | Human | the complement of nucleotides 2065000 to 2118000 of NT_034779.1 | intron:exon junction | 17599 | 17600 | 16 |
| Gemin5 | Same as above | Human | the complement of nucleotides 2065000 to 2118000 of NT_034779.1 | exon | 17600 | 17682 | 16 |
| Gemin5 | Same as above | Human | the complement of nucleotides 2065000 to 2118000 of NT_034779.1 | intron:exon junction | 17682 | 17683 | 16 |
| Gemin5 | Same as above | Human | the complement of nucleotides 2065000 to 2118000 of NT_034779.1 | intron | 17683 | 18921 | 16 |
| Gemin5 | Same as above | Human | the complement of nucleotides 2065000 to 2118000 of NT_034779.1 | intron:exon junction | 18921 | 18922 | 16 |
| Gemin5 | Same as above | Human | the complement of nucleotides 2065000 to 2118000 of NT_034779.1 | exon | 18922 | 19058 | 16 |
| Gemin5 | Same as above | Human | the complement of nucleotides 2065000 to 2118000 of NT_034779.1 | intron:exon junction | 19058 | 19059 | 16 |
| Gemin5 | Same as above | Human | the complement of nucleotides 2065000 to 2118000 of NT_034779.1 | intron | 19059 | 21020 | 16 |
| Gemin5 | Same as above | Human | the complement of nucleotides 2065000 to 2118000 of NT_034779.1 | intron:exon junction | 21020 | 21021 | 16 |
| Gemin5 | Same as above | Human | the complement of nucleotides 2065000 to 2118000 of NT_034779.1 | exon | 21021 | 21094 | 16 |
| Gemin5 | Same as above | Human | the complement of nucleotides 2065000 to 2118000 of NT_034779.1 | intron:exon junction | 21094 | 21095 | 16 |

TABLE 1-continued

Gene Targets, Synonyms and Features

| Target Name | Synonyms | Species | Genbank # | Feature | Feature Start Site | Feature Stop Site | SEQ ID NO |
|---|---|---|---|---|---|---|---|
| Gemin5 | Same as above | Human | the complement of nucleotides 2065000 to 2118000 of NT_034779.1 | intron | 21095 | 21845 | 16 |
| Gemin5 | Same as above | Human | the complement of nucleotides 2065000 to 2118000 of NT_034779.1 | intron:exon junction | 21845 | 21846 | 16 |
| Gemin5 | Same as above | Human | the complement of nucleotides 2065000 to 2118000 of NT_034779.1 | exon | 21846 | 22027 | 16 |
| Gemin5 | Same as above | Human | the complement of nucleotides 2065000 to 2118000 of NT_034779.1 | intron:exon junction | 22027 | 22028 | 16 |
| Gemin5 | Same as above | Human | the complement of nucleotides 2065000 to 2118000 of NT_034779.1 | intron | 22028 | 25986 | 16 |
| Gemin5 | Same as above | Human | the complement of nucleotides 2065000 to 2118000 of NT_034779.1 | intron:exon junction | 25986 | 25987 | 16 |
| Gemin5 | Same as above | Human | the complement of nucleotides 2065000 to 2118000 of NT_034779.1 | exon | 25987 | 26126 | 16 |
| Gemin5 | Same as above | Human | the complement of nucleotides 2065000 to 2118000 of NT_034779.1 | intron:exon junction | 26126 | 26127 | 16 |
| Gemin5 | Same as above | Human | the complement of nucleotides 2065000 to 2118000 of NT_034779.1 | intron | 26127 | 27126 | 16 |
| Gemin5 | Same as above | Human | the complement of nucleotides 2065000 to 2118000 of NT_034779.1 | intron:exon junction | 27126 | 27127 | 16 |
| Gemin5 | Same as above | Human | the complement of nucleotides 2065000 to 2118000 of NT_034779.1 | exon | 27127 | 27298 | 16 |
| Gemin5 | Same as above | Human | the complement of nucleotides 2065000 to 2118000 of NT_034779.1 | intron:exon junction | 27298 | 27299 | 16 |
| Gemin5 | Same as above | Human | the complement of nucleotides 2065000 to 2118000 of NT_034779.1 | intron | 27299 | 31206 | 16 |
| Gemin5 | Same as above | Human | the complement of nucleotides 2065000 to 2118000 of NT_034779.1 | intron:exon junction | 31206 | 31207 | 16 |
| Gemin5 | Same as above | Human | the complement of nucleotides 2065000 to 2118000 of NT_034779.1 | exon | 31207 | 31434 | 16 |
| Gemin5 | Same as above | Human | the complement of nucleotides 2065000 to 2118000 of NT_034779.1 | intron:exon junction | 31434 | 31435 | 16 |
| Gemin5 | Same as above | Human | the complement of nucleotides 2065000 to 2118000 of NT_034779.1 | intron | 31435 | 33548 | 16 |
| Gemin5 | Same as above | Human | the complement of nucleotides 2065000 to 2118000 of NT_034779.1 | intron:exon junction | 33548 | 33549 | 16 |
| Gemin5 | Same as above | Human | the complement of nucleotides 2065000 to 2118000 of NT_034779.1 | exon | 33549 | 33662 | 16 |
| Gemin5 | Same as above | Human | the complement of nucleotides 2065000 to 2118000 of NT_034779.1 | intron:exon junction | 33662 | 33663 | 16 |
| Gemin5 | Same as above | Human | the complement of nucleotides 2065000 to 2118000 of NT_034779.1 | intron | 33663 | 34395 | 16 |
| Gemin5 | Same as above | Human | the complement of nucleotides 2065000 to 2118000 of NT_034779.1 | intron:exon junction | 34395 | 34396 | 16 |
| Gemin5 | Same as above | Human | the complement of nucleotides 2065000 to 2118000 of NT_034779.1 | exon | 34396 | 34518 | 16 |
| Gemin5 | Same as above | Human | the complement of nucleotides 2065000 to 2118000 of NT_034779.1 | intron:exon junction | 34518 | 34519 | 16 |

TABLE 1-continued

| Gene Targets, Synonyms and Features | | | | | | | |
|---|---|---|---|---|---|---|---|
| Target Name | Synonyms | Species | Genbank # | Feature | Feature Start Site | Feature Stop Site | SEQ ID NO |
| Gemin5 | Same as above | Human | the complement of nucleotides 2065000 to 2118000 of NT_034779.1 | intron | 34519 | 35849 | 16 |
| Gemin5 | Same as above | Human | the complement of nucleotides 2065000 to 2118000 of NT_034779.1 | intron:exon junction | 35849 | 35850 | 16 |
| Gemin5 | Same as above | Human | the complement of nucleotides 2065000 to 2118000 of NT_034779.1 | exon | 35850 | 35945 | 16 |
| Gemin5 | Same as above | Human | the complement of nucleotides 2065000 to 2118000 of NT_034779.1 | intron:exon junction | 35945 | 35946 | 16 |
| Gemin5 | Same as above | Human | the complement of nucleotides 2065000 to 2118000 of NT_034779.1 | intron | 35946 | 36348 | 16 |
| Gemin5 | Same as above | Human | the complement of nucleotides 2065000 to 2118000 of NT_034779.1 | intron:exon junction | 36348 | 36349 | 16 |
| Gemin5 | Same as above | Human | the complement of nucleotides 2065000 to 2118000 of NT_034779.1 | exon | 36349 | 36486 | 16 |
| Gemin5 | Same as above | Human | the complement of nucleotides 2065000 to 2118000 of NT_034779.1 | intron:exon junction | 36486 | 36487 | 16 |
| Gemin5 | Same as above | Human | the complement of nucleotides 2065000 to 2118000 of NT_034779.1 | intron | 36487 | 37540 | 16 |
| Gemin5 | Same as above | Human | the complement of nucleotides 2065000 to 2118000 of NT_034779.1 | intron:exon junction | 37540 | 37541 | 16 |
| Gemin5 | Same as above | Human | the complement of nucleotides 2065000 to 2118000 of NT_034779.1 | exon | 37541 | 37688 | 16 |
| Gemin5 | Same as above | Human | the complement of nucleotides 2065000 to 2118000 of NT_034779.1 | intron:exon junction | 37688 | 37689 | 16 |
| Gemin5 | Same as above | Human | the complement of nucleotides 2065000 to 2118000 of NT_034779.1 | intron | 37689 | 39722 | 16 |
| Gemin5 | Same as above | Human | the complement of nucleotides 2065000 to 2118000 of NT_034779.1 | intron:exon junction | 39722 | 39723 | 16 |
| Gemin5 | Same as above | Human | the complement of nucleotides 2065000 to 2118000 of NT_034779.1 | exon | 39723 | 39842 | 16 |
| Gemin5 | Same as above | Human | the complement of nucleotides 2065000 to 2118000 of NT_034779.1 | intron:exon junction | 39842 | 39843 | 16 |
| Gemin5 | Same as above | Human | the compleme of nucleotides 2065000 to 2118000 of NT_034779.1 | intron | 39843 | 40382 | 16 |
| Gemin5 | Same as above | Human | the compleme of nucleotides 2065000 to 2118000 of NT_034779.1 | intron:exon junction | 40382 | 40383 | 16 |
| Gemin5 | Same as above | Human | the compleme of nucleotides 2065000 to 2118000 of NT_034779.1 | exon | 40383 | 40593 | 16 |
| Gemin5 | Same as above | Human | the compleme of nucleotides 2065000 to 2118000 of NT_034779.1 | intron:exon junction | 40593 | 40594 | 16 |
| Gemin5 | Same as above | Human | the compleme of nucleotides 2065000 to 2118000 of NT_034779.1 | intron | 40594 | 42690 | 16 |
| Gemin5 | Same as above | Human | the compleme of nucleotides 2065000 to 2118000 of NT_034779.1 | intron:exon junction | 42690 | 42691 | 16 |
| Gemin5 | Same as above | Human | the compleme of nucleotides 2065000 to 2118000 of NT_034779.1 | exon | 42691 | 42942 | 16 |
| Gemin5 | Same as above | Human | the compleme of nucleotides 2065000 to 2118000 of NT_034779.1 | intron:exon junction | 42942 | 42943 | 16 |

TABLE 1-continued

Gene Targets, Synonyms and Features

| Target Name | Synonyms | Species | Genbank # | Feature | Feature Start Site | Feature Stop Site | SEQ ID NO |
|---|---|---|---|---|---|---|---|
| Gemin5 | Same as above | Human | the compleme of nucleotides 2065000 to 2118000 of NT_034779.1 | intron | 42943 | 46480 | 16 |
| Gemin5 | Same as above | Human | the compleme of nucleotides 2065000 to 2118000 of NT_034779.1 | intron:exon junction | 46480 | 46481 | 16 |
| Gemin5 | Same as above | Human | the compleme of nucleotides 2065000 to 2118000 of NT_034779.1 | exon | 46481 | 46643 | 16 |
| Gemin5 | Same as above | Human | the compleme of nucleotides 2065000 to 2118000 of NT_034779.1 | intron:exon junction | 46643 | 46644 | 16 |
| Gemin5 | Same as above | Human | the compleme of nucleotides 2065000 to 2118000 of NT_034779.1 | intron | 46644 | 47287 | 16 |
| Gemin5 | Same as above | Human | the compleme of nucleotides 2065000 to 2118000 of NT_034779.1 | intron:exon junction | 47287 | 47288 | 16 |
| Gemin5 | Same as above | Human | the compleme of nucleotides 2065000 to 2118000 of NT_034779.1 | exon | 47288 | 47789 | 16 |
| Gemin5 | Same as above | Human | the compleme of nucleotides 2065000 to 2118000 of NT_034779.1 | intron:exon junction | 47789 | 47790 | 16 |
| Gemin5 | Same as above | Human | the compleme of nucleotides 2065000 to 2118000 of NT_034779.1 | intron | 47790 | 49614 | 16 |
| Gemin5 | Same as above | Human | the compleme of nucleotides 2065000 to 2118000 of NT_034779.1 | intron:exon junction | 49614 | 49615 | 16 |
| Gemin5 | Same as above | Human | the compleme of nucleotides 2065000 to 2118000 of NT_034779.1 | exon | 49615 | 49711 | 16 |
| Gemin5 | Same as above | Human | the compleme of nucleotides 2065000 to 2118000 of NT_034779.1 | intron:exon junction | 49711 | 49712 | 16 |
| Gemin5 | Same as above | Human | the compleme of nucleotides 2065000 to 2118000 of NT_034779.1 | intron | 49712 | 50659 | 16 |
| Gemin5 | Same as above | Human | the compleme of nucleotides 2065000 to 2118000 of NT_034779.1 | intron:exon junction | 50659 | 50660 | 16 |
| Gemin5 | Same as above | Human | the compleme of nucleotides 2065000 to 2118000 of NT_034779.1 | exon | 50660 | 51724 | 16 |
| Gemin5 | Same as above | Human | the compleme of nucleotides 2065000 to 2118000 of NT_034779.1 | stop codon | 50825 | 50827 | 16 |
| Gemin5 | Same as above | Human | the compleme of nucleotides 2065000 to 2118000 of NT_034779.1 | 3'UTR | 50828 | 51741 | 16 |
| Gemin6 | FLJ23459; GEM-associated protein 6; gemin 6; hypothetical protein FLJ23459 | Human | BG944981.1 | exon | 2 | 73 | 17 |
| Gemin6 | Same as above | Human | BG944981.1 | 5'UTR | 7 | 92 | 17 |
| Gemin6 | Same as above | Human | BG944981.1 | exon:exon junction | 73 | 74 | 17 |
| Gemin6 | Same as above | Human | BG944981.1 | exon | 74 | 220 | 17 |
| Gemin6 | Same as above | Human | BG944981.1 | start codon | 93 | 95 | 17 |
| Gemin6 | Same as above | Human | BG944981.1 | exon:exon junction | 220 | 221 | 17 |
| Gemin6 | Same as above | Human | BG944981.1 | exon | 221 | 404 | 17 |
| Gemin6 | Same as above | Human | BI600222.1 | 5'UTR | 30 | 86 | 18 |
| Gemin6 | Same as above | Human | BI600222.1 | exon:exon junction | 67 | 68 | 18 |
| Gemin6 | Same as above | Human | BI600222.1 | start codon | 87 | 89 | 18 |
| Gemin6 | Same as above | Human | BI600222.1 | exon:exon junction | 216 | 217 | 18 |

TABLE 1-continued

Gene Targets, Synonyms and Features

| Target Name | Synonyms | Species | Genbank # | Feature | Feature Start Site | Feature Stop Site | SEQ ID NO |
|---|---|---|---|---|---|---|---|
| Gemin6 | Same as above | Human | BI600222.1 | stop codon | 596 | 598 | 18 |
| Gemin6 | Same as above | Human | NM_024775.1 | 5'UTR | 1 | 86 | 19 |
| Gemin6 | Same as above | Human | NM_024775.1 | exon:exon junction | 67 | 68 | 19 |
| Gemin6 | Same as above | Human | NM_024775.1 | exon | 68 | 214 | 19 |
| Gemin6 | Same as above | Human | NM_024775.1 | start codon | 87 | 89 | 19 |
| Gemin6 | Same as above | Human | NM_024775.1 | CDS | 87 | 530 | 19 |
| Gemin6 | Same as above | Human | NM_024775.1 | exon:exon junction | 214 | 215 | 19 |
| Gemin6 | Same as above | Human | NM_024775.1 | stop codon | 528 | 530 | 19 |
| Gemin6 | Same as above | Human | NM_024775.1 | 3'UTR | 531 | 703 | 19 |
| Gemin6 | Same as above | Human | NM_024775.1 | stop codon | 589 | 591 | 19 |
| Gemin6 | Same as above | Human | NM_024775.8 | 5'UTR | 1 | 57 | 20 |
| Gemin6 | Same as above | Human | NM_024775.8 | exon:exon junction | 38 | 39 | 20 |
| Gemin6 | Same as above | Human | NM_024775.8 | exon | 39 | 185 | 20 |
| Gemin6 | Same as above | Human | NM_024775.8 | start codon | 58 | 60 | 20 |
| Gemin6 | Same as above | Human | NM_024775.8 | start codon | 58 | 60 | 20 |
| Gemin6 | Same as above | Human | NM_024775.8 | CDS | 58 | 561 | 20 |
| Gemin6 | Same as above | Human | NM_024775.8 | exon:exon junction | 185 | 186 | 20 |
| Gemin6 | Same as above | Human | NM_024775.8 | stop codon | 498 | 500 | 20 |
| Gemin6 | Same as above | Human | NM_024775.8 | stop codon | 559 | 561 | 20 |
| Gemin6 | Same as above | Human | NM_024775.8 | 3'UTR | 562 | 646 | 20 |
| Gemin6 | Same as above | Human | nucleotides 5647000 to 5653000 of NT_005367.10 | exon | 1043 | 1114 | 21 |
| Gemin6 | Same as above | Human | nucleotides 5647000 to 5653000 of NT_005367.10 | intron:exon junction | 1114 | 1115 | 21 |
| Gemin6 | Same as above | Human | nucleotides 5647000 to 5653000 of NT_005367.10 | intron | 1115 | 1804 | 21 |
| Gemin6 | Same as above | Human | nucleotides 5647000 to 5653000 of NT_005367.10 | intron:exon junction | 1804 | 1805 | 21 |
| Gemin6 | Same as above | Human | nucleotides 5647000 to 5653000 of NT_005367.10 | exon | 1805 | 1951 | 21 |
| Gemin6 | Same as above | Human | nucleotides 5647000 to 5653000 of NT_005367.10 | start codon | 1824 | 1826 | 21 |
| Gemin6 | Same as above | Human | nucleotides 5647000 to 5653000 of NT_005367.10 | intron:exon junction | 1951 | 1952 | 21 |
| Gemin6 | Same as above | Human | nucleotides 5647000 to 5653000 of NT_005367.10 | intron | 1952 | 2090 | 21 |
| Gemin6 | Same as above | Human | nucleotides 5647000 to 5653000 of NT_005367.10 | intron:exon junction | 2090 | 2091 | 21 |
| Gemin6 | Same as above | Human | nucleotides 5647000 to 5653000 of NT_005367.10 | exon | 2091 | 2274 | 21 |
| Gemin6 | Same as above | Human | nucleotides 5647000 to 5653000 of NT_005367.10 | intron:exon junction | 2274 | 2275 | 21 |
| Gemin6 | Same as above | Human | nucleotides 5647000 to 5653000 of NT_005367.10 | intron | 2275 | 4356 | 21 |
| Gemin6 | Same as above | Human | nucleotides 5647000 to 5653000 of NT_005367.10 | intron:exon junction | 4356 | 4357 | 21 |
| Gemin6 | Same as above | Human | nucleotides 5647000 to 5653000 of NT_005367.10 | exon | 4357 | 4926 | 21 |
| Gemin6 | Same as above | Human | nucleotides 5647000 to 5653000 of NT_005367.10 | stop codon | 4669 | 4671 | 21 |
| Gemin6 | Same as above | Human | nucleotides 5647000 to 5653000 of NT_005367.10 | stop codon | 4730 | 4732 | 21 |
| Gemin7 | Gemin 7; hypothetical protein FLJ13956 | Human | AI022330.1 | intron:exon junction | 117 | 118 | 22 |
| Gemin7 | Same as above | Human | BM009097.1 | exon | 2 | 86 | 23 |
| Gemin7 | Same as above | Human | BM009097.1 | exon | 2 | 86 | 23 |
| Gemin7 | Same as above | Human | BM009097.1 | exon:exon junction | 86 | 87 | 23 |
| Gemin7 | Same as above | Human | BM009097.1 | start codon | 95 | 97 | 23 |
| Gemin7 | Same as above | Human | BM009097.1 | stop codon | 489 | 491 | 23 |
| Gemin7 | Same as above | Human | BQ438140.1 | start codon | 76 | 78 | 24 |
| Gemin7 | Same as above | Human | BQ438140.1 | CDS | 76 | 471 | 24 |
| Gemin7 | Same as above | Human | BQ438140.1 | CDS | 76 | 471 | 24 |
| Gemin7 | Same as above | Human | BQ438140.1 | stop codon | 469 | 471 | 24 |
| Gemin7 | Same as above | Human | NM_024707.1 | 5'UTR | 1 | 221 | 25 |
| Gemin7 | Same as above | Human | NM_024707.1 | exon | 2 | 90 | 25 |
| Gemin7 | Same as above | Human | NM_024707.1 | exon | 2 | 90 | 25 |

TABLE 1-continued

| Gene Targets, Synonyms and Features | | | | | | | |
|---|---|---|---|---|---|---|---|
| Target Name | Synonyms | Species | Genbank # | Feature | Feature Start Site | Feature Stop Site | SEQ ID NO |
| Gemin7 | Same as above | Human | NM_024707.1 | exon:exon junction | 90 | 91 | 25 |
| Gemin7 | Same as above | Human | NM_024707.1 | exon | 91 | 213 | 25 |
| Gemin7 | Same as above | Human | NM_024707.1 | exon | 91 | 213 | 25 |
| Gemin7 | Same as above | Human | NM_024707.1 | exon:exon junction | 213 | 214 | 25 |
| Gemin7 | Same as above | Human | NM_024707.1 | exon | 214 | 1631 | 25 |
| Gemin7 | Same as above | Human | NM_024707.1 | exon | 214 | 1631 | 25 |
| Gemin7 | Same as above | Human | NM_024707.1 | start codon | 222 | 224 | 25 |
| Gemin7 | Same as above | Human | NM_024707.1 | CDS | 222 | 617 | 25 |
| Gemin7 | Same as above | Human | NM_024707.1 | stop codon | 615 | 617 | 25 |
| Gemin7 | Same as above | Human | NM_024707.1 | 3'UTR | 618 | 1631 | 25 |
| Gemin7 | Same as above | Human | nucleotides 1708000 to 1723000 of NT_011109.12 | exon | 1467 | 1551 | 26 |
| Gemin7 | Same as above | Human | nucleotides 1708000 to 1723000 of NT_011109.12 | intron:exon junction | 1551 | 1552 | 26 |
| Gemin7 | Same as above | Human | nucleotides 1708000 to 1723000 of NT_011109.12 | intron | 1552 | 2178 | 26 |
| Gemin7 | Same as above | Human | nucleotides 1708000 to 1723000 of NT_011109.12 | exon | 1561 | 1649 | 26 |
| Gemin7 | Same as above | Human | nucleotides 1708000 to 1723000 of NT_011109.12 | intron:exon junction | 1649 | 1650 | 26 |
| Gemin7 | Same as above | Human | nucleotides 1708000 to 1723000 of NT_011109.12 | intron | 1650 | 2178 | 26 |
| Gemin7 | Same as above | Human | nucleotides 1708000 to 1723000 of NT_011109.12 | intron:exon junction | 2178 | 2179 | 26 |
| Gemin7 | Same as above | Human | nucleotides 1708000 to 1723000 of NT_011109.12 | exon | 2179 | 2301 | 26 |
| Gemin7 | Same as above | Human | nucleotides 1708000 to 1723000 of NT_011109.12 | intron:exon junction | 2301 | 2302 | 26 |
| Gemin7 | Same as above | Human | nucleotides 1708000 to 1723000 of NT_011109.12 | intron | 2302 | 12378 | 26 |
| Gemin7 | Same as above | Human | nucleotides 1708000 to 1723000 of NT_011109.12 | intron:exon junction | 12378 | 12379 | 26 |
| Gemin7 | Same as above | Human | nucleotides 1708000 to 1723000 of NT_011109.12 | exon | 12379 | 13796 | 26 |
| Gemin7 | Same as above | Human | nucleotides 1708000 to 1723000 of NT_011109.12 | start codon | 12387 | 12389 | 26 |
| Gemin7 | Same as above | Human | nucleotides 1708000 to 1723000 of NT_011109.12 | CDS | 12387 | 12782 | 26 |
| Gemin7 | Same as above | Human | nucleotides 1708000 to 1723000 of NT_011109.12 | stop codon | 12780 | 12782 | 26 |
| Gemin7 | Same as above | Human | nucleotides 1708000 to 1723000 of NT_011109.12 | 3'UTR | 12783 | 13796 | 26 |

Small Non-Coding RNA-Regulated Regions

Small non-coding RNA molecules play important roles in regulation of gene expression, developmental timing, viral surveillance, and immunity. Not only the classic transfer RNAs (tRNAs) and ribosomal RNAs (rRNAs), but also small nuclear RNAs (snRNAs), small nucleolar RNAs (snoRNAs), small interfering RNAs (siRNAs), tiny non-coding RNAs (tncRNAs) and microRNAs (miRNAs) are now known to act in diverse cellular processes such as chromosome maintenance, gene imprinting, pre-mRNA splicing, guiding RNA modifications, transcriptional regulation, and the control of mRNA translation (Eddy, Nat. Rev. Genet., 2001, 2, 919-929; Kawasaki and Taira, Nature, 2003, 423, 838-842). RNA-mediated processes are now also believed to direct heterochromatin formation, genome rearrangements, and DNA elimination (Cerutti, *Trends Genet.,* 2003, 19, 39-46; Couzin, *Science,* 2002, 298, 2296-2297). In one embodiment, regions of target genes that are targets of small non-coding RNAs are suitable targets for oligomeric compounds of the invention.

One class of small non-coding RNAs known as microRNAs (miRNAs) participates in regulation of gene expression. Mature miRNAs originate from long endogenous primary transcripts (pri-miRNAs) that are often hundreds of nucleotides in length (Lee et al., *EMBO J.,* 2002, 21, 4663-70). These pri-miRNAs are processed by a nucleolar enzyme in the RNase III family known as Drosha, into approximately 70 nucleotide-long pre-miRNAs (also known as stem-loop, hairpin or foldback precursors) which are subsequently processed by the Dicer RNase into mature miRNAs (Lee et al., *Nature,* 2003, 425, 415-419). The current model is that the primary miRNA transcript is processed by Drosha in the nucleus, and the pre-miRNA hairpin precursor is exported from the nucleus through the action of the nuclear export protein exportin-5 (Bohnsack et al., *RNA,* 2004, 10, 185-191; Lund et al., *Science,* 2004, 303, 95-98; Yi et al., *Genes Dev.,* 2003, 17, 3011-3016). Once in the cytoplasm, the pre-miRNA is cleaved by Dicer to yield a double-stranded intermediate, but only one strand of this short-lived intermediate accumulates as the mature miRNA (Ambros et al., *RNA,* 2003, 9, 277-279; Bartel and Bartel, *Plant Physiol.,* 2003, 132, 709-717; Shi, *Trends Genet.,* 2003, 19, 9-12). miRNAs are believed to primarily direct translation repression but have recently been shown to trigger cleavage events.

More than 200 miRNA genes have been detected in the human genome. Naturally occurring miRNAs are characterized by imperfect complementarity to their target sequences. Artificially modified miRNAs with sequences completely complementary to their target RNAs have been designed and found to function as siRNAs that inhibit gene expression by reducing RNA transcript levels. Accordingly, regions of Gemin Genes targeted by naturally occurring or artificially modified miRNAs are contemplated as suitable target sites for the oligomeric compounds of the present invention.

Modulation of Target Expression

As used herein, "modulation" means a perturbation of function, for example, either an increase (stimulation or induction) or a decrease (inhibition or reduction) in expression. As another example, modulation of expression can include perturbing splice site selection of pre-mRNA processing. "Expression" includes all the functions by which a gene's coded information is converted into structures present and operating in a cell and "modulation of expression" means the perturbation of such functions. The functions of DNA to be modulated can include replication and transcription. Replication and transcription, for example, can be from an endogenous cellular template, a vector, a plasmid construct or otherwise. The functions of RNA to be modulated can include translocation functions, which include, but are not limited to, translocation of the RNA to a site of protein translation, translocation of the RNA to sites within the cell which are distant from the site of RNA synthesis, and translation of protein from the RNA. RNA processing functions that can be modulated include, but are not limited to, splicing of the RNA to yield one or more RNA species, capping of the RNA, 3' maturation of the RNA and catalytic activity or complex formation involving the RNA which may be engaged in or facilitated by the RNA. Modulation of expression can result in the increased level of one or more nucleic acid species or the decreased level of one or more nucleic acid species, either temporally or by net steady state level. One result of such interference with target nucleic acid function is modulation of the expression of a Gemin Gene. Thus, in one embodiment modulation of expression can mean increase or decrease in target RNA or protein levels. In another embodiment modulation of expression can mean an increase or decrease of one or more RNA splice products, or a change in the ratio of two or more splice products.

The effect of oligomeric compounds of the present invention on target nucleic acid expression can be tested in any of a variety of cell types provided that the target nucleic acid is present at measurable levels. The effect of oligomeric compounds of the present invention on target nucleic acid expression can be routinely determined using, for example, PCR or Northern blot analysis. Useful cell lines include, e.g., 1321rX3-7; 3T3-L1, differentiated; 3T3-L1, undifferentiated; 70Z3; 7D4; 7F2 (osteoblast); A10; A20; A375; A431; A549; AML-12; ARIP; differentiated Adipocytes; B104; B16-F10; B50; BALC; BB88; BC3H1; BCL; BEAS2B; BHK-21 (fibroblast, kidney); BLO-11 (skeletal muscle); BT-474; BW5147.3 (ATCC TIB-47); BaF3; Mouse primary bone marrow-derived osteoclasts; C2C12; C3A; C3H/10T1/2; C58; C6; CHO (Ovary); CMT-93; COS-7; CT26.WT; Caco-2; ConA; D1 TNC1; D1B; DA-3; DDT1-MF2; DU 145 (prostate); Peripheral Blood Monocyte derived Human Primary Dendritic Cells; E14; EL4; EMT-6; F11; FAT 7 (epithelial, nasal squamous cell carcinoma); Human Primary Dermal Fibroblasts; Mouse Embryonic Primary Fibroblasts; G-361; GH1; GH3; H-4-II-E; H2.35; H8; H9 (Human T Lymphocyte); H9c2(2-1); HASMC (Human Aortic Smooth Muscle Cells); HC252 (differentiated rat neuronal progenitor cell line); HC252 (undifferentiated rat neuronal progenitor cell line); HCT116; HEK A-Z (rt-SLC tx); HEK-293; HEK-293 (Rat VR1 Transfected); HEPA1-6; HFN 36.3; HK-2 (human HPV-16 transformed proximal tubule kidney); HL-60; HMEC (Normal Human Mammary Epithelial Cells); HMVEC-L (Lung Endothelial); HMVEC-d Ad (Human Adult Dermal Endothelial); HMVEC-d Neo (Human Neonatal Dermal Endothelial); HPAEC (Human Pulmonary Artery Endothelial Cells); HT-1080; HeLa; Hec-1A; HepB3; HepG2; Human Primary Hepatocytes; Mouse Primary Hepatocytes; Rabbit Primary Hepatocytes; Rat Primary Hepatocytes; HuT 78 (Human cutaneous T lymphocyte); HuVEC; Huh7; Human H-ras transformed rat intestinal epithelial cells; IC21; IEC-6; IW32; JAR; JEG-3; JUG-3; Jurkat; K-562; K204; Mouse Primary Keratinocytes; L2 (lung); L6; LA4; LBRM-33; LC-540; LL/6; LL2; LLC1; LNcAP; M-3 (Mouse melanoma; skin; melanocyte); MCF7 (breast adenocarcinoma, w/t p53); MDA; MDA MB 468; MDA MB231; MEF; MH-S; MLE12; MLg2908; MMT 060562; MRC-5; Human Primary Macrophages; Mouse Peritoneal Macrophages; Rat Peritoneal Macrophages; Human Primary Melanocytes; Mia Paca; Human Primary Monocytes; N1S1 (liver); NBT-II; NCCIT; NCI-H292; NCTC 3749; ND7/23; NG108-15 (mouse); NG108-15 (rat); NHDC (Dendritic Cells); NHDF; NHEK (Human Primary Keratinocytes); NHEK-Ad (Human Primary Adult Keratinocytes); NHEK-Neo (Human Primary Neonatal Keratinocytes); NIH/3T3 (mouse fibroblast); NIT-1; NOR-10 (Mouse muscle); NR-8383; NRK; NTERA-2 c1.D1; Rat Primary Neurons; Mouse primary Osteoblasts; Rat primary Osteoblasts; P-19; P388D1 (IL-1) adherent; P388D1 suspension; PANC-1; PC-12; PC-3 (prostate); White Preadipocytes; R2C; R6; RAW264.7; RB++; RBL-2H3; RFL-6; RK3E; RMC; ROS 17/2.8; Raji; Rat Tissue—Cerebellum; Rat Tissue—Cerebrum; Rat Tissue—Hippocampus; Rat-2; Human Primary Renal Proximal Tubule Epithelial Cell; Rin-5F; Rin-M; SK-MEL-28; SKBR; SMT/2A LNM; SV40 MES 13; SW480; SW97; Shionogi; Human Primary Smooth Muscle Bronchial Cell; Mouse Primary Splenocytes; Human Synoviocytes; Mouse Synoviocytes; Rat Synoviocytes; T cell hybridoma 2B4; T-24; T-49 D; T3-3A1; T47D (breast adenocarcinoma, mutant p53); T47D+p53 (breast adenocarcinoma, mutant p53, transfected with wild-type p53); TCMK-1 (kidney); TF1.8; THLE-3; THP-1; TM-3; TM4; TRAMP-C1; U-20S; U-87 MG; U373; U937; UMR-106 (osteosarcoma); VERO C1008; WEHI 231; WISH; Y-1; Y13-238 (spleen); Y13-259 (spleen); YB2/0 (spleen); Yac-1; b.END; mIMCD-3; and sw872. The culture of such cells is routine to those skilled in the art. Other cell types well known to one of skilled in the art can be routinely used. Many cell lines and instructions for growing them are obtainable from the American Type Culture Collection (ATCC) (Manassas, Va.).

Assaying Modulation of Expression

Modulation of Gemin Gene expression can be assayed in a variety of ways known in the art. Gemin Gene mRNA levels can be quantitated by, e.g., Northern blot analysis, competitive polymerase chain reaction (PCR), or real-time PCR. RNA analysis can be performed on total cellular RNA or poly(A)+mRNA by methods known in the art. Methods of RNA isolation are taught in, for example, Ausubel, F. M. et al., *Current Protocols in Molecular Biology*, Volume 1, pp. 4.1.1-4.2.9 and 4.5.1-4.5.3, John Wiley & Sons, Inc., 1993.

Northern blot analysis is routine in the art and is taught in, for example, Ausubel, F. M. et al., *Current Protocols in Molecular Biology*, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Levels of a protein encoded by a Gemin Gene can be quantitated in a variety of ways well known in the art, such as immunoprecipitation, Western blot analysis (immunoblotting), ELISA or fluorescence-activated cell sorting (FACS). Antibodies directed to a protein encoded by a Gemin Gene can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., Current Protocols in Molecular Biology, Volume 2, pp. 11.12.1-11.12.9, John Wiley & Sons, Inc., 1997. Preparation of monoclonal antibodies is taught in, for example, Ausubel, F. M. et al., Current Protocols in Molecular Biology, Volume 2, pp. 11.4.1-11.11.5, John Wiley & Sons, Inc., 1997.

Immunoprecipitation methods are standard in the art and can be found at, for example, Ausubel, F. M. et al., Current Protocols in Molecular Biology, Volume 2, pp. 10.16.1-10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1-11.2.22, John Wiley & Sons, Inc., 1991.

Suitable Target Regions

Once one or more target regions, segments or sites have been identified, oligomeric compounds are chosen which are sufficiently complementary to the target, i.e., hybridize sufficiently well and with sufficient specificity, to give the desired effect.

The oligomeric compounds of the present invention can be targeted to features of a target nucleobase sequence, such as those described in Table 1. All regions of a nucleobase sequence to which an oligomeric compound can be targeted, wherein the regions are greater than or equal to 8 and less than or equal to 80 nucleobases, are described as follows:

Let R(n, n+m−1) be a region from a target nucleobase sequence, where "n" is the 5'-most nucleobase position of the region, where "n+m−1" is the 3'-most nucleobase position of the region and where "m" is the length of the region. A set "S(m)", of regions of length "m" is defined as the regions where n ranges from 1 to L−m+1, where L is the length of the target nucleobase sequence and L>m. A set, "A", of all regions can be constructed as a union of the sets of regions for each length from where m is greater than or equal to 8 and is less than or equal to 80.

This set of regions can be represented using the following mathematical notation:

$$A = \bigcup_m S(m) \text{ where } m \in N \mid 8 \leq m \leq 80$$

and $$S(m) = \{R_{n,n+m-1} \mid n \in \{1, 2, 3, \ldots, L-m+1\}\}$$

where the mathematical operator | indicates "such that", where the mathematical operator ∊ indicates "a member of a set" (e.g. y ∊ Z indicates that element y is a member of set Z), where x is a variable, where N indicates all natural numbers, defined as positive integers, and where the mathematical operator Å indicates "the union of sets".

For example, the set of regions for m equal to 8, 20 and 80 can be constructed in the following manner. The set of regions, each 8 nucleobases in length, S(m=8), in a target nucleobase sequence 100 nucleobases in length (L=100), beginning at position 1 (n=1) of the target nucleobase sequence, can be created using the following expression:

$$S(8)=\{R_{1,8} \mid n \in \{1,2,3, \ldots, 93\}\}$$

and describes the set of regions comprising nucleobases 1-8, 2-9, 3-10, 4-11, 5-12, 6-13, 7-14, 8-15, 9-16, 10-17, 11-18, 12-19, 13-20, 14-21, 15-22, 16-23, 17-24, 18-25, 19-26, 20-27, 21-28, 22-29, 23-30, 24-31, 25-32, 26-33, 27-34, 28-35, 29-36, 30-37, 31-38, 32-39, 33-40, 34-41, 35-42, 36-43, 37-44, 38-45, 39-46, 40-47, 41-48, 42-49, 43-50, 44-51, 45-52, 46-53, 47-54, 48-55, 49-56, 50-57, 51-58, 52-59, 53-60, 54-61, 55-62, 56-63, 57-64, 58-65, 59-66, 60-67, 61-68, 62-69, 63-70, 64-71, 65-72, 66-73, 67-74, 68-75, 69-76, 70-77, 71-78, 72-79, 73-80, 74-81, 75-82, 76-83, 77-84, 78-85, 79-86, 80-87, 81-88, 82-89, 83-90, 84-91, 85-92, 86-93, 87-94, 88-95, 89-96, 90-97, 91-98, 92-99, 93-100.

An additional set for regions 20 nucleobases in length, in a target sequence 100 nucleobases in length, beginning at position 1 of the target nucleobase sequence, can be described using the following expression:

$$S(20)=\{R_{1,20} \mid n \in \{1,2,3, \ldots, 81\}\}$$

and describes the set of regions comprising nucleobases 1-20, 2-21, 3-22, 4-23, 5-24, 6-25, 7-26, 8-27, 9-28, 10-29, 11-30, 12-31, 13-32, 14-33, 15-34, 16-35, 17-36, 18-37, 19-38, 20-39, 21-40, 22-41, 23-42, 24-43, 25-44, 26-45, 27-46, 28-47, 29-48, 30-49, 31-50, 32-51, 33-52, 34-53, 35-54, 36-55, 37-56, 38-57, 39-58, 40-59, 41-60, 42-61, 43-62, 44-63, 45-64, 46-65, 47-66, 48-67, 49-68, 50-69, 51-70, 52-71, 53-72, 54-73, 55-74, 56-75, 57-76, 58-77, 59-78, 60-79, 61-80, 62-81, 63-82, 64-83, 65-84, 66-85, 67-86, 68-87, 69-88, 70-89, 71-90, 72-91, 73-92, 74-93, 75-94, 76-95, 77-96, 78-97, 79-98, 80-99, 81-100.

An additional set for regions 80 nucleobases in length, in a target sequence 100 nucleobases in length, beginning at position 1 of the target nucleobase sequence, can be described using the following expression:

$$S(80)=\{R_{1,80} \mid n \in \{1,2,3, \ldots, 21\}\}$$

and describes the set of regions comprising nucleobases 1-80, 2-81, 3-82, 4-83, 5-84, 6-85, 7-86, 8-87, 9-88, 10-89, 11-90, 12-91, 13-92, 14-93, 15-94, 16-95, 17-96, 18-97, 19-98, 20-99, 21-100.

Thus, in this example, A would include regions 1-8, 2-9, 3-10 . . . 93-100, 1-20, 2-21, 3-22 . . . 81-100, 1-80, 2-81, 3-82 . . . 21-100.

The union of these aforementioned example sets and other sets for lengths from 10 to 19 and 21 to 79 can be described using the mathematical expression $$A = \bigcup_m S(m)$$

where Å represents the union of the sets obtained by combining all members of all sets.

The mathematical expressions described herein defines all possible target regions in a target nucleobase sequence of any length L, where the region is of length m, and where m is greater than or equal to 8 and less than or equal to 80 nucleobases and, and where m is less than L, and where n is less than L−m+1.

Validated Target Segments

The locations on the target nucleic acid to which the suitable oligomeric compounds hybridize are hereinbelow referred to as "validated target segments." As used herein the term "validated target segment" is defined as at least an 8-nucleobase portion of a target region to which an active oligomeric compound is targeted. While not wishing to be bound by theory, it is presently believed that these target segments represent portions of the target nucleic acid which are accessible for hybridization.

Target segments can include DNA or RNA sequences that comprise at least the 8 consecutive nucleobases from the 5'-terminus of a validated target segment (the remaining nucleobases being a consecutive stretch of the same DNA or RNA beginning immediately upstream of the 5'-terminus of the target segment and continuing until the DNA or RNA contains about 8 to about 80 nucleobases). Similarly suitable validated target segments are represented by DNA or RNA sequences that comprise at least the 8 consecutive nucleobases from the 3'-terminus of a validated target segment (the remaining nucleobases being a consecutive stretch of the same DNA or RNA beginning immediately downstream of the 3'-terminus of the target segment and continuing until the DNA or RNA contains about 8 to about 80 nucleobases). It is also understood that a validated oligomeric target segment can be represented by DNA or RNA sequences that comprise at least 8 consecutive nucleobases from an internal portion of the sequence of a validated target segment, and can extend in either or both directions until the oligonucleotide contains about 8 about 80 nucleobases.

Screening for Modulator Compounds

In another embodiment, the validated target segments identified herein can be employed in a screen for additional compounds that modulate the expression of a Gemin Gene. "Modulators" are those compounds that modulate the expression of a Gemin Gene and which comprise at least an 8-nucleobase portion which is complementary to a validated target segment. The screening method comprises the steps of contacting a validated target segment of a nucleic acid molecule encoding a Gemin Gene with one or more candidate modulators, and selecting for one or more candidate modulators which perturb the expression of a nucleic acid molecule encoding a Gemin Gene. Once it is shown that the candidate modulator or modulators are capable of modulating the expression of a nucleic acid molecule encoding a Gemin Gene, the modulator can then be employed in further investigative studies of the function of a Gemin Gene, or for use as a research, diagnostic, or therapeutic agent. The validated target segments can also be combined with a second strand as disclosed herein to form stabilized double-stranded (duplexed) oligonucleotides for use as a research, diagnostic, or therapeutic agent.

Phenotypic Assays

Once modulator compounds of a Gemin Gene have been identified by the methods disclosed herein, the compounds can be further investigated in one or more phenotypic assays, each having measurable endpoints predictive of efficacy in the treatment of a particular disease state or condition. Phenotypic assays, kits and reagents for their use are well known to those skilled in the art and are herein used to investigate the role and/or association of a Gemin Gene in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the genotype of the cell (measurement of the expression of one or more of the genes of the cell) after treatment is also used as an indicator of the efficacy or potency of the Gemin Gene modulators. Hallmark genes, or those genes suspected to be associated with a specific disease state, condition, or phenotype, are measured in both treated and untreated cells.

The following phenotypic assays are useful in the study of the compounds and compositions of the present invention.

Cell Proliferation and Survival

Unregulated cell proliferation is a characteristic of cancer cells, thus most current chemotherapy agents target dividing cells, for example, by blocking the synthesis of new DNA required for cell division. However, cells in healthy tissues are also affected by agents that modulate cell proliferation.

In some cases, a cell cycle inhibitor will cause apoptosis in cancer cells, but allow normal cells to undergo growth arrest and therefore remain unaffected (Blagosklonny, *Bioessays,* 1999, 21, 704-709; Chen et al., *Cancer Res.,* 1997, 57, 2013-2019; Evan and Littlewood, *Science,* 1998, 281, 1317-1322; Lees and Weinberg, *Proc. Natl. Acad. Sci. USA,* 1999, 96, 4221-4223). An example of sensitization to anti-cancer agents is observed in cells that have reduced or absent expression of the tumor suppressor genes p53 (Bunz et al., *Science,* 1998, 282, 1497-1501; Bunz et al., *J. Clin. Invest.,* 1999, 104, 263-269; Stewart et al., *Cancer Res.,* 1999, 59, 3831-3837; Wahl et al., *Nat. Med.,* 1996, 2, 72-79). However, cancer cells often escape apoptosis (Lowe and Lin, *Carcinogenesis,* 2000, 21, 485-495; Reed, *Cancer J. Sci. Am.,* 1998, 4 Suppl 1, S8-14). Further disruption of cell cycle checkpoints in cancer cells can increase sensitivity to chemotherapy while allowing normal cells to take refuge in G1 and remain unaffected. Cell cycle assays can be employed to identify genes, such as p53, whose inhibition will sensitize cells to anti-cancer agents.

Caspase Activity

Programmed cell death, or apoptosis, is an important aspect of various biological processes, including normal cell turnover, as well as immune system and embryonic development. Apoptosis involves the activation of caspases, a family of intracellular proteases through which a cascade of events leads to the cleavage of a select set of proteins. The caspase family can be divided into two groups: the initiator caspases, such as caspase-8 and -9, and the executioner caspases, such as caspase-3, -6 and -7, which are activated by the initiator caspases. The caspase family contains at least 14 members, with differing substrate preferences (Thornberry and Lazebnik, *Science,* 1998, 281, 1312-1316). For example, a caspase assay can be used to identify genes whose inhibition selectively cause apoptosis in breast carcinoma cell lines, without affecting normal cells, and to identify genes whose inhibition results in cell death in p53-deficient T47D cells, and not in MCF7 cells which express p53 (Ross et al., *Nat. Genet.,* 2000, 24, 227-235; Scherf et al., *Nat. Genet.,* 2000, 24, 236-244).

Angiogenesis

Angiogenesis is the growth of new blood vessels (veins and arteries) by endothelial cells. This process is important in the development of a number of human diseases, and is believed to be particularly important in regulating the growth of solid tumors. Without new vessel formation it is believed that tumors will not grow beyond a few millimeters in size. In addition to their use as anti-cancer agents, inhibitors of angiogenesis have potential for the treatment of diabetic retinopathy, cardiovascular disease, rheumatoid arthritis and psoriasis (Carmeliet and Jain, *Nature,* 2000, 407, 249-257; Freedman and Isner, *J. Mol. Cell. Cardiol.,* 2001, 33, 379-393; Jackson et al., *Faseb J.,* 1997, 11, 457-465; Saaristo et al., *Oncogene,* 2000, 19, 6122-6129; Weber and De Bandt, *Joint Bone Spine,* 2000, 67, 366-383; Yoshida et al., *Histol. Histopathol.,* 1999, 14, 1287-1294).

During the process of angiogenesis, endothelial cells perform several distinct functions, including the degradation of the extracellular matrix (ECM), migration, proliferation and the formation of tube-like structures (Liekens et al., *Biochem. Pharmacol.,* 2001, 61, 253-270). Endothelial cells must regulate the expression of many genes in order to perform the functions necessary for angiogenesis. This gene regulation has been the subject of intense scrutiny, and many genes have been identified as being important for the angiogenic phenotype. For example, the expression levels of the following genes, previously identified as being highly expressed in angiogenic endothelial cells, can be measured as indicators: Integrin beta3, endoglin/CD105, TEM5 and MMP-14/MT-MMP1.

Integrin beta3 is part of a family of heterodimeric transmembrane receptors that consist of alpha and beta subunits (Brooks et al., *J. Clin. Invest.,* 1995, 96, 1815-1822). Each subunit recognizes a unique set of ECM ligands, thereby allowing cells to transmit angiogenic signals from the extracellular matrix. Integrin beta3 is prominently expressed on proliferating vascular endothelial cells, and it plays roles in allowing new blood vessels to form at tumor sites as well as allowing the epithelial cells of breast tumors to spread (Brooks et al., *J. Clin. Invest.,* 1995, 96, 1815-1822; Drake et al., *J. Cell Sci.,* 1995, 108 (Pt 7), 2655-2661). Blockage of integrin beta3 with monoclonal antibodies or low molecular weight antagonists inhibits blood vessel formation in a variety of in-vivo models, including tumor angiogenesis and neovascularization during oxygen-induced retinopathy (Brooks et al., *Science,* 1994, 264, 569-571; Brooks et al., *J. Clin. Invest.,* 1995, 96, 1815-1822; Hammes et al., *Nat. Med.,* 1996, 2, 529-533).

Endoglin is a transforming growth factor receptor-associated protein highly expressed on endothelial cells, and present on some leukemia cells and minor subsets of bone marrow cells (Burrows et al., *Clin. Cancer Res.,* 1995, 1, 1623-1634; Haruta and Seon, *Proc. Natl. Acad. Sci. USA,* 1986, 83, 7898-7902). Its expression is upregulated in endothelial cells of angiogenic tissues and is therefore used as a prognostic indicator in various tumors (Burrows et al., *Clin. Cancer Res.,* 1995, 1, 1623-1634). Endoglin functions as an ancillary receptor influencing binding of the transforming growth factor beta (TGF-beta) family of ligands to signaling receptors, thus mediating cell survival (Massague and Chen, *Genes Dev.,* 2000, 14, 627-644).

Tumor endothelial marker 5 (TEM5) is a putative 7-pass transmembrane protein (GPCR) (Carson-Walter et al., *Cancer Res.,* 2001, 61, 6649-6655). The mRNA transcript, designated KIAA1531, encodes one of many tumor endothelium markers (TEMs) that display elevated expression (greater than 10-fold) during tumor angiogenesis (St Croix et al., *Science,* 2000, 289, 1197-1202). TEM5 is coordinately expressed with other TEMs on tumor endothelium in humans and mice.

Matrix metalloproteinase 14 (MMP-14), a membrane-type MMP covalently linked to the cell membrane, is involved in matrix detachment and migration. MMP-14 is thought to promote tumor angiogenesis; antibodies directed against the catalytic domain of MMP-14 block endothelial-cell migration, invasion and capillary tube formation in vitro (Galvez et al., *J. Biol. Chem.,* 2001, 276, 37491-37500). MMP-14 can degrade the fibrin matrix that surrounds newly formed vessels potentially allowing the endothelial cells to invade further into the tumor tissue (Hotary et al., *J. Exp. Med.,* 2002, 195, 295-308). MMP-14 null mice have impaired angiogenesis during development, further demonstrating the role of MMP-14 in angiogenesis (Vu and Werb, *Genes Dev.,* 2000, 14, 2123-2133; Zhou et al., *Proc. Natl. Acad. Sci. USA,* 2000, 97, 4052-4057).

Angiogenesis is stimulated by numerous factors that promote interaction of endothelial cells with each other and with extracellular matrix molecules, resulting in the formation of capillary tubes. This morphogenic process is necessary for the delivery of oxygen to nearby tissues and plays an essential role in embryonic development, wound healing, and tumor growth (Carmeliet and Jain, *Nature,* 2000, 407, 249-257). Moreover, this process can be reproduced in a tissue culture assay that evaluated the formation of tube-like structures by endothelial cells. There are several different variations of the assay that use different matrices, such as collagen I (Kanayasu et al., *Lipids,* 1991, 26, 271-276), Matrigel (Yamagishi et al., *J. Biol. Chem.,* 1997, 272, 8723-8730) and fibrin (Bach et al., *Exp. Cell Res.,* 1998, 238, 324-334), as growth substrates for the cells. For example, HUVECs can be plated on a matrix derived from the Engelbreth-Holm-Swarm mouse tumor, which is very similar to Matrigel (Kleinman et al., *Biochemistry,* 1986, 25, 312-318; Madri and Pratt, *J. Histochem. Cytochem.,* 1986, 34, 85-91). Untreated HUVECs form tube-like structures when grown on this substrate. Loss of tube formation in vitro has been correlated with the inhibition of angiogenesis in vivo (Carmeliet and Jain, *Nature,* 2000, 407, 249-257; Zhang et al., *Cancer Res.,* 2002, 62, 2034-2042), which supports the use of in vitro tube formation as an endpoint for angiogenesis.

Adipocyte Differentiation and Insulin Signaling Assays

Insulin is an essential signaling molecule throughout the body, but its major target organs are the liver, skeletal muscle and adipose tissue. Insulin is the primary modulator of glucose homeostasis and helps maintain a balance of peripheral glucose utilization and hepatic glucose production. The reduced ability of normal circulating concentrations of insulin to maintain glucose homeostasis manifests in insulin resistance which is often associated with diabetes, central obesity, hypertension, polycystic ovarian syndrome, dyslipidemia and atherosclerosis (Saltiel, *Cell,* 2001, 104, 517-529; Saltiel and Kahn, *Nature,* 2001, 414, 799-806).

Insulin promotes the differentiation of preadipocytes into adipocytes. The condition of obesity, which results in increases in fat cell number, occurs even in insulin-resistant states in which glucose transport is impaired due to the antilipolytic effect of insulin. Inhibition of triglyceride breakdown requires much lower insulin concentrations than stimulation of glucose transport, resulting in maintenance or expansion of adipose stores (Kitamura et al., *Mol. Cell. Biol.,* 1999, 19, 6286-6296; Kitamura et al., *Mol. Cell. Biol.,* 1998, 18, 3708-3717).

One of the hallmarks of cellular differentiation is the upregulation of gene expression. During adipocyte differentiation, the gene expression patterns in adipocytes change considerably. Some genes known to be upregulated during adipocyte differentiation include hormone-sensitive lipase (HSL), adipocyte lipid binding protein (aP2), glucose transporter 4 (Glut4), and peroxisome proliferator-activated receptor gamma (PPAR-gamma). Insulin signaling is improved by compounds that bind and inactivate PPAR-gamma, a key regulator of adipocyte differentiation (Olefsky, *J. Clin. Invest.,* 2000, 106, 467-472). Insulin induces the translocation of GLUT4 to the adipocyte cell surface, where it transports glucose into the cell, an activity necessary for triglyceride synthesis. In all forms of obesity and diabetes, a major factor contributing to the impaired insulin-stimulated glucose transport in adipocytes is the downregulation of GLUT4. Insulin also induces hormone sensitive lipase (HSL), which is the predominant lipase in adipocytes that functions to promote fatty acid synthesis and lipogenesis (Fredrikson et al., *J. Biol. Chem.,* 1981, 256, 6311-6320). Adipocyte fatty acid binding protein (aP2) belongs to a multi-gene family of fatty acid and retinoid transport proteins. aP2 is postulated to serve as a lipid shuttle, solubilizing hydrophobic fatty acids and delivering them to the appropriate metabolic system for utilization (Fu et al., *J. Lipid Res.,* 2000, 41, 2017-2023; Pelton et al., *Biochem. Biophys. Res. Commun.,* 1999, 261, 456-458). Together, these genes play important roles in the uptake of glucose and the metabolism and utilization of fats.

Leptin secretion and an increase in triglyceride content are also well-established markers of adipocyte differentiation. While it serves as a marker for differentiated adipocytes, leptin also regulates glucose homeostasis through mechanisms (autocrine, paracrine, endocrine and neural) independent of the adipocyte's role in energy storage and release. As adipocytes differentiate, insulin increases triglyceride accumulation by both promoting triglyceride synthesis and inhibiting triglyceride breakdown (Spiegelman and Flier, *Cell,* 2001, 104, 531-543). As triglyceride accumulation correlates tightly with cell size and cell number, it is an excellent indicator of differentiated adipocytes.

Insulin mediates its effects by suppressing the RNA expression levels of enzymes important for gluconeogenesis and glycogenolysis, and also by controlling the activities of some metabolic enzymes by post-translational mechanisms (Hall and Granner, *J. Basic Clin. Physiol. Pharmacol.,* 1999, 10, 119-133; Moller, *Nature,* 2001, 414, 821-827; Saltiel and Kahn, *Nature,* 2001, 414, 799-806). However, the mechanisms by which insulin regulates these genes are not fully understood. Genes in liver cells cells that are involved in regulating glucose metabolism are identified by monitoring changes in the expression of selective insulin-responsive genes in a cell culture model. Primary human hepatocytes are difficult to obtain and work with in culture. Therefore, the insulin signaling assay as used in the Examples can be performed in the hepatocellular carcinoma cell line HepG2. Insulin responsive genes that can be evaluated in this assay are phosphoenolpyruvate carboxykinase (PEPCK), insulin-like growth factor binding protein 1 (IGFBP-1) and follistatin.

IGFBP-1 is one of a family of six secreted proteins that bind insulin-like growth factor (IGF) with high affinity and thereby modulate IGFs action in vivo (Baxter, *Am. J. Physiol. Endocrinol. Metab.,* 2000, 278, E967-976; Lee et al., *Proc. Soc. Exp. Biol. Med.,* 1997, 216, 319-357). IGFBP-1 is characterized by dynamic variability of levels in circulation due to the regulation of its hepatic secretion (Lee et al., *Proc. Soc. Exp. Biol. Med.,* 1997, 216, 319-357). The multi-hormonal regulation of PEPCK and IGFBP-1 are similar. Glucocorticoids and cyclic AMP (cAMP) stimulate transcription of the IGFBP-1 gene expression whereas insulin acts in a dominant manner to suppress both basal and cAMP or glucocorticoid-stimulated IGFBP-1 gene transcription (O'Brien and Granner, *Physiol. Rev.,* 1996, 76, 1109-1161). PEPCK catalyzes the rate-limiting step in gluconeogenesis, and thereby contributes to hepatic glucose output (Hall and Granner, *J. Basic Clin. Physiol. Pharmacol.,* 1999, 10, 119-133; Moller, *Nature,* 2001, 414, 821-827; Saltiel and Kahn, *Nature,* 2001, 414, 799-806). In hepatoma cells, studies have shown that the expression of PEPCK is stimulated by glucocorticoids, glucagon (via cAMP), and retinoic acid. Insulin acts in a dominant manner to suppress these stimulations as well as basal transcription (O'Brien and Granner, *Physiol. Rev.,* 1996, 76, 1109-1161). In HepG2 cells, prolonged serum starvation induces the expression of PEPCK and subsequent insulin stimulation significantly reduces the PEPCK mRNA level.

Follistatin is significantly stimulated by insulin in HepG2 cells. Interestingly, follistatin levels have been shown to be higher in women with polycystic ovary syndrome (PCOS) (Norman et al., *Hum. Reprod.,* 2001, 16, 668-672). PCOS is a metabolic as well as a reproductive disorder, and an important cause of type 2 diabetes mellitus in women. It is often associated with profound insulin resistance and hyperinsulinemia as well as with a defect in insulin secretion (Dunaif, *Endocr. Rev.,* 1997, 18, 774-800; Nestler et al., *Fertil. Steril.,* 2002, 77, 209-215).

Inflammation Assays

Inflammation assays are designed to identify genes that regulate the activation and effector phases of the adaptive immune response. During the activation phase, T lymphocytes (also known as T-cells) receiving signals from the appropriate antigens undergo clonal expansion, secrete cytokines, and upregulate their receptors for soluble growth factors, cytokines and co-stimulatory molecules (Cantrell, *Annu. Rev. Immunol.,* 1996, 14, 259-274). These changes drive T-cell differentiation and effector function. In the effector phase, response to cytokines by non-immune effector cells controls the production of inflammatory mediators that can do extensive damage to host tissues. The cells of the adaptive immune systems, their products, as well as their interactions with various enzyme cascades involved in inflammation (e.g., the complement, clotting, fibrinolytic and kinin cascades) all represent potential points for intervention in inflammatory disease. The inflammation assay measures hallmarks of the activation phase of the immune response.

Dendritic cells can be used to identify regulators of dendritic cell-mediated T-cell costimulation. The level of interleukin-2 (IL-2) production by T-cells, a critical consequence of T-cell activation (DeSilva et al., *J. Immunol.,* 1991, 147, 3261-3267; Salomon and Bluestone, *Annu. Rev. Immunol.,* 2001, 19, 225-252), is used as an endpoint for T-cell activation. T lymphocytes are important immunoregulatory cells that mediate pathological inflammatory responses. Optimal activation of T lymphocytes requires both primary antigen recognition events as well as secondary or costimulatory signals from antigen presenting cells (APC). Dendritic cells are the most efficient APCs known and are principally responsible for antigen presentation to T-cells, expression of high levels of costimulatory molecules during infection and disease, and the induction and maintenance of immunological memory (Banchereau and Steinman, *Nature,* 1998, 392, 245-252). While a number of costimulatory ligand-receptor pairs have been shown to influence T-cell activation, a principal signal is delivered by engagement of CD28 on T-cells by CD80 (B7-1) and CD86 (B7-2) on APCs (Boussiotis et al., *Curr. Opin. Immunol.,* 1994, 6, 797-807; Lenschow et al., *Annu. Rev. Immunol.,* 1996, 14, 233-258). While not adhering to a specific mechanism, inhibition of T-cell co-stimulation by APCs holds promise for novel and more specific strategies of immune suppression. In addition, blocking costimulatory signals may lead to the development of long-term immunological anergy (unresponsiveness or tolerance) that would offer utility for promoting transplantation or dampening autoimmunity. T-cell anergy is the direct consequence of failure of T-cells to produce the growth factor IL-2 (DeSilva et al., *J. Immunol.,* 1991, 147, 3261-3267; Salomon and Bluestone, *Annu. Rev. Immunol.,* 2001, 19, 225-252).

The cytokine signaling assay identifies genes that regulate the responses of non-immune effector cells (initially endothelial cells) to cytokines such as interferon-gamma (IFN-gamma). The effects of the oligomeric compounds of the present invention on the regulation of the production of intercellular adhesion molecule-1 (ICAM-1), interferon regulatory factor 1 (IRF1) and small inducible cytokine subfamily B (Cys-X-Cys), member 11 (SCYB 11), which regulate other parameters of the inflammatory response, can be monitored in response to cytokine treatment.

Kits, Research Reagents, and Diagnostics

The oligomeric compounds of the present invention can be utilized for diagnostics, therapeutics, prophylaxis and as research reagents and kits. Furthermore, antisense compounds, which are able to inhibit gene expression with exquisite specificity, are often used by those of ordinary skill to elucidate the function of particular genes or to distinguish between functions of various members of a biological pathway.

For use in kits and diagnostics, the oligomeric compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more compounds or compositions of the present invention are compared to control cells or tissues not treated with compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.,* 2000, 480, 17-24; Celis, et al., *FEBS Lett.,* 2000, 480, 2-16), SAGE (serial analysis of gene expression) (Madden, et al., *Drug Discov. Today,* 2000, 5, 415-425), READS (restriction enzyme amplification of digested cDNAs) (Prashar and Weissman, *Methods Enzymol.,* 1999, 303, 258-72), TOGA (total gene expression analysis) (Sutcliffe, et al., *Proc. Natl. Acad. Sci. U.S.A.,* 2000, 97, 1976-81), protein arrays and proteomics (Celis, et al., *FEBS Lett.,* 2000, 480, 2-16; Jungblut, et al., *Electrophoresis,* 1999, 20, 2100-10), expressed sequence tag (EST) sequencing (Celis, et al., *FEBS Lett.,* 2000, 480, 2-16; Larsson, et al., *J. Biotechnol.,* 2000, 80, 143-57), subtractive RNA fingerprinting (SuRF) (Fuchs, et al., *Anal. Biochem.,* 2000, 286, 91-98; Larson, et al., *Cytometry,* 2000, 41, 203-208), subtractive cloning, differential display (DD) (Jurecic and Belmont, *Curr. Opin. Microbiol.,* 2000, 3, 316-21), comparative genomic hybridization (Carulli, et al., *J. Cell Biochem. Suppl.,* 1998, 31, 286-96), FISH (fluorescent in situ hybridization) techniques (Going and Gusterson, *Eur. J. Cancer,* 1999, 35, 1895-904) and mass spectrometry methods (To, *Comb. Chem. High Throughput Screen,* 2000, 3, 235-41).

Therapeutics

The specificity and sensitivity of antisense technology is also harnessed by those of skill in the art for therapeutic uses. Antisense compounds have been employed as therapeutic moieties in the treatment of disease states in animals, including humans. Antisense drugs have been safely and effectively administered to humans and numerous clinical trials are presently underway. It is thus established that antisense compounds are useful therapeutic modalities that can be configured to be useful in treatment regimes for the treatment of cells, tissues and animals, especially humans.

For therapeutics, an animal, such as a human, suspected of having or at risk of having a disease or disorder which can be treated by modulating the expression of a Gemin Gene is treated by administering compounds in accordance with this invention. For example, in one non-limiting embodiment, the methods comprise the step of administering to said animal, a therapeutically effective amount of an antisense compound that inhibits expression of a Gemin Gene. In one embodiment, the antisense compounds of the present invention effectively inhibit the levels or function of a Gemin Gene RNA. Because reduction in Gemin Gene mRNA levels can lead to alteration in Gemin Gene protein products of expression as well, such resultant alterations can also be measured. In one embodiment, the antisense compounds of the invention inhibit the expression of a Gemin Gene causing a reduction of RNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of a Gemin Gene can be measured in a bodily fluid, tissue or organ of the animal. Bodily fluids include, but are not limited to, blood (serum or plasma), lymphatic fluid, cerebrospinal fluid, semen, urine, synovial fluid and saliva and can be obtained by methods routine to those skilled in the art. Tissues or organs include, but are not limited to, blood (e.g., hematopoietic cells, such as human hematopoietic progenitor cells, human hematopoietic stem cells, CD34+ cells CD4+ cells), lymphocytes and other blood lineage cells, skin, bone marrow, spleen, thymus, lymph node, brain, spinal cord, heart, skeletal muscle, liver, pancreas, prostate, kidney, lung, oral mucosa, esophagus, stomach, ilium, small intestine, colon, bladder, cervix, ovary, testis, mammary gland, adrenal gland, and adipose (white and brown). Samples of tissues or organs can be routinely obtained by biopsy. In some alternative situations, samples of tissues or organs can be recovered from an animal after death.

The cells contained within said fluids, tissues or organs being analyzed can contain a nucleic acid molecule encoding a Gemin Gene protein and/or the Gemin Gene-encoded protein itself For example, tissues or fluids procured from patients can be evaluated for expression levels of the target mRNA or protein. Additionally, the mRNA or protein expression levels of other genes known or suspected to be associated with the specific disease state, condition or phenotype can be assessed. mRNA levels can be measured or evaluated by real-time PCR, Northern blot, in situ hybridization or DNA array analysis. Protein levels can be measured or evaluated by ELISA, immunoblotting, quantitative protein assays, protein activity assays (for example, caspase activity assays) immunohistochemistry or immunocytochemistry. Furthermore, the effects of treatment can be assessed by measuring biomarkers associated with the disease or condition in the aforementioned tissues and fluids, collected from a patient or subject receiving treatment, by routine clinical methods known in the art. These biomarkers include but are not limited to: glucose, cholesterol, lipoproteins, triglycerides, free fatty acids and other markers of glucose and lipid metabolism; liver transaminases, bilirubin, albumin, blood urea nitrogen, creatine and other markers of kidney and liver function; interleukins, tumor necrosis factors, intracellular adhesion molecules, C-reactive protein and other markers of inflammation; testosterone, estrogen and other hormones; tumor markers; vitamins, minerals and electrolytes.

Pharmaceuticals and Methods of Treatment

The compounds of the present invention can be utilized in pharmaceutical compositions by adding an effective amount of a compound to a suitable pharmaceutically acceptable diluent or carrier. In one aspect, the compounds of the present invention inhibit the expression of a Gemin Gene. Consequently, the compounds are useful in the treatment of disorders and diseases related to Gemin Gene expression. Use of the compounds, compositions and methods of the invention may also be useful prophylactically. The compounds of the invention can also be used in the manufacture of a medicament for the treatment of diseases and disorders related to Gemin Gene expression.

Methods whereby bodily fluids, cells or tissues are contacted with an effective amount of one or more of the antisense compounds or compositions of the invention are also contemplated. Bodily fluids, cells or tissues can be contacted with one or more of the compounds of the invention resulting in modulation of Gemin Gene expression in the bodily fluids, cells or tissues. An effective amount can be determined by monitoring the modulatory effect of the antisense compound or compounds or compositions on target nucleic acids or their products by methods routine to the skilled artisan. Further contemplated are ex vivo methods of treatment whereby cells or tissues are isolated from a subject, contacted with an effective amount of the antisense compound or compounds or compositions and reintroduced into the subject by routine methods known to those skilled in the art.

Further contemplated herein is a method for the treatment of a subject suspected of having or at risk of having a disease or disorder comprising administering to a subject an effective amount of an isolated single stranded RNA or double stranded RNA oligonucleotide directed to a Gemin Gene. The ssRNA or dsRNA oligonucleotide may be modified or unmodified. That is, the present invention provides for the use of an isolated double stranded RNA oligonucleotide targeted to a Gemin Gene, or a pharmaceutical composition thereof, for the treatment of a disease or disorder.

In one embodiment, provided are uses of a compound of an isolated double stranded RNA oligonucleotide in the manufacture of a medicament for inhibiting Gemin Gene expression or overexpression. Thus, provided herein is the use of an isolated double stranded RNA oligonucleotide targeted to a Gemin Gene in the manufacture of a medicament for the treatment of a disease or disorder by means of the method described above.

Salts, Prodrugs and Bioequivalents

The oligomeric compounds of the present invention comprise any pharmaceutically acceptable salts, esters, or salts of such esters, or any other functional chemical equivalent which, upon administration to an animal including a human, is capable of providing (directly or indirectly) the biologically active metabolite or residue thereof Accordingly, for example, the disclosure is also drawn to prodrugs and pharmaceutically acceptable salts of the oligomeric compounds of the present invention, pharmaceutically acceptable salts of such prodrugs, and other bioequivalents.

The term "prodrug" indicates a therapeutic agent that is prepared in an inactive or less active form that is converted to an active form (i.e., drug) within the body or cells thereof by the action of endogenous enzymes or other chemicals and/or conditions. In particular, prodrug versions of the oligonucleotides of the invention are prepared as SATE ((S-acetyl-2-thioethyl)phosphate) derivatives according to the methods disclosed in WO 93/24510 or WO 94/26764.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.,* 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 22 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfoc acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine. Sodium salts of antisense oligonucleotides are useful and are well accepted for therapeutic administration to humans. In another embodiment, sodium salts of dsRNA compounds are also provided.

Formulations

The oligomeric compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756.

The present invention also includes pharmaceutical compositions and formulations which include the oligomeric compounds of the invention. The pharmaceutical compositions of the present invention may be administered in a number of ways depending upon whether local or systemic treatment is desired and upon the area to be treated. Administration may be topical (including but not limited to ophthalmic and to mucous membranes including vaginal and rectal delivery), pulmonary, e.g., by inhalation or insufflation of powders or aerosols, including by nebulizer (intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Sites of administration are known to those skilled in the art. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the oligomeric compound which may be present as a solution in the aqueous phase, oily phase or itself as a separate phase. Microemulsions are included as an embodiment of the present invention. Emulsions and their uses are well known in the art and are further described in U.S. Pat. No. 6,287,860.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

Formulations of the present invention include dendrimers, which are hyperbranched polymers. Dendrimers are built around a central core to which the branch points are attached. Thus the core is encapsulated in a web of branch points. Dendrimers form a monodisperse material of uniform molecular weight providing more predictable pK and biodistribution properties. Hyperbranched dendrimers offer a unique opportunity of polyfunctionalization with desired carrier or targeting molecules for targeted drug delivery. Short dendrimers can also be used to attach multiple carriers to a single oligomeric compound thus increasing chances of uptake by the cluster effect. Dendrimers can be attached to oligomeric compounds of the invention to target solid tumors which have a leaky vasculature while avoiding glomelular filtration by virtue of their large size. Due to dendrimers' cage like structure they protect their core and thus an oligomeric compound can be protected from degradation by encapsulating it within a dendrimer. Dendrimers can be programmed to self-destruct under certain pH, oxidative and enzymatic conditions and thus can be used as osmotic bombs attached to oligomeric compounds to disrupt lysosomal membranes and release attached oligomeric compounds. Dendrimers have also been used to target molecules to specific organs and intracellular compartments; therefore, such uses can be applied to oligomeric compounds of the invention. Dendrimers can also serve as biocompatible carriers for oligomeric compounds of the invention to increase their plasma circulation time.

The pharmaceutical formulations and compositions of the present invention may also include surfactants. The use of surfactants in drug products, formulations and in emulsions is well known in the art. Surfactants and their uses are further described in U.S. Pat. No. 6,287,860.

In one embodiment, the present invention employs various penetration enhancers to effect the efficient delivery of oligomeric compounds, particularly oligonucleotides. In addition to aiding the diffusion of non-lipophilic compounds across cell membranes, penetration enhancers also enhance the permeability of lipophilic compounds. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860.

In general, a composition's bioavailability is said to be "enhanced" when its relative bioavailability is greater than the bioavailability of a composition substantially consisting of pure oligomeric compound, i.e. oligomeric compound in the absence of a penetration enhancer.

Organ bioavailability refers to the concentration of compound in an organ. Organ bioavailability may be measured in test subjects by a number of means, such as by whole-body radiography. Organ bioavailability may be modified, e.g. enhanced, by one or more modifications to the oligomeric compound, by use of one or more carrier compounds or excipients, etc. as discussed in more detail herein. In general, an increase in bioavailability will result in an increase in organ bioavailability.

Suitable embodiments provided herein are compositions comprising one or more pharmaceutically acceptable penetration enhancers, and methods of using such compositions, which result in the improved bioavailability of oligonucleotides administered via non-parenteral modes of administration. Heretofore, certain penetration enhancers have been used to improve the bioavailability of certain drugs. See Muranishi, *Crit. Rev. Ther. Drug Carrier Systems,* 1990, 7, 1 and Lee et al., *Crit. Rev. Ther. Drug Carrier Systems,* 1991, 8, 91. It has been found that the uptake and delivery of oligonucleotides can be greatly improved even when administered by non-parenteral means through the use of a number of different classes of penetration enhancers.

In some embodiments, compositions for non-parenteral administration include one or more modifications from naturally-occurring oligonucleotides (i.e. full-phosphodiester deoxyribosyl or full-phosphodiester ribosyl oligonucleotides). Such modifications may increase binding affinity, nuclease stability, cell or tissue permeability, tissue distribution, or other biological or pharmacokinetic property. In some embodiments, compositions for administration to a subject, and in particular oral compositions for administration to an animal or human subject, will comprise modified oligomeric compounds having one or more modifications for enhancing affinity, stability, tissue distribution, or other biological property.

Oral compositions for administration of non-parenteral oligomeric compounds can be formulated in various dosage forms such as, but not limited to, tablets, capsules, liquid syrups, soft gels, suppositories, and enemas. The term "alimentary delivery" encompasses e.g. oral, rectal, endoscopic and sublingual/buccal administration. A common requirement for these modes of administration is absorption over some portion or all of the alimentary tract and a need for efficient mucosal penetration of the nucleic acid(s) so administered. Consequently, such oral oligomeric compound compositions can be referred to as "mucosal penetration enhancers."

Delivery of a drug via the oral mucosa, as in the case of buccal and sublingual administration, has several desirable features, including, in many instances, a more rapid rise in plasma concentration of the drug than via oral delivery (Harvey, Chapter 35 *In: Remington's Pharmaceutical Sciences,* 18th Ed., Gennaro, ed., Mack Publishing Co., Easton, Pa., 1990, page 711).

Oligomeric compounds, such as oligonucleotides, may be delivered orally, in granular form including sprayed dried particles, or complexed to form micro or nanoparticles. Oligonucleotide complexing agents and their uses are further described in U.S. Pat. No. 6,287,860. Oral formulations for oligonucleotides and their preparation are described in detail in U.S. application Ser. No. 09/108,673 (filed Jul. 1, 1998), Ser. No. 09/315,298 (filed May 20, 1999) and Ser. No. 10/071,822, filed Feb. 8, 2002.

Endoscopy may be used for drug delivery directly to an interior portion of the alimentary tract. For example, endoscopic retrograde cystopancreatography (ERCP) takes advantage of extended gastroscopy and permits selective access to the biliary tract and the pancreatic duct (Hirahata et al., *Gan To Kagaku Ryoho,* 1992, 19(10 Suppl.), 1591). Pharmaceutical compositions, including liposomal formulations, can be delivered directly into portions of the alimentary canal, such as, e.g., the duodenum (Somogyi et al., *Pharm. Res.,* 1995, 12, 149) or the gastric submucosa (Akamo et al., *Japanese J. Cancer Res.,* 1994, 85, 652) via endoscopic means. Gastric lavage devices (Inoue et al., *Artif. Organs,* 1997, 21, 28) and percutaneous endoscopic feeding devices (Pennington et al., *Ailment Pharmacol. Ther.,* 1995, 9, 471) can also be used for direct alimentary delivery of pharmaceutical compositions.

In some embodiments, oligomeric compound formulations may be administered through the anus into the rectum or lower intestine. Rectal suppositories, retention enemas or rectal catheters can be used for this purpose and may be preferred when patient compliance might otherwise be difficult to achieve (e.g., in pediatric and geriatric applications, or when the patient is vomiting or unconscious). Rectal administration can result in more prompt and higher blood levels than the oral route (Harvey, Chapter 35 *In: Remington's Pharmaceutical Sciences,* 18th Ed., Gennaro, ed., Mack Publishing Co., Easton, Pa., 1990, page 711). Because about 50% of the drug that is absorbed from the rectum will bypass the liver, administration by this route significantly reduces the potential for first-pass metabolism (Benet et al., Chapter 1 *In:*

*Goodman & Gilman's The Pharmacological Basis of Therapeutics,* 9th Ed., Hardman et al., eds., McGraw-Hill, New York, N.Y., 1996).

In one embodiment, oral oligomeric compound compositions comprise at least one member of the group consisting of surfactants, fatty acids, bile salts, chelating agents, and non-chelating surfactants. Further embodiments comprise oral oligomeric compound comprising at least one fatty acid, e.g. capric or lauric acid, or combinations or salts thereof. One combination is the sodium salt of lauric acid, capric acid and UDCA. Other embodiments comprise methods of enhancing the oral bioavailability of an oligomeric compound, the method comprising co-administering the oligomeric compound and at least one penetration enhancer.

Other excipients that may be added to oral oligomeric compound compositions include surfactants (or "surface-active agents"), which are chemical entities which, when dissolved in an aqueous solution, reduce the surface tension of the solution or the interfacial tension between the aqueous solution and another liquid, with the result that absorption of oligomeric compounds through the alimentary mucosa and other epithelial membranes is enhanced. In addition to bile salts and fatty acids, surfactants include, for example, sodium lauryl sulfate, polyoxyethylene-9-lauryl ether and polyoxyethylene-20-cetyl ether (Lee et al., *Critical Reviews in Therapeutic Drug Carrier Systems,* 1991, page 92); and perfluorochemical emulsions, such as FC-43 (Takahashi et al., *J. Pharm. Phamacol.,* 1988, 40, 252).

Fatty acids and their derivatives which act as penetration enhancers and can be used in compositions of the compounds of the present invention include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glyceryl 1-monocaprate, 1-dodecylazacycloheptan-2-one, acylcarnitines, acylcholines and mono- and di-glycerides thereof and/or physiologically acceptable salts thereof (i.e., oleate, laurate, caprate, myristate, palmitate, stearate, linoleate, etc.) (Lee et al., *Critical Reviews in Therapeutic Drug Carrier Systems,* 1991, 8:2, 91-192; Muranishi, *Critical Reviews in Therapeutic Drug Carrier Systems,* 1990, 7:1, 1-33; El-Hariri et al., *J. Pharm. Pharmacol.,* 1992, 44, 651-654). Examples of some fatty acids are sodium caprate (C10) and sodium laurate (C12), used singly or in combination at concentrations of 0.5 to 5%.

In one embodiment, oligomeric compound compositions for oral delivery comprise at least two discrete phases, which phases may comprise particles, capsules, gel-capsules, microspheres, etc. Each phase may contain one or more oligomeric compounds, penetration enhancers, surfactants, bioadhesives, effervescent agents, or other adjuvant, excipient or diluent. In one embodiment, one phase comprises at least one oligomeric compound and at least one penetration enhancer. In one embodiment, a first phase comprises at least one oligomeric compound and at least one penetration enhancer, while a second phase comprises at least one penetration enhancer. In one embodiment, a first phase comprises at least one oligomeric compound and at least one penetration enhancer, while a second phase comprises at least one penetration enhancer and substantially no oligomeric compound. In one embodiment, at least one phase is compounded with at least one degradation retardant, such as a coating or a matrix, which delays release of the contents of that phase. In one embodiment, a first phase comprises at least one oligomeric compound and at least one penetration enhancer, while a second phase comprises at least one penetration enhancer and a release-retardant. In particular embodiments, an oral oligomeric compound comprises a first phase comprising particles containing an oligomeric compound and a penetration enhancer, and a second phase comprising particles coated with a release-retarding agent and containing penetration enhancer.

A variety of bile salts also function as penetration enhancers to facilitate the uptake and bioavailability of drugs. The physiological roles of bile include the facilitation of dispersion and absorption of lipids and fat-soluble vitamins (Brunton, Chapter 38 *In: Goodman & Gilman's The Pharmacological Basis of Therapeutics,* 9th Ed., Hardman et al., eds., McGraw-Hill, New York, N.Y., 1996, pages 934-935). Various natural bile salts, and their synthetic derivatives, act as penetration enhancers. Thus, the term "bile salt" includes any of the naturally occurring components of bile as well as any of their synthetic derivatives. Bile salts contemplated herein include, for example, cholic acid (or its sodium salt, sodium cholate, or other pharmaceutically acceptable salts), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (CDCA, sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems,* 1991, page 92; Swinyard, Chapter 39 *In: Remington's Pharmaceutical Sciences,* 18th Ed., Gennaro, ed., Mack Publishing Co., Easton, Pa., 1990, pages 782-783; Muranishi, *Critical Reviews in Therapeutic Drug Carrier Systems,* 1990, 7, 1-33; Yamamoto et al., *J. Pharm. Exp. Ther.,* 1992, 263, 25; Yamashita et al., *J. Pharm. Sci.,* 1990, 79, 579-583). UDCA and CDCA have been used effectively as penetration enhancers for oligonucleotides, and even more effectively when combined.

In one embodiment, penetration enhancers useful in some embodiments are mixtures of penetration enhancing compounds. One such penetration enhancer is a mixture of UDCA (and/or CDCA) with capric and/or lauric acids or salts thereof e.g. sodium. Such mixtures are useful for enhancing the delivery of biologically active substances across mucosal membranes, in particular intestinal mucosa. Other penetration enhancer mixtures comprise about 5-95% of bile acid or salt(s) UDCA and/or CDCA with 5-95% capric and/or lauric acid. Particular penetration enhancers are mixtures of the sodium salts of UDCA, capric acid and lauric acid in a ratio of about 1:2:2 respectively. Anther such penetration enhancer is a mixture of capric and lauric acid (or salts thereof) in a 0.01:1 to 1:0.01 ratio (mole basis). In particular embodiments capric acid and lauric acid are present in molar ratios of e.g. about 0.1:1 to about 1:0.1, in particular about 0.5:1 to about 1:0.5.

Other excipients include chelating agents, i.e. compounds that remove metallic ions from solution by forming complexes therewith, with the result that absorption of oligomeric compound through the alimentary and other mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315). Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., *Critical Reviews in Thera-*

*peutic Drug Carrier Systems,* 1991, page 92; Muranishi, *Critical Reviews in Therapeutic Drug Carrier Systems,* 1990, 7, 1; Buur et al., *J. Control Rel.,* 1990, 14, 43).

As used herein, non-chelating non-surfactant penetration enhancers may be defined as compounds that demonstrate insignificant activity as chelating agents or as surfactants but that nonetheless enhance absorption of oligonucelotides through the alimentary and other mucosal membranes (Muranishi, *Critical Reviews in Therapeutic Drug Carrier Systems,* 1990, 7, 1). This class of penetration enhancers includes, but is not limited to, unsaturated cyclic ureas, 1-alkyl- and 1-alkenylazacyclo-alkanone derivatives (Lee et al., *Critical Reviews in Therapeutic Drug Carrier Systems,* 1991, page 92); and non-steroidal anti-inflammatory agents such as diclofenac sodium, indomethacin and phenylbutazone (Yamashita et al., *J. Pharm. Pharmacol.,* 1987, 39, 621).

Some oral oligonucleotide compositions also incorporate carrier compounds in the formulation. As used herein, "carrier compound" or "carrier" can refer to a nucleic acid, or analog thereof, which may be inert (i.e., does not possess biological activity per se) or may be necessary for transport, recognition or pathway activation or mediation, or is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.,* 1995, 5, 115; Takakura et al., *Antisense & Nucl. Acid Drug Dev.,* 1996, 6, 177).

A "pharmaceutical carrier" or "excipient" may be a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, EXPLOTAB); and wetting agents (e.g., sodium lauryl sulphate, etc.).

Oral oligomeric compositions may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers.

One of skill in the art will recognize that formulations are routinely designed according to their intended use, i.e. route of administration.

Formulations for topical administration include those in which the oligomeric compounds of the invention are in admixture with a topical delivery agent such as lipids, liposomes, fatty acids, fatty acid esters, steroids, chelating agents and surfactants. Lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligomeric compounds of the invention may be encapsulated within liposomes or may form complexes thereto, in particular to cationic liposomes. Alternatively, oligonucleotides may be complexed to lipids, in particular to cationic lipids. Fatty acids and esters, pharmaceutically acceptable salts thereof, and their uses are further described in U.S. Pat. No. 6,287,860. Topical formulations are described in detail in U.S. patent application Ser. No. 09/315,298 filed on May 20, 1999.

Combinations

In accordance with the present invention certain pharmaceutical compositions contain one or more antisense compounds and one or more other agents which function by a non-antisense mechanism. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one can achieve therapeutic efficacy with lower dosages of each agent, thus reducing the potential for adverse side effects.

Chemotherapeutic Agents

For example, in the treatment of cancer, one or more of the agents can be chemotherapeutic agents. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin, pemetrexed and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention.

NONLIMITING DISCLOSURE AND INCORPORATION BY REFERENCE

While certain compounds, compositions and methods of the present invention have been described with specificity in accordance with certain embodiments, the following examples serve only to illustrate the compounds of the invention and are not intended to limit the same. Each of the references, GenBank accession numbers, and the like recited in the present application is incorporated herein by reference in its entirety.

Example 1

The effect of oligomeric compounds on target nucleic acid expression was tested in one or more of the following cell types.

3T3-L1 cells: The mouse embryonic adipocyte-like cell line 3T3-L1 was obtained from the American Type Culture Collection (Manassas, Va.). 3T3-L1 cells were routinely cultured in DMEM, high glucose (Invitrogen Life Technologies, Carlsbad, Calif.) supplemented with 10% fetal bovine serum (Invitrogen Life Technologies, Carlsbad, Calif.). Cells were routinely passaged by trypsinization and dilution when they reached approximately 80% confluence. Cells were seeded into 96-well plates (Falcon-Primaria #3872) at a density of approximately 4000 cells/well for use in oligomeric compound transfection experiments.

A10 cells: The rat aortic smooth muscle cell line A10 was obtained from the American Type Culture Collection (Manassas, Va.). A10 cells were routinely cultured in DMEM, high glucose (American Type Culture Collection, Manassas, Va.) supplemented with 10% fetal bovine serum (Invitrogen Life Technologies, Carlsbad, Calif.). Cells were routinely passaged by trypsinization and dilution when they reached approximately 80% confluence. Cells were seeded into 96-well plates (Falcon-Primaria #3872) at a density of approximately 2500 cells/well for use in oligomeric compound transfection experiments.

A549 cells: The human lung carcinoma cell line A549 was obtained from the American Type Culture Collection (Manassas, Va.). A549 cells were routinely cultured in DMEM, high glucose (Invitrogen Life Technologies, Carlsbad, Calif.) supplemented with 10% fetal bovine serum, 100 units per ml penicillin, and 100 micrograms per ml streptomycin (Invitrogen Life Technologies, Carlsbad, Calif.). Cells were routinely passaged by trypsinization and dilution when they reached approximately 90% confluence. Cells were seeded into 96-well plates (Falcon-Primaria #3872) at a density of approximately 5000 cells/well for use in oligomeric compound transfection experiments.

AML-12 cells: AML12 (alpha mouse liver 12) cell line was established from hepatocytes from a mouse (CD 1 strain, line MT42) transgenic for human TGF alpha. Cells are cultured in a 1:1 mixture of DMEM and Ham's F12 medium (Invitrogen Life Technologies, Carlsbad, Calif.) supplemented with 10% fetal bovine serum, 0.005 mg/ml insulin, 0.005 mg/ml transferrin, 5 ng/ml selenium, and 40 ng/ml dexamethasone (Invitrogen Life Technologies, Carlsbad, Calif.). Cells were routinely passaged by trypsinization and dilution when they reached approximately 90% confluence. Cells were seeded into 96-well plates (Falcon-Primaria #3872) at a density of approximately 5000 cells/well for use in oligomeric compound transfection experiments.

b.END cells: The mouse brain endothelial cell line b.END was obtained from Dr. Werner Risau at the Max Plank Institute (Bad Nauheim, Germany). b.END cells were routinely cultured in DMEM, high glucose (Invitrogen Life Technologies, Carlsbad, Calif.) supplemented with 10% fetal bovine serum (Invitrogen Life Technologies, Carlsbad, Calif.). Cells were routinely passaged by trypsinization and dilution when they reached approximately 90% confluence. Cells were seeded into 96-well plates (Falcon-Primaria #3872) at a density of approximately 3000 cells/well for use in oligomeric compound transfection experiments.

B16-F10 cells: The mouse melanoma cell line B16-F10 was obtained from the American Type Culture Collection (Manassas, Va.). B16-F10 cells were routinely cultured in DMEM, high glucose (Invitrogen Life Technologies, Carlsbad, Calif.) supplemented with 10% fetal bovine serum (Invitrogen Life Technologies, Carlsbad, Calif.), Cells were routinely passaged by trypsinization and dilution when they reached approximately 90% confluence. Cells were seeded into 96-well plates (Falcon-Primaria #3872) at a density of approximately 7000 cells/well for use in oligomeric compound transfection experiments.

CHO cells: The Chinese hamster ovary cell line CHO was obtained from the American Type Culture Collection (ATCC) (Manassas, Va.). CHO cells were routinely cultured in Ham's F12K media (Invitrogen Life Technologies, Carlsbad, Calif.) supplemented with 10% fetal bovine serum and 2 mM L-glutamine, which was adjusted to contain 1.5 g/L sodium bicarbonate (Invitrogen Life Technologies, Carlsbad, Calif.). Cells were routinely passaged by trypsinization and dilution when they reached approximately 90% confluence. Cells were seeded into 96-well plates (Falcon-Primaria #3872) at a density of approximately 6000 cells/well for use in oligomeric compound transfection experiments.

HEPA 1-6 cells: The mouse hepatoma cell line HEPA 1-6 is a derivative of the BW7756 mouse hepatoma that arose in a C57/L mouse and is supplied by the American Type Culture Collection (Manassas, Va.). The cells are propagated in DMEM, high glucose, supplemented with 10% fetal bovine serum and 1% penicillin/streptomycin. Cells were routinely passaged by trypsinization and dilution when they reached approximately 80% confluence. Cells were seeded into 96-well plates at a density of approximately 4000 cells/well for use in oligomeric compound transfection experiments.

Primary mouse hepatocytes: Primary mouse hepatocytes were prepared from CD-1 mice purchased from Charles River Labs. Primary mouse hepatocytes were routinely cultured in Hepatocyte Attachment Media supplemented with 10% fetal bovine serum, 1% penicillin/streptomycin, 1% antibiotic-antimitotic (Invitrogen Life Technologies, Carlsbad, Calif.) and 10 nM bovine insulin (Sigma-Aldrich, St. Louis, Mo.). Cells were seeded into 96-well plates (Falcon-Primaria #3872) coated with 0.1 mg/ml collagen at a density of approximately 10,000 cells/well for use in oligomeric compound transfection experiments.

HepG2 cells: The human hepatoblastoma cell line HepG2 was obtained from the American Type Culture Collection (Manassas, Va.). HepG2 cells were routinely cultured in Eagle's MEM supplemented with 10% fetal bovine serum, 1 mM non-essential amino acids, and 1 mM sodium pyruvate (Invitrogen Life Technologies, Carlsbad, Calif.). Cells were routinely passaged by trypsinization and dilution when they reached approximately 90% confluence. Multiwell culture plates are prepared for cell culture by coating with a 1:100 dilution of type 1 rat tail collagen (BD Biosciences, Bedford, Mass.) in phosphate-buffered saline. The collagen-containing plates were incubated at 37° C. for approximately 1 hour, after which the collagen was removed and the wells were washed twice with phosphate-buffered saline. Cells were seeded into 96-well plates (Falcon-Primaria #3872) at a density of approximately 8,000 cells/well for use in oligomeric compound transfection experiments.

HUVEC cells: The human umbilical vein endothilial cell line HuVEC was obtained from the American Type Culture Collection (Manassas, Va.). HuVEC cells were routinely cultured in EBM (Cambrex Bio Science, Walkersville, Md.) supplemented with SingleQuots supplements (Cambrex Bio Science, Walkersville, Md.). Cells were routinely passaged by trypsinization and dilution when they reached approximately 90% confluence were maintained for up to 15 passages. Cells were seeded into 96-well plates (Falcon-Primaria #3872) at a density of approximately 10000 cells/well for use in oligomeric compound transfection experiments.

MLg2908 cells: The mouse lung cell line MLg2908 was obtained from the American Type Culture Collection (ATCC) (Manassas, Va.). MLg2908 cells were routinely cultured in MEM (Invitrogen Life Technologies, Carlsbad, Calif.) supplemented with 10% fetal bovine serum, 2 mM L-glutamine, Earle's BSS adjusted to contain 1.5 g/L sodium bicarbonate, 0.1 mM non-essential amino acids, and 1.0 mM sodium pyruvate (Invitrogen Life Technologies, Carlsbad, Calif.). Cells were routinely passaged by trypsinization and dilution when they reached approximately 90% confluence. Cells were seeded into 96-well plates (Falcon-Primaria #3872) at a density of approximately 3000 cells/well for use in oligomeric compound transfection experiments.

P388D1 cells: The murine macrophage cell line P388D1 was obtained from the American Type Culture Collection (ATCC) (Manassas, Va.). P388D1 cells were routinely cultured in RPMI 1640 media supplemented with 10% fetal bovine serum, 2 mM L-glutamine and 1% sodium pyruvate (Invitrogen Life Technologies, Carlsbad, Calif.). Cells were routinely passaged by trypsinization and dilution when they reached approximately 65-75% confluence. Cells were seeded into 96-well plates (Falcon-Primaria #3872) at a density of approximately 15,000 cells/well for use in oligomeric compound transfection experiments.

T-24 cells: The transitional cell bladder carcinoma cell line T-24 was obtained from the American Type Culture Collection (ATCC) (Manassas, Va.). T-24 cells were routinely cultured in complete McCoy's 5A basal media (Invitrogen Life Technologies, Carlsbad, Calif.) supplemented with 10% fetal bovine serum (Invitrogen Life Technologies, Carlsbad, Calif.). Cells were routinely passaged by trypsinization and dilution when they reached approximately 90% confluence. Cells were seeded into 96-well plates (Falcon-Primaria #3872) at a density of approximately 4000-6000 cells/well for use in oligomeric compound transfection experiments.

Treatment with antisense compounds: When cells reached approximately 65-75% confluency, they were treated with oligonucleotide. Oligonucleotide was mixed with LIPOFECTIN™ (Invitrogen Life Technologies, Carlsbad, Calif.) to achieve a final concentration of 3 μg/mL LIPOFECTIN™ per 100 nM oligonucleotide in 1 mL OPTI-MEM™-1 or Eagle's MEM (Invitrogen Life Technologies, Carlsbad, Calif.). For cells grown in 96-well plates, wells were washed once with 100 μL OPTI-MEM™-1, Eagle's MEM or serum-free culture medium and then treated with 130 μL of the oligonucleotide/OPTI-MEM™-1 or Eagle's MEM/LIPOFECTIN™ cocktail. Cells were treated and data were obtained in duplicate or triplicate. After 4-7 hours of treatment at 37° C., the medium was replaced with fresh medium. Cells were harvested 16-24 hours after oligonucleotide treatment.

Control oligonucleotides are used to determine the optimal oligomeric compound concentration for a particular cell line. Furthermore, when oligomeric compounds of the invention are tested in oligomeric compound screening experiments or phenotypic assays, control oligonucleotides are tested in parallel with compounds of the invention. In some embodiments, the control oligonucleotides are used as negative control oligonucleotides, i.e., as a means for measuring the absence of an effect on gene expression or phenotype. In alternative embodiments, control oligonucleotides are used as positive control oligonucleotides, i.e., as oligonucleotides known to affect gene expression or phenotype.

Control oligonucleotides are shown in Table 2. "Target Name" indicates the gene to which the oligonucleotide is targeted. "Species of Target" indicates species in which the oligonucleotide is perfectly complementary to the target mRNA. "Motif" is indicative of chemically distinct regions comprising the oligonucleotide. Certain compounds in Table 2 are composed of 2'-O-(2-methoxyethyl) nucleotides, also known as 2'-MOE nucleotides, and designated as "Uniform MOE". Certain compounds in Table 2 are chimeric oligonucleotides, composed of a central "gap" region consisting of 2'-deoxynucleotides, which is flanked on both sides (5' and 3') by "wings". The wings are composed of 2'-O-(2-methoxyethyl) nucleotides, also known as 2'-MOE nucleotides. The "motif" of each gapmer oligonucleotide is illustrated in Table 2 and indicates the number of nucleotides in each gap region and wing, for example, "5-10-5" indicates a gapmer having a 10-nucleotide gap region flanked by 5-nucleotide wings. Similarly, the motif "5-9-6" indicates a 9-nucleotide gap region flanked by 5-nucleotide wing on the 5' side and a 6-nucleotide wing on the 3' side. ISIS 15839 is a "hemimer" composed of two regions of distinct chemistry, wherein the first 12-nucleotides are 2'-deoxynucleotides and the last 8 nucleotides are 2'-MOE nucleotides. ISIS 15344 is a "hemimer" composed of two regions of distinct chemistry, wherein the first 9 nucleotides are 2'-deoxynucleotides and the last 11 are 2'-MOE nucleotides. ISIS 13513 is a chimeric oligonucleotide composed of multiple regions of distinct chemistry, denoted with a motif of "6-8-5-1" and comprised of a 6-nucleotide wing flanking an 8-nucleotide gap region followed by 5 2'-MOE nucleotides and terminating with a 2'-deoxynucleotide at the 3' end. The internucleoside (backbone) linkages are phosphorothioate throughout the oligonucleotides in Table 2. Unmodified cytosines are indicated by "uC" in the nucleotide sequence; all other cytosines are 5-methylcytosines.

TABLE 2

Control oligonucleotides for cell line testing, oligomeric compound screening and phenotypic assays

| ISIS # | Target Name | Species of Target | Sequence (5' to 3') | Motif | SEQ ID NO |
|---|---|---|---|---|---|
| 117386 | C/EBP alpha | Human | CCCTACTCAGTAGGCATTGG | 5-10-5 | 27 |
| 15839 | CD54 | Cynomolgus monkey; Human; Rhesus monkey | G$^u$C$^u$C$^u$CAAG$^u$CTGG$^u$CAT$^u$C$^u$CGT$^u$CA | Hemimer | 28 |

TABLE 2-continued

Control oligonucleotides for cell line testing, oligomeric compound screening and phenotypic assays

| ISIS # | Target Name | Species of Target | Sequence (5' to 3') | Motif | SEQ ID NO |
|---|---|---|---|---|---|
| 113131 | CD86 | Human | CGTGTGTCTGTGCTAGTCCC | 5-10-5 | 29 |
| 289865 | forkhead box O1A (rhabdomyosarcoma) | Human | GGCAACGTGAACAGGTCCAA | 5-10-5 | 30 |
| 186515 | insulin-like growth factor binding protein 1 | Human | AGGTAGCTTTGATTATGTAA | 5-10-5 | 31 |
| 25237 | integrin beta 3 | Human | GCCCATTGCTGGACATGC | 4-10-4 | 32 |
| 196103 | integrin beta 3 | Human | AGCCCATTGCTGGACATGCA | 5-10-5 | 33 |
| 134062 | Interleukin 8 | Human | GCTTGTGTGCTCTGCTGTCT | 5-10-5 | 34 |
| 148715 | Jagged 2 | Human; Mouse; Rat | TTGTCCCAGTCCCAGGCCTC | 5-10-5 | 35 |
| 15346 | Jun N-Terminal Kinase-1 | Human | CTCTCTGTAGG"C"C"CGCTTGG | 5-9-6 | 36 |
| 18076 | Jun N-Terminal Kinase-1 | Human | CTTTC"CGTTGGA"C"CCCTGGG | 5-9-6 | 37 |
| 18078 | Jun N-Terminal Kinase-2 | Human | GTGCG"CG"CGAG"C"C"CGAAATC | 5-9-6 | 38 |
| 101759 | Jun N-Terminal Kinase-2 | Mouse; Rat | GCTCAGTGGACATGGATGAG | 5-10-5 | 39 |
| 183881 | kinesin-like 1 | Human | ATCCAAGTGCTACTGTAGTA | 5-10-5 | 40 |
| 342672 | Mir-143 | Human; Mouse; Rat | ATACCGCGATCAGTGCATCTTT | Uniform MOE | 41 |
| 342673 | Mir-143 | Human; Mouse; Rat | AGACTAGCGGTATCTTTATCCC | Uniform MOE | 42 |
| 29848 | none | none | NNNNNNNNNNNNNNNNNNNN | 5-10-5 | 43 |
| 129695 | none | none | TTCTACCTCGCGCGATTTAC | 5-10-5 | 44 |
| 129700 | none | none | TAGTGCGGACCTACCCACGA | 5-10-5 | 45 |
| 226844 | Notch (*Drosophila*) homolog 1 | Human; Mouse | GCCCTCCATGCTGGCACAGG | 5-10-5 | 46 |
| 105990 | Peroxisome proliferator-activated receptor gamma | Human | AGCAAAAGATCAATCCGTTA | 5-10-5 | 47 |
| 13513 | Protein kinase C-delta | Human; Mouse | GGA"C"C"CCGAAAGAC"CA"C"CAG | 6-8-5-1 | 48 |
| 116847 | PTEN | Human; Mouse; Rabbit; Rat | CTGCTAGCCTCTGGATTTGA | 5-10-5 | 49 |
| 15344 | Raf kinase B | Human | CTGCCTGGATGGGTGTTTTT | Hemimer | 50 |
| 13650 | Raf kinase C | Human | TCCCGC"CTGTGA"CATGCATT | 6-9-6 | 51 |
| 336806 | Raf kinase C | Human | TACAGAAGGCTGGGCCTTGA | 5-10-5 | 52 |
| 15770 | Raf kinase C | Mouse; Murine sarcoma virus; Rat | ATGCATT"CTG"C"C"C"C"CAAGGA | 5-10-5 | 53 |
| 30748 | Ship-2 | Human; Mouse; Rat | CCAACCTCAAATGTCCCA | 4-10-4 | 54 |

TABLE 2-continued

| Control oligonucleotides for cell line testing, oligomeric compound screening and phenotypic assays | | | | | |
|---|---|---|---|---|---|
| ISIS # | Target Name | Species of Target | Sequence (5' to 3') | Motif | SEQ ID NO |
| 153704 | STAT 1 | Human; Rat | AGGCATGGTCTTTGTCAATA | 5-10-5 | 55 |
| 23722 | Survivin | Human | TGTGCTATTCTGTGAATT | 4-10-4 | 56 |
| 13920 | Ras-Ha | Human | T“C“CGTCATCGCT“C“CT“CAGGG | 3-9-8 | 475 |

The concentration of oligonucleotide used varies from cell line to cell line. To determine the optimal oligonucleotide concentration for a particular cell line, the cells are treated with a positive control oligonucleotide at a range of concentrations. Positive controls are shown in Table 2. For human and non-human primate cells, the positive control oligonucleotide is selected from either ISIS 13650 (SEQ ID NO: 51), ISIS 336806 (SEQ ID NO: 52) or ISIS 18078 (SEQ ID NO: 38). For mouse or rat cells the positive control oligonucleotide is ISIS 15770 (SEQ ID NO: 53) or ISIS 15346 (SEQ ID NO: 36). The concentration of positive control oligonucleotide that results in 80% inhibition of the target mRNA, for example, human Raf kinase C for ISIS 13650, is then utilized as the screening concentration for new oligonucleotides in subsequent experiments for that cell line. If 80% inhibition is not achieved, the lowest concentration of positive control oligonucleotide that results in 60% inhibition of the target mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 2

Real-Time Quantitative PCR Analysis of Target Gene mRNA Levels

Quantitation of Gemin Gene mRNA levels was accomplished by real-time quantitative PCR using the ABI PRISM™ 7600, 7700, or 7900 Sequence Detection System (PE-Applied Biosystems, Foster City, Calif.) according to manufacturer's instructions.

Prior to quantitative PCR analysis, primer-probe sets specific to the target gene being measured were evaluated for their ability to be "multiplexed" with a GAPDH amplification reaction. After isolation the RNA is subjected to sequential reverse transcriptase (RT) reaction and real-time PCR, both of which are performed in the same well. RT and PCR reagents were obtained from Invitrogen Life Technologies (Carlsbad, Calif.). RT, real-time PCR was carried out in the same by adding 20 μL PCR cocktail (2.5×PCR buffer minus $MgCl_2$, 6.6 mM $MgCl_2$, 375 μM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 μL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by RT, real-time PCR were normalized using either the expression level of GAPDH, a gene whose expression is constant, or by quantifying total RNA using RiboGreen™ (Molecular Probes, Inc. Eugene, Oreg.). GAPDH expression was quantified by RT, real-time PCR, by being run simultaneously with the target, multiplexing, or separately. Total RNA was quantified using RiboGreen™ RNA quantification reagent (Molecular Probes, Inc. Eugene, Oreg.).

170 μL of RiboGreen™ working reagent (RiboGreen™ reagent diluted 1:350 in 10 mM Tris-HCl, 1 mM EDTA, pH 7.5) was pipetted into a 96-well plate containing 30 μL purified cellular RNA. The plate was read in a CytoFluor 4000 (PE Applied Biosystems) with excitation at 485 nm and emission at 530 nm.

Presented in Table 3 are primers and probes used to measure GAPDH expression in the cell types described herein. The GAPDH PCR probes have JOE covalently linked to the 5' end and TAMRA covalently linked to the 3' end, where JOE is the fluorescent reporter dye and TAMRA is the quencher dye. In some cell types, primers and probe designed to a GAPDH sequence from a different species are used to measure GAPDH expression. For example, a human GAPDH primer and probe set is used to measure GAPDH expression in monkey-derived cells and cell lines.

TABLE 3

| GAPDH primers and probes for use in real-time PCR | | | | |
|---|---|---|---|---|
| Target Name | Species | Sequence Description | Sequence (5' to 3') | SEQ ID NO |
| GAPDH | Human | Forward Primer | CAACGGATTTGGTCGTATTGG | 57 |
| GAPDH | Human | Reverse Primer | GGCAACAATATCCACTTTACCAGAGT | 58 |
| GAPDH | Human | Probe | CGCCTGGTCACCAGGGCTGCT | 59 |

TABLE 3-continued

GAPDH primers and probes for use in real-time PCR

| Target Name | Species | Sequence Description | Sequence (5' to 3') | SEQ ID NO |
|---|---|---|---|---|
| GAPDH | Human | Forward Primer | GAAGGTGAAGGTCGGAGTC | 60 |
| GAPDH | Human | Reverse Primer | GAAGATGGTGATGGGATTTC | 61 |
| GAPDH | Human | Probe | CAAGCTTCCCGTTCTCAGCC | 62 |
| GAPDH | Human | Forward Primer | GAAGGTGAAGGTCGGAGTC | 60 |
| GAPDH | Human | Reverse Primer | GAAGATGGTGATGGGATTTC | 61 |
| GAPDH | Human | Probe | TGGAATCATATTGGAACATG | 63 |
| GAPDH | Mouse | Forward Primer | GGCAAATTCAACGGCACAGT | 64 |
| GAPDH | Mouse | Reverse Primer | GGGTCTCGCTCCTGGAAGAT | 65 |
| GAPDH | Mouse | Probe | AAGGCCGAGAATGGGAAGCTTGTCATC | 66 |
| GAPDH | Rat | Forward Primer | TGTTCTAGAGACAGCCGCATCTT | 67 |
| GAPDH | Rat | Reverse Primer | CACCGACCTTCACCATCTTGT | 68 |
| GAPDH | Rat | Probe | TTGTGCAGTGCCAGCCTCGTCTCA | 69 |

Probes and primers for use in real-time PCR were designed to hybridize to target-specific sequences. The primers and probes and the target nucleic acid sequences to which they hybridize are presented in Table 4. The target-specific PCR probes have FAM covalently linked to the 5' end and TAMRA covalently linked to the 3' end, where FAM is the fluorescent dye and TAMRA is the quencher dye.

TABLE 4

Gene target-specific primers and probes for use in real-time PCR

| Target Name | Species | Target SEQ ID NO | Sequence Description | Sequence (5' to 3') | SEQ ID NO |
|---|---|---|---|---|---|
| Gemin2 | Human | 7 | Forward Primer | CAAATTGACCCAAAGAAGTTGAAA | 70 |
| Gemin2 | Human | 7 | Reverse Primer | GTTGCTGTTGCCATTGAAGTGT | 71 |
| Gemin2 | Human | 7 | Probe | ACCCGCCCCTGAAGGTTATTCCCC | 72 |
| Gemin4 | Human | 12 | Forward Primer | GAAGTGCAGGGTCCCAATTC | 73 |
| Gemin4 | Human | 12 | Reverse Primer | TTCATCCAGACGGTTTCTTTGA | 74 |
| Gemin4 | Human | 12 | Probe | TCTGCCACTTTCATGGTGTCAT | 75 |
| Gemin5 | Human | 14 | Forward Primer | GCAAAAGCTCCTCCTCTTACCA | 76 |
| Gemin5 | Human | 14 | Reverse Primer | GTCACCCTCTCCACGAAAGG | 77 |
| Gemin5 | Human | 14 | Probe | ACTTGGAACACGGGCACCGAAG | 78 |
| Gemin6 | Human | 20 | Forward Primer | GAGAAGAACCACATCCCCATCA | 79 |
| Gemin6 | Human | 20 | Reverse Primer | GACCCCAGCCACACAGAGA | 80 |
| Gemin6 | Human | 20 | Probe | TGAACAGGGAGACGCTCCAAGGA | 81 |
| Gemin7 | Human | 25 | Forward Primer | CCTTCAAGCCATAAAGATATTGTGTTC | 82 |
| Gemin7 | Human | 25 | Reverse Primer | TTGGGAGGCCTGGGATACA | 83 |
| Gemin7 | Human | 25 | Probe | CTTTTCTGCTTGAGGCTAAGGCA | 84 |

Example 3

Treatment of Cultured Cells with Oligomeric Compounds

Oligomeric compounds targeted to Gemin Genes presented in Table 1 were tested for their effects on gene target expression in cultured cells. Table 5 shows the experimental conditions, including cell type, transfection method, dose of oligonucleotide and control SEQ ID NO used to evaluate the inhibition of gene expression by the oligomeric compounds of the invention. The control oligonucleotide was chosen from the group presented in Table 2, and in these experiments was used as a negative control. Each cell type was treated with the indicated dose of oligonucleotide as described by other examples herein.

TABLE 5

Treatment conditions of cultured cells with oligomeric compounds

| Target Name | Cell Type | Transfection Method | Dose of Oligonucleotide (nM) | Control SEQ ID NO |
|---|---|---|---|---|
| Gemin2 | A549 | Lipofectin | 150 | 38 |
| Gemin4 | T-24 | Lipofectin | 150 | 38 |
| Gemin5 | A549 | Lipofectin | 150 | 38 |
| Gemin6 | T-24 | Lipofectin | 150 | 38 |
| Gemin7 | T-24 | Lipofectin | 150 | 38 |

Example 4

Antisense Inhibition of Gene Targets by Oligomeric Compounds

A series of oligomeric compounds was designed to target different regions of the Gemin Genes, using sequences cited in Table 1. The oligomeric compounds and the data describing the degree to which they inhibit gene expression are shown in Table 6.

All oligomeric compounds in Table 6 are chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-0-(2-methoxyethyl) nucleotides, also known as 2'-MOE nucleotides. The internucleoside (backbone) linkages are phosphorothioate throughout the oligonucleotide. All cytidine residues are 5-methylcytidines.

The oligomeric compounds were analyzed for their effect on gene target mRNA levels by quantitative real-time PCR as described in other examples herein. Data are averages from experiments in which cultured cells, as indicated for each target in Table 5, were treated with the disclosed oligomeric compounds. A reduction in expression is expressed as percent inhibition in Table 6. If the target expression level of oligomeric compound-treated cell was higher than control, percent inhibition is expressed as zero inhibition. If present, "N.D." indicates "not determined". The target regions to which these oligomeric compounds are inhibitory are herein referred to as "validated target segments."

As shown in Table 6, SEQ ID NOs 87, 89, 90, 91, 92, 94, 103, 104, 105, 106, 109, 110, 111, 112, 113, 114, 115, 116, 117, 118, 119, 121, 122, 123, 125, 127, 128, 129, 130, 131, 132, 135, 136, 137, 138, 139, 140, 141, 142, 145, 146, 147, 148, 149, 150, 151, 152, 153, 156, 157, 158, 161, 163, 166, 177, 178, 180, 188, 193, 195, 210, 225, 228, 229, 232, 238, 241, 242, 243, 244, 245, 246, 249, 250, 251, 252, 253, 254, 255, 256, 257, 259, 260, 261, 262, 263, 264, 265, 266, 267, 268, 269, 270, 271, 272, 274, 275, 276, 277, 278, 279, 280, 281, 282, 283, 284, 285, 286, 291, 294, 295, 296, 297, 298, 299, 300, 301, 302, 303, 304, 305, 306, 307, 308, 309, 311, 313, 315, 316, 317, 319, 320, 326, 328, 329, 330, 332, 333, 334, 335, 336, 337, 338, 339, 340, 341, 342, 343, 344, 346, 347, 348, 349, 350, 351, 352, 353, 354, 356, 357, 358, 359, 360, 361, 362, 363, 364, 366, 368, 369, 370, 371, 372, 373, 374, 375, 376, 377, 378, 380, 381, 382, 383, 384, 385, 387, 388, 393, 394, 395, 396, 397, 398, 399, 401, 402, 403, 410, 411, 412, 414, 415, 417, 418, 419, 420, 421, 422, 423, 424, 425, 426, 427, 428, 429, 430, 432, 433, 434, 435, 436, 437, 438, 439, 440, 441, 442, 443, 444, 445, 450, 451, 452, 457, 458, 462, 467, 468, 469, 470, 471, 472, 473, 474, demonstrated at least 50% inhibition of a Gemin Gene in this assay. In some embodiments of the invention, oligomeric compounds of the invention comprise at least one of these sequences. In other embodiments, oligomeric compounds of the invention consist of at least one of these sequences.

The target sites to which these sequences are complementary are examples of "validated target sites" and are therefore sites for designing other oligomeric compounds of the present invention.

TABLE 6

Modulation of Gemin Gene mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 297287 | 1 | 510 | TTACTGTTGCTTGTACATAA | 28 | 85 |
| 297288 | 2 | 735 | GTCAAAATACCACTAAGAGC | 2 | 86 |
| 297289 | 3 | 81 | TGCTTCGATCCGGCAATAGC | 59 | 87 |
| 297292 | 4 | 1317 | CAATAAAATTTTATATGTAT | 5 | 88 |
| 297293 | 4 | 1356 | TAGGAGTCAAACAAAATTTT | 51 | 89 |
| 297294 | 4 | 1381 | GCTAAGGCCATCCATTGTCT | 54 | 90 |
| 297295 | 4 | 1394 | TTTTAATTCTGATGCTAAGG | 53 | 91 |
| 297296 | 4 | 1412 | GCCATTTAATCCAGATTATT | 52 | 92 |
| 297297 | 4 | 1418 | CACATTGCCATTTAATCCAG | 35 | 93 |
| 297298 | 4 | 1432 | TTGCTGACTATGAACACATT | 57 | 94 |
| 297299 | 4 | 1439 | AATTTTATTGCTGACTATGA | 43 | 95 |
| 297290 | 5 | 539 | GCCATCTTCCCTGATTCATT | 10 | 96 |
| 297291 | 6 | 399 | GAAAACCAATCATTGTCACA | 8 | 97 |
| 297230 | 7 | 44 | CGCAGGCGCACTAATAGACA | 17 | 98 |
| 297231 | 7 | 51 | GTCACAGCGCAGGCGCACTA | 38 | 99 |
| 297232 | 7 | 57 | TTCTAGGTCACAGCGCAGGC | 37 | 100 |
| 297233 | 7 | 71 | GGCGCATGCGCCCATTCTAG | 13 | 101 |
| 297234 | 7 | 95 | TTTTCAAACCAGCCAGTTCC | 48 | 102 |
| 297235 | 7 | 174 | GTCAAGTCGCAAGGCTCTAC | 81 | 103 |
| 297236 | 7 | 270 | GCTACCACAACATCTGGACA | 77 | 104 |
| 297237 | 7 | 287 | TCTTTGGGTCAATTTGAGCT | 92 | 105 |
| 297238 | 7 | 294 | TTCAACTTCTTTGGGTCAAT | 88 | 106 |
| 297239 | 7 | 308 | CACTTTGCTTCCTTTTCAAC | 45 | 107 |
| 297240 | 7 | 329 | ATCCTGAAAGAGAAATATTC | 19 | 108 |
| 297241 | 7 | 374 | GTTGCCATTGAAGTGTTGGG | 81 | 109 |

TABLE 6-continued

Modulation of Gemin Gene mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 297242 | 7 | 378 | TGCTGTTGCCATTGAAGTGT | 90 | 110 |
| 297243 | 7 | 389 | GTGCCACTTGTTGCTGTTGC | 86 | 111 |
| 297244 | 7 | 406 | TCGAACAGTTGAAAACTGTG | 61 | 112 |
| 297245 | 7 | 419 | TGTTCACATTCTGTCGAACA | 71 | 113 |
| 297246 | 7 | 577 | ATAATCTATTCCAGGACTTT | 68 | 114 |
| 297247 | 7 | 630 | GCCTGATTCATTCTGCTAAC | 78 | 115 |
| 297248 | 7 | 633 | GTTGCCTGATTCATTCTGCT | 83 | 116 |
| 297249 | 7 | 649 | CAAGACACTAGTTACTGTTG | 77 | 117 |
| 297250 | 7 | 652 | TTCCAAGACACTAGTTACTG | 74 | 118 |
| 297251 | 7 | 657 | AGATATTCCAAGACACTAGT | 74 | 119 |
| 297252 | 7 | 671 | CAAACCAATTACTCAGATAT | 33 | 120 |
| 297253 | 7 | 682 | GTCTCTTTCTCCAAACCAAT | 52 | 121 |
| 297254 | 7 | 687 | GTAAAGTCTCTTTCTCCAAA | 53 | 122 |
| 297255 | 7 | 692 | CTGGAGTAAAGTCTCTTTCT | 82 | 123 |
| 297256 | 7 | 697 | CAATTCTGGAGTAAAGTCTC | 47 | 124 |
| 297257 | 7 | 702 | CTTCCCAATTCTGGAGTAAA | 65 | 125 |
| 297258 | 7 | 706 | CCATCTTCCCAATTCTGGAG | 43 | 126 |
| 297259 | 7 | 735 | TTTTCAAGACAAGCCAATAA | 55 | 127 |
| 297260 | 7 | 738 | GGCTTTTCAAGACAAGCCAA | 66 | 128 |
| 297261 | 7 | 742 | CAAAGGCTTTTCAAGACAAG | 51 | 129 |
| 297262 | 7 | 746 | GTAACAAAGGCTTTTCAAGA | 57 | 130 |
| 297263 | 7 | 762 | AGTGAATGAGCCTCAGGTAA | 85 | 131 |
| 297264 | 7 | 873 | AAATACCTGCTAACCAAGCA | 57 | 132 |
| 297265 | 7 | 876 | TCAAAATACCTGCTAACCAA | 24 | 133 |
| 297266 | 7 | 900 | GGCTCATCAGCTAAATCACG | 0 | 134 |
| 297267 | 7 | 903 | GATGGCTCATCAGCTAAATC | 65 | 135 |
| 297268 | 7 | 908 | ATCAAGATGGCTCATCAGCT | 79 | 136 |
| 297269 | 7 | 916 | TCAGCTACATCAAGATGGCT | 71 | 137 |
| 297270 | 7 | 941 | AGAAATATCTTCTATCCCTG | 68 | 138 |
| 297271 | 7 | 970 | GTTTTCCTCAGAGTTAGGCT | 83 | 139 |
| 297272 | 7 | 1004 | AAGATGTGTTGAAATCTGTA | 77 | 140 |
| 297273 | 7 | 1017 | TCACATAGTGTTGAAGATGT | 79 | 141 |
| 297274 | 7 | 1023 | AACCCTTCACATAGTGTTGA | 80 | 142 |
| 297275 | 7 | 1031 | AAGATGTGAACCCTTCACAT | 0 | 143 |
| 297276 | 7 | 1037 | CAGGTTAAGATGTGAACCCT | 18 | 144 |
| 297277 | 7 | 1055 | GTATCAATCTGAATTGCACA | 81 | 145 |

TABLE 6-continued

Modulation of Gemin Gene mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 297278 | 7 | 1105 | GTGGGATTTTCCATTGATAT | 69 | 146 |
| 297279 | 7 | 1110 | ACTGAGTGGGATTTTCCATT | 83 | 147 |
| 297280 | 7 | 1114 | AAAACTGAGTGGGATTTTC | 82 | 148 |
| 297281 | 7 | 1121 | GTTCATCAAAAACTGAGTGG | 74 | 149 |
| 297282 | 7 | 1131 | TGTTCAAACTGTTCATCAAA | 75 | 150 |
| 297283 | 7 | 1144 | GATTACAGAAAACTGTTCAA | 64 | 151 |
| 297284 | 7 | 1150 | CTGCTTGATTACAGAAAACT | 79 | 152 |
| 297285 | 7 | 1164 | AATTTCTATGCAAGCTGCTT | 89 | 153 |
| 297286 | 7 | 1182 | TGTAAAATTTCATCATACAA | 48 | 154 |
| 297300 | 8 | 1981 | TAAGTAACCCATTTAAAGAC | 36 | 155 |
| 297301 | 8 | 4803 | ATCCTGAAAGCTAGAGATCA | 58 | 156 |
| 297302 | 8 | 5344 | TGTTCACATTCTAAAGGAAG | 60 | 157 |
| 297303 | 8 | 7356 | GGAATAAGGTTATCTACCTT | 71 | 158 |
| 297304 | 8 | 14948 | CAAAGAAAGCTAATTTGTTT | 42 | 159 |
| 297305 | 8 | 18873 | TGCAACTTACCACTAAGAGC | 36 | 160 |
| 297306 | 8 | 19918 | TAATCACTGTACAGTCAAGA | 64 | 161 |
| 297307 | 8 | 20524 | TTAACTATACCTGCTAACCA | 28 | 162 |
| 297452 | 9 | 6 | TGGGCACAGAGCAATCACAC | 75 | 163 |
| 297450 | 9 | 129 | CAATCACACGGCCACAGGAT | 45 | 164 |
| 297451 | 9 | 427 | CAATCACACAGCCACAGGAT | 41 | 165 |
| 297453 | 9 | 892 | CAAGACGGTGAATGAGATCC | 53 | 166 |
| 297446 | 10 | 7 | CTTAGGCCTGCTCACAACCT | 0 | 167 |
| 297447 | 10 | 12 | CCGCGCTTAGGCCTGCTCAC | 0 | 168 |
| 297448 | 10 | 41 | CACGATGGGAGACGCAGGAG | 13 | 169 |
| 297449 | 10 | 80 | CTCCCCTCCGAGAACTCGAA | 44 | 170 |
| 297454 | 11 | 63 | TCCTTCCAGTCAAAAACAAG | 31 | 171 |
| 297455 | 11 | 90 | TTTCAGGGAAACGGTCCACC | 49 | 172 |
| 297386 | 12 | 15 | CCTAGGTCCATGGCGGCGAC | 0 | 173 |
| 297387 | 12 | 22 | CAAGGGTCCTAGGTCCATGG | 0 | 174 |
| 297388 | 12 | 24 | TTCAAGGGTCCTAGGTCCAT | 0 | 175 |
| 297389 | 12 | 53 | CATGCAGAATAGTCATTTCT | 40 | 176 |
| 297390 | 12 | 108 | GTTAATTCTGCCAGTGCCTT | 53 | 177 |
| 297391 | 12 | 203 | TCTTCCAGGCAAAGGGCTGG | 59 | 178 |
| 297392 | 12 | 210 | GCTTTCTTCTTCCAGGCAAA | 27 | 179 |
| 297393 | 12 | 282 | TGCCACCGTGTCTCTGTGTC | 62 | 180 |
| 297394 | 12 | 471 | TCTTCGGCAGAAGTGTCAAC | 43 | 181 |

TABLE 6-continued

Modulation of Gemin Gene mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 297395 | 12 | 694 | GATCCGACTCTGGATCTGTG | 35 | 182 |
| 297396 | 12 | 767 | CCTCTGTCAGCGCAAACACA | 25 | 183 |
| 297397 | 12 | 837 | GAGTTCCACACAGAGATCAC | 28 | 184 |
| 297398 | 12 | 843 | GTGTCCGAGTTCCACACAGA | 19 | 185 |
| 297399 | 12 | 849 | TTCTGGGTGTCCGAGTTCCA | 42 | 186 |
| 297400 | 12 | 980 | CCCGCAGCAGGTGGTGCAGG | 0 | 187 |
| 297401 | 12 | 1076 | TCTGGCTGAAGGAAGTCAGA | 52 | 188 |
| 297402 | 12 | 1164 | AGGAAGTCCCTGACACACTC | 0 | 189 |
| 297403 | 12 | 1173 | GTTTTCCTCAGGAAGTCCCT | 48 | 190 |
| 297404 | 12 | 1199 | AGGCCCTGTTCTTCAGCACC | 42 | 191 |
| 297405 | 12 | 1215 | GCTGTGATATCCTCCAAGGC | 42 | 192 |
| 297406 | 12 | 1269 | CACACTTCCATATGGCGGTC | 62 | 193 |
| 297407 | 12 | 1302 | AAGGCCCACTTCTTCTCAGA | 18 | 194 |
| 297408 | 12 | 1337 | TGTTACTCCCCAGGCAGGCT | 55 | 195 |
| 297409 | 12 | 1374 | AGCCTCAACACCAAGTCTGG | 31 | 196 |
| 297410 | 12 | 1469 | CTGCGTAACATTCCAGGATC | 45 | 197 |
| 297411 | 12 | 1559 | CATAAGCCAGCAACTTTTCA | 32 | 198 |
| 297412 | 12 | 1579 | GTCTTCCTGAAAACCCTCCA | 38 | 199 |
| 297413 | 12 | 1584 | TTGAGGTCTTCCTGAAAACC | 43 | 200 |
| 297414 | 12 | 1655 | GGGCCACGGAGGCCACAGCT | 18 | 201 |
| 297415 | 12 | 1686 | ACCGTGACTTCCGGGTGCAC | 0 | 202 |
| 297416 | 12 | 1724 | TGCCGAGATTGACCACAGCC | 48 | 203 |
| 297417 | 12 | 1762 | AGGGAAGGCAGTGAGAATCT | 33 | 204 |
| 297418 | 12 | 1781 | CTTCCACAAACCTAAGGGCA | 46 | 205 |
| 297419 | 12 | 1857 | GGTGTAGAGAACTTCATCCA | 31 | 206 |
| 297420 | 12 | 1887 | AGGAGCTCTAAAAATTGCTT | 23 | 207 |
| 297421 | 12 | 1938 | AGAGCAGCCACTGGAATCCC | 25 | 208 |
| 297422 | 12 | 1982 | AGAAAGGCAGGACAAATTCC | 20 | 209 |
| 297423 | 12 | 2018 | TCAGACTGAGGTCTACCTCT | 51 | 210 |
| 297424 | 12 | 2244 | AAGGTCTCAGCATTGGCTGA | 25 | 211 |
| 297425 | 12 | 2282 | GGAGCCAGGACAGGGACTTG | 49 | 212 |
| 297426 | 12 | 2289 | TTGCGGTGGAGCCAGGACAG | 49 | 213 |
| 297427 | 12 | 2323 | CCTCAGGCCCACAGTCCAGT | 45 | 214 |
| 297428 | 12 | 2471 | AGCAGCACTCCATCCAGGCC | 0 | 215 |
| 297429 | 12 | 2541 | ACCTCCTCAGGATTGCCCAC | 43 | 216 |
| 297430 | 12 | 2550 | AACAGTCTGACCTCCTCAGG | 26 | 217 |

TABLE 6-continued

Modulation of Gemin Gene mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 297431 | 12 | 2616 | CGCTGCCACTCCTGAGGGCT | 38 | 218 |
| 297432 | 12 | 2633 | TGGTCAGCTGGTGAAGGCGC | 38 | 219 |
| 297433 | 12 | 2719 | AAAGGGCTTCAGGTTGAGCA | 40 | 220 |
| 297434 | 12 | 2778 | TGGCTGCAGAGAAACTGGAA | 44 | 221 |
| 297435 | 12 | 2793 | CAATTACGACAGCTATGGCT | 43 | 222 |
| 297436 | 12 | 3037 | GCAGGTGAGGGTTTCCAAGG | 0 | 223 |
| 297437 | 12 | 3077 | AGGAGCTGACAGAAGGGTTG | 12 | 224 |
| 297438 | 12 | 3086 | TCTGGAGCAAGGAGCTGACA | 53 | 225 |
| 297439 | 12 | 3189 | ACGCCAAGTCAGAAGCTGCT | 0 | 226 |
| 297440 | 12 | 3228 | GATCTTCTGCAGACCCGCCA | 34 | 227 |
| 297441 | 12 | 3263 | CAGCTTTTTCGCTCCCGCAC | 61 | 228 |
| 297442 | 12 | 3291 | ACCCCTACAGACCTGCCATG | 53 | 229 |
| 297443 | 12 | 3304 | CTGCTCGGGTCTGACCCCTA | 48 | 230 |
| 297444 | 12 | 3326 | TCACATAACTGTAAAGTCCA | 45 | 231 |
| 297445 | 12 | 3348 | CCATGACTTTTTGTGGACAG | 71 | 232 |
| 297456 | 13 | 1818 | CGGCACCCACCTAGGTCCAT | 25 | 233 |
| 297457 | 13 | 2360 | GTGATACCTCAGGAGCGCAG | 0 | 234 |
| 297458 | 13 | 2691 | ATAAGGACACTGAGGCGCAG | 38 | 235 |
| 297459 | 13 | 4041 | GGCCCTAGCTCTGTGGGAGA | 19 | 236 |
| 297460 | 13 | 4137 | ATAAACTTGCCTTGGGAACA | 46 | 237 |
| 297461 | 13 | 4300 | AATCACACAGCCACAGGGTA | 54 | 238 |
| 297462 | 13 | 5440 | GGCGAGACCCTCCAGCAAAG | 15 | 239 |
| 297463 | 13 | 5918 | TTCAAGGGTCCTGCACACAG | 43 | 240 |
| 297551 | 14 | 43 | CCTCCAAAACAGCTAGATAC | 54 | 241 |
| 297552 | 14 | 64 | AGATCCCATTGCAACAGTTC | 87 | 242 |
| 297553 | 14 | 112 | TCTGATGAGGCACTGAAGAG | 83 | 243 |
| 297554 | 14 | 203 | TCTATCCATTGATGTAGAAA | 64 | 244 |
| 297555 | 14 | 275 | GTATGCAAACCCACCAAGGG | 76 | 245 |
| 297556 | 14 | 531 | GATATGTGCTAGAAATCTGT | 67 | 246 |
| 297557 | 14 | 612 | GGGAAGGTCTGTCTCCTTCT | 39 | 247 |
| 297558 | 14 | 650 | TAAGACAATCCCTTCTCCTC | 30 | 248 |
| 297559 | 14 | 677 | TCCACTAAGCTTCCAGGGAT | 84 | 249 |
| 297560 | 14 | 939 | TGGAGCCAGAGGCCATCAGA | 85 | 250 |
| 297561 | 14 | 960 | GCACGTAAATGACTGCATTG | 77 | 251 |
| 297562 | 14 | 991 | GGGCTGCTCTCTATGACAGT | 52 | 252 |
| 297563 | 14 | 1076 | ATGTGGGCTCCACGCCACAC | 62 | 253 |

TABLE 6-continued

Modulation of Gemin Gene mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 297564 | 14 | 1230 | CCCCTGAATAGATGCAGTCT | 81 | 254 |
| 297565 | 14 | 1291 | TGAGGAGGCCGGGAATGATC | 66 | 255 |
| 297566 | 14 | 1377 | TTCTCAAGGTGGGCTTTTTC | 66 | 256 |
| 297567 | 14 | 1843 | ATCATTCTATACAGGGTAGC | 63 | 257 |
| 297568 | 14 | 1864 | TGACCTTTTCCTTCAATATC | 33 | 258 |
| 297569 | 14 | 1893 | GAAATAACTCAGGGTGGCCA | 56 | 259 |
| 297570 | 14 | 1935 | GGAGAACACCTTTGAGATCC | 70 | 260 |
| 297571 | 14 | 1982 | CATAGCCACAAGGTTGTCTG | 64 | 261 |
| 297572 | 14 | 2002 | TGGTAGCCAGCTGCTGGTGC | 75 | 262 |
| 297573 | 14 | 2073 | AAGCAGCCTTGACATACTGA | 88 | 263 |
| 297574 | 14 | 2117 | CAGCTCCACCGCTTCATACA | 70 | 264 |
| 297575 | 14 | 2369 | ATCCTCTCCTACGATGGCAG | 83 | 265 |
| 297576 | 14 | 2395 | CTGAGAGCCAGGGAAGCAGA | 83 | 266 |
| 297577 | 14 | 2431 | ACCCAGTTGTTGGCCAGAAG | 79 | 267 |
| 297578 | 14 | 2477 | CTGACCCTGTAGACTTTCAT | 71 | 268 |
| 297579 | 14 | 2681 | GTTCTGCAGCTTCTGAAAGG | 68 | 269 |
| 297580 | 14 | 2748 | AGTCATGGCAAATGTGAAGC | 78 | 270 |
| 297581 | 14 | 2782 | GAGGCCATCTGTTGGCTCAG | 58 | 271 |
| 297582 | 14 | 2865 | ACACTTCCTGCATGATGGTG | 79 | 272 |
| 297583 | 14 | 2896 | TGGTCACAGCCATCAGGGAG | 25 | 273 |
| 297584 | 14 | 3088 | GCAGTGTCTAACTGCTGGCT | 74 | 274 |
| 297585 | 14 | 3125 | TGGCTGAGAAGTTTCAGGGT | 66 | 275 |
| 297586 | 14 | 3390 | TACACTGGCTCTGAGAACTG | 69 | 276 |
| 297587 | 14 | 3460 | ATTCTCTGATTTGCCTCGGT | 79 | 277 |
| 297588 | 14 | 3662 | TGTGAAAATTCACATACAGA | 57 | 278 |
| 297589 | 14 | 3739 | GAGTGAATGTCTGGTGAGGC | 78 | 279 |
| 297590 | 14 | 3794 | AAACTTAATCCTTGTTTGTA | 54 | 280 |
| 297591 | 14 | 3822 | GTTGTCTATGGGTAGGCAGG | 80 | 281 |
| 297592 | 14 | 3982 | TTTGGGTGACGACAGAAGTT | 78 | 282 |
| 297593 | 14 | 4024 | GAAGTATTTACAAAGGTAGC | 74 | 283 |
| 297594 | 14 | 4057 | TCTCAAACAAGCATGACACA | 51 | 284 |
| 297595 | 14 | 4092 | AAAGGTATCAATAGTCCTAA | 77 | 285 |
| 297596 | 14 | 4182 | GGCCTATTTCATATTCAAAC | 87 | 286 |
| 297597 | 14 | 4360 | TTCCTGAGCTATTTGACTGC | 42 | 287 |
| 297598 | 14 | 4375 | TGAAACAGTAATTTATTCCT | 37 | 288 |
| 297599 | 14 | 4492 | AATAATCCAAAGGTCATCTA | 45 | 289 |

TABLE 6-continued

Modulation of Gemin Gene mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 297600 | 14 | 4527 | TTAAATAGTATTTAGGGTCC | 45 | 290 |
| 297601 | 15 | 20 | GAAGCTGCCACAGCCGACCG | 57 | 291 |
| 297602 | 15 | 35 | CCGTCAGAGACAAGAGAAGC | 49 | 292 |
| 297603 | 15 | 55 | TCCTGCCCCATAACTACAAG | 31 | 293 |
| 297604 | 15 | 163 | CGGACAAGGAAGACGGAGGT | 63 | 294 |
| 297605 | 15 | 233 | GTGTCCCACCAACTCTCCTA | 64 | 295 |
| 297606 | 15 | 249 | CAGAGACCCTTTCGGTGTGT | 86 | 296 |
| 297607 | 15 | 359 | ATGTTCTGTCACAACTGTTT | 76 | 297 |
| 297608 | 15 | 421 | ACTATTAAGTCCTTTACTCG | 54 | 298 |
| 297609 | 15 | 477 | GGCTGTCATTTCTGTTAAAC | 62 | 299 |
| 297610 | 15 | 498 | TGGGTTCTATAAAGAGGTGC | 76 | 300 |
| 297611 | 15 | 580 | ATTATCACCACTATGCCATC | 63 | 301 |
| 297612 | 15 | 632 | ATCATCATGGCCTCGAAGCC | 82 | 302 |
| 297613 | 15 | 658 | GGACACCAGGCTATGGAGTG | 65 | 303 |
| 297614 | 15 | 769 | AAGTAGCAACCTTTTGTTAC | 65 | 304 |
| 297615 | 15 | 783 | TGCTTCCAGTGGCTAAGTAG | 86 | 305 |
| 297616 | 15 | 803 | GATTCGAATGGTTTGATCTT | 60 | 306 |
| 297617 | 15 | 827 | CCCTCGGCCTCTAGAACAGC | 77 | 307 |
| 297618 | 15 | 890 | TTTAACAGTTGGGTCTATAC | 67 | 308 |
| 297619 | 15 | 931 | GGTTGATTGCTGGGCCAATG | 62 | 309 |
| 297620 | 15 | 1516 | CCTTCTCCTCCAAGTGACAT | 39 | 310 |
| 297621 | 15 | 2049 | CATCCCACACCTGGGCTGTA | 54 | 311 |
| 297622 | 16 | 19049 | AAGAACTCACTTTGATTGAA | 0 | 312 |
| 297623 | 16 | 19178 | CAGCCTTATAAGAACATTTA | 62 | 313 |
| 297624 | 16 | 22018 | CCAAAGTTACCTATGACAGT | 4 | 314 |
| 297625 | 16 | 30470 | GGTTGCCATGCCTTTCTGGT | 60 | 315 |
| 297626 | 16 | 34509 | ATTTTTGTACCTCTGGAGTG | 58 | 316 |
| 297627 | 16 | 44650 | AGCTGCTGTAAACATTTGTG | 52 | 317 |
| 297628 | 16 | 49702 | TAACTCTTACCTTAATGCTC | 5 | 318 |
| 297694 | 17 | 28 | GGTACTCAGCAACCATGCTT | 83 | 319 |
| 297695 | 17 | 33 | CTCTGGGTACTCAGCAACCA | 80 | 320 |
| 297696 | 17 | 207 | AGAACCTTGGCAGAGACTGG | 44 | 321 |
| 297697 | 18 | 713 | TTTACCGACACATCCAAGAA | 0 | 322 |
| 297698 | 18 | 770 | GCCCTAAGTTCATTAATTTC | 3 | 323 |
| 297699 | 18 | 807 | CTGCGCCTAATCTTAAGCCA | 7 | 324 |
| 297700 | 18 | 916 | ACCTGAAGATTGCCCCATGG | 7 | 325 |

TABLE 6-continued

Modulation of Gemin Gene mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 297630 | 20 | 8 | CTCCTCGCAACTCTGGGTAC | 70 | 326 |
| 297631 | 20 | 29 | CTGGCTAAATCAGTTAAAAA | 16 | 327 |
| 297632 | 20 | 36 | TTGCCACCTGGCTAAATCAG | 63 | 328 |
| 297633 | 20 | 40 | ATGATTGCCACCTGGCTAAA | 63 | 329 |
| 297634 | 20 | 50 | CCATTCACTCATGATTGCCA | 87 | 330 |
| 297635 | 20 | 55 | TTCATCCATTCACTCATGAT | 44 | 331 |
| 297636 | 20 | 84 | TGTAATCTTGCCATTCTAAG | 58 | 332 |
| 297637 | 20 | 90 | TGTAAATGTAATCTTGCCAT | 73 | 333 |
| 297638 | 20 | 93 | CTTTGTAAATGTAATCTTGC | 65 | 334 |
| 297639 | 20 | 103 | ACTCGGACCTCTTTGTAAAT | 51 | 335 |
| 297640 | 20 | 112 | CTGGCTGTCACTCGGACCTC | 78 | 336 |
| 297641 | 20 | 116 | CTCACTGGCTGTCACTCGGA | 88 | 337 |
| 297642 | 20 | 119 | CTTCTCACTGGCTGTCACTC | 58 | 338 |
| 297643 | 20 | 125 | CTCATTCTTCTCACTGGCTG | 81 | 339 |
| 297644 | 20 | 148 | GTAGTTAAAACCCATCCTTT | 56 | 340 |
| 297645 | 20 | 152 | GTCTGTAGTTAAAACCCATC | 57 | 341 |
| 297646 | 20 | 156 | CTGGGTCTGTAGTTAAAACC | 66 | 342 |
| 297647 | 20 | 159 | AGACTGGGTCTGTAGTTAAA | 57 | 343 |
| 297648 | 20 | 166 | TTGGCAGAGACTGGGTCTGT | 82 | 344 |
| 297649 | 20 | 176 | AAGGACAATATTGGCAGAGA | 24 | 345 |
| 297650 | 20 | 190 | TCAAGGAAGTTCACAAGGAC | 59 | 346 |
| 297651 | 20 | 197 | GCCATCTTCAAGGAAGTTCA | 78 | 347 |
| 297652 | 20 | 199 | CTGCCATCTTCAAGGAAGTT | 58 | 348 |
| 297653 | 20 | 211 | GTCACAGACATGCTGCCATC | 77 | 349 |
| 297654 | 20 | 214 | CCGGTCACAGACATGCTGCC | 88 | 350 |
| 297655 | 20 | 232 | ACAGCATGTCCCATAATTCC | 53 | 351 |
| 297656 | 20 | 240 | CAGTCTGCACAGCATGTCCC | 80 | 352 |
| 297657 | 20 | 244 | TCAACAGTCTGCACAGCATG | 68 | 353 |
| 297658 | 20 | 256 | TCATTCATAGTTTCAACAGT | 53 | 354 |
| 297659 | 20 | 262 | TCCCCTTCATTCATAGTTTC | 36 | 355 |
| 297660 | 20 | 267 | TATGGTCCCCTTCATTCATA | 63 | 356 |
| 297661 | 20 | 269 | TCTATGGTCCCCTTCATTCA | 62 | 357 |
| 297662 | 20 | 297 | TGAACAAATGCATCAGCTTC | 59 | 358 |
| 297663 | 20 | 303 | CAGACGTGAACAAATGCATC | 76 | 359 |
| 297664 | 20 | 315 | CTTTGCAGTCTCCAGACGTG | 84 | 360 |
| 297665 | 20 | 327 | CTGGGCTGTATGCTTTGCAG | 79 | 361 |

TABLE 6-continued

Modulation of Gemin Gene mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 297666 | 20 | 333 | GATCCTCTGGGCTGTATGCT | 68 | 362 |
| 297667 | 20 | 336 | CCAGATCCTCTGGGCTGTAT | 74 | 363 |
| 297668 | 20 | 346 | TTTCTCTCTTCCAGATCCTC | 54 | 364 |
| 297669 | 20 | 369 | CAAGCCATTTCTTTAGGCTG | 32 | 365 |
| 297670 | 20 | 372 | TCTCAAGCCATTTCTTTAGG | 60 | 366 |
| 297671 | 20 | 374 | CTTCTCAAGCCATTTCTTTA | 48 | 367 |
| 297672 | 20 | 377 | GTTCTTCTCAAGCCATTTCT | 68 | 368 |
| 297673 | 20 | 379 | TGGTTCTTCTCAAGCCATTT | 71 | 369 |
| 297674 | 20 | 381 | TGTGGTTCTTCTCAAGCCAT | 80 | 370 |
| 297675 | 20 | 385 | GGGATGTGGTTCTTCTCAAG | 65 | 371 |
| 297676 | 20 | 404 | GTCTCCCTGTTCAGTGATGG | 86 | 372 |
| 297677 | 20 | 424 | ACACAGAGAGTCCTTGGAGC | 65 | 373 |
| 297678 | 20 | 429 | CAGCCACACAGAGAGTCCTT | 66 | 374 |
| 297679 | 20 | 433 | ACCCCAGCCACACAGAGAGT | 69 | 375 |
| 297680 | 20 | 447 | GGTCTATAGTCAGGACCCCA | 62 | 376 |
| 297681 | 20 | 454 | TATGGTGGGTCTATAGTCAG | 54 | 377 |
| 297682 | 20 | 457 | TCATATGGTGGGTCTATAGT | 59 | 378 |
| 297683 | 20 | 468 | AATTTTCTGGATCATATGGT | 21 | 379 |
| 297684 | 20 | 472 | CTGCAATTTTCTGGATCATA | 83 | 380 |
| 297685 | 20 | 481 | TTAGAGCTGCTGCAATTTTC | 84 | 381 |
| 297686 | 20 | 485 | CTCATTAGAGCTGCTGCAAT | 81 | 382 |
| 297687 | 20 | 499 | CGCGACAGAATAATCTCATT | 89 | 383 |
| 297688 | 20 | 511 | AGATCCTGAACACGCGACAG | 63 | 384 |
| 297689 | 20 | 550 | CTGGCCTCTCATTGGGAAGC | 58 | 385 |
| 297690 | 20 | 590 | GATAAAATATAGTCTTTTTC | 27 | 386 |
| 297691 | 20 | 595 | TGAGGGATAAAATATAGTCT | 76 | 387 |
| 297692 | 20 | 603 | ACATTTTATGAGGGATAAAA | 70 | 388 |
| 297693 | 20 | 610 | ATTTAAAACATTTTATGAGG | 32 | 389 |
| 297701 | 21 | 1302 | TCTCCGCTGGATCCCGCCAT | 36 | 390 |
| 297702 | 21 | 1452 | ACATTCCAAATCGCTTTCAC | 21 | 391 |
| 297703 | 21 | 1795 | CTGGCTAAATCTGAAACAAC | 18 | 392 |
| 297704 | 21 | 1942 | GCATACTCACTTGGCAGAGA | 81 | 393 |
| 297705 | 21 | 2844 | TCTTTTAAGAGATATAGTGA | 58 | 394 |
| 297706 | 21 | 4327 | AAAGTAAGTTTAGAGGCATC | 55 | 395 |
| 297707 | 21 | 4347 | AAGGACAATACTTTGGAGGA | 65 | 396 |
| 297769 | 22 | 144 | AGAGCCCAACACTTAGGTCA | 55 | 397 |

TABLE 6-continued

Modulation of Gemin Gene mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 297770 | 22 | 152 | TAGATTCAAGAGCCCAACAC | 61 | 398 |
| 297771 | 22 | 269 | TCCCTGGTGACCTGGCCCCA | 80 | 399 |
| 297772 | 22 | 325 | TTAAGAAAGATCACACAGGG | 34 | 400 |
| 297773 | 22 | 349 | GGTGTGACCTGATAAGAAAC | 59 | 401 |
| 297774 | 22 | 383 | GTGCCCCATGTAGAAAGGCA | 73 | 402 |
| 297775 | 22 | 410 | AGAGGGAGCAAACTCAGGTC | 66 | 403 |
| 297776 | 22 | 416 | GGAGGAAGAGGGAGCAAACT | 39 | 404 |
| 297766 | 23 | 58 | CGGCTACTGGTGTCCCCACT | 23 | 405 |
| 297767 | 23 | 66 | GAGGTCCGCGGCTACTGGTG | 30 | 406 |
| 297768 | 23 | 77 | ATTGTCTTGGCGAGGTCCGC | 26 | 407 |
| 297785 | 24 | 56 | TGTCTTGGCTCTTTCCGTCA | 29 | 408 |
| 297708 | 25 | 81 | GCCGCCAGACCTCTTTCCGT | 19 | 409 |
| 297709 | 25 | 94 | TGTCAACAGAGAAGCCGCCA | 82 | 410 |
| 297710 | 25 | 98 | GAGTTGTCAACAGAGAAGCC | 68 | 411 |
| 297711 | 25 | 106 | AACCAGCTGAGTTGTCAACA | 77 | 412 |
| 297712 | 25 | 113 | GGTGTGGAACCAGCTGAGTT | 48 | 413 |
| 297713 | 25 | 167 | GAGAGGAGATCAGCTCAGTG | 62 | 414 |
| 297714 | 25 | 176 | GGTGCTCCAGAGAGGAGATC | 72 | 415 |
| 297715 | 25 | 204 | ATTGTCTTGGCTCCCTCCTG | 36 | 416 |
| 297716 | 25 | 213 | GGAGTTTGCATTGTCTTGGC | 68 | 417 |
| 297717 | 25 | 224 | GAATGTTCACTGGAGTTTGC | 83 | 418 |
| 297718 | 25 | 231 | GGCACGGGAATGTTCACTGG | 76 | 419 |
| 297719 | 25 | 328 | CTGGATTTCAGGAACCTCTG | 74 | 420 |
| 297720 | 25 | 339 | ATGGGACACTCCTGGATTTC | 65 | 421 |
| 297721 | 25 | 347 | CTTGAGCTATGGGACACTCC | 86 | 422 |
| 297722 | 25 | 374 | CCCGCTGCTCCTGGGATTCC | 75 | 423 |
| 297723 | 25 | 507 | AAGTTGGCCACATCCAGGTC | 82 | 424 |
| 297724 | 25 | 513 | ACGTAGAAGTTGGCCACATC | 83 | 425 |
| 297725 | 25 | 527 | TCTGCAGCTGTGACACGTAG | 89 | 426 |
| 297726 | 25 | 537 | CCTATGGGAGTCTGCAGCTG | 83 | 427 |
| 297727 | 25 | 540 | ACACCTATGGGAGTCTGCAG | 90 | 428 |
| 297728 | 25 | 544 | TTGCACACCTATGGGAGTCT | 86 | 429 |
| 297729 | 25 | 550 | CTCTGCTTGCACACCTATGG | 87 | 430 |
| 297730 | 25 | 572 | TGTCACTACATCGGAGCAGC | 0 | 431 |
| 297731 | 25 | 594 | GGCTTGAAGGTATATGAAAT | 76 | 432 |
| 297732 | 25 | 607 | ACAATATCTTTATGGCTTGA | 85 | 433 |

TABLE 6-continued

Modulation of Gemin Gene mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 297733 | 25 | 680 | GCCCAGAGTTCCTGGCTCGG | 70 | 434 |
| 297734 | 25 | 701 | GGGAGCTCATAACTCCATGG | 72 | 435 |
| 297735 | 25 | 725 | TTAAAGCTTGGCTCAAAATT | 51 | 436 |
| 297736 | 25 | 741 | AGGAGTCCAGACTTGCTTAA | 74 | 437 |
| 297737 | 25 | 751 | AGGAGGTCTCAGGAGTCCAG | 84 | 438 |
| 297738 | 25 | 792 | CTTAGAATTCCTAGAGTTGC | 78 | 439 |
| 297739 | 25 | 808 | TTCCTTCCAATGGGATCTTA | 84 | 440 |
| 297740 | 25 | 822 | TGTGAGGTAGAGCATTCCTT | 93 | 441 |
| 297741 | 25 | 831 | TCAGAGTTCTGTGAGGTAGA | 86 | 442 |
| 297742 | 25 | 858 | GGCAGCAGGCCCATATTTCT | 76 | 443 |
| 297743 | 25 | 885 | ACCTCGATGCCCCGGTCTTC | 76 | 444 |
| 297744 | 25 | 907 | AGGTTGTATCCTTTATCACC | 83 | 445 |
| 297745 | 25 | 941 | ACTTTGCAGCCTCTTTAATA | 37 | 446 |
| 297746 | 25 | 1020 | AAACAGGAGTCGAATTTTCC | 30 | 447 |
| 297747 | 25 | 1059 | AAGATGACTCCATCCCCGTC | 28 | 448 |
| 297748 | 25 | 1070 | ACCAGCCCCTAAAGATGACT | 38 | 449 |
| 297749 | 25 | 1083 | GGATAACCACCCTACCAGCC | 61 | 450 |
| 297750 | 25 | 1114 | ACTTGGCCCAGCTCCACTGG | 50 | 451 |
| 297751 | 25 | 1161 | GACTTGCGGCCGTGCAGCCC | 66 | 452 |
| 297752 | 25 | 1171 | CTTTCCAGGAGACTTGCGGC | 43 | 453 |
| 297753 | 25 | 1188 | ATGCCGGTCACTCCAGCCTT | 44 | 454 |
| 297754 | 25 | 1303 | TCCACAGCAACCACAGGTGG | 19 | 455 |
| 297755 | 25 | 1331 | GGGACAGCGAATCTGCTGTC | 20 | 456 |
| 297756 | 25 | 1405 | CACCCTGATCGCGAATCCTC | 56 | 457 |
| 297757 | 25 | 1414 | GTGAAGTTGCACCCTGATCG | 59 | 458 |
| 297758 | 25 | 1442 | TGCAAGGCTGGAGAGAAGAG | 48 | 459 |
| 297759 | 25 | 1477 | AGGCTTAGTGAAGCGCGTGA | 40 | 460 |
| 297760 | 25 | 1504 | ATGCGCTGGAAGGTTACTAG | 38 | 461 |
| 297761 | 25 | 1515 | CTTTTTAAACAATGCGCTGG | 54 | 462 |
| 297762 | 25 | 1524 | AACTGCTTTCTTTTTAAACA | 14 | 463 |
| 297763 | 25 | 1574 | GAAGGCTTCGCTTACATCCT | 37 | 464 |
| 297764 | 25 | 1592 | ACACACCTTTACTTAATGGA | 0 | 465 |
| 297765 | 25 | 1601 | CGAAACGACACACACCTTTA | 10 | 466 |
| 297777 | 26 | 1542 | TTGTACTCACCGAGGTCCGC | 51 | 467 |
| 297778 | 26 | 1640 | GCGGTCCTACCTCTTTCCGT | 51 | 468 |
| 297779 | 26 | 1647 | TGCAGGCGCGGTCCTACCTC | 68 | 469 |

TABLE 6-continued

Modulation of Gemin Gene mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 297780 | 26 | 2169 | GCCGCCAGACCTAATTAATT | 54 | 470 |
| 297781 | 26 | 4301 | AGACACTAGGAACGCAATGA | 80 | 471 |
| 297782 | 26 | 8747 | ATGCTATGATGTTGAATGTG | 63 | 472 |

TABLE 6-continued

Modulation of Gemin Gene mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 297783 | 26 | 8992 | CTATGCTGTTATCAGGATTC | 78 | 473 |
| 297784 | 26 | 12369 | ATTGTCTTGGCTGTTGAGTG | 61 | 474 |

What is claimed is:

1. A method of modulating expression of a Gemin gene in a cell comprising contacting the cell with an oligomeric compound of from 13 to 30 nucleobases in length and having a nucleobase sequence comprising at least 8 contiguous nucleobases complementary to an equal length portion of nucleobases 1110 to 1183 of SEQ ID NO. 7, and wherein said nucleobase sequence is at least 90% complementary to SEQ ID NO:7 as measured over the entirety of the oligomeric compound, and thereby modulating expression of the Gemin gene.

2. The method of claim 1, wherein said oligomeric compound is 20 nucleobases in length.

3. The method of claim 1, wherein said oligomeric compound is chimeric.

4. The method of claim 1, wherein said oligomeric compound comprises at least one modified internucleoside linkage.

5. The method of claim 4, wherein the modified internucleoside linkage comprises a phosphorothioate internucleoside linkage.

6. The method of claim 1, wherein said oligomeric compound comprises at least one modified sugar moiety.

7. The method of claim 6, wherein said modified sugar moiety comprises a 2'-O-methoxyethyl sugar moiety.

8. The method of claim 1, wherein said oligomeric compound comprises at least one modified nucleobase.

9. The method of claim 8, wherein said modified nucleobase comprises a 5-methylcytosine.

10. The method of claim 1, wherein said oligomeric compound is an antisense, chimeric oligonucleotide 20 nucleobases in length and comprises at least one phosphorothioate internucleoside linkage and at least one 2'-O-methoxyethyl sugar moiety and at least one 5-methylcytosine.

11. The method of claim 1, wherein the expression of the Gemin gene is reduced by at least 50%.

12. The method of claim 1, wherein the cell is in an animal.

13. The method of claim 12, wherein the animal is a human.

14. The method of claim 1, wherein said nucleobase sequence is at least 95% complementary to SEQ ID NO:7 as measured over the entirety of the oligomeric compound.

15. The method of claim 1, wherein said nucleobase sequence is 100% complementary to SEQ ID NO:7 as measured over the entirety of the oligomeric compound.

16. The method of claim 10, wherein said nucleobase sequence is 100% complementary to SEQ ID NO:7 as measured over the entirety of the oligomeric compound.

* * * * *

SEQUENCE LISTING

```
<160> NUMBER OF SEQ ID NOS: 475

<210> SEQ ID NO 1
<211> LENGTH: 815
<212> TYPE: DNA
<213> ORGANISM: Homo sapiens

<400> SEQUENCE: 1

atgcgccgag cggaactggc tggtttgaaa accatggcgt gggtaccagc ggagtccgca     60

gtggaagagt tgatgcctcg gctattgccg gtagagcctt gcgacttgac ggaaggtttc    120

gatccctcgg tacccccgag gacgcctcag gaatacctga ggcgggtcca gatcgaagca    180

gctcaatgtc cagatgttgt ggtagctcaa attgacccaa agaagttgaa aaggaagcaa    240

agtgtgaata tttctctttc aggatgccaa cccgcccctg aaggttattc cccaacactt    300

caatggcaac agcaacaagt ggcacagttt tcaactgttc gacagaatgt gaacaaacat    360

agaagtcact ggaaatcaca acagttggat agtaatgtga caatgccaaa atctgaagat    420

gaagaaggct ggaagaaatt ttgtctgggt gaaaagttat gtgctgacgg ggctgttgga    480

ccagccacaa atgaaagtcc tggaatagat tatgtacaag caacagtaac tagtgtcttg    540

gaatatctga gtaattggtt tggagaaaga gactttactc cagaattggg aagatggctt    600

tatgctttat tggcttgtct tgaaaagcct ttgttacctg aggctcattc actgattcgg    660

cagcttgcaa gaaggtgctc tgaagtgagg ctcttagtgg atagcaaaga tgatgagagg    720

gttcctgctt tgaatttatt aatctgcttg gttagcaggt attttgacca acgtgattta    780

gctgatgagc catcttgatg tagctgatct ctcag                               815


<210> SEQ ID NO 2
<211> LENGTH: 801
<212> TYPE: DNA
<213> ORGANISM: Homo sapiens

<400> SEQUENCE: 2

atgcgccgag cggaactggc tggtttgaaa accatggcgt gggtaccagc ggagtccgca     60

gtggaagagt tgatgcctcg gctattgccg gtagagcctt gcgacttgac ggaaggtttc    120

gatccctcgg tacccccgag gacgcctcag gaatacctga ggcgggtcca gatcgaagca    180

gctcaatgtc cagatgttgt ggtagctcaa attgacccaa agaagttgaa aaggaagcaa    240

agtgtgaata tttctctttc aggatgccaa cccgcccctg aaggttattc cccaacactt    300

caatggcaac agcaacaagt ggcacagttt tcaactgttc gacagaatgt gaacaaacat    360

agaagtcact ggaaatcaca acagttggat agtaatgtga caatgccaaa atctgaagat    420
```

```
gaagaaggct ggaagaaatt ttgtctgggt gaaaagttat gtgctgacgg ggctgttgga    480

ccagccacaa atgaaagtcc tggaatagat tatgtacaaa ttggttttcc tcccttgctt    540

agtattgtta gcagaatgaa tcaggcaaca gtaactagtg tcttggaata tctgagtaat    600

tggtttggag aaagagactt tactccagaa ttgggaagat ggctttatgc tttattggct    660

tgtcttgaaa agcctttgtt acctgaggct cattcactga ttcggcagct tgcaagaagg    720

tgctctgaag tgaggctctt agtggtattt tgaccaacgt gatttagctg atgagccatc    780

ttgatgtagc tgatctctca g                                              801
```

<210> SEQ ID NO 3
<211> LENGTH: 825
<212> TYPE: DNA
<213> ORGANISM: Homo sapiens

<400> SEQUENCE: 3

```
atgcgccgag cggaactggc tggtttgaaa accatggcgt gggtaccagc ggagtccgca     60

gtggaagagt tgatgcctcg gctattgccg gatcgaagca gctcaatgtc cagatgttgt    120

ggtagctcaa attgacccaa agaagttgaa aaggaagcaa agtgtgaata tttctctttc    180

aggatgccaa cccgcccctg aaggttattc cccaacactt caatggcaac agcaacaagt    240

ggcacagttt tcaactgttc gacagaatgt gaacaaacat agaagtcact ggaaatcaca    300

acagttggat agtaatgtga caatgccaaa atctgaagat gaagaaggct ggaagaaatt    360

ttgtctgggt gaaaagttat gtgctgacgg ggctgttgga ccagccacaa atgaaagtcc    420

tggaatagat tatgtacaaa ttggttttcc tcccttgctt agtattgtta gcagaatgaa    480

tcaggcaaca gtaactagtg tcttggaata tctgagtaat tggtttggag aaagagactt    540

tactccagaa ttgggaagat ggctttatgc tttattggct tgtcttgaaa agcctttgtt    600

acctgaggct cattcactga ttcggcagct tgcaagaagg tgctctgaag tgaggctctt    660

agtggatagc aaagatgatg agagggttcc tgctttgaat ttattaatct gcttggttag    720

caggtatttt gaccaacgtg atttagctga tgagccatct tgatgtagct gatctctcag    780

ggatagaaga tatttctcat gaaggcagcc taactctgag gaaaa                    825
```

<210> SEQ ID NO 4
<211> LENGTH: 1553
<212> TYPE: DNA
<213> ORGANISM: Homo sapiens

<400> SEQUENCE: 4

```
gctgtgacct agaatgggcg catgcgccga gcggaactgg ctggtttgaa aaccatggcg     60

tgggtaccag cggagtccgc agtggaagag ttgatgcctc ggctattgcc ggtagagcct    120

tgcgacttga cggaaggttt cgatccctcg gtacccccga ggacgcctca ggaatacctg    180

aggcgggtcc agatcgaagc agctcaatgt ccagatgttg tggtagctca aattgaccca    240

aagaagttga aaaggaagca aagtgtgaat atttctcttt caggatgcca acccgcccct    300

gaaggttatt ccccaacact tcaatggcaa cagcaacaag tggcacagtt ttcaactgtt    360

cgacagaatg tgaacaaaca tagaagtcac tggaaatcac aacagttgga tagtaatgtg    420

acaatgaggt ggggttttgc catgttggcc aggctggtct tgaactcctg acttcatgtg    480

atcgcctgcc tcggcctccc aaagtgctgg gattacaggc gtgaaccacc gcacccggcc    540

taagccaaaa tctgaagatg aagaaggctg gaagaaattt tgtctgggtg aaaagttatg    600

tgctgacggg gctgttggac cagccacaaa tgaaagtcct ggaatagatt atgtacaaat    660
```

tggttttcct cccttgctta gtattgttag cagaatgaat caggcaacag taactagtgt 720
cttggaatat ctgagtaatt ggtttggaga aagagacttt actccagaat tgggaagatg 780
gctttatgct ttattggctt gtcttgaaaa gcctttgtta cctgaggctc attcactgat 840
tcggcagctt gcaagaaggt gctctgaagt gaggctctta gtggatagca aagatgatga 900
gagggttcct gctttgaatt tattaatctg cttggttagc aggtattttg accaacgtga 960
tttagctgat gagccatctt gatgtagctg atctctcagg gatagaagat atttctcatg 1020
aaggcagcct aactctgagg aaaacaatgc caattcaagt acagatttca acacatcttc 1080
aacactatgt gaagggttca catcttaacc tgtgcaattc agattgatac tcagaatatg 1140
ggttgatttg aatatctgaa atatcaatgg aaaatcccac tcagtttttg atgaacagtt 1200
tgaacagttt tctgtaatca agcagcttgc atagaaattg tatgatgaaa ttttacatag 1260
gttcttggtg ctgttttgtt ctttttttgt tttttgttgt tttgttattt acttatatac 1320
atataaaatt ttattgaaaa tatgttttgg ttactaaaat tttgtttgac tcctaacaaa 1380
agacaatgga tggccttagc atcagaatta aaataatctg gattaaatgg caatgtgttc 1440
atagtcagca ataaaattaa acatttttcc ctttaaaaaa aaaaaaaaaa aaaaaaaaaa 1500
aaaaaaaaaa aaaaaaaaaa aaaaaaaaaa aaaaaaaaaa aaaaaaaaaa aaa 1553

<210> SEQ ID NO 5
<211> LENGTH: 681
<212> TYPE: DNA
<213> ORGANISM: Homo sapiens
<220> FEATURE:
<221> NAME/KEY: misc_feature
<222> LOCATION: 681
<223> OTHER INFORMATION: n is a, c, g, or t

<400> SEQUENCE: 5
gggctggttt gaaaaccatg gcgtgggtac cagcggagtc cgcagtggaa gagttgatgc 60
ctcggctatt gccggtagag ccttgcgact tgacggaagg tttcgatccc tcggtacccc 120
cgaggacgcc tcaggaatac ctgaggcggg tccagatcga agcagctcaa tgtccagatg 180
ttgtggtagc tcaaattgac ccaaagaagt tgaaaaggaa gcaaagtgtg aatatttctc 240
tttcaggatg ccaacccgcc cctgaaggtt attccccaac acttcaatgg caacagcaac 300
aagtggcaca gttttcaact gttcgacaga atgtgaacaa acatagaagt cactggaaat 360
cacaacagtt ggatagtaat gtgacaatgc caaaatctga agatgaagaa ggctggaaga 420
aattttgtct gggtgaaaag ttatgtgctg acggggctgt tggaccagcc acaaatgaaa 480
gtcctggaat agattatgta caaattggtt ttcctccctt gcttagtatt gttagcagaa 540
tgaatcaggg aagatggctt tatgctttat tggcttgtct tgaaaagcct ttgttacctg 600
aggctcattc actgattcgg cagcttgcaa gaaggtgctc tgaagtgagg ctcttagtgg 660
atagcaaaga tgatgagagg n 681

<210> SEQ ID NO 6
<211> LENGTH: 822
<212> TYPE: DNA
<213> ORGANISM: Homo sapiens

<400> SEQUENCE: 6
agcgggcgcc gagcggaact ggctggtttg aaaaccatgg cgtgggtacc agcggagtca 60
gcagtggaag agttgatgcc tcggctattg ccggtagagc cttgcgactt gacggaaggt 120
ttcgatccct cggtaccccc gaggacgcct caggaatacc tgaggcgggt ccagatcgaa 180
gcagctcaat gtccagatgt tgtggtagct caaattgacc caaagaagtt gaaaaggaag 240
caaagtgtga atatttctct ttcaggatgc caacccgccc ctgaaggtta ttccccaaca 300
cttcaatggc aacagcaaca attggcacag ttttcaactg ttcgacagaa tgtgaacaaa 360
catagaagtc actggaaatc acaacagttg gatagtaatg tgacaatgat tggttttcct 420
cccttgctta gtattgttag cagaatgaat cagggaagat ggctttatgc tttattggct 480
tgtcttgaaa agcctttgtt acctgaggct cattcactga ttcggcagct tgcaagaagg 540
tgctctgaag tgaggctctt agtggatagc aaagatgatg agagggttcc tgctttgaat 600
ttattaatct gcttggttag caggtatttt gaccaacgtg atttagctga tgagccatct 660
tgatgtagct gatctctcag ggatagaaag atatttctca tgaagggcag cctaactctg 720
aggaaaacaa tgccaattca agtacagatt tcaacacatc ttcaacacta tgtgaacggt 780
tcacatcttt acctgtgcaa tcagattgat actcagaata tg 822

<210> SEQ ID NO 7
<211> LENGTH: 1285
<212> TYPE: DNA
<213> ORGANISM: Homo sapiens
<220> FEATURE:
<221> NAME/KEY: misc_feature
<222> LOCATION: 25
<223> OTHER INFORMATION: n is a, c, g, or t

<400> SEQUENCE: 7
taacgctccc taaactgcca cttgntcagc tccgcgccta aggtgtctat tagtgcgcct 60
gcgctgtgac ctagaatggg cgcatgcgcc gagcggaact ggctggtttg aaaaccatgg 120
cgtgggtacc agcggagtcc gcagtggaag agttgatgcc tcggctattg ccggtagagc 180
cttgcgactt gacggaaggt ttcgatccct cggtaccccc gaggacgcct caggaatacc 240
tgaggcgggt ccagatcgaa gcagctcaat gtccagatgt tgtggtagct caaattgacc 300
caaagaagtt gaaaaggaag caaagtgtga atatttctct ttcaggatgc caacccgccc 360
ctgaaggtta ttccccaaca cttcaatggc aacagcaaca agtggcacag ttttcaactg 420
ttcgacagaa tgtgaacaaa catagaagtc actggaaatc acaacagttg gatagtaatg 480
tgacaatgcc aaaatctgaa gatgaagaag gctggaagaa attttgtctg ggtgaaaagt 540
tatgtgctga cggggctgtt ggaccagcca caaatgaaag tcctggaata gattatgtac 600
aaattggttt tcctcccttg cttagtattg ttagcagaat gaatcaggca acagtaacta 660
gtgtcttgga atatctgagt aattggtttg gagaaagaga ctttactcca gaattgggaa 720
gatggcttta tgctttattg gcttgtcttg aaaagccttt gttacctgag gctcattcac 780
tgattcggca gcttgcaaga aggtgctctg aagtgaggct cttagtggat agcaaagatg 840
atgagagggt tcctgctttg aatttattaa tctgcttggt tagcaggtat tttgaccaac 900
gtgatttagc tgatgagcca tcttgatgta gctgatctct cagggataga agatatttct 960
catgaaggca gcctaactct gaggaaaaca atgccaattc aagtacagat ttcaacacat 1020
cttcaacact atgtgaaggg ttcacatctt aacctgtgca attcagattg atactcagaa 1080
tatgggttga tttgaatatc tgaaatatca atggaaaatc ccactcagtt tttgatgaac 1140
agtttgaaca gttttctgta atcaagcagc ttgcatagaa attgtatgat gaaattttac 1200
ataggttctt ggtgctgttt tgttcttttt ttgttttttg ttgttttgtt atttacttat 1260
atacatataa aattttattg aaaat 1285

<210> SEQ ID NO 8

<211> LENGTH: 25001
<212> TYPE: DNA
<213> ORGANISM: Homo sapiens

<400> SEQUENCE: 8

```
ttatcaccaa aatgttggac gacaggagta tttctcccta ttctaagtct gtttttccca     60
aaaccagtga aaatttgtta accaaataac tgtagtttgc agccaggtga tatctttcca    120
agtgtcccaa ttgtttagtt acagttccta agcattaagt acttaaataa gctaaggact    180
atcctcactt tatcttcaat ttagacttac atcctggttt gaaatcaatt ccttgcaaac    240
taaaggcagt gccataaata aaaattttta accttctaaa ataaacatca gtgttagaaa    300
ataagtcaat tgtattcact caattgtatt tgtttagaaa taatcagata ttatacttgt    360
ttcttgcaca ttcttgcctt gtttcctcac ctatgaaatg gagataataa tactatctac    420
ctaacaagat tgacctaaca tttttgttaa tttctgggtg ttagcattag tttcattttt    480
ttcactattt gtatttaaac gaagagattt ttctttaaaa caaaaattaa aaagtgctgg    540
ctattctagg agtaatattc attccaaata aacatacagt gatctttgaa gtggtcaagc    600
actagaaatt tctgtagaaa attaattttt cattcatttg gcatcgcata aatctaggtt    660
ggaattggtt cttcctcttt ggaaggtcag tccctgccct aagagagcgg tatattacca    720
cccacttcac aagactgttc taagaatcaa atgagaaaat gtgtttatga agagtttaag    780
aatttagagc tccatgaatg ataattacag taatattgtt cattaattca aaaaacattt    840
ttaaggatcc ctcactacta gggatgcata aaagttgcta accctcggcc tttacccagc    900
gttagaagac aaaacagagg gtaaaagtcc cagaaacgcg ttcgaaccaa ttcagctagg    960
aattaaattc tcagatcctt tattacacca ccggagcctt aaccttgagg caagcagcaa   1020
tttgttcatg cgcagttaac gctccctaaa ctgccacttg ctcagctccg cgcctaaggt   1080
gtctattagt acgcctgcgc tgtgacctag aatgggcgca tgcgccgagc ggaactggct   1140
ggtttgaaaa ccatggcgtg ggtaccagcg gagtccgcag tggaagagtt gatgcctcgg   1200
ctattgccgg tagagccttg cgacttgacg gaaggtttcg atccctcggt acccccgagg   1260
acgcctcagg aatacctgag gcgggtccag tgagtgattc ggccctgggc gggtgggctg   1320
gtcttctgcc ctgcccctgg gtacagccct cggtgctcta ttcccgttcc agtctgttgc   1380
gagttcaggt ctattcagga ttctggatta catcctaacg tgggcgagtt tctgttgaac   1440
gtgattgcac gtatcaagat gtgtgctctt agatttgttt tcaatccaga taatttcaga   1500
aatacattgt ttagtacctc aattggaagt ctgaattttt ttctgatttc acaatgaact   1560
gtggaagtgg atcgcttgtt ttactacacc tgagcaaagc acaacagaaa tttaatttat   1620
cgcgtttatt acttatttgt aggatcgaag cagctcaatg tccagatgtt gtggtagctc   1680
aaattgaccc aaagaagttg aaaaggaagc aaagtgtgaa tatttctgtg agttttatta   1740
accgtctgga gattaccccc aaccccccaa ttaaaagact aacgctcttc ctatagtatc   1800
tgacagcatc aattatgacg taagatttga ctactccgtg caaagttaga cattcgcttg   1860
tactttttcc ttcagaaaga caattggcat ttactgcctc taaagaggct ttctgtaact   1920
ctagcctttg tggagtgttg cccatcttac ttcaggacat tatccagtcc tttcaaagga   1980
gtctttaaat gggttactta tgttatcttt tattttttgc ttgtttgttt gtttatagag   2040
agggagtctc tgttgccagc tggtctggaa ctcctggcct caagtgatcc tccctcctct   2100
gccacccaaa gcgttgggat cacaggcgtg agccacctca cctggcccct ttattttttta   2160
aggaactttt tccagttatt ggattggtgt ttaatcttag tgtgctttgc atgttctgaa   2220
```

-continued

```
tttgaccaag tttcactttt tttaagaata gaaacccaga tgtcttacac tttttttttt   2280

tttttttttg agacagtttc actcttgttg cccaggctgc agtgcagtgg tgcgatctca   2340

gctcactgca acctctgcct tccggtttca agcgattacc gtgcctcagc ctcccgagta   2400

gctgggatta caggcgccca ccaccacacc cggctaattt ttgtattttt agtagagacg   2460

gggtttcacc atgttgtcca gtctggtctt gaactcctga cctcgtgatg cgcccacctc   2520

tgcctcccaa actgctggga ttacaggtgt gagccaccat acccggcctt acacttttat   2580

agctacttgc acactctgga cattttcatt tatttattta tccagcacat ctttaattaa   2640

gcaactaggt tgtgccgggc attgggaatt caacagaggg taagacaaaa aaggttccta   2700

cccttgtaga gtttacatac cctcctgagg aagacagaga gtaaacaagc aaacaaataa   2760

ttacatattg tgattattgc tatgaagaaa ataagcatgt ataataatca ataaatgaca   2820

gaactactgt agaggaatca tagaagggct ctctttttcc ccttttttt tttgcgtctc   2880

aatttttcgc ccaggctgga gtgcagtggc acaatctcag ctcatcacaa cctctgcctc   2940

tcaggttcaa gagcttctct tgcctcagcc ccctgagtag ctaggattac aggcgtgtgc   3000

caccacacct gactaatttt tgtattttta gtagagacgt ggttttacca tgttggccag   3060

gctggtctca aactcctgac ctgaagtgat ctgcctgcct ctgcctccta aagtgctggg   3120

attacagatg tgagccacca cgcctggcca gcaaaggtct ctctaaggag gtgctattta   3180

acctaagctc aaaggagggt ggcattttat tttatttctt tttctttttt tttttttttt   3240

gagatggagt ctcagagtct cgctctgtcg cccaggctgg agtgcagtgg cgcgatctcg   3300

gctcactgca acctctgcct cccgggttca caccattctc ctgcctcagc ctcccgagta   3360

gctgggacta caggcgcctg ggagagtggc attttaaata gttgatagta atttcctttt   3420

catgctcaaa gtagtttctc tgatacttgt aatcaggaaa ttttaattca gacactgtaa   3480

tttttcctat aattcctctt cagggttttt tagttgatgg acatttaatg gaacagaatg   3540

tcttaatata cctaatttga tggattgatt gattgattga ttgagacagg gtctcgcttt   3600

gttgcacagg ccagagtaca gtgccacgat catagctcac tgcagcctcg agttcttggg   3660

ctcaagccat cctcccacct cagtctcccc agtagctgag atgacaagca tgtgccaccg   3720

tgcccagcta attgtatttt ttgtagcgac ggggtcttga tatgttgctc aggctgtatg   3780

tgctctttta gaaaacagaa gtatggctgg gcttagtggc tcacacctgt aatcccagca   3840

ctttgggagg ccaagtcagg cggatcacct gaggtgggga gttcaagacc agcccgacca   3900

acatggagaa accccatctc tactaaaaat acaaaattag ccgggtgtgg tggcacatgc   3960

ctgtaatccc agctactcgg gaggctgagg caggagaatt gcttgaaccc gggagacgga   4020

gattgcagtg agctgagatg gccattgcac tccagcctga gcaacaggag cgaaactccg   4080

tctcaaaaaa aaaaaaaaag aaaacagaag tagacaattt aaagttaagc gtctttaagt   4140

acattttgcc cataccaaag ttcttatttt taattttatt gatacataat aatcataatt   4200

tcatgcttta tcacgcaggc acaataataa ttgtacatat ttatggagta tatgtgatat   4260

tttgatacat gcatacaatg tataataatc agtaattagg atagccatca cctcatttat   4320

catttctttc ttttgggaac attcaaatct tctagctgtt ttgaaatata caataaatta   4380

ttgttaactg tagtcactct actgtgctat tgaatgctag aactcattcc ttctaactgt   4440

atttcatacc agaattcttt atttgtggta tatctctctt tttgtttctg ttttgctatt   4500

ctagaaaggc aggtagggct agatcatatt ctccaggctc atgtcattta gatttcatag   4560

aaactccaac tataaacctt tccagatttc tctgattaag gtgactaagg ctctttccct   4620
```

```
aatattttta actgagatat aaataataaa gtgaaatgcc tactttttta catctgcaaa   4680
aatattttat tttcttgtat aatctttatt ttattataca ctttatcttg gttttacttt   4740
tgctttgcag aggcatgaga ttctagtttt gacactaatg ttgatcctaa tatttgtgaa   4800
cttgatctct agctttcagg atgccaaccc gcccctgaag gttattcccc aacacttcaa   4860
tggcaacagc aacaagtggc acagttttca actgttcgac aggtaagtgt catatttaat   4920
ctaattaagc ccctgttgga tttatttctg ttcttagact gtagctggaa aaataaaatt   4980
tatgatccta aagtatacag aatattcatg aattaattac caaattattt ttataatcat   5040
tagacatgat acagtttgaa atattttcta agttttgttt atttttattt gtttgtttat   5100
ttatttcaat agttttgggg aacaggtggt ttttggttac atggataagt tctttagtgg   5160
tgatttctga gattttggtg cacttgtcac ccaagtagtg tactctgtac ccaatacatg   5220
gtcttttaca tctcaccccc tcccaccttt cccatttttc aagttttaga tggttacaat   5280
tttgtgcaga aactgatttc agttatccat tttttgaaga gtaccatcta atgtctaagt   5340
tttcttcctt tagaatgtga acaaacatag aagtcactgg aaatcacaac agttggatag   5400
taatgtgaca atggtatgta agtttctcag ttttaagatg tacaatgtat acctgattga   5460
aagagtctat atttacttcc agtcgttaaa gattcacttg cctagtcagt gttactttca   5520
ttctcttcaa tataccatta atagtaacaa ttcattacat tagtagcctg gaaagtatag   5580
attttcatga caaatttttt tttttttttt ttttgagaca gggtcttgct ctgtctccca   5640
ggctagagtg cagtcatggc tcactgcagc cttgacctcc tgggctcaag tgatcctccc   5700
accaccgcct tccaagtagc tcgaacttaa ggcatatacc accatgccca gctaattgtt   5760
aaaatttttt gtagagacaa ggtctccctg tgttacccag gctggtctct tactcctggg   5820
ctcaagtgat cctcctgccc tagcctcccc gagtgctgga ttacaggcat gagctactgt   5880
acccagcctt tcatgtcaat tttaattcac aatatcttgg gggactttgg ataggtgact   5940
gtgaaacttc cacaagtttt taaggattct tctagacatt tactttctag gaaataaata   6000
cattttcaat atttacaaaa aaaattgaat aaagccttaa tggattttcc tgatgaggtg   6060
atggtgccat gcagtaaact cacatgttta cagaacttgt gaatggattc tgcttctgct   6120
taatgtgatg agtctgtgtc acaattccag tgacatataa gtgaaacctg tcatgtatat   6180
tgtcatgcat atgtcctata ttttatcagt ttagatataa ctttaagccc tttagtagat   6240
atatcaggac taccaaatga aaaaaggagt tggaaagatg atacattgtc tcaggacagt   6300
agtttttaac cttttagggg acttcatatt ctttcgtaga atctaatgaa agctatttat   6360
cttcagaggg aaaaaaaatg cacctatgca caacatttta gtttcaggta gttcatagat   6420
tttagatttt agaagcttcc tttaggcagt gcttcctgat atcttttaca tggtgacaca   6480
ttagaataaa tgactgcttg catattcttc ctgaaaccag ccgaaagctg agagattcag   6540
tatatggcat ctctgtatgc ttctgcatac catttggaag ctctgctcca ggaaaagcgt   6600
gaagggaagt aacttatcac ttgccaatgg tcatttaact tgtaaaaggt atagctagtc   6660
cttctatcaa agaagcatgc gcacataaac acacaaaagg tatgcttaag gttcaaaccc   6720
aagttggtct gtctctaaag cctgtgtgcc tttgactatg caatggtgcc ttcctagtac   6780
caaggatgta tgtatgtagt agggacaggg ctaggtaggt aaatatattt tttttcttac   6840
ttagcggaag gccttttggg tgcatgccca ctaactaaaa aagaagccac atcagtaaca   6900
ttatgacttg ataaaatttt gtcaaaaatg gaaatgacct aacataattg attcaataaa   6960
ctatggtcca tcagaacagt ggaatattat gtagcaattt taagtgtttg tcatggcaaa   7020
```

-continued

```
tgcaaacatc atataagtaa taaaatgaaa atgttttaaa gtacactctg agccaggcac   7080

agtggctcat gcctataatc ccagcacttt gggaggctga ggtgggcaga tcacctgagc   7140

tcaggagttc gagaccagcc tgggcaacat ggcaaaaccc tgtctctatt taaattattt   7200

aaaaaataaa gtacactgtg atggcaactg tgtgaaaaca taaacatttg tttattaatt   7260

gatccaataa tttaagcatg tgctatattt aataatcagg atattcagta ctaactgaaa   7320

cagaaacagc ttctgaccta atagagtgtt aggaaaaggt agataacctt attccaagac   7380

aatagggttt aactttgtag tggtctcatg ttcatcgtga ggttttattt tattttattt   7440

tattttattt attttttga gatggagttt tgctcttgtt gcccagtctg gagtgcagtg   7500

gcacaatctt ggctcactgc aacctctgtc tcttggattc aagcaattct cctgcctcag   7560

cctcccaagt agctgggatt acaggtgcct gccaccacac ccagctaatt tttgtatttt   7620

tagtagagac ggggtttcac catatttcca ggctagtctc gaactcctga cctcaggtga   7680

ttcatcctaa ggatttaatg aaagctactt atccctaggg ggaaaatgca cctatgcaaa   7740

gtaatataca aggtgatatg tacaaacaaa ggttattttg ttaaggaggt tatattgagc   7800

tgaatgcttc tcccaaatag tcctgcgtcc tgctttttct gtctggcagc atgagtagat   7860

ctgtttcttc tttgactgga caacccttca aatatgtgaa atatgtaatc atgtctcttt   7920

acatgggata aatatccttc attctattaa gtgttcttgg tgcatttttt cccccatact   7980

tatttctgtc tttatcatcc tcttttggac acaccattgt ctgtcagtgt ccactaaagt   8040

cttgtccaaa ctaaacacat cttggctggg cacagtggct cacacttgta atcccagcac   8100

tttgggaagc caaagcagaa gaattgcttg aggccaggag tttgagacca gcctgggcaa   8160

catagtgaga caactatctc tacaaaaaaa atttaaaaat tatcaggcat ggtggcacat   8220

gcctgtagtc ccagctactc aagaggctga ggtggcagaa ttatttgagc ccgagattca   8280

ggctgcaatg aactgtaatc acacctctgc actccaactt gggcgacaga gcaagaccct   8340

gtctcaaaaa atgtaataat aaggaaaaac aacatgtccc acatattgtg tagccactta   8400

ggcactatgt ttgtcagggc tgccataaca gactaggtgg attaaacaac agaaatgtat   8460

ttattttctc agtcttgaag gctgaaagtc aaagaacaag gtggcagcaa ggttggtctc   8520

tttttgtttg tttgtttgtt ttttgaggca gagtttcgct cttgttgccc aggctagagt   8580

gcaatgacgc aatctctgct cactgcagcc tccgcctccc aggctcgagt gattctcctg   8640

cctcagcctc tgggtagctg ggattacagg tgtgcaccac cacatccggc taattttttt   8700

ttttttgta tttttagtag aggtggggtt ttgccatgtt ggccaggctg gtcttgaact   8760

cctgacttca tgtgatcgcc tgcctcggcc tcccaaagtg ctgggattac aggcgtgaac   8820

caccgcaccc ggcctaaggt tggtctcttc tgaggctttt ctccttggct tgcatagggc   8880

caccttctcc ctgttttctc acgtggtctt tcctctgtgt gtgggagtcc ctggtgtctc   8940

tttgtgaatc caaatttcct cttataagga cactagtaag attggattac ggctcaccct   9000

aatggcctca atttaaatta atcacttctt taaaggccct gtctccaaat acagtcacat   9060

tctgaggtac tggagtttaa ggttttaaca tacaaatttg gggcagagaa ttctccccat   9120

aactggctcc gtatctttgg gttgcggtaa tgggaatatg gaaggactta acttcttttt   9180

ttttactgtt cagtgtaaaa attaatacac aggaataaat cagttttttt ttttttcttt   9240

tagccaaaat ctgaagatga agaaggctgg aagaaatttt gtctgggtga aaagttatgt   9300

gctgacgggg ctgttggacc agccacaaat gaaagtcctg gaatagatta tgtacaagta   9360

agggctgtgt ggataaacag aacaaaaagc attttaattt tggtgcacca cttaatataa   9420
```

-continued

```
ggggtcagca aactctaccc tgggccaagt ccagttcatg gccttttttta tatccatgag   9480
ctaaggattg tttttaggtt ttgaaagagt aaaaaagaaa caaataatat gtggctgaga   9540
ctttatgtgg cctgcaaagc ctaaaatatt tgctgtctga ctcttgatag aaaatgtttg   9600
ccaacccaga cttagtttat tagctcttca acctaacaaa acagcttagt ttctgaaaca   9660
atttactgtg acttttttta gtttggcttc atatccctta tgtttggctt ggtaatcatt   9720
ttatgagttg gataagattc atagtttttt taaatgatga ggcatcaggc aaacagtgtt   9780
atgagtagcc agggaaaaaa tggaaatcga cacaattaga tgctttaaaa tgcataatca   9840
catctatcac ttcatgggcc tgtaaaaaat aaatcacata ttctaaagat gaaatgttga   9900
ggatatcttt aaaattcatg tggctgtaat cataagttat gtagacaact ccttgtcctt   9960
caggatttac ctgcccccaa gtttgcaggt gttccttgag aatccagtgc atgcctctgc  10020
attagcgctt actccctata gcatgtagtt cttttcagtt caacaggtat ttattatttg  10080
ctatatggtg ccacattgtg tttttcacat ttaaaactaa tttttcctaa aaatgtaaaa  10140
agccccaaga atcaataaaa agaccaagaa tcacccctcc cctgcccaag aaaaaatagc  10200
caaaggatat agatacctca cagaaaggaa ataaaattat tcttatatga caagatgcca  10260
aaaatcactt gtaatagaag tataacataa ctatgccaag gtgctatttt tcaggtaaca  10320
tattggccaa gaaagtttga tacaccatat tgacaagagc tggggaaaca agcactctta  10380
gacgtggtac aggagtataa atagactcaa atcttaggga agttaatttg gtactctttc  10440
tatataacca attgatcttt tggatgatat ccttaacata tgctacattt caaaaatagc  10500
tatatatata tatatatata tatttttttt tttttttttt tttttttttt ttgagacagg  10560
gtcttcttcc gtcatccagg ctggagtgca gtagtgcact catagctcat tacagcttca  10620
acctcctggg ctcaagcaat cctcccacgt cagccttcaa cataccaggg gcagcaggca  10680
cccaccacca cacccagcta atttttaaat tttttgtagc gataagtttt ttaatttttt  10740
aaaaaaattt ttttgtagag agaagttttc accatgttgc aaggttggcc tgaaactcct  10800
gggctcaggc aatcctcctg ctgggattat aggcatgagc tatcatggct agccaaaaat  10860
ggtttttaat ttataaagaa ttaaaactta cttatttagc ttattttcag agaatacata  10920
caagtaaaat acaccatgtt aaaaaaaacc cttaaggaag taagcgttta atgtatatcc  10980
tcttaagttt ctcacaaatc agtggtattt tcataattag caatcacagc ctcagactcc  11040
aaagtagact tttaaaaatt gaatcaaatt aggttttaaa aatgtcattc taattcaagt  11100
gtccttaatt cttgaaaata ttagctttag ctgaagattt tgaaatggtg tatacaacat  11160
attaatgtca tcttatcaat gttacagttt tattggatat acttaataag ttagtttttt  11220
caagtactat catgtaaaaa atttttagtc tttaacattt tacttactaa aatcatactt  11280
tatttaaaaa tttacaaatt cagaccaggt gaggtggctc atgcctgtaa tcacagcact  11340
ttgggaggct ctggcaggta gatcacttga gctcaggagt tccagaccaa cctgggcaac  11400
atggcaaaac ctcatctcta ccaaaaatac aaaaaaatta gctgggcgtg ttgacatgca  11460
cctgtggtcc tagctactcg tgaggctgag gtgggagcat cacctgagcc caggaagcag  11520
aggttgcagt gagccaagat cgcgccacta cactccagcc tgggtgacag agtgagaccc  11580
catctaaaaa aaaaattaca tattcaaaat ttaaggcgtt attttcttcc gcattacaaa  11640
catagtagtt tccggaatgt ctcattgtta tggacaatga aagaattttc ttttatttgt  11700
tctttgtttc taaacaacag tgtggcaaga aattcaccag tttgaaaaaa aaaaatgaag  11760
cttataatac catttagtaa aattcagtct catttttttct ttcagattgg ttttcctccc  11820
```

```
ttgcttagta ttgttagcag aatgaatcag gtaaaattaa taatagagat atatgcattc  11880
ttttgtttgc attgtgtgtg aaagtatttg aattgttaat acatatactg aattcttaca  11940
gtatgcaaga ctttgtccta agctctttaa tggttcttat ttaatcctta ctacaaccct  12000
ctatggagag ttattattga taactacttt ttatagatga ggaaacagca tttgaggtta  12060
agtaacttgc aggtggtttt tcagcaagta aatggcagta ctgagattca gtgccaggta  12120
gatctaactc cagagctcat gctctgtctt aatcatggtg ctagagtatt catttctgta  12180
gctttcagtt ataagtctta gattctgggg tttgaattaa atacaaggtc cctgacttac  12240
aatggttcag tttaggattc ctttttttccc accatgcctg gctaattttt gtattttcag  12300
tagagagagg attttgtcat gttggccacg ttggtctcga actcctggcc tcaactgatc  12360
cacccacctt ggcctcccaa agtgctggaa ttacaggcat gagccaccat gcccagccat  12420
tttaggaatt ttcaacttta caatgtgttt atcagcacat aaccccattg caagttcagg  12480
ggcatctgta ctaaggttag attgctattt ctagttctag atgtcctata cattctatta  12540
agattgaaat atgggccggg cgcggtggct tatgcctgta atcccggcac tttgggaggt  12600
caaggcaggt ggatcacaag gtcaggagtt cgagaccagc ctggccaaca tggtaaaacc  12660
ccatctctac taaaaataca aaaattagct ggatgtggag gtgtgcactt gtaatcccag  12720
ctatttggga ggctgaggca ggagaatcgc ttgaacctgg gaggcagagg ttgcagtgag  12780
ccgagatcgt gccattgcac tccagcctgg gcgacagggc gagactctgt ctcaaaaaaa  12840
aaaaaaagaa agattgaaat atatgatttc ttggatcaaa agggaagaat tatggagttt  12900
ggttcttcag tttttagga gtaaggactc ttattcattt aaaaagcaaa taaaaattta  12960
attttatctt cacatagcat tgggtacctt tggaagcctt tttttttttt tttggcaggg  13020
tctcattctc ttgcccatgc tggagtacag tgatgtgatc ttggctcact gcagtcttgt  13080
actttggggc tcaggcaatc ctcccacctc agcctcctgg tagctgggac cacaggcatg  13140
tgctaccatg cctggctaat tttgtttatt tttggtagag acaaggtctc actgtgttgt  13200
ccaggctggt ctggaactcc tgagctcaag cgatcctccc acctcagcct cccaaagtgc  13260
tgggaataca ggtgtgaacc actgggccca gccaacaatt ttttttgtgg gtgatattct  13320
cttggaaata atacacaagc tgacagtgtt acttaatcat ttgcattaag atattgtagc  13380
agtcatacta aattccatca gtgtcatttt tgttgtaacc atcaactgta tttgaataaa  13440
ccagagatta ttttcaagag tttgataaat ccatctgtat agtttaagaa cagatttttc  13500
tccacctaaa tttttattca gatttgtact ttgatttaat ttgaatttag aaataaactg  13560
atggtttttt tgttttgttt tgttttgttt tgttttttga gagggagtct cgctctgtcg  13620
ccaggctgga gtgcagtggc acaatcttgg ctcactgcaa cctccacctc ccaggttcaa  13680
gcaattcccc tgcctcagcc tccctagtag ctaggactac aggcgcacac catcacaccc  13740
agctaatttt ttgtatttta gcagggatgg ggtttaccgt gttggccagg atggtctttg  13800
tctcccgacc ttgtgatcca cccgcctcag cctcccaaag tgctgggatt ataggcatga  13860
gcccaccgcg cctggccaac tgatggtatt tttacaaata catctttttt tttttttttt  13920
tttgagacag agtttcgcct tttgcccagg ctgtactgaa gcggcaggat ctcagctcac  13980
tgcaacctct gcctcctggg ttcaagcagt tctcctgtct cagcctcccg agtagctagg  14040
attacagacc ccgccaccat gcctggctaa tttttgtatt tttagtagag acggggtttt  14100
gccgtgttgg ccaggctggt ctcaaactcc tgacctcagg tgtgccattg tttttttttt  14160
tttttttttt ttttgagaca gagtctcact ctgttgccca ggctggagtg cagtggcaaa  14220
```

```
atcctggctc actgcaacct ctgcctccca ggttcaaggg attccccggc ctcagcctcc  14280
ctagtagctg ggactgcatt cactcaccac catgcccggc taatttttgt atttttagta  14340
gagatggggt ttcaccatgt tggcctggct ggtctcaaac tgacatcaag tgatccacct  14400
gcctcggcct cccaaagtgc tgagattact ggcaagagcc actgagcctg gccacaaata  14460
cattttcttt taaccttgtg aagtctttca agtagttaca aactaaatta ttaatagtta  14520
caaactaaat cctaggattt aaaccaaggt gttagttgat atttgaaagt gtgaaaatat  14580
ttgttttaaa agcctcactg gggctaggcg cggtgcctca cacctgtgat cgcagcactt  14640
tgggaggccg aggagggcgg atcacctgag gtcgagagtt cgaccagcct gaccaacatg  14700
cagaaaccct gtctctacta aaaatacaaa aattagccgg acgtggtggt gcacgcatgt  14760
aatctcagct actcaggggg ctgaggcagg agaattgctt gaacccggga ggcggaggtt  14820
gcagtgagcc aagatcgcac cagtgcgctc cagcctgggc aacagagtga gactctatct  14880
caaaaaaaaa aaaaaaaaaa aaaaaaagcc tcattggata agccgcctaa tcaaactaat  14940
tagagtcaaa caaattagct ttctttgaaa gtttaaagaa tgaggccatt tttaacatca  15000
gagttgcttt ctaaataaac ttaatgaaac tcatgttgaa ttcatgtttt attattaata  15060
caactcttct ccacccccctc tttttttttt taggcaacag taactagtgt cttggaatat  15120
ctgagtaatt ggtttggaga aagagacttt actccagaat tggtagtatt gcatgttttt  15180
cttttcataa tgtaggcaaa aattagacgt tttgggtcaa ctgtgggcca catatacaat  15240
ggtgctccta taggattata atactgtatt tttactgcac attttctttt tttcttttct  15300
tttttttttt tttttttttt ttgagacaag gtctcgctct gttacccagg ctggggtgca  15360
gtattacaat catagctcac tgcaaccttg atctccccag ctcaagcaat cctcctgcct  15420
caatctcctg agtagctggg actacaggcg catgcagcca cgcccagttt tttttgtttt  15480
ttgtttttttg tttttttttat tagagacaag gtctcactgt gttgtccagg ctggtcttga  15540
actgagtcca aatgatcctg cctcctcacc ctcccaaaat gctgggaatt acaggcatga  15600
gccaccatgt gtgcggcctt ttgtgttttt taaatagaga cgaggtctca ccatgttccc  15660
caggctgatc tcagactcct aggctcaagt gttcttccca ccttggcctc ccaaactgtt  15720
tggattacaa gcatgagcca ctgagcccgg ctcctttcca gtatttaaat atgtttagat  15780
ctggccaggc acagtggctc atgcctgtaa tcccaactac tagggagggc tgaggcagga  15840
ggatcaccta aggccaggga ggttgaggct gcagtgagcc atgattgtgc cactgcactg  15900
cactctagcc tgagtgacag agtgagaccc tatcttaaga aataaatata tggttttttt  15960
ggatgcacaa atgtttacca ttatgttaca gttgcctaca gtattcagta tagtaatgtg  16020
ctatataggt ttgtagccta ggagcaattg gctatgcaat atagtctagg tatagtagac  16080
tataccatct aggtttgtgt aagtatactc tatgatgttc atccagggtc aaaaatcacc  16140
taacaatgca tttctcagaa tatatctccc ttcattaagt gatgcatgac tgtacttgat  16200
gtgatgctac ggtatttatt tattttttat ttatttgttt gttttgacat ggaatctccc  16260
tctgttgccc aggctggagt gcagtagcgc gatctcggct cactgcagcc tccacctcct  16320
ggtttcaagt gattctcctg cctcagcctc ccaagtagct gggattacag gcacctgcca  16380
ccacacccag ctaatttttg tatttttgta gagacaggct ttctccatgt tggccagact  16440
ggtcttgaac tcatgacctc aggtgatctg cccgcctcca cctctcaaag tgttggaatt  16500
acaggcgtga gccactgcac ccagccagta tttatattta tatttatatt tgtatatgtg  16560
tgtgtgtgtg tatatacata tgtataatct gaactatact tgtttgtagt caaataagaa  16620
```

-continued

```
acactagaat gtaaatcaac atactacttc cttcattgag aaagtcttgg agaaaaaaag  16680
tcaatgaaag agttgatgta tatcctggta caaggtacaa actccttatc tcattgcaga  16740
caagtttgtt tttttttttt tttttttttt ttgagatgga gtctcactct gtcacccagg  16800
ctgcagtgca gtggtgccat ctcggctcac tgcaacctct gcctcccaag ttcaagcaat  16860
cctcctgcct cagcctcctg agtagctggg acaagtgtag agaatattta atttaaatta  16920
aatatttaat ttaaatgcta gctttacata gtaaatgtat cccttaaaat ttgagtcaag  16980
ttgaaacata taattttttt ttatagaaaa agaattccac aatttgtaaa agaaacctgg  17040
atttgaatct ttttctgtaa gaaaaagtct taactattga tttgagtttg cctgaggaac  17100
ccatttagtg tgttgtataa attgctattt aaattttgtc ctaatatttt ttaggtttcc  17160
ccgaagtgat atgttgctta gaataaacaa agttgtatat actactggtg gaaatacaaa  17220
tttggtataa cctttccagg atacaatctg gtgatcatat ctgaaaaacc ttgatgaata  17280
tacataccct ttgtcaccat tttacttgca atacttaata aactttcccc atgttgttaa  17340
atgagattaa acaagggaat gttattaaat actctaaaca agacacttaa cattcccttg  17400
ttaatcccat ttaactacaa gggatggctg agtggggtgg ctcactcctg taatcccagc  17460
acttagggag gccgaggtgg gcggatcact tgaggtcagg agttcgacac cagcctggcc  17520
aacatggtga aaccccccatc tctactaaaa atacaaaaat tagctgagca tggtggcggg  17580
cgcctgttgt cccagctact caggaggctg aggcaggagg attgcttgaa cctgggaggc  17640
agaggttgca gtgagccgag atggcaccac tgcactccag cctggatgac agaacgagac  17700
tccatctcga aaaaaaaaag aaaaaggaca aaaacaacat ggtaaacatt ttattatgta  17760
ttataaataa aaaagatggc tacaagatga tattacaact gatgaaattg tattgaaaaa  17820
aggttgtaca gccgggcatg gtggctcacg cctgtaatct caccactttg ggaggctaag  17880
gcaggcagat cacttgaggt caggagttcg agaccagcct gaacaacatg gtgaaacccg  17940
gtctctatta aaaatacaaa attagccggg tgtggtggta catgcctgta attccaggta  18000
ctcaggatgc tgagacagga gaattgcttg aacccgggag gcagaggttg cagtgagccg  18060
agatcgcgcc attgcactcc agcctgggca acaagagtga aactctgtct caaaaaaaaa  18120
gaaagttgta catacgaata ggaaaaacaa gaacattttt aaagtgaatc aaagtttgat  18180
ctggaatgtt gggactgcag gtttttttctt gtgcttgtgg tattcttcac agtttttctg  18240
catcaaatat gtattcattt tgtagctgaa aaccccattt taaaagggag tggggataca  18300
ttgagcctgt caaagtattt ataaaagtgt caaaagatta tttcatctgt agtatagttt  18360
ctttgtatgt ccccagagga caaaattata caattataaa atgatttcta tatctgtcca  18420
tacagaacaa agaaaaaaat gtatcttaat tttttccagt atttatattc atcttaatgt  18480
agtgttctgc ttacaaatga gaacttccta tcataagaat atctgaaaca aactctttgg  18540
agatcaggga atattttgag gtatccaatg tcctgtgtct gtaattatag gatacaagag  18600
ataacacctg gctctccaaa tgaggctttc ttgtctatac ccaaacataa tatagttaaa  18660
tgttctatga atttattcat agcagataat caggcataac attggacatt taaaaaataa  18720
acttctggtt cagtatttgt ctaaatatta attttttgaa tttttttttta gggaagatgg  18780
ctttatgctt tattggcttg tcttgaaaag cctttgttac ctgaggctca ttcactgatt  18840
cggcagcttg caagaaggtg ctctgaagtg aggctcttag tggtaagttg caacttactg  18900
tttaaaatta aaagcaccca ccaatttata tggtggtaaa gaaggagttc agtgaaatag  18960
gaaaacacat ggaatatttt attggtggca attagatttg taaagcccaa aataatagta  19020
```

```
gcttaaataa tatggaaatg ttttctgaga taaagaagtc tgagccgggc gtggtggctc  19080
acacctataa tcccagcact ttgggaggct gaggcgggtg gctcacctga ggtcaggagt  19140
ttgagaccaa cctggcccac atggtgaaac cccgtctcta ctaaaaatac aaaatttagc  19200
tgggtgtggt ggtgggtgct tgtcatccca gctactcagg aggctgaggc aggagaatcg  19260
ttcgaaccca ggaggcggag gttgcagtga gctgagattg caccactgca ctcctgcctg  19320
ggcaacagag caagactctg tctcaaaaaa gaagtaggta aaaaaattag atttttacta  19380
agatggcagt aacccaccca cacctttgag ttttgtcata tgtggctttc atcctcatgc  19440
tcatcttatg atccaagatg gctgctgtag cttcagcctt tttttttttt tttttttttt  19500
cttttattgt gagatggagt ctcgctctgt caccgaggct ggagtgcaat ggtgcggtct  19560
cggctcactg caacctccgc ttcccaggtt caagcaattc tcctgcctta gcctccagag  19620
tagctgagat tacaggtgcc cgccaccatg cctggctaat tttgtattt ttagtagaga  19680
cagggtttca ccatgttggc cagactggtc tcaaactgct gacttcaagt gatccacctg  19740
cctcagcctc ccaaagtgct gggattacag gcatgagcta ctgcacctgg tgtgtgtgtg  19800
tgtgtgtgtg tgtgtatata tatgtgtgtg tgtgtgtgtg tatatatata tatctttata  19860
tatatatctt tatataattc agtaatgaat atatataaga acagtaagaa tcctgtgtct  19920
tgactgtaca gtgattaata tatattatat atattcatat atattctata tatatcctca  19980
catatattgt atgcattata tagaggaaca ataagaatcc tgtgtcttga ctacagtgat  20040
aaatatattt attcatatat gtatattaat atatatttat tatatatgaa tacatattca  20100
ctacagttaa gacacatata taatatatat gaatatatat atatatattc atcactgtac  20160
agttaagaca caggattctt attgttcctt tagtaggaac cagggaaaaa tttcccccaa  20220
gttatccccc ttagatccct ctttattttt ttttccctat tcagaatctt tatttaaaag  20280
atagtcttag atgtttctca aggaatcatt aactctacag ttctctgctt tttctttgag  20340
ggctcctatt tccacatgat gattactgtc atataataaa gttttcatgt ttcgtgtttt  20400
acatcttaat agaaaattta tttcaaaagt aataggaaca gacaatattt aaatttttct  20460
tttttttttt ttaggatagc aaagatgatg agagggttcc tgctttgaat ttattaatct  20520
gcttggttag caggtatagt taatccttgg cttctttatt atttatcagt gaggtcagtg  20580
aggttagatc gtatttatta catttggttt ttgtttggtt ggtttttttt tgagtctcac  20640
tctgttgcta tagttagggt gcagtggcgc aatcacagct cactagagct ttaacttcct  20700
gggctccagc aatcctccca cctcagcctc ctgagtagct aggaccacaa ccaagcacca  20760
ccacacctgg ctaattaaaa aaaattgttc gtagagacag ggtctcacta tgttgcccag  20820
gctggtctca aaactcctgg gctcaagcga tcctcccacc taagcctccg aaagtgcagg  20880
gattacaggt gtaaagccac tgcattcagc ctgcattttt gtttaattgc ctgtgtcctg  20940
cgttcatttt cagttgtggc atatttttat ttagtatctg ttttatttca tttcttacat  21000
agaaattctt cttggaattt atttgaaaac tttttttgtt gttttgtttt gagacagagt  21060
ctcgctctgt tgcccaggct ggagtgcaat ggcaccatct cggctcacta caaccttcac  21120
ctcctgggtt caagcaattc tccccctca gcctcccaag tagctgggct tacaggcacc  21180
tgccatcatg cccggctaat tttgtaatt ttgtggagac ggagtttcac cattattggc  21240
caggcagtaa aacacacata tttattttag gtctcctcct ggacatattt ttgttccata  21300
gatcagtgtt tttatttcat tgccagtacc tttttaaagc tttataatat acttaaatat  21360
tgggaaggca agtaatcttg tttccatatt ttcacatatt caatatctag tttcttgatc  21420
```

```
tacaataatt atgctgctga tgataattaa catttactgg gcaatttgtg ccaagcattt  21480
ttcttagtga ggaacccatt taatccttct aaggtgggta ctgttaacag tttacagatg  21540
aggaaaccat ggcagagaga ggttaaataa tattactacc atcacaaagc tagtaagtgt  21600
tagagtaatg atccaaaccc aggcaacttt gactccggag ctaaactttt aactatgctg  21660
atcaaaaatt aagctaatac ctacctcatc tgttggtagt agcagttaaa tgagatgata  21720
tagcattgcc ctacttactt tatgtatagt atctctactc tttacaatag atcagagttg  21780
tgtttttgtt tttgtttttg ttttaataaa tttttccttt tcagctctgt tggacttgat  21840
tttttccctt ttacagataa tgacacagat tcagaaaggt taagtaattg gtagctcagc  21900
aaaccagtaa ttaatgaaac ctcagacaag tatagtttct gactgcctca gttgagattt  21960
tacagtatta tgcaattatg aaagcaaaaa cattcaagtg tattttttgc cctcaaaaag  22020
ttagataaaa atggaaaaag ttctagacta caaaaggttc tgaagctaac agctttacaa  22080
tagaagacac aaagatttga aagtttagga aaaaaaggac cgggcatggt ggctcatacc  22140
tgtaatccca ccactttggg aggccaaggc gggtggatca ccttaagtca ggagttcaag  22200
actagcctgg ccaacatggt gaaacctcgc ctctactaaa aataggaaaa ttagccgggc  22260
acggtggttc acgcctgtaa tcccagctac tcgggatggt gaggcaggag aatcacttga  22320
acctgggagg tggaggttgc agtgagctga gatcgtgcca ttgcactcca gcctgggcaa  22380
caagaacgaa actccatctc aaaaaaaaaa gaaaaaagaa aaaaaaaagg aaagctgggc  22440
acagtgactc acacctgtaa gcccagtgct ttgggaggtc aaggtgggag gattgcttga  22500
gtccaggggt tcaagaatgc agtgagccat gacaaaatct gattagtgat tttccttttt  22560
atttaatctt ataattacat aaaatagtta ccttgccaaa gttaaaatta taattcaagg  22620
tacatttgga gtattttagc atccatcttt atcctcatta tcctcttttt tcctttctcc  22680
tctagttaac cattgtatta ctaatttttg tttcatcttt tcattcattg tttcttttta  22740
aaagtataag taggccgcat gtggtggctc aagcctgtaa ttccagcact tcgagagact  22800
gaggctggag aattgtttga gcccaggagt tcaagaccag tctgggaaat gagccatgat  22860
catgccactg cactccagcc tgggtgacag agtgagacct tgtctcaaaa aggaaaagaa  22920
aaatataaac aaacacgtat attggcagtc ctacacatac tcacataagg tagcatacag  22980
aacaatctgt tctgtacttc gttttttttc acttaataaa tcctggaaat catactttag  23040
cagtataaat acgttcctca tactttagca gtataaatat ttccctcatt tctcttttta  23100
tggcttcata attttccact atgtagacat actatagctt atttaaccag tttcttattg  23160
atggacgttt gggttgctta tggtctttgg ctattaaaaa tagtgctaca gttaatatct  23220
ttatacataa attttttgtt ttttttttac taggtatttt gaccaacgtg atttagctga  23280
tgagccatct tgatgtagct gatctctcag ggatagaaga tatttctcat gaaggcagcc  23340
taactctgag gaaaacaatg ccaattcaag tacagatttc aacacatctt caacactatg  23400
tgaagggttc acatcttaac ctgtgcaatt cagattgata ctcagaatat gggttgattt  23460
gaatatctga aatatcaatg gaaaatccca ctcagttttt gatgaacagt ttgaacagtt  23520
ttctgtaatc aagcagcttg catagaaatt gtatgatgaa attttacata ggttcttggt  23580
gctgttttgt tctttttttg ttttttgttg ttttgttatt tacttatata catataaaat  23640
tttattgaaa atatgttttg gttactaaaa ttttgtttga ctcctaacaa aagacaatgg  23700
atggccttag catcagaatt aaaataatct ggattaaatg gcaatgtgtt catagtcagc  23760
aataaaatta aacatttttc cctttaagct cagcactttt tttttttttt ttttttttc  23820
```

```
tttgagatgg agtctcgctc tgtcatccag gctggagtgc agtggcagga tctcagctca  23880

ctgcaacctc tgcctcccag gttcaagtga ttctcctgcc ccaggctccc gagtagctgg  23940

atctacaggt gtccgccacc aagcctggct aatttttgta tttttagtag aaacagggtt  24000

tcaccatgct ggccaggctg ctcttgaact cctgatctca ggtgatccgc ccgcctcagc  24060

ctcccaaagt gctgggatta caggcatgag ccactgtgcc tggcctcaat atttttattt  24120

ttaaatgctt tattgcacaa atagaacttt atctaacaaa tcactttcaa aaataacagg  24180

tcaactgttt taatttgttt atgtcactta taacttacct atttctgtat caggtaggaa  24240

tgttttctgc tttaagtaac acaaaagatc caagtggcaa tggttcttca aataggggtt  24300

tttctcagat aacaagaagt ctaaaggagc tggccactgg cattggttta gtgactcagt  24360

gatatcaggg gctcagattc ctttagcctt tctgtcatgg aaacaagatg gccattgcag  24420

ttcaagccaa tgtgtctgta ttcaagacaa aaagaagggg aagcagggcc ttccacatct  24480

gatccttttc tcataaatgt aaaatctttt ctagaaattt agatcagact tgtgttcatc  24540

tgctagccat aaatgtacaa catgatcacc ccttgttccc aggaaagtgg gaaaatgaag  24600

ctgtacgcct ttccagtctc actaatggaa ggtgggaaag gaaaatgggg attgggaatt  24660

accatggatc agacaaccaa cagttttgcc accagttata attagagcag aggtcatttt  24720

atatttgaat cttttctgta atgtcttcat aaagctcact ttattattat ttttgtttgt  24780

ttttgagacg agtctcgctt ggttgcccag gctggagtgc agtgacgcaa tctcggctca  24840

cgcaacctcc acctcccagg ttcaagtgat tctcccacct cagcctcctg agcagctggg  24900

actacagaca tgcaccaccg cacccagcta attttttttgt gtttttagta gagaccgggt  24960

ttcaccatgt tggtcaggct ggtttcaaac tcctgacttc a                      25001
```

<210> SEQ ID NO 9
<211> LENGTH: 4752
<212> TYPE: DNA
<213> ORGANISM: Homo sapiens

<400> SEQUENCE: 9

```
tggccgtgtg attgctctgt gcccattacc ctgtggccgt gtgactgctg ctgtgcccat     60

taccctgtgg ccgtgtgatt gctgctgtgc ccattaccct gtggccgtgt gattgctctg    120

tgcccattat cctgtggccg tgtgattgct ctgtgcccat taccctgtgg ccgtgtgatt    180

gctctgtgcc cattaccctg tggccgtgtg attgctctgt gcccattatc ctgtggccgt    240

gtgattgctc tgtgcccatt atcctgtggc cgtgtgattg ctctgtgccc attatcctgt    300

ggccgtgtga ttgctctgtg cccattatcc tgtggccgtg tgattgctgc tgtgcccatt    360

accctgtggc cgtgtgattg ctctgtgccc attatcctgt ggccgtgtga ttgctctgtg    420

cccattatcc tgtggctgtg tgattgctct gtgcccatta tcctgtagcc gtgtgattgc    480

ttctgtgccc attaccctgt ggctgtgtga ttgctgctgt gcccattatc ctgtggctgt    540

gtgattgctg ctgtgcccat taccctgtgg ctgtgtgatt gctctgtgcc cattaccctg    600

tggctgtgtg attgctctgt gcccattatc ctgtggccgt gtgattgctg ctgtgcctgt    660

taccctgtgg ctgtgtgatt gctctgtgcc cattaccctg tggctatgct cccttcatct    720

gtcatgagaa gctcagctgt catgtcctgt ggtacatgct cagtggcccc tgtagtttgt    780

actgtcctcc tatttctaaa cccctctccc cacatcctct gctggcccag cctttgctgg    840

agggtctcgc ctcagcagcc cagctttttc ttttcacaca cttttcctga aggatctcat    900

tcaccgtctt ggttccggtg atcccctctg ggcagatacc tctcagaatc acatttccca    960
```

```
gcttacttcc ctcctgaact tccacctggc atttccgttg ctggaggaca tctgtacctt   1020

gatggccaaa gctgaactca tctttcctca cacctgctct gattctcctc cattccctgt   1080

atgtgatgtc acctggtggc ctcccagttc ccaggctgga gagctcggaa gccattctgg   1140

attcctcggc caagtccttc tgactccagc tgtgcagtgg ctcttgtagt catccattct   1200

ccccgtccgc tgatgtcctt taaaaccctt gtcatctcaa accatgacag cctactaaca   1260

gcagtggcca tctggaaaca ttttcactat actgtcttat ttggcttgtc tgtgtgcagg   1320

acccttgaac atctgtgaag aaatgactat tctgcatgga ggcttcttgc tggccgagca   1380

gctgttccac cctaaggcac tggcagaatt aacaaagtct gactgggaac gtgttggacg   1440

gcccatcgtg gaggccttaa gggagatctc ctcggctgca gcacactccc agccctttgc   1500

ctggaagaag aaagccctga tcatcatctg ggccaaggtt ctgcagccgc accccgtgac   1560

cccgtccgac acagagacac ggtggcagga agacctgttc ttctcggtgg gcaacatgat   1620

ccccaccatc aaccacacca tcctcttcga gctgctcaaa tccctggaag cttctggact   1680

ctttatccag ctcctgatgg ccctgcccac caccatctgc catgcagaac tagagcgctt   1740

tctggaacat gtgaccgttg acacttctgc cgaagacgtg gccttcttcc tggacgtctg   1800

gtgggaggtg atgaagcaca agggtcaccc gcaggacccc ctgctctccc agtttagtgc   1860

aatggcccat aagtacctgc ctgccttaga tgagttcccc catcctccaa agaggcttag   1920

gtcagaccca gacgcgtgcc ccaccatgcc cctgttggcc atgctgctcc gcgggctgac   1980

acagatccag agtcggatcc tgggcccggg gaggaagtgc tgtgcgctgg ccaacctggc   2040

tgacatgctg actgtgtttg cgctgacaga ggacgacccc caggaggtgt ctgcaaccgt   2100

gtatctggac aaactggcca cggtgatctc tgtgtggaac tcggacaccc agaatcccta   2160

ccaccagcag gcgctggcag agaaggtgaa ggaggcagaa cgggatgtca gcctgacctc   2220

gctggccaaa ctccccagtg agaccatttt cgtgggctgc gagttcctgc accacctgct   2280

gcgggagtgg ggggaggagt tgcaggccgt gctccgcagc agccagggga caagttacga   2340

cagctaccgg ctgtgcgaca gtctgacttc cttcagccag aacgcgacgc tctacctgaa   2400

ccgcaccagc ctgtccaagg aggacaggca ggtggtctct gagctggcgg agtgtgtcag   2460

ggacttcctg aggaaaacga gcacggtgct gaagaacagg gccttggagg atatcacagc   2520

ttccattgcc atggccgtca tccagcagaa gatggaccgc catatggaag tgtgctacat   2580

ttttgcctct gagaagaagt gggccttctc ggacgagtgg gtagcctgcc tggggagtaa   2640

cagggccctc ttccgagagc cagacttggt gttgaggctg ctggaaacag tgatagacgt   2700

cagcacagct gacagagcca tccctgagtc tcagatccgg caggtgatcc acctgatcct   2760

ggaatgttac gcagacctct ccctgccagg taaaaataaa gtccttgcag gtatcctgcg   2820

ttcctggggg cgaaagggcc tctctgaaaa gttgctggct tatgtggagg gttttcagga   2880

agacctcaat acaactttta accagctcac tcagagtgcc tccgaacagg gcttggcaaa   2940

agctgtggcc tccgtggccc gcctggtcat agtgcacccg gaagtcacgg tgaagaaaat   3000

gtgcagcctg gctgtggtca atctcggcac ccacaagttc ctggcccaga ttctcactgc   3060

cttccctgcc cttaggtttg tggaagtgca gggtcccaat tcatctgcca ctttcatggt   3120

gtcatgcctc aaagaaaccg tctggatgaa gttctctaca cccaaggaag aaaagcaatt   3180

tttagagctc ctgaactgcc tgatgagtcc cgtgaaaccc caagggattc cagtggctgc   3240

tcttcttgag ccagacgagg tgctgaagga atttgtcctg cctttcttga ggttagatgt   3300

tgaagaggta gacctcagtc tgaggatctt catccagact ctagaggcaa acgcgtgtcg   3360
```

```
agaggaatac tggctccaga cctgctcccc gtttccactc ctcttcagct tgtgccagct   3420

cttggaccgc ttcagcaaat actggcagct tcccaaggag aagcggtgcc tctctttgga   3480

taggaaggat ctagcgatcc atatcctgga gctcctgtgt gagattgtat cagccaatgc   3540

tgagaccttc tccccggatg tctggatcaa gtccctgtcc tggctccacc gcaagttaga   3600

acagctagac tggactgtgg gcctgaggct gaagagcttc ttcgaggggc acttcaagtg   3660

tgaagtgcca gccacacttt ttgagatctg taagctttca gaagacgagt ggacctccca   3720

ggcccaccca gggtacgggg ctggcacggg gctcctggcc tggatggagt gctgctgcgt   3780

ctccagcggc atctcggaga ggatgctgtc tctcttggtg gtggacgtgg gcaatcctga   3840

ggaggtcaga ctgttcagca aaggctttct ggtggccctg gtgcaagtca tgccttggtg   3900

cagccctcag gagtggcagc gccttcacca gctgaccagg agactgctgg agaagcagct   3960

cctccatgtc ccttatagcc tggaatatat tcagtttgtt cccctgctca acctgaagcc   4020

ctttgcccag gagttgcaac tctccgtcct cttcctgagg actttccagt ttctctgcag   4080

ccatagctgt cgtaattggc ttcctctgga aggctggaac cacgtggtca aactcctctg   4140

tggcagtctg acccgcctcc tggactcagt cagggcgata caggcagctg gcccttgggt   4200

tcaaggacca gagcaggacc tgacccagga agccctgttt gtttacaccc aggtgttctg   4260

ccatgctctg cacatcatgg ccatgctcca cccggaggtc tgtgagccac tctacgtttt   4320

agccttggaa accctcacct gctatgagac tttgagcaag accaaccctt ctgtcagctc   4380

cttgctccag agggcacacg agcagcgctt cttaaagtcc attgctgagg gcattggccc   4440

tgaagaacgg cgccaaaccc tgttgcagaa gatgagcagc ttctgacttg gcgtggggag   4500

ctgggcccca acatggcggg tctgcagaag atcagcagct tcttacctgt gcgggagcga   4560

aaaagctggg cttcaacatg gcaggtctgt aggggtcaga cccaagcagc ctggacttta   4620

cagttatgtg aaactgtcca caaaaagtca tggcaataat ggtgtaaaga aaatagtttc   4680

ttgggtattt gtaacgtaca aactatcata aaaattctcc tctttcccaa aaaaaaaaaa   4740

aaaaaaaaaa aa                                                       4752
```

<210> SEQ ID NO 10
<211> LENGTH: 720
<212> TYPE: DNA
<213> ORGANISM: Homo sapiens
<220> FEATURE:
<221> NAME/KEY: misc_feature
<222> LOCATION: 458
<223> OTHER INFORMATION: n is a, c, g, or t

<400> SEQUENCE: 10

```
agcgggaggt tgtgagcagg cctaagcgcg gccgccgtgg ctcctgcgtc tcccatcgtg     60

ccgtgcgtcc cgcgccgcgt tcgagttctc ggaggggagg gggcgttagc cccgcgcagc    120

cgccggcgtc gccgccatgg acctagaccc ttgaacatct gtgaagaaat gactattctg    180

catggaggct tcttgctggc cgagcagctg ttccacccta aggcactggc agaattaaca    240

aagtctgact gggaacgtgt tggacggccc atcgtggagg ccttaaggga gatctcctcg    300

gctgcagcac actcccagcc ctttgcctgg aagaagaaag ccctgatcat catctgggcc    360

aaggttctgc agccgcaccc cgtgaccccg tccgacacag agacacggtg gcaggaagac    420

ctgttcttct cggtgggcaa catgatcccc accatcanac acaccatcct cttcgagctg    480

ctcaaatccc tggaagcttc tggactcttt atccagctcc tgatggccct gcccaccacc    540

atctgccatg cagaactaga gcgctttctg gaacatgtga ccgttgacac ttctgccgaa    600
```

```
gacgtgagct tcttcctgga cgtctggtgg gaggtgatga agcacaaggg tcacccgcag    660

gacccctgct ctcccagttt agtgaaatgg cccataagta cctgactgcc ttagatgaga    720
```

```
<210> SEQ ID NO 11
<211> LENGTH: 671
<212> TYPE: DNA
<213> ORGANISM: Homo sapiens

<400> SEQUENCE: 11

agcggagtcc cgcgcagccg ccggcgtcgc cgccatggac ctagagctag ggccatgagt     60

accttgtttt tgactggaag gagctgtggg gtggaccgtt tccctgaaag ctagaagaat    120

gtttgaagcc tgttcccaag gacccttgaa catctgtgaa gaaatgacta ttctgcatgg    180

aggcttcttg ctggccgagc agctgttcca ccctaaggca ctggcagaat taacaaagtc    240

tgactgggaa cgtgttggac ggcccatcgt ggaggcctta agggagatct cctcggctgc    300

agcacactcc cagccctttg cctggaagaa gaaagccctg atcatcatct gggccaaggt    360

tctgcagccg caccccgtga ccccgtccga cacagagaca cggtggcagg aagacctgtt    420

cttctcggtg ggcaacatga tccccagcat caagcacacc atcctcttcg agctgctcaa    480

atccctggaa gcttctggac tctttatcca gctcctgatg gccctgccca caacatctgc    540

catgcagaac tagagcgctt tctggaacat gtgaccgttg acacttctgc cgaagacgtg    600

ggcttcttcc tggacgtctg gtgggaggtg atgaagcaca agggtcaccc gcaggacccc    660

ctgctctccc a                                                         671
```

```
<210> SEQ ID NO 12
<211> LENGTH: 3472
<212> TYPE: DNA
<213> ORGANISM: Homo sapiens

<400> SEQUENCE: 12

tggcggccgc cggcgtcgcc gccatggacc taggaccctt gaacatctgt gaagaaatga     60

ctattctgca tggaggcttc ttgctggccg agcagctgtt ccaccctaag gcactggcag    120

aattaacaaa gtctgactgg gaacgtgttg gacggcccat cgtggaggcc ttaagggaga    180

tctcctcggc tgcagcacac tcccagccct ttgcctggaa gaagaaagcc ctgatcatca    240

tctgggccaa ggttctgcag ccgcaccccg tgaccccgtc cgacacagag acacggtggc    300

aggaagacct gttcttctcg gtgggcaaca tgatccccac catcaaccac accatcctct    360

tcgagctgct caaatccctg gaagcttctg gactctttat ccagctcctg atggccctgc    420

ccaccaccat ctgccatgca gaactagagc gctttctgga acatgtgacc gttgacactt    480

ctgccgaaga cgtggccttc ttcctggaca tctggtggga ggtgatgaag cacaagggtc    540

acccgcagga cccccctgctc tcccagttta gtgcaatggc ccataagtac ctgcctgcct    600

tagatgagtt cccccatcct ccaaagaggc ttaggtcaga cccagacgcg tgccccacca    660

tgcccctgtt ggccatgctg ctccgcgggc tgacacagat ccagagtcgg atcctgggcc    720

cggggaggaa gtgctgtgcg ctggccaacc tggctgacat gctgactgtg tttgcgctga    780

cagaggacga cccccaggag gtgtctgcaa ccgtgtatct ggacaaactg gccacggtga    840

tctctgtgtg gaactcggac acccagaatc cctaccacca gcaggcgctg gcagagaagg    900

tgaaggaggc agaacgggat gtcagcctga cctcgctggc caaactcccc agtgagacca    960

ttttcgtggg ctgcgagttc ctgcaccacc tgctgcggga gtgggggggag gagttgcagg   1020

ccgtgctccg cagcagccag ggggacaagtt acgacagcta ccggctgtgc gacagtctga   1080
```

-continued

```
cttccttcag ccagaacgcg acgctctacc tgaaccgcac cagcctgtcc aaggaggaca   1140
ggcaggtggt ctctgagctg gcggagtgtg tcagggactt cctgaggaaa acgagcacgg   1200
tgctgaagaa cagggccttg gaggatatca cagcttccat tgccatggcc gtcatccagc   1260
agaagatgga ccgccatatg gaagtgtgct acatttttgc ctctgagaag aagtgggcct   1320
tctcggacga gtgggtagcc tgcctgggga gtaacagggc cctcttccga gagccagact   1380
tggtgttgag gctgctggaa acagtgatag acgtcagcac agctgacaga gccatccctg   1440
agtctcagat ccggcaggtg atccacctga tcctggaatg ttacgcagac ctctccctgc   1500
caggtaaaaa taaagtcctt gcaggtatcc tgcgttcctg gggcgaaag ggcctctctg    1560
aaaagttgct ggcttatgtg gagggttttc aggaagacct caatacaact tttaaccagc   1620
tcactcagag tgcctccgaa cagggcttgg caaaagctgt ggcctccgtg gcccgcctgg   1680
tcatagtgca cccggaagtc acggtgaaga aaatgtgcag cctggctgtg gtcaatctcg   1740
gcacccacaa gttcctggcc cagattctca ctgccttccc tgcccttagg tttgtggaag   1800
tgcagggtcc caattcatct gccactttca tggtgtcatg cctcaaagaa accgtctgga   1860
tgaagttctc tacacccaag gaagaaaagc aatttttaga gctcctgaac tgcctgatga   1920
gtcccgtgaa accccaaggg attccagtgg ctgctcttct tgagccagac gaggtgctga   1980
aggaatttgt cctgcctttc ttgaggttag atgttgaaga ggtagacctc agtctgagga   2040
tcttcatcca gactctagag gcaaacgcgt gccgagagga atactggctc cagacctgct   2100
ccccgtttcc actcctcttc agcttgtgcc agctcttgga ccgctttagc aaatactggc   2160
cgcttcccaa ggagaagcgg tgcctctctt tggataggaa ggatctagcg atccatatcc   2220
tggagctcct gtgtgagatt gtatcagcca atgctgagac cttctccccg gatgtctgga   2280
tcaagtccct gtcctggctc caccgcaagt tagaacagct agactggact gtgggcctga   2340
ggctgaagag cttcttcgag ggcacttca agtgtgaagt gccagccaca ctttttgaga    2400
tctgtaagct ttcagaagac gagtggacct cccaggccca cccagggtac ggggctggca   2460
cggggctcct ggcctggatg gagtgctgct gcgtctccag cggcatctcg gagaggatgc   2520
tgtctctctt ggtggtggac gtgggcaatc ctgaggaggt cagactgttc agcaaaggct   2580
ttctggtggc cctggtgcaa gtcatgcctt ggtgcagccc tcaggagtgg cagcgccttc   2640
accagctgac caggagactg ctggagaagc agctcctcca tgtcccttat agcctggaat   2700
atattcagtt tgttcccctg ctcaacctga agccctttgc ccaggagttg caactctccg   2760
tcctcttcct gaggactttc cagtttctct gcagccatag ctgtcgtaat tggcttcctc   2820
tggaaggctg gaaccacgtg gtcaaactcc tctgtggcag tctgacccgc ctcctggact   2880
cagtcagggc gatacaggca gctggccctt gggttcaagg accagagcag gacctgaccc   2940
aggaagccct gtttgtttac acccaggtgt tctgccatgc tctgcacatc atggccatgc   3000
tccacccgga ggtctgtgag ccactctacg ttttagcctt ggaaaccctc acctgctatg   3060
agactttgag caagaccaac ccttctgtca gctccttgct ccagagggca cacgagcagc   3120
gcttcttaaa gtccattgct gagggcattg gccctgaaga acggcgccaa accctgttgc   3180
agaagatgag cagcttctga cttggcgtgg ggagctgggc cccaacatgg cgggtctgca   3240
gaagatcagc agcttcttac ctgtgcggga gcgaaaaagc tgggcttcaa catggcaggt   3300
ctgtaggggt cagacccgag cagcctggac tttacagtta tgtgaaactg tccacaaaaa   3360
gtcatggcaa taatggtgta aagaaaatag tttcttgggt atttgtaacg tacaaactat   3420
cataaaaatt ctcctctttc gcatctcaaa aaaaaaaaaa aaaaaaaaaa aa           3472
```

<210> SEQ ID NO 13
<211> LENGTH: 11001
<212> TYPE: DNA
<213> ORGANISM: Homo sapiens
<220> FEATURE:
<221> NAME/KEY: misc_feature
<222> LOCATION: (1)...(11001)
<223> OTHER INFORMATION: n is a, c, g, or t

<400> SEQUENCE: 13

```
ggtaggccct gtgttccagt gggggctttt ggacttgact ttagtgttta ggaggacaga      60
gtccctctcc cctctgtggt gctggggtat tagtaaatca gccttgaaga gataaggggc     120
tggggcctca acctcccaag aggctgtcac tggagaatgg tctcctgccc tcagatcttg     180
ggcatttcca cagcacactg tccccctcgt ccttccaaat acctacatac gctcttgtaa     240
taggagagct gggaactcca cccaaaacca tacaaaaagt tagtctgtgt atttggacgc     300
ctccccagca ctcagtcacc gagtttctcc tttccaacag cagtcactct catgcagttt     360
aagtgattta ttgatgtctc ggctaagctt gcgacagttt caggacattt cagccatcaa     420
ggtctaagaa gccctttcca ttcccgagga gccctcagcc agcctccttc ttcctcatct     480
cctcactctg gccgcgtagc ccctcatggc gtccatcttg gacgcccctt tgttcgcgct     540
ccacgccccc cacttccttc ttcgtcagct cctccacttt ggccgcgtag cccctcatgg     600
cgtccatctt ggacgcccct ttgttcgcgc tccacgcccc ccacttcctt cttcgtcagc     660
tcctccactt tggccgcgta gcccctcatg gcgtccatct tggacgcccc tttgttcgcg     720
ctccacgccc cccacttcct tcttcgtcag ctcctccact ttggccgcgt agcccctcat     780
ggcgtccatc ttgcacgccc ctttgttcgc gctccacgcc ccccacttcc ttcttcgtca     840
gctcctccac tttggccgcg tagcccctca tggcgtccat cttggacgcc cctttttttcg     900
cgctccaagc ctcccacttg gccctggctc tcacgtctga ggccggaggg ccggggatgt     960
cgcagtcgcc ctgggtggcc tgtttgtaca agccgtagac cagcagcttc tcctgatcgc    1020
tcacgggacc cttcagctgc ttgagggccg cgcagctcga actccacttg gcacatgggg    1080
tggtggaggc ggtccctggt gctagaagct ggaggtggag agttggagtg gctgttacta    1140
ctcgatctca gggggaggag acaggcacgc gatgtttgtg ttttgtcaag cacagattgc    1200
aagctcgggg tccagcgtaa accccaccat gtttgggctc acacggcgca ttttctgggg    1260
aggaccagcc gtcaaaaagc gtctaggatc cggaacgctg ctgtctggag ggggcggcgc    1320
ggcaggagcg cgttgaggga ctgtatgtgg cgcgagctgg gcgggtggga gtggaagcct    1380
cgcgtggtgc ggccgcgctg ggtggtgggc gtcccggggg aggcgctcgg tgggggtgaa    1440
ctgtgtgcgg ggcacgcccg gggttaccgg gtgagggtga atgcggggcc ggggaatcat    1500
gagcccgacc cgctgggacc ccggaagagg ggccgggcag gggacggtgc ggaggggtct    1560
agtgagcgac gtccgggtac ttgagggctg gtgggagggc tctgccggaa ggcggcgctg    1620
tgcgcttggc gcgctcgtta gtaagaactg cgcgtgcgcg gcggaggctg tgggcggggc    1680
cgggcggagg ttgtgagcag gcctaagcgc ggccgccgtg gctcctgcgt ctcccatcgt    1740
gccgtgcgtc ccgcgccgcg ttcgagttct cggaggggag ggggcgttag ccccgcgcag    1800
ccgccggcgt cgccgccatg gacctaggtg ggtgccgcgg ctccccggcc ccgggctgcg    1860
tccagcaatg cgccaccaga gcggtgctgc cccgtcgcgt ctcctcctgt cgcgcacgct    1920
cgcgcgggcc cggaccgaaa cgtcccccgc gtcggggcgg gtctaggggt cccggggtgg    1980
ccttggcggg gggtggtccg ggtcccgccg cgcgttgggc cgcgtcttgc cgcctccggc    2040
```

-continued

```
ccccctgcgct tgaaaacacg gagcagacgt gaagttagag cccttggaag cgcccggggc   2100
tcgcgcacgt gctttgggaa acgggctccc tccgagcacc cctgggcgcc ccgacggcct   2160
catttcctga acggcagctg cgttcttgag caagtgtctt aacgctccaa gtgtcttacg   2220
ctcatgacgt ttcctcatcg acagagcggg gagaatggaa gtgtgtctcc ccactgagtt   2280
ttgggcgact ttgcattgag atcgccgagg tacagtgtcc cttgtggggt tgcgcgggtc   2340
acacccgcgg tgggggcggc tgcgctcctg aggtatcact ttgtgaacct gcgtgcgtcc   2400
ggattcagaa tcttacaggc aaggtctggg agggagccca taggaactag atgctccctg   2460
ctaaatcttg gcacacgctg ctaagaccag gaggctgttc tgggagagct gggggtgagg   2520
caccccgaga tgtgtcagca gtagtaggct ggggggaaat ggtctggtcc ccgcccccag   2580
acagcttttc aggagcggaa tggcagagct ctaagggctt ggagcccctc agccgtaatt   2640
gcttcccagc cccaccacat tcaggctggg acaccctcag caaatcgttt ctgcgcctca   2700
gtgtccttat ctctagagca ggaatactag tcctcaaaag gtgattgtga atagaagaga   2760
tcttacctgt gtaccaccta gcacagtgtc tggcatggag taggtgctta ataaacctaa   2820
gaagcgggct gtggcaagca ctagttaacc atccatgata gagtaccgga gtattttcca   2880
gctagtaacc gccctgggac ttactacttc aaactgtgcg tacttaatgc gcctggaagg   2940
caggtgttta gggccaaaca tctgctcaac taagccaata atgcaataaa attaaattta   3000
cagcgtcagg agggactata ttttgggacc ctgggagagc ctcctgagcc agaaagaagg   3060
gcggtaaccc ccagggaggt ccccttcgca gcgtaaccct ccctgggagt cggtctcagc   3120
cactgtgaga tgagatggat tgcctccaca agtgggttac atagtgctga gcccttggcc   3180
tgctgccgct cccataaatg gtgggagggg taagatggtc cttagtctcc tggagtcagt   3240
gttttctctg ctggtgtctg gcctgtgaaa atggggaata tgagctcttg ggggcatgac   3300
agactgagga aggagtagca tctctcactc ctgggaaagg ggagatgact caggaatgag   3360
gaatagggag cagtgtttgc accctcgttt tagtttctgg gccaaaggaa acatacctga   3420
taaagaccta catcctttga tgtttctgag ctgggggagg caaagaatag tgacaagatt   3480
ctggtcttgc caaccatgaa aaggtttggg gaaaccaaca tttactgagc acctaattag   3540
actctgtaac tggattctta ctgtagctct atctcattta tccatcatag cgtcccgggg   3600
agatggggtc aggagatagc agtgccaacc cactagcaag ggcttgactg gtatatatca   3660
catgatcccc aaaggcataa catgaagtct gtattatccc cacatatgca gaaggaaggc   3720
ttggagaagc aatctgacca agatcacatc cctttttttt tttcggagat ggagggggag   3780
tctcactgtg ttaccccagc tagtcttgaa ctcctggcct cagggatcca cctgcctcag   3840
ccccccaagt agctgggatt acaagtgcta gccactgaac ctggccagaa tcacatcatt   3900
tttaaatggc tgaactagga tttaaaccca tgtctgatta aacatcccaa gatgttttcc   3960
atggtaagtc tgtgtcaatc gttagttccc tgaaggaagg cttaatctag cacagtattt   4020
tctgtatcta ctccctggtt tctcccacag agctagggcc atgagtacct tgtttttgac   4080
tggaaggagc tgtggggtgg accgtttccc tgaaagctag aagaatgttt gaagcctgtt   4140
cccaaggcaa gtttataaag agtgaaggca gggcttgtct gattccttct gtgcccattg   4200
ctctgtggct atgtgattgc tctgtgccca ttaccctgtg gctgtgtgac tgctgctgtg   4260
cccgttaccc tgtggctgcg tgattgctgc tgtgcccatt accctgtggc tgtgtgattg   4320
ctctgtgccc attatcctgt ggccgtgtga tcgctctgtg cccattaccc tgtagccgtg   4380
tgattgctgc tgtgcccatt accttgtggc tgtgtgattg ctgctgtgcc cattatcctg   4440
```

-continued

```
tggctgtgtg attgctctgt gcccattatc ctgtggctgt gtgattgctc tgtgcccatt   4500
atcctgtagc cgtgtgattg cttctgtgcc cattaccctg tggctgtgtg attgctgctg   4560
tgcccattat cctgtggccg tgtgattgct gctgtgccca ttaccctgtg gccgtgtgat   4620
tgctctgtgc ccattaccct gtggccgtgt gactgctgct gtgcccatta ccctgtggcc   4680
gtgtgattgc tgctgtgccc attaccctgt ggccgtgtga ttgctctgtg cccattatcc   4740
tgtggccgtg tgattgctct gtgcccatta ccctgtggcc gtgtgattgc tctgtgccca   4800
ttaccctgtg gccgtgtgat tgctctgtgc ccattatcct gtggccgtgt gattgctctg   4860
tgcccattat cctgtggccg tgtgattgct ctgtgcccat tatcctgtgg ccgtgtgatt   4920
gctctgtgcc cattaccctg tggccgtgtg attgctgctg tgcccattac cctgtggccg   4980
tgtgattgct ctgtgcccat tatcctgtgg ccgtgtgatt gctctgtgcc cattatcctg   5040
tggctgtgtg attgctctgt gcccattatc ctgtagccgt gtgattgctt ctgtgcccat   5100
taccctgtgg ctgtgtgatt gctgctgtgc ccattatcct gtggctgtgt gattgctgct   5160
gtgcccatta ccctgtggct gtgtgattgc tctgtgccca ttaccctgtg gctgtgtgat   5220
tgctctgtgc ccattatcct gtggccgtgt gattgctgct gtgcctgtta ccctgtggct   5280
gtgtgattgc tctgtgccca ttaccctgtg gctatgctcc cttcatctgt catgagaagc   5340
tcagctgtca tgtcctgtgg tacatgctca gtggcccctg tagtttgtac tgtcctccta   5400
tttctaaacc cctctcccca catcctctgc tggcccagcc tttgctggag ggtctcgcct   5460
cagcagccca gctttttctt ttcacacact tttcctgaag gatctcattc accgtcttgg   5520
ttccggtgat cccctctggg cagatacctc tcagaatcac atttcccagc ttacttccct   5580
cctgaacttc cacctggcat ttccgttgct ggaggacatc tgtaccttga tggccaaagc   5640
tgaactcatc tttcctcaca cctgctctga ttctcctcca ttccctgtat gtgatgtcac   5700
ctggtggcct cccagttccc aggctggaga gctcggaagc cattctggat tcctcggcca   5760
agtccttctg actccagctg tgcagtggct cttgtagtca tcccttctcc ccgtccgctg   5820
atgtccttta aaacccttgt catctcaaac catgacagcc tactaacagc agtggccatc   5880
tggaaacatt ttcactatac tgtcttattt ggcttgtctg tgtgcaggac ccttgaacat   5940
ctgtgaagaa atgactattc tgcatggagg cttcttgctg gccgagcagc tgttccaccc   6000
taaggcactg gcagaattaa caaagtctga ctgggaacgt gttggacggc ccatcgtgga   6060
ggccttaagg gagatctcct cggctgcagc acactcccag ccctttgcct ggaagaagaa   6120
agccctgatc atcatctggg ccaaggttct gcagccgcac cccgtgaccc cgtccgacac   6180
agagacacgg tggcaggaag acctgttctt ctcggtgggc aacatgatcc ccaccatcaa   6240
ccacaccatc ctcttcgagc tgctcaaatc cctggaagct tctggactct ttatccagct   6300
cctgatggcc ctgcccacca ccatctgcca tgcagaacta gagcgctttc tggaacatgt   6360
gaccgttgac acttctgccg aagacgtggc cttcttcctg gacgtctggt gggaggtgat   6420
gaagcacaag ggtcacccgc aggacccccct gctctcccag tttagtgcaa tggcccataa   6480
gtacctgcct gccttagatg agttccccca tcctccaaag aggcttaggt cagacccaga   6540
cgcgtgcccc accatgcccc tgttggccat gctgctccgc gggctgacac agatccagag   6600
tcggatcctg ggcccgggga ggaagtgctg tgcgctggcc aacctggctg acatgctgac   6660
tgtgtttgcg ctgacagagg acgacccccca ggaggtgtct gcaaccgtgt atctggacaa   6720
actggccacg gtgatctctg tgtggaactc ggacacccag aatccctacc accagcaggc   6780
gctggcagag aaggtgaagg aggcagaacg ggatgtcagc ctgacctcgc tggccaaact   6840
```

-continued

```
ncccagtga gaccattttc gtgggctgcg agttcctgca ccacctgctg cgggagtggg 6900
gggnaggagt tgcaggccgt gctccgcagc agccagggga caagttacga cagctaccgg 6960
ctgtgcgaca gtctgacttc cttcagccag aacgcgacgc tctacctgaa ccgcaccagc 7020
ctgtccaagg aggacaggca ggtggtctct gagctggcgg agtgtgtcag ggacttcctg 7080
aggaaaacga gcacggtgct gaagaacagg gccttggagg atatcacagc ttccattgcc 7140
atggccgtca tccagcagaa gatggaccgc catatggaag tgtgctacat tttgcctct 7200
gagaagaagt gggccttctc ggacgagtgg gtagcctgcc tggggagtaa cagggccctc 7260
ttccgacagc cagacttggt gttgaggctg ctggaaacag tgatagacgt cagcacagct 7320
gacagagcca tccctgagtc tcagatccgg caggtgatcc acctgatcct ggaatgttac 7380
gcagacctct ccctgccagg taaaaataaa gtccttgcag gtatcctgcg ttcctggggg 7440
cgaaagggcc tctctgaaaa gttgctggct tatgtggagg gttttcagga agacctcaat 7500
acaactttta accagctcac tcagagtgcc tccgaacagg gcttggcaaa agctgtggcc 7560
tccgtggccc gcctggtcat agtgcacccg gaagtcacgg tgaagaaaat gtgcagcctg 7620
gctgtggtca atctcggcac ccacnaagtt cctggcccag attctcactg ccttccctgc 7680
ccttaggttt gtggaagagc agggtcccaa ttcatctgcc actttcatgg tgtcatgcct 7740
caaagaaacc gtctggatga agttctctac acccaaggaa gaaaagcaat tttagagct 7800
cctgaactgc ctgatgagtc ccgtgaaacc ccaagggatt ccagtggctg ctcttcttga 7860
gccagacgag gtgctgaagg aatttgtcct gcctttcttg aggttagatg ttgaagaggt 7920
agacctcagt ctgaggatct tcatccagac tctagaggca aacgcgtgcc gagaggaata 7980
ctggctccag acctgctccc cgtttccact cctcttcagc ttgtgccagc tcttggaccg 8040
cttcagcaaa tactggcagc ttcccaagga gaagcggtgc ctctctttgg ataggaagga 8100
tctagcgatc catatcctgg agctcctgtg tgagattgta tcagccaatg ctgagacctt 8160
ctccccggat gtctggatca agtccctgtc ctggctccac cgcaagttag aacagctaga 8220
ctggactgtg ggcctgaggc tgaagagctt cttcgagggg cacttcaagt gtgaagtgcc 8280
agccnacanc tttttgagat ctgtaagctt tcagaagacg agtggacctc ccaggcccac 8340
ccagggtacg gggctggcac ggggctcctg gcctggatgg agtgctgctg cgtctccagc 8400
ggcatctcgg agaggatgct gtctctcttg gtggtggacg tgggcaatcc tgaggaggtc 8460
agactgttca gcaaaggctt tctggtggcc ctggtgcaag tcatgccttg gtgcagccct 8520
caggagtggc agcgccttca ccagctgacc aggagactgc tggagaagca gctcctccat 8580
gtcccttata gcctggaata tattcagttt gttcccctgc tcaacctgaa gccctttgcc 8640
caggagttgc aactctccgt cctcttcctg aggactttcc agtttctctg cagccatagc 8700
tgtcgtgatt ggcttcctct ggaaggctgg aaccacgtgg tcaaactcct ctgtggcagt 8760
ctgacccgcc tcctggactc agtcagggcg atacaggcag ctggcccttg ggttcaagga 8820
ccagagcagg acctgaccca ggaagccctg tttgtttaca cccaggtgtt ctgccatgct 8880
ctgcacatca tggccatgct ccacccggag gtctgtgagc cactctacgt tttagccttg 8940
gaaaccctca cctgctatga gactttgagc aagaccaacc cttctgtcag ctccttgctc 9000
cagagggcac acgagcagcg cttcttaaag tccattgctg agggcatcgg ccctgaagaa 9060
cggcgccaaa ccctgttgca gaagatgagc agcttctgac ttggcgtggg gagctgggcc 9120
ccaacatggc gggtctgcag aagatcagca gcttcttacc tgtgcgggag cgaaaaagct 9180
gggcttcaac atggcaggtc tgtaggggtc agacccgagc agcctggact ttacagttat 9240
```

```
gtgaaactgt ccacaaaaag tcatggcaat aatggtgtaa agaaaatagt ttcttgggta   9300
tttgtaacgt acaaactatc ataaaaattc tcctctttcg catctcactt tgtctcttct   9360
aagtcggcct cagcaatagc ccaggattaa atatgctctg aaattgggtt tagtgtcttc   9420
aagatcaaat ccagccagga ggaacatgtt cataactgga cttttccatc ctagattttg   9480
gcaaataagc ccaaagttga aaccatgtga gtggaaaaag cattacatgg tacgtataac   9540
ccccttcaag agttatttcg tcttttaatg tttttttctt gaggtatctt ggaaaggaca   9600
gcagcttgga aaagaatcca gtccagccct ggctctgcct ctggccatga gactgctgtg   9660
cccgagaggc ctgcacaatt ctaaaatgag aggattggag gaccaagata aactcagtgg   9720
cgaggggcta ggttagtgac ctcaagaaaa tgggtcccct ctgaattgag gagtgtgtac   9780
agtctttgtt gctcagacta gccttgaacc cctggactca agtgatcctc ccacctcagc   9840
ctcctgagta gctgggacaa taagcacacc cacttcccat acagtcttaa ctccatctat   9900
tcagtcaccc ccaaaggggc tactgtgaag acgagacctg gcaaacccag cagagatgtg   9960
ctgaatggat gggtcacgtt agcttttgcc tcaggagggg ttgtcaagat ttggatgaat  10020
gaatggtttg gataagggaa tgatgtgtgc aggaacataa aaaatgagtt tgggccaggt  10080
gcggtgactc acacctgtaa tctcagcact ttgggaggcc gaggcgggag gatcacttga  10140
gaccagccaa catatggaag ccctgtctct acaaaaaaaa aaccacaaaa attagctagg  10200
tgtggtgaca cacagctgta gtcccagcta ctcagggttc taaagcagga ggctcacttg  10260
atcctgggag gtagaggctg cagtaagctg agatcagacc actgcactcc agccttggtg  10320
acagagtgag accctgtcta aaacaaaaaa aaaaaaaatt gagagtgggc taggcatggt  10380
ggctcacacc tgtaataatc ccagtgcttt gggaggctga ggcaggagga tcacttgagg  10440
ccaggagttt gagaccagcc tgggcaacag agataacctg tctctacaaa aagaaaaaaa  10500
aatgagttta aggtgtctga ggtatgagga aactatgaaa attggctggg gacatgttta  10560
atgtgtgaga tgaaaggggg aaaaaatatg tcccatcact ccctccatat ccacaccctc  10620
cttcacaatg gggcattact caggttctcc tcaggtaaag taggcttggc tccctgacca  10680
ataatcggtc ttccactctc ccaattccta gtaagattca cttatgaaga gaagaaacgg  10740
tctcaagtta cgtgtgacca ctacgcttga actctgggaa ccttcaatgt attactgaga  10800
ccatgaacca caaaaatagg tttgagtgag gtgtgagcta gacctttctg gaggctgaaa  10860
gcattcacac acacacccct ctgctagtta catggacaca gaccttgagc cacagcacac  10920
ggcagccagt cgagctaggt cacaggatga ttcttacagg acactgatat tgatgtattt  10980
cacaaatgag aataagttgg g                                            11001
```

<210> SEQ ID NO 14
<211> LENGTH: 4586
<212> TYPE: DNA
<213> ORGANISM: Homo sapiens

<400> SEQUENCE: 14

```
acgcgtcgac tccattggcc cagcaatcaa ccaacacagc tggtatctag ctgttttgga     60
ggtgaactgt tgcaatggga tctcactcaa tcttggagac ggaaatacac cctcttcagt    120
gcctcatcag aagggcaaaa tcattcaaga attgtgttta atttatgtcc tttacaaaca    180
gaggatgaca aacagctgtt actttctaca tcaatggata gagatgtaaa atgttgggac    240
atagccacct tggagtgcag ctggaccctt ccttcccttg gtgggtttgc atacagcctg    300
gctttctctt ctgtggacat aggctctttg gccataggtg ttggggatgg catgatccgt    360
```

```
gtatggaata cactctccat aaagaacaac tatgatgtga aaaatttttg gcaaggcgtg    420
aagtccaagg ttacagcgct gtgctggcac ccaaccaagg aaggttgctt agcttttgga    480
actgatgatg gaaaagtggg attgtatgac acctactcca acaagcctcc acagatttct    540
agcacatatc ataagaagac tgtatatacg ttagcctggg ggccaccagt accccccatg    600
tcacttggag gagaaggaga cagaccttcc cttgctttat acagctgtgg aggagaaggg    660
attgtcttac agcataatcc ctggaagctt agtggagaag cctttgacat caacaaactc    720
atcagggaca ccaattcaat caaatacaaa ttgcctgtac acacagagat aagttggaaa    780
gcagatggca aaatcatggc tcttggcaat gaagatggat caatagaaat atttcagatt    840
cccaacctga aactgatctg tactatccaa cagcatcaca agcttgtgaa taccattagc    900
tggcatcatg agcatggcag ccagccagaa ttgagctatc tgatggcctc tggctccaac    960
aatgcagtca tttacgtgca caacctgaag actgtcatag agagcagccc tgagtctcca   1020
gtgaccatta cagagcccta ccggaccctc tcagggcata cggccaagat taccagtgtg   1080
gcgtggagcc cacatcatga tggaaggctg gtatctgctt cctatgatgg tacagcccag   1140
gtgtgggatg ctctccggga agagcccctg tgcaatttcc gaggacatca aggtcgactg   1200
ctttgtgtgg catggtctcc tttggatcca gactgcatct attcaggggc agatgacttt   1260
tgtgtgcaca agtggctcac ttccatgcaa gatcattccc ggcctcctca aggcaaaaaa   1320
agtattgaat tggagaaaaa acggctctct caacctaagg caaagcccaa aaagaagaaa   1380
aagcccacct tgagaactcc tgtaaagctg gaatcgattg atggaaatga agaagaaagc   1440
atgaaggaga actcaggacc tgttgagaat ggtgtgtcag accaagaagg ggaggagcaa   1500
gcacgggagc cggaattacc ctgtggcctt gctccagcgg tttctagaga accagttatc   1560
tgcactccag tttcctcagg ctttgaaaag tcaaaagtca ccattaataa caaagtcatt   1620
ttactgaaaa aggagccacc aaaagagaag ccagaaacct taatcaagaa gagaaaagct   1680
cgttccttgc ttcccctgag tacaagcctg gaccacagat ccaaagagga gcttcatcag   1740
gactgtttgg tactagcaac tgcaaagcac tccagagagc tgaatgaaga tgtgtctgct   1800
gatgttgagg aaagatttca tctggggctt ttcacagaca gggctaccct gtatagaatg   1860
attgatattg aaggaaaagg tcacttagaa aatggccacc ctgagttatt tcaccagctt   1920
atgctttgga aaggggatct caaaggtgtt ctccagactg cagcagaaag aggggagctg   1980
acagacaacc ttgtggctat ggcaccagca gctggctacc atgtgtggct atgggctgtg   2040
gaagcttttg ccaaacagct gtgttttcag gatcagtatg tcaaggctgc ttctcaccta   2100
ctttccatcc acaaagtgta tgaagcggtg gagctgctca agtcaaacca tttttacagg   2160
gaagctattg cgattgccaa ggcccggctg cgcccggagg acccagtcct gaaggacttg   2220
tacctcagct ggggaaccgt cctagaaaga gatggccact atgctgtagc tgccaaatgc   2280
tatttagggg ccacttgtgc ttatgatgca gccaaagttt tggccaaaaa gggggatgcg   2340
gcatcactta gaacggctgc agagttggct gccatcgtag gagaggatga gttgtctgct   2400
tccctggctc tcagatgtgc ccaagagctg cttctggcca acaactgggt gggagcccag   2460
gaagccctgc agctgcatga aagtctacag ggtcagagat tggtgttttg ccttctggag   2520
ctactgtcca ggcatctgga ggaaaagcag ctttcagagg gcaaaagctc ctcctcttac   2580
cacacttgga acacgggcac cgaagggcct ttcgtggaga gggtgactgc agtgtggaag   2640
agcatcttca gccttgacac ccctgagcag tatcaggaag cctttcagaa gctgcagaac   2700
atcaagtacc catctgctac aaataacaca cctgccaaac agctcctgct tcacatttgc   2760
```

```
catgacttga ccctggcagt gctgagccaa cagatggcct cctgggacga ggctgtgcag   2820
gcgctccttc gggcggtggt ccggagctat gactcaggga gcttcaccat catgcaggaa   2880
gtgtactcag cctttctccc tgatggctgt gaccacctaa gagacaagtt gggggaccat   2940
caatcccctg ccacaccagc tttcaaaagt ttggaggcct tttttcttta tgggcgtctg   3000
tatgaattct ggtggtctct ctccagacct tgcccaaatt ccagtgtctg ggtaagggct   3060
ggtcacagaa cactctctgt tgagccaagc cagcagttag acactgccag cactgaagaa   3120
acggaccctg aaacttctca gccagagcca aacaggcctt cagaactaga cttgagactc   3180
acagaagaag gtgagcgaat gctgagtact tttaaggagc tcttttcaga aaagcatgcc   3240
agtctccaaa actcacagag aactgttgct gaagtccaag agaccttggc agaaatgatc   3300
cgacaacacc aaaagagtca actctgtaaa tccacagcaa atggtcctga taagaatgaa   3360
ccggaagtag aagcagagca gcccctctgc agttctcaga gccagtgtaa agaagaaaaa   3420
aatgagccac tttctctgcc tgagttaacc aaaaggctta ccgaggcaaa tcagagaatg   3480
gcaaaatttc ctgagagcat taaggcctgg cccttcccag atgtgctgga gtgctgcctc   3540
gtcctgcttc tcatcaggtc ccactttcct ggctgtctgg cccaggaaat gcagcagcag   3600
gcccaagagc tccttcagaa atacggcaac acgaaaactt acagaagaca ctgccagacc   3660
ttctgtatgt gaattttcac acaccttgaa gaaactgcca aattgaaaat gtttgacatc   3720
tttcacctct gcagttatgc ctcaccagac attcactctg gtccctagat gtttttgcag   3780
taatccaaaa gaatacaaac aaggattaag tttgaatcaa ccctgcctac ccatagacaa   3840
cggtggatct gactttagac tcaattgtgg tctcctactg gagggaagat catgaaaagc   3900
ccacagtagt tattcagaac taacacctgc agagtgttgg tcatctctac agccttaggc   3960
aggtttcacc aaaagaggag aaacttctgt cgtcacccaa agtgttacat gcttaaaaca   4020
caagctacct ttgtaaatac ttcatctgat cagaagtgtg tcatgcttgt ttgagatgga   4080
gttgctgcat tttaggacta ttgatacctt tttttaattg tttttataat atttaatttg   4140
aaagaggaga cccttctctc tctactcttt catagactga agtttgaata tgaaataggc   4200
cttaaccatc atgttgactc tcctgtcaga attttaggtt ggaaatttgg ttttattctt   4260
tcatgtaatt gcttatttga acagatcact tactaaagct ttagaagaag tgattcaaat   4320
gtgtgttttc ccttcagttt tataacaaat ggattgatgg cagtcaaata gctcaggaat   4380
aaattactgt ttcaatggtt cttaaacttt cttggatcat aggatccttt tgagaatcag   4440
attaaagcca aagatactct ttggagaaaa atgcatattc ctaattttgc atagatgacc   4500
tttggattat tggactctga ctattgggac cctaaatact atttaattat aaatctttct   4560
tttctcctca aaaaaaaaaa aaaaaa                                        4586
```

<210> SEQ ID NO 15
<211> LENGTH: 2301
<212> TYPE: DNA
<213> ORGANISM: Homo sapiens

<400> SEQUENCE: 15

```
ccacgcgtcc ggctacgagc ggtcggctgt ggcagcttct cttgtctctg acggcttgta     60
gttatggggc aggagccgcg gacgctgccg ccctccccca actggtactg cgcccgctgc    120
agcgatgccg tgcccggggg cctctttggc ttcgccgcgc ggacctccgt cttccttgtc    180
cgcgtgggcc cgggcgcagg cgagagtcca gggacacccc cgtttcgagt cataggagag    240
ttggtgggac acaccgaaag ggtctctggc ttcacatttt ctcatcaccc tggtcagtac    300
```

-continued

```
aacctctgtg ccaccagctc cgacgatggg actgtgaaaa tatgggatgt agagacaaaa    360
acagttgtga cagaacatgc actccatcag catacgatat caacattaca ttggtctcct    420
cgagtaaagg acttaatagt atctggggat gaaaaaggag tagttttctg ttactggttt    480
aacagaaatg acagccagca cctctttata gaacccagga caattttctg tcttacttgt    540
tcacctcatc atgaagattt agtagccatt ggctacaagg atggcatagt ggtgataatt    600
gacatcagta agaaaggaga agttattcat aggcttcgag gccatgatga tgaaatccac    660
tccatagcct ggtgtcccct gcctggtgaa gattgtttat ctataaacca agaggaaact    720
tcagaagaag ctgaaattac caacgggaat gctgtagcac aagctccagt aacaaaaggt    780
tgctacttag ccactggaag caaagatcaa accattcgaa tctggagctg ttctagaggc    840
cgaggggtga tgattttgaa attgcccttt ctgaagagaa gaggaggggg tatagaccca    900
actgttaaag agcgcctttg gttgacactc cattggccca gcaatcaacc aacacagctg    960
gtatctagct gttttggagg tgaactgttg caatgggatc tcactcaatc ttggagacgg   1020
aaatacaccc tcttcagtgc ctcatcagaa gggcaaaatc attcaagaat tgtgtttaat   1080
ttatgtcctt tacaaacaga ggatgacaaa cagctattac tttctacatc aatggataga   1140
gatgtaaaat gttgggacat agccaccttg gagtgcagct ggacccttcc ttcccttggt   1200
gggtttgcat acagcctggc tttctcttct gtggacatag gctctttggc cataggtgtt   1260
ggggatggca tgatccgtgt atggaataca ctctccataa agaacaacta tgatgtgaaa   1320
aatttttggc aaggcgtgaa gtccaaggtt acagcgctgt gctggcaccc aaccaaggaa   1380
ggttgcttag cttttggaac tgatgatgga aaagtgggat tgtatgacac ctactccaac   1440
aagcctccac agatttctag cacatatcat aagaagactg tatatacttt agcctggggg   1500
ccaccagtac cccccatgtc acttggagga gaaggagaca gaccttccct tgctttatac   1560
agctgtggag gagaagggat tgtcttacag cataatccct ggaagcttag tggagaagcc   1620
tttgacatca acaaactcat cagggacacc aattcaatca aatacaaatt gcctgtacac   1680
acagagataa gttggaaagc agatggcaaa atcatggctc ttggcaatga agatggatca   1740
atagaaatat ttcagattcc caacctgaaa ctgatctgta ctatccaaca gcatcacaag   1800
cttgtgaata ccattagctg gcatcatgag catggcagcc agccagaatt gagctatctg   1860
atggcctctg gctccaacaa tgcagtcatt tacgtgcaca acctgaagac tgtcatagag   1920
agcagccctg agtctccagt gaccattaca gagccctacc ggaccctctc agggcatacg   1980
gccaagatta ccagtgtggc gtggagccca catcatgatg gaaggctggt atctgcttcc   2040
tatgatggta cagcccaggt gtgggatgct ctccgggaag agcccctgtg caatttccga   2100
ggacatcgag gtcgactgct ttgtgtggca tggtctcctt tggatccaga ctgcatctat   2160
tcaggggcag atgacttttg tgtgcacaag tggctcactt ccatgcaaga tcattcccgg   2220
cctcctcaag gcaaaaaaag tattgaattg gagaaaaaac ggctctctca acctaaggca   2280
aagcccaaaa aaaaaaaaaa a                                             2301
```

<210> SEQ ID NO 16
<211> LENGTH: 53001
<212> TYPE: DNA
<213> ORGANISM: Homo sapiens

<400> SEQUENCE: 16

```
tggagtgcag tggcgcaatc tctgctcact gcaacttccg cctcccaggt tcaagcgatt     60
ctcctgcctc agcctcccta gtatttgttg tctagggatt gttgcatttt actttttttt    120
```

-continued

```
tttttttgag atggagtctc gctgtgtggc caggctagag tgcagtggcg tgatctccgc    180
tcacagcaac ttccgcctcc cgggttcaag cgattctcct gcctcagcct cccgagcagc    240
tgggattaca ggcgcctgcc accacacccg gcttatttta ttattttatt ttatttttgt    300
tttttaatag agacgaggtt tcactatgct gaccaggccg gtcttttaac tcctgacctc    360
gtgatcctcc cgcctcggcc tcccaaagtg ctgggattac aggcgtgagc caccgcaccc    420
ggcctcttgt gcatatcttt aaaacacctc cacaactagc aaagtgccct ggcacatagc    480
gctcaaaaaa cgttggacgg gatagtggtt gaacagctcc aaataataaa ctggtagcct    540
ggggcggtgg ttccactagt ctaatcctct aattttgtgc ctttctgtgg gaagtgagaa    600
tgcttaacct cggggctgtg ctcaggcagc acctgaccct agccagggtt ggggcggacc    660
tcctaccgcg ggctaggtac tgagggccag tgcagcacgc gtggtcccgc ccttcccagc    720
ccggcggtag cgggaacgca acgcgcggtg ctggctgggc ctcgacgcgc accgtagcga    780
ctgcccgaga aggcggggct cggagttcac cccgccccgc tccctaccta aggcgtgagg    840
ctacgagcgg tcggctgtgg cagcttctct tgtctctgac ggcttgtagt tatggggcag    900
gagccgcgga cgctgccgcc ctcccccaac tggtactgcg cccgctgcag cgatgccgtg    960
cccgggggcc tctttggctt cgccgcgcgg acctccgtct tccttgtccg cgtgggcccg   1020
ggcgcaggcg agagtccagg gacacccccg tttcgaggta actcaccacc cttgggcccg   1080
agacttactg ccctttgtac gctccccagg ggcgccgagt ggacgactcc accccgtttt   1140
ctacagctag ggaaactgag gcccaggctg ggaggagagg cagcccacag tcactaagct   1200
gagttgcttc tggtctccta atgagctaca ccatgctgtg gccgagcggt cccgcctcct   1260
ggagcttcca cgtggggccg cttgcttact gaaaagttag ccttgtatag tctcggccat   1320
ttatatggct cccctgccca gcctggtgcg cgccagcccc ccgggagcct tcctggggtt   1380
gggggctaac cacagctgca ggccctaagc aagatcctgc aacgtgtggc attccttact   1440
gtaagatgaa tgggttgaac cagatgcttt caggctccaa actaggcttt gattgtgcct   1500
taggatatga catgccaggt gatttattct ggccacatct aaataagagt cactttcaca   1560
ttatttgagc tgctttccag tctgtgaact aagcagagca aggtatatca acattcattt   1620
cacagttgag aagctgaggc tcagagactt gttcgaagtc acgtggcaca gccaatatca   1680
gcacttggga attctgagtg taagtccgtc ggtgtttcag ttataccatg ggttaagtaa   1740
ctccaaagca tctgctcact tgtcatccaa caacagtatg attctgccag gaaccttgga   1800
tagcacttcg attaacctag cgtctggttt tgcttaaagt cataggagag ttggtgggac   1860
acaccgaaag ggtctctggc ttcacatttt ctcatcaccc tggtcagtac aacctctgtg   1920
ccaccagctc cgacgatggg actgtgaaaa tatgggatgt agagacaaaa acagttgtga   1980
cagaacatgc actccatcag gtaccatggc ttactggttt ctcaaaccgt ttttatctat   2040
ctgtgctgag ggttcttctg ttgcaagcta gttttgctag ctcatctgtg caaagtaact   2100
tgtaattgtg ttcattaatt agataagaaa ctatattgta agatgtctca actttttttg   2160
aaaggagata tatacaaacc agaggttggc aaactgctct gtgcctgttt ttgcaaatag   2220
gttttattag aatacaacca cactaattca tttaagtatt gtctatgact gctttcatgc   2280
tacaagagtt gagtagttgc aacaggcatg gtatggccca caaggtctaa aacaattacc   2340
ctctggttat tgatacaaat ggactcctga tatagactgt aaatgcgtga atgaaactca   2400
tttctaagct agatagttac ttgatgtacc tgccttttga gagaacaaag gaaaagacct   2460
acttaataag aactttgcat taagctattt aaaaaatttt taatgattat ttgatcccca   2520
```

```
gtagtctaaa tcttcccacc attttgttaa tatcgtgttg ctatagaagt actactaata   2580
agtattaatt actttttttt ttttttttga gacggagtct ggctctgtcg cccaggctgg   2640
agtgcaatgg cgggatcttg gctcactgca agctccgcct cctgggttga cgccattctc   2700
ctgcctcagc ctctcgagta gctggaacta caggagccca ccaccacgcc cggctaattt   2760
ttttatgttt ttagcagaga tggggtttca ccatgttagc caggatggtc tcgatctcct   2820
tacctggtga tccacccgcc tcggcctccc aaagtgctgg gattacaggc gtgagccacc   2880
gcgcccggcc gtattaatta cttttaatgt gtatatgtag cattatgctg gtttgtgata   2940
caagttaaaa attaagtaga acttcagcat tgacaataac aaatttttgt tttgttttaa   3000
agcatacgat atcaacatta cattggtctc ctcgagtaaa ggacttaata gtatctgggg   3060
atgaaaaagg agtagttttc tgttactggt ttaacagaaa tgacagccag cacctcttta   3120
tagaacccag gacaattttc tgtcttactt gttcacctca tcatgaagat ttagtagcca   3180
ttgggtaagt actatgccat ctgtattgat gatttttgtt tgtttatgat cgtgttttgc   3240
attttcttta ccttctctgt ccttttattc ctcaaaggaa accatctaca gatgttaacc   3300
actccccctg agcccctggc atcatttatt cctccaggtc tttactgtct ctgccactcc   3360
gtttttgttt ccttggtttc catggtactg tactttcttc gtttttcgga tctaactcct   3420
ccaatcaacc tttacgtgta ggaaatgtcc tctttcacct ttttcgcttt ctctactgcc   3480
cgttgataca acatgaactc ccaggtgtca gatgactttg ctgggtctct ctagttctga   3540
gcgctccctt tagattggga aagtgatgcg gcattgggat ctgtttcctt gttgatcacc   3600
aaggttgttt cacatgagct gcctgaatat acatccccgt ttctttcacc atttcatgta   3660
cttctcactg aaagatgtct attttctcta atttgaagac ttaagcaatt tccctagaat   3720
gttgaaggag aaattctgat tggagtggat ttgaaagact gggggctaag gcaatagaga   3780
tacacaaaga gacaacaact ctttcacaaa gtttgttgta aaaatgtgca tatacatgaa   3840
gccagagggg atagatgggg tcaagggagt attaaatgga aaataccagg gacctgtttt   3900
tatgctgatg aaagtaaggc ttgaaaagag gaagagcttg ttgcaggagt aaactatgat   3960
aaatgcaggg gtattgctga aaagtcaaga ggggattgga ttcagatgac aagaagaaag   4020
aacagctggg aatatagaaa taggtgcagg tagatttgta gatgtgcttg gaagaaaaag   4080
gtgttctatt ctggtatttc tgattttctc attgaggcat aagtcagagt ggtagagtca   4140
agttcatcat ggggttgaaa ctggatatgc aaagaaggta tgaaaatggt caaagagaat   4200
aggaaaacga atgtactaag gaaaattata ggcccagtgt tcactgttga gtggcaaaca   4260
aagaatcgtg gccataaatt taaagtaaac ccaaactgtt tgagaaagga gatggttgga   4320
ttcagccagg tttggggctt tgtggagtaa gtactcttga gggagaggga gaaggagacg   4380
gggcgtacgg gtatttttaa aagttgatga taaggctggg cgcagtggct cacacctgta   4440
atcccaacac tttgggaggc cgaggcgggt ggatcacctg aggtcaggag ttcaagacca   4500
gcccggccaa catggtgaag ccccatctct actaaaaata aaaaatcagg ccaggtgcag   4560
tggtgcacgc ctgtaatccc agcactttga gaggccgagg tgggcaaatc acctgtggtt   4620
gggagttcaa gaccagcatg gagaaacccc gtctctatta aaaacacaaa attagccagg   4680
catggtggcg catgcctgta atcccagcta ctagggaggc tgaggcagga ggatcacttg   4740
aacccaggag gtagaggttg tggtgagcca ggattgagcc attgcacccc agcctgggca   4800
acaagagcga aactctgtct caaaaaaaca aacaaacaaa aattagccag acttggtggc   4860
gcacacctgt aagcccagct actcaggagg gtgaggcagg agaatcgctt gaacctgggc   4920
```

```
agtggaggtt gcagtgagat gagattgcac cactgcactc cagcctgagc gacagagcaa   4980
gactctatct caaaaaaaaa agtcaatgat agtgatggat catgaaatct gtgctgcatt   5040
gggtaggggg atgtatggaa agacaggtgt gggtgagtga tagtgaaaat ggaaggggac   5100
tggatcggca gtctcttgaa gtgggagcag tgttgtagta gggttgatag agaggatgaa   5160
cagaaaggtg gtaggcagga gtcaggggag gatcttcaga atagtattat tcccagaaag   5220
cttgattcag atttctaaat agcttgatct gttggtgatt aggttgcata acttggcagt   5280
tttcaaagtc cgggtcttca aaggttgaca tactctagtg tttcttttaa aaaaaaaaaa   5340
taaataaagc tgtgctggtg ttcttccctg tcgaatgctg taatgtgtag gaagtgtgaa   5400
taggtacagc cactttgtat aatgcagttt tgtactttct aataaaaatg catatatctt   5460
aacatcctgg cagttccatt actagtcatc aaacctgaaa ttgtcttaga tgtgtacatg   5520
aacattaata gcattttttt gttgtaaaaa agtggaagcc cttcaaaagg aaaatgaata   5580
aactttgaaa tattcacaca gtgcagtact aatacaatag tgtaatgact ggccaggaac   5640
tagagttacg tgtatcaaca tggatgaatt acaaacagaa tgagtgaaaa aaacaagctg   5700
caggaaaata gatgatagca tttatgtgca gttttaaaat atgcaaaatc tatatcttat   5760
ttaggaatat atacaaagaa aggctaggaa tgatataaca caattcacaa atagagtttg   5820
acctctgggt agaggaagaa aaggagaaga gatctggcaa ggagagaggt ttgattgaag   5880
tggaatgtac agaggacttc agctctattg gtaattattt ttcttaggca gggtagtaga   5940
ttactttttt tatgtatctg aagtcattca tttttaaaaa gctattagaa tttctcagtt   6000
tcttttgaat tcataaaatg acagccttgg aatatgcagg tctagagtgt agaattctgc   6060
aacttttgtt aagttcacag tttaaaaagt agtatcactt ataaagaaag agattatttt   6120
ccagtgcact aggacaaaat tatctctagt tagaagagtt ggccgggtgt ggtggctgat   6180
gcctataatc ccatcacttt aggaggccaa cgcaggtaga ttgcttgagc ccaggagttt   6240
gagaccagcc atgagcaaca tggtgaaacc tcatctctac aaaaaaatac aaaaattagc   6300
tgggcatggc atgtaccttt agtcccagct actcagtccc aggctgaggt gggaggattg   6360
cttgagcctg ggaagtcaag gctgcagtaa gtggtgattg tgccactgca ctccagcctg   6420
ggcaacagag aaggaaaaaa gaagagttgc tgcacccttg caaaaactat gaaaattccc   6480
ttagaacaaa atcatggtcc actgtgagtt ttgtaccagg caacatacat agtattacct   6540
agtgccaaga gtttgatcat agagagaagg gttttaacaa aaccaggagg cataaggtga   6600
gcactttaaa aaaaggaaaa agcaaaatta ttttttgtcc tcttccctcc tccgccaccc   6660
caaatgcacc taactttaag gaatgcgcca atggtaactc caagccaaaa tgtttactag   6720
agactctgtt ctgtcttcat ttttttagta atatttctaa ctcttgtttt ttagctacaa   6780
ggatggcata gtggtgataa ttgacatcag taagaaagga gaagttattc ataggcttcg   6840
aggccatgat gatgaaatcc actccatagc ctggtgtccc ctgcctggtg aagattgttt   6900
atctataaac caagaggaaa cttcaggtag agatggttta agggaaagtt aagtccactt   6960
gagacctgaa gaacagaacg ggtacaatta tatcattttt tatttattat ttatttttgg   7020
agacggagtt ttgcttttgt tgcctaggct ggagcgtgat ctcggctcac cgcaacctcc   7080
gcctcccggg ttcaagcgat tctcctgcct cagcctcccg agtagccggg attacaggca   7140
tgcgccacca cgcccagcta attttgtatt tttagtagag acaggtttct ccatgttggt   7200
caggctggtc ttgaactccc gacctcaggt gatccacctg cctcagcctc ccaaaatgct   7260
gggattacag gcgtgagcca ctgcaccagg ccgaattata tcattttaat tatacctaaa   7320
```

```
acttcaaatt ttatagttca gacctatgaa agagatagct aagttttgga aactcttgca   7380
aactaatttt tttatattag tgcgtgttta atgtaaatta aaaacaaaat tgccacctat   7440
ctcatagaag aagctgaaat taccaacggg aatgctgtag cacaagctcc agtaacaaaa   7500
ggttgctact tagccactgg aagcaaagat caaaccattc gaatctggag ctgttctaga   7560
ggccgaggta agattgatct ttcttttgtg atgtaaccta tgttgatctg gtggaagtag   7620
agggttttct gttcttattg tcctgagggt gtgtcatcta tttgagagca gttcttcact   7680
ttttggtcta gaattctgct tcctcatttg agcctggcct agactctcta ttctctcaac   7740
atctggcctt agagattagt atttcccatg cattccagga gaagacaagg atctcttgct   7800
ttatagaagg gtcagtgttt ggcatggaga gcagaatatt tgtaataaaa acaggaatat   7860
tagaacatga tatggcctaa gccaggagaa tggaaaatat cttaagagtt agagctttta   7920
atgcacaaat gcagaataaa ttacatacac ccagcataga attatgtgta aaagctcatt   7980
ttatccaaat tatagagccc ctcaatcatt tagctttccc aaatgtctct ttgaacagaa   8040
cttttatctt taagtttaaa aattgagaga aactctaggc ataatgaata tttatagtat   8100
atcatagaat ataaccttta tagtaaaaat cttgtttttc tctttctagc gggcttctct   8160
tctttcttca ttttatttta tttttttgg cagtttttta agctgtggtg gaaaatataa   8220
catttgccat ctttatcact tttaagtgta catttaagtg gtatgaagta cactctaaag   8280
ttgtgcaact gtcacagcca cccatctcca gaattctact ctccatttcc ccctccccca   8340
ggccctggca accatcattc tgctttcagc tctatgattt tgactactct gagtatttcc   8400
tttgagtgaa gttatacata tgatatgtct ttttgtgatt ggcttatttc acttagcata   8460
tatccccgag gttcattgat gttggtaccg tatgtcagca tatccttcct ttctaaggct   8520
gaataatatt ccattgtgtg tatgtcccac attttactta cccactcatc cacttgttat   8580
aaataaaatt tcggtgtggc aaaagaaata gcactcaaat ataaaacttt ctttttaatt   8640
ctcagcaagg caatgtactt ctatagaagg gtgcgccctt acagatggag caatggtgag   8700
cgcacacttg gacaacggag gggaggggtt cttatccctg acgcatgtgg cccctgctgc   8760
tgtgtcgttc ccctatcagc tagggttaga ccgcacaggc taaactaatt ctgattcgct   8820
gatttaaaga gagtgccggg gtaagtggtt tgatgggaga aaatggttat ggcaggaaaa   8880
atggttatgg cagagcagga aatcagaatg agtcagggtg gagcaggtaa tcggaatgag   8940
tcaggatgga gcaggtaatc gaaaaaggtt gcttttacga ggaagttaag tttaaaaaca   9000
gaagccaaat aattgaacat actgacatat tgattctttg aagagaaatt tagaactcat   9060
atctcacaca ctgatggaca tttgggttgc ttccatgttt tactattcta aataatatgc   9120
tatgagcatg gatgtacttt ctactttatt tgaaaccatg atagttttat catatttgcc   9180
caaatgcatg taaagcaagt agcacagcac ttggaatgtc atccaggctt catcagtggt   9240
aggtaactaa tagtataatt tgggaagaca gaactttttt aaggtttaca ggctacttct   9300
tggcatactg cagctaaaac tccaagtggg aacataaggc tgaggatccc tccaggaggg   9360
taacctctag acttagaggt gtctggtaaa atggccttca attgtggttg tgcagcagaa   9420
tcagctggag agtctttgga aaaatgtagg ttcttgtacc ccacctcaga tctactgagt   9480
ccgaatctct aggagttagg ccctggcgta tgtatttttt aaagttccac ctgtggttcc   9540
gatgcacaat acagcttaaa aaacggtgat tagaagcatg tcgggtggag gtactcccca   9600
cccacagcac gttcactgcc aaatttttct ttgttggatt tcttgccgac tagaaatagt   9660
aatcccaacc tctgtccttt tcactttgga gttatgtcac tgcaatactt ttgggtacac   9720
```

-continued

```
aactcagctg tgttactagc tgggttctca gttttacttg ggaactcatt ttcccagacg    9780
aaaaaatact ctttttcttt tgaggcagag tctctctctg tcgcccaggc tggagtgcag    9840
tggcacgatc tcagctcact gcaagctcca cctcctgggt tcatgccatt ctcctgcctc    9900
agcctcccga gtagctggga ctacaggtgc ctgccaccac gcccggctaa tttttttgta    9960
tttttagtag agacagggtt tcaccatgtt agccaggatg gtctcgatct cctgacctcg   10020
tgatcctccc gcctcggcct ctcaaagtgc tgggattaca ggcatgagcc accgcgcccg   10080
gccaaaaaaa aaaaatactc ttaatacgtt gaggttgtca agatagcctg tcgaagcttg   10140
tttgacctaa atgtagctag actagtatta accagtattt atagtgatta aaattataac   10200
cataataatg gttaaaattg taaccattgg aaaatgagat ctgaattcta agtagccaaa   10260
ctaacaagct tttacagcgc agactgtgtg ttatgaacca ccggtgactt catgcatgta   10320
gtttcactgt cttgagtgcc cactggcctt ctttttaatc tgcaggggtg atgattttga   10380
aattgccctt tctgaagaga agaggagggg gtatagaccc aactgttaaa gagcgccttt   10440
ggttgacact ccattggccc agcaatcaac caacacagct ggtatctagc tgttttgggt   10500
aagtcttttt tggtcatgct ttctcagata tattttgttt ttctatttgg cctcaagtcc   10560
tcctaggatg gagaaagtaa tggccaaggc ttgtattatg atgggccatt tgaaatggaa   10620
aaattatgag actaatgcct gtgctatcta ctaacagagc tgtaaaaaga tcacataagt   10680
atagtccggc agttaggaat atggactctg aagtcagaac taaatttcag aatcactttg   10740
tcacttactg ccttgtattc ctgagcaaga ccctttactt ttctgagctt cagtcacttc   10800
aagtgtagaa aggggagatg gttataatat tttctcttag gttggatggc tatgcccatt   10860
cagtaaacaa agttcattga ctacctactt ctagtggctg gagataaatc tgtttaaagg   10920
gtagtccaat atactcacat ggttcaagaa gaacgaaagt atataataaa ctgtctttct   10980
gtcttcccta gctacttggt tccccttctt gtgattaaat tttttttttt ttttgaaaca   11040
gggtcttgct ctgtcaccca ggctggagtg cagtggtgca aacacagctc actgcagcct   11100
caacctcctg ggctcaagca attctcccac ctcagcctcc caagtaactg ggaccataga   11160
tgtgcaccac catgcccaac taattttttt aattgtttgt agggacggtc tcactttgtt   11220
gcccaggctg gtcttgagat cggggcttca agcaatcctc ctgccttggc ctcctagaat   11280
gctgagatta cagatgtgaa ctactgcacc cagccttccc agagatattt tgtgcatatt   11340
ttcagcatat gcaatttttc tctccttaaa cgacaacaaa tcattttgca gctatgagcc   11400
cagactctgt ctcaacagtc acttgttttc agatcgtttg taaaagaact aatgcttatg   11460
tttttccttc acagaggtga actgttgcaa tgggatctca ctcaatcttg gagacggaaa   11520
tacaccctct tcagtgcctc atcagaaggg caaaatcatt caagaattgt gtttaattta   11580
tgtcctttac aaacagagga tgacaaacag ctattacttt ctacatcaat ggatagagat   11640
gtaagaatgc ttattttcac tcagcattgt agagcagcag tttacaactt gggtgggatg   11700
agagggcttt ttcaaagcac ctgtcaagtc gtaatactcc acccctgact ccaatttcag   11760
agttactgct acagatcagc actgaatata tcaatagctc acatgtaagg agaatgtgaa   11820
gacccaccaa aatagttttt tgttaaagca gacataataa agaagggtag ttttgcccag   11880
ggaaggatgt attaggtcaa gcttgtccaa cccacagctc aggatggttt taagttcatc   11940
agctgttgtt agtgttagtg tttttttttt ttctgagaca gagtcttgct ctgtctccca   12000
ggctggagtg cagtggtgtg atcttggctc actgcaagct ccacctcccc agttttacgc   12060
cattctcctg cctcagcctc tcgagtagct aggactacag gcgtgtatca cctacgccca   12120
```

```
gctaatttt tgtgtgtgtt tttagtagag atggagtttc actgtgttgg ccaggatggc  12180
ctcgatctcc tgacctcgtg atctgcctgc ctcagcctcc caaagtgctg ggattacagg  12240
cgtgagccac ggcgcctggc ctagtgttag tgtacttttt gtgtggccca agacaattct  12300
gcttccagtg tggccccaga aagccaaaag attggacacc cctgtgttag gtcctcatgc  12360
tatggtttat cctggtttgt agtgtatgta gcagaataga aatctttcag agagaattga  12420
ctttatttga aagcctatta ccttactgtt ttgcagttaa gctaggctta tttggtagac  12480
ttcattttct cccaagcctg tctcttaaac aagtgatgat taaaaattta ccactcctcc  12540
ttccctgggt atgataaggt gttttgcctt ttgagagagc agttctttga tttttccact  12600
gtgctgaggc catcttcttc cttagagttt gccaaatgag gggttacca gtgctataat  12660
aggacagaaa gaccaccgaa cttggagaca ggaggcgtgg gttctggttt attaattgtg  12720
taaccctgaa ttcacgtgac atctttggga ataaatatat tttaagatcc ctttaagcaa  12780
cataatttat tactattttt tttttcttag cagtgctttc ttcaattcct gctggaagac  12840
atgcattatc cttacccagt ctttgagcct atcccatttg acatatcagg tttttttttcc  12900
tatttctctg ttctttttta tgtttaggcc cttaccgtta atctttgcag gtaaaatgtt  12960
gggacatagc caccttggag tgcagctgga cccttccttc ccttggtggg tttgcataca  13020
gcctggcttt ctcttctgtg gacataggct ctttggccat aggtgttggg gatggcatga  13080
tccgtgtatg gaatacactc tccataaaga acaactatga tgtgaaaaat ttttggcaag  13140
gcgtgaagtc caaggttaca gcggtaagga ttcttttttt gagcttgttt tgaacttttt  13200
tttttccaaa taattctctt ttatgcctgt tcatttaaat gcgctctgtt gagaatcaaa  13260
agttttaaag tattttcaat gaagtttgaa actaggaaag cagaatgatc ctgtaaccaa  13320
acccattatc ctccagagtt taaatttatt aaggctctgt tcatctcagc atttttteta  13380
atagtaagaa gttagaaata gcctgactgt atattcatag aaaatgcgtt aagttataag  13440
ataaccaaat gttggaatgg catcaaatta ttgaaaatga taatgtagat tccttcttcc  13500
ttgatgtgga aaggtatata aatgatttat gaaaaatgtc aattataaaa catggaaagc  13560
aggttataaa acagtatgtg taattttttt ggttttctct aaaatgatac ctttcttttg  13620
gctattgaat ctaaaggtaa taaattttta tggtttaaaa agaaaatcaa acaacacaaa  13680
aatagagaaa ggaaacattt ttttcctacc ctaccctcca ctccagtccc ccacttgaat  13740
aatccagaga accactgtgg acagtttatg atctatcttt tcaaattttg taaactattt  13800
aatattaata gaactgtatt ttctaaattc ttccagaatc tcttattccg actcgacagt  13860
gtataatgca tatcatttac gtatttgaac tcatttgttt ttttcaattg tgtataagtt  13920
tattcacaaa aatatctgga aagagagata caacatctgc agtcggtttt ttgaatgaaa  13980
gattacagat gacattgact ttgttttttt tgttgttttg ttttgttttg ttttttgaga  14040
cagagtctca ctctgtcgcc caggctggag tgcagtggca caatctcggc tcactgcaag  14100
ctccgcctcc cgggttcacg cctttctcct gcctcagcct cccgagtagc tgggactaca  14160
ggcgcccgcc accacgcctg gctaattttt tgtattttta gtagaggcag ggtttcactg  14220
tgttagccag gatggtctcg atctcctgac ctcgtgatcc gcccgcctct gcctcccaaa  14280
gtgctgggat tacaggcgtg agccactgcg cccggccgac tttgttttta ataccctttt  14340
tctcctttaa ataatgaaga aatcagagca agacagtttt ccctttggat gcttaaaggg  14400
taatgtaagg attcctttaa ctatatgccc cacttcttat attctcactt ggaaactctt  14460
tttttgtag ctgtgctggc acccaaccaa ggaaggttgc ttagcttttg gaactgatga  14520
```

```
tggaaaagtg ggattgtatg acacctactc caacaagtaa gaaatgggtg attcttcttc  14580
cattgtggcc cggggagcca aaaggttggc cacccctgct ctagaataat ccctcacttt  14640
ccttttcata acgttgcctt ttcaatttga agaccacaaa tcagttgttt ggtagactct  14700
tccacatttt ggacttgtca gttatctcct tgtggtagct tctaactcat ttccctgttc  14760
cctatgtttc gtatgaacta gaagttatgt ctagaactac attctccact acagtagtca  14820
ttaaccacag gtgattactg atcacttgaa aggtgccaag tccgaactga gatgtgctgt  14880
aagtgtaaaa tacacaccag agttccgagt cttaatattt aaagaaaatt aaaaatctca  14940
ataattattt tattttgatt acattttaaa taatactttc agtgggctga gttaaataaa  15000
atacattact aaaattttac ttttttcttt tgcttttta aaatatggct actagaaaac  15060
tttaggttac atatacagtt catctttgtg gcttacattg tttatttttg tacaccgctg  15120
ctctagaggc ttgattagaa tccagacctg tgttgttcag tctggtagcc acatgtggct  15180
atttatactt aaagtaatta aaatgaaata gaaattcagt tcctcagtca cactagccct  15240
attttaaatg cacaagaggc atccgtgact aatggctacc ttattgaaca acactgttct  15300
agaccaggcg ttggtgaacc atggtccatg aattaagaat ggttttgctt tttaagtggc  15360
tggagaaaaa tcaaaagaat gttttatgac atatgaagat taaataaaat tcagatttca  15420
gtgtctgtaa gtgaaatttt attgggacat ggctgcactc ctttgtttac attctgtctg  15480
gctgctttca tactaccaca gcagagtgga gtagttgtgg cagggaccac atggctcaca  15540
aagcctgaaa tatttacaga aaaggttggc cagcctctgt cttagatcat tcatttctga  15600
gtgaaaatca tttatgatac tgcagagctg tcctttttt tttggagaca gagtttcgct  15660
cttcttgccc aggctggagt gcagtggtac gatctcagct caccaaaacc ttcgccttct  15720
gggttcaagc gattctcctg cctcagcctc ctgagtagct gggattacag gcatgtgcca  15780
ccacacctgg ctaattttgt atctttagta gagacagaca gggtttctcc gtgttggtca  15840
ggctggtctt gaactcctaa cctcaggtga tccaccctca gcctcccaaa gtgctgggat  15900
tacagatgtt agctaccgtg cccggccaga gctgtccttt gtatatgcag ttcttgaagt  15960
attcatgtag aacctacatg cagttgacta ttctcctttt ttaactctca aaaaagaaca  16020
ctattttaag gcctggcacg gtggctcacg cctgtaatcc caacactttg ggaggctgag  16080
gcgggcggat cctgaggtca ggagattgag accatcctgg ctaacacggt gaaagcccgt  16140
ctctactaaa aatacaaaaa attagctgga tgtggtagtg ggcgcctgta ttctcagcta  16200
ctcgggaggc tgaggtagga gaattgcttg aacccaggag gcggaggttg cggtgagccg  16260
agatcgtgcc actgtgctcc agcctgggca acagagcaag actccatctc aaaaaaaaaa  16320
aaaaaaactg ttttaaagat ttatttaaag tacactgttt ttaatcaaat aaaacttaaa  16380
tagttctata tcaccatgaa attgctaatt ctattaaatt attatatcct ggttattata  16440
agctgaatat tcagactaac agtacaaaag ccatgtaata gccagagagt ggtgggtatt  16500
gccctagagc tattgttagg cattttgcca gaactgctta ttctatttct tttagatata  16560
ggctaaagta ggccgggcac agtggctgcc agcactttgg gaggccgacg cgggcagatc  16620
acgaggtcag gagatcgaga ccatcctggc taacactgtg aaaccccatc tctactaaaa  16680
gtacaaaaaa ttagccgggc ttggtggcag gtgcctgtag tcccagctac tccagaggct  16740
gaggcaggag aatggtgtga acccaggagg cggagcttgc agtgagcgga gattgcacca  16800
ctgcactcca gcctgggtga cagagcgaga ctccgtctct aaaacagaaa aaaagaaaat  16860
aaataggcta aagtataaat tagcctgttt ataaaatata aatttctttt agaaattttg  16920
```

-continued

```
atttattctc tagattgatc actataaatt tgtcagataa atggaagtaa gtcagctgct  16980
aattattcat aggctctgga attctacaat catacaaaga atgtatgata atttatggta  17040
aaagaaataa caatgctgcc tggttttttc tacaaagtta agcattcttt actgacacat  17100
cacatatcat taccacaaca accttcaaaa atgctcttag gagtacgcct tctttaaaag  17160
acaatcacaa actgaaaatc tctctaccct gaaatcttgt ctcaatttag gaaatgtgat  17220
gttaatggca cagagtaagt ctaaaatgac ttctcatctt ttacatgacc gtaaagtgaa  17280
tacatttggg tggtgataat atatgttctg gctagatggg taagagtaac atttttttggg  17340
gggtaaaata tgtttgggac ttaatcgttt tggtagtaaa tgtcattatt tgatatttaa  17400
atataattta aatgtaaata ttatatgata attaactgct ttacagtcaa ctatttggag  17460
caagatattg ttgaattatt tttctccaat tattagtagt tatgtttata atggggacct  17520
tttagaaaaa gatggtctgt ttttcattat gcctttttgt ttaaatctcc atttgttctc  17580
tctccctgct cttctaaagg cctccacaga tttctagcac atatcataag aagactgtat  17640
atactttagc ctgggggcca ccagtacccc ccatgtcact tggtaagtat ctgaacaatt  17700
ccataacaaa tatgagagta ttcttccttc agtttaatcc taaaatatta aagatggaaa  17760
gagtcataaa tggtctagtg cactgactgc ttatgtgggc tacttatgtc cccaggggtt  17820
catgaagaca gtagtggcag atgataaatc acagttcctg ggagaaacca tttacccata  17880
ataagcttcc ccaaactcac taaagcattg ttcttctatt tgatctgaaa tttttcattg  17940
tatgtatagt tatcatgctg ggtcctgata cccagtctaa tattcttcac taaaacttgc  18000
tgtctctttt taattttatc agaattagaa tgatacttca gtatattaat ggaataatat  18060
ctattttcac ccacaggaaa agcaaactta gagtttctga aatgatctct tgcctttgat  18120
tcagcattct gctcctttcc ctcttctagc ccctcagcct tgtctttctt tttcttattc  18180
ctaaagtaat gagtcttttc tattagcttt ttacataagt gtattcatca aaagtctctg  18240
ataaactttt cttaaccatc tatgatgaaa catctgtaaa tttctatagg aattgcatta  18300
catagagagg ataagtagat ttatcagaac tcaagtagca ttggaatttg tagttcattt  18360
atgcaacaaa tgtttactgg gtatttgatt tgtgatctac cagtggtaaa agtaaaactt  18420
gctcttatag aaacccacca gaattactgt ttgcttctta aaaattaaca agaagattgc  18480
tgtgatacta aggaaatcac tgctttgatg acatctcttt gttataagac atagaaagtc  18540
ctactgtgct atgtaattcc caaagagtac tcatttctgg aagaaaaagc aaattctcag  18600
aagcttttga gaacatatat gtttgttttc tgatcccagc ttttggaccc ctattattat  18660
gaataccaga agactgttta aagcaaatat gttacatcac ataaattaac ctagaattat  18720
agtagtatag ttttttttact tctgctccca acaactgtgt tcaggtggaa agaacagtga  18780
ttttattcca atgtattaga atgtttcaaa tatatagttc ttttaaaaca actatgtagt  18840
atggtatggt catactatag caacaaatag ttaagctgat gaagtacaaa actgataagt  18900
ttcttttctt atttcataca ggaggagaag gagacagacc ttcccttgct ttatacagct  18960
gtggaggaga agggattgtc ttacagcata atccctggaa gcttagtgga gaagcctttg  19020
acatcaacaa actcatcagg gacaccaatt caatcaaagt gagttcttgt ggtcctgaag  19080
tattttcttt ttacatcaca gatccctctg tgtttcccat cttgcaaaat aaatgctgtt  19140
attggagatt accatcatca tactaagtca gatttcttaa atgttcttat aaggctgtgc  19200
atgaatttgt gagttatata tcttaggagt ctttatcctc gaataaaaca aagaggtact  19260
tctcagacag tgagtatgag gcaaaaaaat aaaaaagcca aaaaagaact actgaaaaaa  19320
```

```
aggtctgtct caattgcaac aatgatttat tataaacttt caggtgttat gtataaagca  19380
tccttttcag gccaaccact ttcaccaaag tgatgctgtg gtaaaaataa caataatata  19440
gtatccaaat gcaactgcat ggtgttttac tcaagacaaa attgtcattt tgtttttaat  19500
tttctagtaa aatgattcta gatttacacg aagctacaaa aataatacac ataatttgct  19560
tatatccttt acccagattc ccacatttaa ttacatttgt gttctcatgc tatcagtatg  19620
tgccagaact gtctttttaa agtcatacct taaatgttga gatttcctta tttccttacc  19680
ctttttgtg tgtgtgacag agtctcactc tgtcactcag gctggagtgc agtggcgtga  19740
tcttggctta ctgcaacctc cggcctccta ggttcatgag attctcctgc ctcagcctcc  19800
caagtatctg ggactgcagg catgggccac catgcccagc taatttttgt attttttaag  19860
tagagatggg gtttcaccat gttggccagg ctggttttga acttctgagc tcaagtgatc  19920
cacctgcttt ggcctcctta ccctttcaaa tgagtatttt tatttattta cttatttatt  19980
ttttgagaca gagccttgtt ctgtcgccca ggctggagtg cggtggtgcg atctcagctc  20040
actgcagcct ccacctcctg gaatcaagtg attctcatgt ctcagccacc tgagtagctg  20100
ggattacagg cacgtgccaa gactggctaa tttttgtgtc tttagtagag acagggtttc  20160
accatgttgg ccaggctgtg atctcggact cctggcctca agtgatccac cccacttggc  20220
ctcccaaagt actgattata ggcatgagcc accatgccca gcccaaatga gcatttttat  20280
attattgctc attactttta tggctagtat aaaagtaaca tttagttata aattgggtta  20340
tattgttgat tatattccct cattgtcttt aattttatct aaacattaac attcagcaat  20400
gaataagaga caaaattcgt gttcctaagt ctcttctaat ttattggcac ttgaatgtgt  20460
ggatcagagg ttcatgctag gagtctgagc tggatataga aattttgaat cccttcacaa  20520
taaagatagt tgaagaagct gtggacatgt atgaggtggg ttaaagagac aattaacaag  20580
agaagagggc ccaggcagcc ttggggaata ccagcatata gatatgggag ggaaatgatt  20640
cagggaaaga agctttgaag ggatagaaaa caaggagagt gtatatagtt ttctttaagg  20700
cctcatggtc cccacattgt ccaagctgat gggcacagat cagtttaatt aagtatatat  20760
ttcacaaggt taagcactgt aaacatttag tacttattgg ccttgggggt ttttttgttt  20820
tgtttttttg gcccagttag gaaatgagaa ttagaatgca tgttcttagt aatcctttta  20880
ctaattatgt agattattta caagaatagc tgttgtataa ttaaaacgtt tttaaactct  20940
agggattttt ttttctcatg ctgtcattgc tgatttgtga gatatgtata tagtcaagat  21000
tggtttgttt tgctttctag tacaaattgc ctgtacacac agagataagt tggaaagcag  21060
atggcaaaat catggctctt ggcaatgaag atgggtatgt atttgcttct ttaagataaa  21120
aaatttgcaa tcgcacatat atttgatcac aagctgacta atgccatctg taatgttagc  21180
tggggcggcc cagttgtatt tggtattttg atttattctt gatatcctcc gctgatccag  21240
tagtgccttg tgtctttgag aactacagaa ttatttagat attttcagcc cattgagagt  21300
atttggctac actgtatttt ggctgtcttg tccctcacaa aatggtcacc tcctatgttg  21360
aactgcataa atctccattt ttttaaagta agcctagtca gaaatgcttt ttaggtctgt  21420
atcctgacca gtgttaatca tagtaacaca gtcataattc agccattgat ctgttaatta  21480
ttttagcttc tccctatcat catttgtcat taatgcctga tgaacacaat tttatcaagc  21540
attgttagaa tgctaggaga ttgttacact gaggtagtgt ggaaagttaa aatttctaaa  21600
aattaatttt tttaagaaaa gaattgttag gatattgcta gaatttttaa aagctaaata  21660
tactttttgg agaataactt tttatacttg attttttatg agagaatgac ctttgcagtg  21720
```

```
atagaaaggg ttatcctttt ccacctcatc tttccttgac tgacggaatg agggagctac  21780
tatttgcatt gtaacttgta atttgatcat ccatctttct tgttttgatg tgtttcttat  21840
tccagatcaa tagaaatatt tcagattccc aacctgaaac tgatctgtac tatccaacag  21900
catcacaagc ttgtgaatac cattagctgg catcatgagc atggcagcca gccagaattg  21960
agctatctga tggcctctgg ctccaacaat gcagtcattt acgtgcacaa cctgaagact  22020
gtcataggta actttggttt ctttcatact ggggatgata tcgtttgttc agctactttc  22080
cattctaatc tttgttactt tttactttat ttttgacatt ataataaaat aagtattatt  22140
cttactactt tttctgtttc aaaagtgata gattcatctt attttaaaat tctttcaaac  22200
atgacaaaaa tggtaacaga aaatgaagtt ggccaggcac agttgctcac acctgtaatc  22260
ctggcacttt aggaggccac aacgagaaga ttatttgtgg ccaggatttt gagaccagcc  22320
tgttaaatag tgaggctccg tctctacaaa aaattgaaaa taaaaaacaa atttgccggg  22380
ttagaggtgc atgcctttag tcccagctac ttgggaggct gagctgagag gatcatctga  22440
ttctaggagt ttgaggctgc agtgagctat atttgcacca ctgcacccta gcctgggtta  22500
cagagcacac cctatctcaa aaaagaaaga aaaaaaaatg aagttttccc ctaaaatttc  22560
atcattcaat aaccagtgtt attggcttgc tatatatttt ctctagattt tataaagtca  22620
tagcctacat atgtatacat gttagtatat attaataggt ttgcacttct gtgtacttgt  22680
gtgaaagaat aatcttctgt tcctagctaa aaataaattg ctatatataa tatatagtgc  22740
ttgcagtttt tttctctaaa tttacaatat ttatcatgga catcttttta tgtcagtaca  22800
caaggatcta tcttgctgtt attaacaaat atctgtcagc caggcgcagt ggctcatacc  22860
tgtaatccta gcactttggg aggccatagt ggaaggatag cttgagacca ggagtttgaa  22920
accagcctgg gcaatgtagg gagaccccac ctatacaaaa aataaaaatt aaaaaaaaaa  22980
cagttacctg ttcattccat tatatgggct taccataatg tatccattcc acaattaaat  23040
gacattcaaa ttatttattt ttttttacaa tttaagtagt attacaataa actgccttat  23100
acatagatct tcgtgaacat gaatgaataa tttttgtata gaaaattcta gaagtggaat  23160
tgctaggtaa aaagatgtag ttttttatac ttactgctaa gcggctctcc aaaaacatta  23220
tgccatttaa tacttccgcc agcagttttt gagtgttaca cacaaacaga ggacacatac  23280
ctcattcccg tgtttgattg catctgattc tcacaatcct gtgagggtga taggtaacgt  23340
tatcctcatt ttcccaatga ttacactgag gcccagaaag gttagctaac ttattcaagc  23400
aagtagcatc gctaatacat gatagggcct agattcaacc ttagagtgtc taattgcagt  23460
gtctgtatgt gttctagcaa gtactattcc atgcttaatg agttaacttt catatgggta  23520
taatttattc cataagaaat cttaaatttc actgaggccc cttcggcacc tggaaaacca  23580
tagtaggtgg tcagaagagc cagttttaaa tatgagtgaa gtgggattac tttttttcct  23640
aatatgaaga aattataatc tgacactaaa ttgttttcag agtgctataa aacatgtgct  23700
ctcagccata gtgaaaatag ttacattttt catttctcta gaatttactt cagtagtttt  23760
ctaagaatcc tatgtgtaac aagaaaaaat atttttggtt ctagtagtga ctcctgagtt  23820
aaaagcaata tggaaaaagt attaaaatgt agatgtgttt tcctagtaat aaatagtaga  23880
cagtgtataa ctaatgaaca taagttagaa agctgattct ggtccttatg attattattg  23940
ggattctaaa ttaatcatcc actttatatc atatctacta aataatagag aaaggaagaa  24000
aactgccaga atccatttta atttttacct tcttattttg aaatatttga gacacagagg  24060
aaagttataa gaattgtaca aagaaatcgc atatactttt tcctattaat agattcaaca  24120
```

```
atttttaatg tgttgtcata ttggctttat tctgtgtgcg tgtatgtatg tagtttttcc 24180
taccaattat cagtttgtta gtttaactta atatataata gtttaatctt tcccttaaaa 24240
tatacacaac tattatttgt caatttaaac aaatagttta ggctacgtgt ggtggctcat 24300
gcctataatc ccaacacttg aggagaccat ggcaggaaga tcacttgatt agctggacat 24360
gatgggtacc tataggccca gttactcaca ggctgaggtg ggaggatccc ttgagcccag 24420
gagttggagg ctacagttag ctatatgact gtcactgtac tccacccttg gccacagggt 24480
aagacctagt ctctttaaaa aaaaaaaaaa aaaaagtaaa atagtgtaat cagccaccca 24540
tattctagtt gtgtcagttg atccaatgat gttcttaata gtgatttttt ttttctccag 24600
tgcagattcc aatgcaggat cacctatttg cattttgttg tcatgtctct ttagtctcct 24660
ttcatctata ataatttctc agtcttttaa aaattattta tttaggccgg gcgtggtggc 24720
tcacgcctat aatcccggca ctttgggagg ccaaggtggg cggatcgcct gaggtccgga 24780
gttcgaaacc agcctggcca acatggtgaa accctgtctc tactaaaaat acaaaaatta 24840
gctgggcttg gtggtgcatg cctataatcc cagctactca ggaggctgag gcaggagaat 24900
ggtttgaacc tgggaggcag aggttgcatt gagccgagat cgtgccattg cactccagcc 24960
tgggagatga gtgaaactcc atctcaaaaa aaaaaaaatt atgtgtgtat ttatttattt 25020
tttagaaact gggtctcact gtattgttca gggtggagtg tagtggtgca gttatagctc 25080
atgacagtct ccaattcctg gactcaagcc gtcctcccac ctcagtctcc tgagtagttg 25140
ggactacagg cacataccac catgcccagc taggttggtt tttgtttttt gtgttttcct 25200
ttttttttga gacagggtct cactctgtca cccaggctgt agtacagtgg cacgatctca 25260
gctcactaca acctctgcct cccaggctca agcagtccac ccatctcagc ctcctatgta 25320
gctgggacta taggtgtgca ccaacacacc cggttaattt ttgtattttt tttttagagt 25380
cagggtttcc acaggccggt cttgaactcc tgaactcaag caatttgccc accttggcct 25440
cccaaagtgc tgggattata ggcgtgagcc gacacgcctg gccaagccag actttttaaa 25500
atcttatgtg acacttttga ggaagatagg gcactcgttt tgtagatgct ttctcatttt 25560
gcatttgtct ggtattttct catgactata ttcaaattat acattttagc tagaatatcc 25620
tataagttat aatgagacct aacacttctt gtggtaatct atatgctaag cactgtggat 25680
gtgtccacac tcttaataac taacaatgtt gcctgctaaa aatcacctag acttgggagg 25740
ctgaggcagg agaatcgctt gaacccagga ggcggaggtt gcagtgagcc gagattgcgc 25800
cattgcattg cgccattgca ctccagcctg agcaacaaga gcgaaactcc atctcaaaaa 25860
aaaaataacc tagaaagtgt atggcaaaat cttgattctt gtcatgtgaa tgccttcctg 25920
gatgtacttt gttttgtttt ttgttattag tagtagcagc agtgatgtct ttcctttgcc 25980
ttttagagag cagccctgag tctccagtga ccattacaga gccctaccgg accctctcag 26040
ggcatacggc caagattacc agtgtggcgt ggagcccaca tcatgatgga aggctggtat 26100
ctgcttccta tgatggtaca gcccaggtac tattgtgtcc ttgtccctgt gggtccttca 26160
ctgtgtactc taacaaattc tttcttcttt tcccccagtt gtgaacaggt tccccctccc 26220
ccattatcat catctactga aggagatttt ctgggctcta ggaggcattt tagtttcatt 26280
ccacataggg cctaggctaa gactgggttt tttttttgt tacttagatg aaggggaaag 26340
tattgatagg agctagctaa ctctaacatt tttacagatt tcattctgac tcactatcag 26400
tatggtggac taatatgata tgcaaagtac tctcttctgt tcagacactg aaatgttggc 26460
taaaaatcac aaaacaattt tttaataata aattggtaag tcagaaatct ccaagttcta 26520
```

```
aataaataaa gatgaaatgc caagccagat ctatgaggga ggacttgtgg atatcagaac  26580
tagagctggg gacttaacat ctgtgatgta tctcgcttag tgttgagttg taattgagat  26640
gtctgcacaa agctgggagc cgcaaagggc tgccttctgt gaaactgagt tcagaataat  26700
tcaagaaata gaaaggaaat tggccaatta ctcaaggagt tggagacaaa agattcacct  26760
atgagaaatt agaagtctaa tttctgtgct agatgtgggc tattttcttc gtgataccag  26820
aatctcaagc ccaaaagtta acatacagta ttggttcgag acagtgaaat ccatgggaca  26880
ccagtagaag ctcattcaaa atcatccccg tagaaatgtc tatgcatctc caagcacaga  26940
agtctctcac aggaaatagc actcttctga aattgaactt ctaagagaaa actctaaatc  27000
acctgaggaa ataagaggcc gcagattgtt tttgtttttt gtttttttgtt tttaattaga  27060
aaacatactg cccaaacaat agaataacca gaaaatgtct tttcggccat gtgcttttgg  27120
gtttaggtgt gggatgctct ccgggaagag cccctgtgca atttccgagg acatcgaggt  27180
cgactgcttt gtgtggcatg gtctcctttg gatccagact gcatctattc aggggcagat  27240
gacttttgtg tgcacaagtg gctcacttcc atgcaagatc attcccggcc tcctcaaggt  27300
cagtcagaac ctagagctta tctaattctt tttctccctt tcttaataat tgagttgatc  27360
aggattgagc aaggaagaca ttcgtgtagg gcattagtgt cagtagggca ggggtctgag  27420
cctaagcaag aaagcagcca caagggcttg agaacaacac cacccacaat aggaaagagc  27480
atacctagca ctcagatctt ggtttctttt ttgagacaga gtctcgctct gttgcccaga  27540
ctggaatgta gtggcgtgat cttggctcgc tgcagcctcc acctcctggg ttaaagcaat  27600
tctcgcacct tgacctccct agtagctggg actacaggtg cgcactacca tgctggctaa  27660
ttttttgtg tttttagtag agacgggatc tagccatgtt ggccaggctg gtctcaaact  27720
cctggcctca agtgatctgc ctatcaacct cccaaagtgc taggattaca ggcatgagcc  27780
accgtgccca gcccagatct tggtttctaa atgacattct ccactaaaaa tgtccatggc  27840
ttcttggaga aatggctggt tccagtctgg gacaggtaga gaacaaactg aacctggaac  27900
attcttatgc cagaaaggaa ggcagtactc aaagaattca ggagacatgt caaaaggaca  27960
aaagaaacag cttgaagagg ttcccactga ccaaatctgg gacaactgtt aaacataagt  28020
aagaggaggc caggtgcgat ggctcacacc tgtaatccca gcactttggg aggccgagat  28080
gggcggatca caaggtcggg agatccgaga ccatcctgac taacaggtga aaccctgtct  28140
ctactaaaaa tacaaaaaat tacccgggcg tgttggcggg tgcctgtagt cccagctact  28200
cgggaggctg aggcaggaga atggcgtgaa gccaggaggc ggagcttgca gtgagccgag  28260
attgcgccac tgtactccag cctgggtgac acagcgagac tccgtctcaa aacaaaaaaa  28320
agagaaagta agaggaaaat tccattcctg gctaagaaag attaattggt atcagacttg  28380
ccataagcaa ctagaaagct agacaaaata tattaagcaa ctgctgggca cagtggctca  28440
tgtctgtatt cccagcactt tgggaagcca aggctagagg atcacttgag gccaggagtt  28500
tgagaccagc ctggcaacag agcgagatcc catttctacc aagaactgca aaataaaagc  28560
aaataggaaa aattggccaa gcatgctggc tcactcctat aatcccaaca ctttgggatg  28620
ccgaggcagg aggatggctt gagcccagga gttcaggact aacctggaca acatagggggg  28680
acactgtctc tgtgaaataa gttttttttt tattttaaat gaaagaatat attaaacaac  28740
tagaaattta cacccaaaga aatgaaatga tgtgtccaca taaagacttg taaaagaatg  28800
ctcatagtag ctttatctgt gatcaccaaa aactggtaac aatccaaatg tccatcatca  28860
gataaatgaa ttaattgtgg tatatcctta cagtaggctt ctattccaca ataaaaagaa  28920
```

```
ggtaacaact gataaagaac aaaatggatg aatctagaaa aacattatgc caagcagaag  28980
cagccaggca caaaagacta catactgtct aattctgttt atgtgaaatt cttttttttt  29040
tttcttgaaa cggagtctta ctctgtcacc caggccagag tgcagtggtg cactctcggc  29100
tcactacaac ctctgcccca caggttcaaa caattctcct gcctcagcct tttgagtagc  29160
tgtgactata ggtgcgtgcc tcacacccag ctaattgttt gtgtttttag tagagacagg  29220
gattcaccat gttggctagg ctggtattga actcttgacc tcagatgatc tgcccgcctc  29280
agcctcccaa agtgctggga ttataggcat gagccactgc gcccggtgta tgtgaaattc  29340
ttcaacaggc aaaactaaac cacagtgaga gcaaattagt gattgcctag ggctcaagca  29400
gggggtatat cttactacaa agaggcttgg tggaaatatt agattagtac aaaagtaatt  29460
gtggtggtgg taggtacttt gtaccaaagt atttaaaaat tggtgtattt tattatatta  29520
cccctcagta aagatgattt taaagtaagc aaaggataaa aaccttaaaa tgtaaatata  29580
gaaaccttaa aaatgtaaat gtaacagtaa tggaagaatt catgagtcca gaccgatata  29640
ataaataaat ggggagaagc acaagctctt ccttgtggta ggatgccaac tagatgccaa  29700
gctcttcctt gtggtagaat gtagagtgaa atcctggaat tagaagttca ccttgtgggc  29760
caggcacagt agctcacgcc tgtaatccca gtactttggg aggcgagctg atcacttgag  29820
cccaggtgtt tgataccagc ctggccaaca tgacaaaacc ccatctctac aaaaaaaaaa  29880
aaaaaaaaaa atacaaaaat tacccaggca tggtgtcgca cacctgtagt cccagctatt  29940
caagaggctg aggcaggagg attgcttgag cctggaaggt caagtaaggc tgccgtgaac  30000
ggagattctg ccaccgcact ccagcccaga caacagagca agaacctgtc tcaaaaaaga  30060
gaaaaaaaga aaaaacaaac tcaccatttg gcagtcatca tagtaacaat ttttaatcaa  30120
gaaacatcag tgaatacaaa aactagtaga tgcaaatact tagtagttaa acaggggaaa  30180
taccctttta gggagtaact tgcaagacac acccttaatc aggtgatcaa agtaaaccaa  30240
atgggacgaa taaaaattag ctgctacctc atagattgcc ctgcatgaac acagcagcac  30300
taatgtgcat tccagctaaa gatgcatacc ctaaatctag tcatgaaaaa catctggcag  30360
acctaaattg agggaaattg gacaaaataa ctgtcttgta atcttcagaa gtttcagatt  30420
atgaaagtca aaggaaaacc atgcaactaa ctgttccagg ctgaagggaa ccagaaaggc  30480
atggcaacca aatgtaccat gtgatcctgg attgattcct tttgctataa aagacatctg  30540
ggtaggccgg gcgtggtggc tcatgcctgt aatcccagca ctttgggagg ccgaggcagg  30600
cagatcacct gaggtcagga gtttgagacc agcctgacca acatggtgaa accccgtctc  30660
tactgaaaat acaaaaatta gctgggcgtg gttgtgcgtg cctgtaatcc cagctactca  30720
ggaggctgaa gcaggagaat cgcttgaacc tgggaggcag aagttgcggt gagctgagat  30780
ctcgccattg cactcccgcc ggggcaagaa gagcgaaacc atctccaaaa aaaaaaaaaa  30840
aaaaaaaaaa aaggacatct gggtaaaatt ggcagaactt aaatagagag tatggagtag  30900
gtggcagtag tgaatcgtgt taatttcctg atttccatgg ttgtactatg gtgacgtcgg  30960
agcatgtcct gttcataaga cacacactaa aatatttggg tgttattggg catcatgttt  31020
atgatttaat gaaatttcaa aagggtttgg ttaatattgt gataatataa ttctaaaagt  31080
tcattgagaa gaaagggaat gggtaaaaat gctattaaag aggaatgaga tattggagtt  31140
taccacctag agtgctttta accaagaatg tatactttag tcagtccttt attgtgattc  31200
ttgtaggcaa aaaaagtatt gaattggaga aaaaacggct ctctcaacct aaggcaaagc  31260
ccaaaaagaa gaaaaagccc accttgagaa ctcctgtaaa gctggaatcg attgatggaa  31320
```

```
atgaagaaga aagcatgaag gagaactcag gacctgttga gaatggtgtg tcagaccaag  31380
aaggggagga gcaagcacgg gagccggaat taccctgtgg ccttgctcca gcgggtatgt  31440
ggcagaatcc tgtgtatcac taggatttca tggtcgtgtc tgggaaacta agctaggtcc  31500
ttactcagtt tgaaacttcg ctgttcccat ttttccaact cttggaaaca gcattagttt  31560
tttttgttaa gctttattca agtctctaaa ataaacatct ttgaagtttt aaaggggttc  31620
tagtggatgt ttgtggtgga aatagtaaag ttctacagag aaaacttctt attcaacttg  31680
ggcaaggtaa aaccgtggga cgaagcgaag ctgggtcagt tgtgtacata ggaacttaca  31740
tgggaaaagt tttaacagta tgacatcagt agccacattt ggtgaaagaa actactgtcc  31800
cttacaaatg tctgacctag aagctaccac cactgtggga acttgcaagc tctcaccccc  31860
ttacgtggag tttgtacgcg gctttctgtc ttctcacaga aaaaaaatgt gtgaatggtt  31920
attaggtttt tctagtgagt taagctgtag tgatggctct cagatgtctc acaaaacagt  31980
gttctatcac taacaaaaaa actgttaggt aaaaatttta gcactctttt tattttgtac  32040
atttactcgg gacctgttga gaatggtttg tcagaccaag tgataaatat ctggtccctg  32100
gtaaaataaa cgattaaata gcaaacagtg taagtagaag cagtaactca tacttaattc  32160
taaaacagaa tccattgatg tgacagtatt gaaatggcta gaatatagga tacaaggcat  32220
tcctgatgct ctccatccca agggatagct gttagacaca tagttggggt aaataaagag  32280
caaaaagcct aatggattta ttattttggc tcatcagaat gcttttctag tcgggtacag  32340
agacacatac ctctagtccc agatcctcag gaggctgagg caggagaacc gcttgaggcc  32400
agcctgggca acacagcaag accccccatc tctttatttt tctttttttt aaaaagtctt  32460
tctttcacaa aatggctata caaaacatgg atcaacaagt tgtttttaaa aagttcctgt  32520
gctcaggatt gtgacaccat attgcataca cctagtattc tctattatta aagttactcc  32580
tgttagtgta attaaatatg caattagtac tttatgacct agaaatgtaa aaagtgcttt  32640
gtcacctgag caaagtatag gaactccttg gcttatggta taaagttgtg gagggctgga  32700
agctttttcc ttagtcaaag ttcaaagtaa ggcgggcatg gtggttcatg cctgtaatcc  32760
cagcactatg ggaggccaag gaaagagact tgcttcaacc caggagcttg agactagcct  32820
aagcaacata gggaaccccc atctttgcaa aaaatataaa aattaccaag ataatggctt  32880
gtgcctatag tcctagccac tctgggaggc tgaggagggg aggatcacct gagcccagga  32940
ggttaaggcc tcagtgactg tgattgcacc cactgcactc cagcctgggc aacagttata  33000
tcttatctct aaccaaaaga aaaaaaaaaa agtaagccag gagcggtggc tcacgcctgt  33060
aatcccagca gtttgggagg ctgaggcagg tggatcacct gaggtcagga gtttgagatc  33120
accctggcca acatggcgaa accctgtctc tactaaaaat acaaaaatta gccaggcatg  33180
gtggcttgtg ccagctactg gcgaggctca ggcaggagaa ttgcttggac ctaggaggca  33240
gaggttgcag taagccaaga ttgcgccact gaatttccag cctgggcgac agagtgagac  33300
ttcgtctcaa aaaaaaaaaa aaaaccaaag taatagactt acagattcct gaaaacagct  33360
agtttgggag gtgggaaagg ggaaactact cctacttctt ttccagtgca ttttatctca  33420
aaagttttgg taatagatga attgattata ttgctaagct tggaatggct cttaattttt  33480
acaaagaact gaaattctgt attattgtta tccttaactt tttttttcct ttttccccca  33540
tgatgtagtt tctagagaac cagttatctg cactccagtt tcctcaggct ttgaaaagtc  33600
aaaagtcacc attaataaca aagtcatttt actgaaaaag gagccaccaa aagagaagcc  33660
aggttggtat ctagtaatta aaatacagta ttttgttaaa gcagcctaaa atattacata  33720
```

```
tattacacgc aactgtcaaa aaacagtgtg gtttcttgtt tgtttttata ggttcaaaat  33780
atttgtaggt tttctgatta tgggtttttt gtttgttttt tgtttgtttt gagacagatt  33840
ttcactccag tcacccaggc tggagtgcag tggcacactc ttggctcact acaaactcca  33900
cttcccgggc tcaagcgatc ctcctgcctc agcctcccga gtagctggga ttacaggcgc  33960
ccgccaccat gcccagctaa cttttgttat ttttagtaga gacggggatt caccatgttg  34020
gccaggctgg tctcgaactg ctggcctcca gtgatccgcc cgcctcagcc tcccaaagtg  34080
ctgggattac aggcgtgagc cattgtgccc agacttccac ttccattttg ggtcatgctt  34140
ttgaattttt tttagcactt gatgaaatgt tttgcagttg ttgacactac atcataaatg  34200
ttagcaagag cgtttttgtg tgtattgtga acaatgcccc cagcaaattt attttgaaag  34260
cctctttatt aggaggagga gctttctctg cctgtggtgt cgtcctgcca gtaggttaca  34320
ttcacacaat aggcattccg ttttatgttt ctgatcagtt ctccttcaga tagtatgtac  34380
tttattaaat ttcagaaacc ttaatcaaga agagaaaagc tcgttccttg cttcccctga  34440
gtacaagcct ggaccacaga tccaaagagg agcttcatca ggactgtttg gtactagcaa  34500
ctgcaaagca ctccagaggt acaaaaatgt acttccttgg cccatccata gtcttccggg  34560
actggtatat aagggatgtt tacttattta ttaaatgaat gcccaaagaa atgtctaaat  34620
tgttttctgt atttttatgt tctccagctc tcccttccct ccacatccct ataccccctac  34680
accttgctgc caaactcccc attgtgaccc accgtcagca ctgccatggc tttgaaatgt  34740
agcgctctgc ttttattcta aatctaattc ctcccagcca tctgtgtgcc agaattggta  34800
tgttggccta agtatctcag catgaataaa ctccttcaac tcttttcccc attgaacagt  34860
atcctatgga gaaaaaaatc tttttttctt attggaaata tgctcataat atggcatttt  34920
tttagaaaaa aatttgatgg aagcttttgc tttgtaagtt ttgttttgaa gggttgtttt  34980
atttttgttt ttcaaagtct tcatttaatg tccactattt tgatatttta ataactttat  35040
tttttaaatt tgaagtttac atgtggaaaa gggatgcaca taataaataa aattgatgct  35100
taaggggctg aagcagaagg atcacttgag ctcactttaa ggccagcctg ggcaacatag  35160
tgagaccctc tctctattta aaaaaaaaaa ttttttttta attttttttt caaagtaaat  35220
cttcctccca gtcctctgtt tctcctcccc aggaatggag gaccatcctc cctcccggtt  35280
actgtctccc actaccctaa caagggtagt cactatcctg ggcttccatt tgtttctttc  35340
ttttgaattt ttgtactgtt ttgtctgtat tgcataatca aactattatc agtttcttgt  35400
gtcttgatgg agatgtttta tgcttttatt atatacatag ccttttttgga gctttgtgat  35460
gacttcctat aacttacata gttaacctag tttcacatta ttttccttac tggaaaatta  35520
ctcagttgac tttttttttg aagcaaagga tgaatattga atccccttgt ggtaagtccc  35580
agtgaatatt aaggactttc ttttgcttat taatattgtt ttgcttgttt tttactgcac  35640
ttaaatatgt tctgatttgg ggttcacttt taacatttta agtgtttttg tgttttgctc  35700
cctttgtaac tgcaggagtc tctgttagag ctctgattct ctcagtgtct gaagtgggtg  35760
ttccaaacat atattcggaa gttattggag agaaaactgt aatcaatgta atgacttcat  35820
ctgatttttt tgccttttta aattaacaga gctgaatgaa gatgtgtctg ctgatgttga  35880
ggaaagattt catctggggc ttttcacaga cagggctacc ctgtatagaa tgattgatat  35940
tgaaggtgag acaaatccag tcaacataat ctcatccatc tttatacttt cccaacattt  36000
tgtgtgcacc tctttgatgg ctgtcatcct gtgatattat aatggttagt tttacgtgtc  36060
agctaactag gttttgagct ccctgattta catattgata caacccttgc atcatcatag  36120
```

-continued

```
gatcctaaac atacagcatt cactctgagt acatgtgaag gtgtgggagt gtacagtgac  36180
caagtgggct tcagatctta ctgtaatcac tctggtaggt gacacccatc agagaatgac  36240
tgcatatttt aggagctcac tttctcttct atcttgcctt tcttttccta caagtcagta  36300
acagatgttt ctgaaacacc ttccaaacat tatctctctt tcaaacagga aaaggtcact  36360
tagaaaatgg ccaccctgag ttatttcacc agcttatgct ttggaaagga gatctcaaag  36420
gtgttctcca gactgcagca gaaagagggg agctgacaga caaccttgtg gctatggcac  36480
cagcaggtat ggtttttgtt tgtttgttct tttcaacaaa agctctatca tctctaggat  36540
acgtccacta aagatggctc ttagcacagt cttaagcttg aaatcactta caaatagata  36600
caaagcaata gacagcaata gacaaactaa taaatccaac ccaacccctt tgaaaaaaag  36660
caggtcactg acactttaat tggcaaaagc ataattggtg agaacttctt gaaggacaat  36720
ttggccatgt ctagtaaatt ttaaaagata taatggcaca agtctgtagt ccccagctgc  36780
tcaggaggct gaggcaggag gattgcttaa ggctaggcgt tcagacctat agcgctctgt  36840
taattgtgcc tgtgaatagc cagtgtattc tagtctgggc aacatcatga gaccttgtct  36900
ctttaaaaaa aaaaaaggct gggtgtggtg attcctgatt catgcctgta ataccagcat  36960
ttcgggaggc cgaggtgggc aggtcacttg atcccaggag tttgagacca gcctaggcaa  37020
catggcaaaa gcccatctct acaaaaaaat taaaaaatta tctgggcatg gtgacatgta  37080
cctgtagtcc ccgctactcg ggaggctgtg gtgggaggat cacctgagcc cggggaggtt  37140
aaggctgcag tgagccatta ttgtgctact gcgctccagc ctgagccaca gagtgagacc  37200
ctgtctcaaa aaacaataaa aggaaagggg aaaaaaaaaa aagcacgtag tcatgttacc  37260
tttggctcat cagttatgat tataggaatt taactgtgct cacacattcc tttctgtatc  37320
ttttcaactt tgtactgttt tgtttgtgtt acataatcaa acaattgatg tttcagaatg  37380
tgtagatgaa gcagatgatc cataatggca gctgaattgg tatctaaatg ttctgctgaa  37440
tgcattgacg aaaacaaggc tttttcaacc caaatgtact gggtattgtt tttacttttt  37500
cttcaactgt ttttttaacc accatctttt attttttcag ctggctacca tgtgtggcta  37560
tgggctgtgg aagcttttgc caaacagctg tgttttcagg atcagtatgt caaggctgct  37620
tctcacctac tttccatcca caaagtgtat gaagcggtgg agctgctcaa gtcaaaccat  37680
ttttacaggt ctgtgtggtc ctagagttgg gataatactt ggacataatg tgaaaataac  37740
ctaaacttct ctattgttaa agtaacataa atagaagaaa cagtcctcct gcttcagccc  37800
cctgagtaac tgggactact caggaggtgc atgccaccac atccaactaa ttttttagtt  37860
ttttgtagag acggagtctt gctgtgttgt ccaagctgat tgccaactcc tgggctcaag  37920
cgatcctcgt gcctcagcct cccaaagtgc tgggattaca ggcatgagcc accatgcttg  37980
gccaagattt tctttttgtt ctaccctgct ttggttttgt tatcttcctt tagagagtgt  38040
taaactttgt tttggtaagt agtaaagttg tgtatcagct tgatcttttc atggcttgtt  38100
tttaaacttc gttagggcaa gtttatcata ttctagaatt agtttggacc tcctacattt  38160
tgatatcttt cttgaatgcc ttatgcattc aacaaatcaa aactcagatg tctccaagtc  38220
ctgagtaagc tctgggaatt gttcagctta cagttaccta gtcattcttt gtttagactt  38280
aaggagtttc ctttacatac gtggctttta atttagccaa agactcaatg ggatctccag  38340
gcagagttgt ggatgtcttt ctctggacag cttcctcctt cctagtatcc tgcccctcag  38400
atttccattg tttcctcttc tcaactcaga gactgctgag gttttgctca ggtttccctt  38460
aggaaaatgg ctttgggcag aaagccagtg ccaagatagg gctcccatca tttgtttctg  38520
```

```
ttctcttagg gctgaccatc ctatgctgcc tgttacctgg tatctaaaaa cagttgtttc  38580
agccattttg tccagttttt tagttttatg gcagaaaggt aagtctggtc ccagttactc  38640
catcatggct ggaagtagaa gtcccaaaat actttcaaaa tattgctctc tctagatcac  38700
tttaatctaa taaaacactt ttttcccagc tacaacttta tgttggctac aactcagcag  38760
ttgtatgtca tttgaaaaat atttgtttac tgagttgttc agatcttcca aatgttaaca  38820
tatcttatta taaaataccc aaaaatacca cattccttac tatcaccatc agtctcatca  38880
gaaaattcta acttatggga aactcaggca cacaagtggt aggtacaagt tttctaaaat  38940
tctaattttt gctagaaaac tcgcatttta tcattagtaa caaatactgt tggttgtttt  39000
taatgaagtg ataggcctac tttgttcatt tttgagaaaa acatctgcca aatacccaac  39060
actgaataac tgttatttat gttagtcatt tttttttttt ttagaagaaa gaaggttcta  39120
tgaaaaagca gccagtttag cttgtaattt gttcatacag gtgttaccta gagacaacca  39180
ttctactttg gaatgcagca gagaacacaa aatgttcttc ccatttgtca cacagaatat  39240
taaagtgttt tggacttgac ggatttagta aaatttgtaa tttttactgc ttcattaagg  39300
gcattcttcc ttttttttcca ctgtaagagc caccgccttc cttcttagat gccaggtttc  39360
ccaatcactg ctttggcaca atcagtgcaa atgtcaacac attttttttt tttaataaaa  39420
aagcacataa ctgactctta gcattgttac gaaaatagtt ttaacctcat gaaccctctg  39480
aaaggttctt gaggaccccc taggaatcca cagaccacaa tttaagaact gctgatctaa  39540
gtgaagaaac gaatgcagca tatgtttcta atttgtctat ataatgcaag tgcagttttt  39600
aaaggaagtt ggaacaataa gacaacacaa aagggacagt ttgtcctgtc ttacagcccc  39660
tcctaggacc atacacagag gagccttttc agattggcta aaggatctgt tcttgccttt  39720
agggaagcta ttgcgattgc caaggcccgg ctgcgcccgg aggacccagt cctgaaggac  39780
ttgtacctca gctggggaac cgtcctagaa agagatggcc actatgctgt agctgccaaa  39840
tggtaagcct gaggagtgga gggatgcttc caacatagga gagcttctgc caggaagggg  39900
aggacaagaa tacaagtaat aagtttagag gtggaggtaa agcagcaagg aattatttaa  39960
aagatatgta tattcaactt agtttcataa gactcatcag gaactacttc ctgatttatt  40020
tatataaatc actataacta ttcaagaaaa acctcagcag cagattaaga aattatgcat  40080
ttttctaatg gtctcttata acatcaaata aaggaacctc aacccatgct ggattgaacc  40140
caacagagga gtcattccct ctcattttcc ttatgtcctt aacctatatg atattgtttc  40200
tcatacactc tgctgagttg tgttggcctc agccttcaca ggaacaaccg gggcagtgac  40260
atacctggga ccacaggaag gcacatgcag caaagtagat agaaagaaat gattccatcc  40320
tctaggaatg ggaataaaaa tctgtttgtg acattttctt cacattttta ttcatattat  40380
agctatttag gggccacttg tgcttatgat gcagccaaag ttttggccaa aaagggggat  40440
gcggcatcac ttagaacggc tgcagagttg gctgccatcg taggagagga tgagttgtct  40500
gcttccctgg ctctcagatg tgcccaagag ctgcttctgg ccaacaactg ggtgggagcc  40560
caggaagccc tgcagctgca tgaaagtcta caggtcagtc tgttatttca tctcctagta  40620
tacaagaggg aagtgtccca aatccttttc tagtcaaatc caagttaata acccagttgc  40680
acaagctgtg ccaatttggc aggcccagca agccctggcc atgctatccc actgaagtac  40740
tatgacttgt tagttgccgt attcagagta agagataata tggtcattca cagtaattcc  40800
cattgcttat ctgtttgtac aaaacacctg tgagccgggc acagtggctc atgcctgtaa  40860
tcccagcact ttgggaggcc gaggcaggca gatcacttga ggtcaggagt ttgagacaag  40920
```

```
cctggacaac atggtgaaac cccgtttcaa ctaaaaatac aaaaattagc cgagcgtggt  40980
ggcacgcttc tgtaatccta gcttacttgg gaggctgagg caggagaatc acttgaaccc  41040
ggaaggcgga ggtggcagcg agccaagatc cagcctgggc aacatagtgg gactctgtct  41100
caaaaaaaaa aaaaaaaaac acaaaaaaaa acaccttagt cagcccaggc cttgggttgg  41160
cagtctaggg tttcttcatt gatgttatca gcactgtctt ccttgaagag agaatggttg  41220
gcctctaaca gaaatcatgg aactctacct gtaaatgccc ctcttaactg taagctatgg  41280
aaaaaaaact gggccagatg cagcagatca cttgagatta ggagttcaag accagcctgg  41340
ccaacatggc gaaatcttgt ctctactaaa aataaaaaaa ttagccaggc atggtggcac  41400
acatctgtaa tttggctact tgagaggcta aggcaggaga attgcttgaa cccaggaggc  41460
agaggttgca atgaaccaag attgtgtcac tgcactgcag cctacgtgac agagtgagac  41520
tcttcagaaa aaaaagagaa aagtgtggga aaatggaaat ctctttatct cttaaatttt  41580
tttgttccca tctgattaaa aatcagtaac ataccactgc ctttttgaca catcaaaaca  41640
gattaaagca ttggcacact tacctagttt ctgaaacatg taaacatttg attcacttta  41700
gataactttg tgagatacta acaagaggtt ttttaagttc ttcattctct aacagagtac  41760
agggcctaca gatggttttt agctgaatat ttagagccca aggaacgtgg tacatgggga  41820
ggtagctttc taggaacagc agaataaaaa tggaggcgaa aataggacac cctaaaagat  41880
aatgccactg ggcattattt ataaaatgac caagtctaga gagattttaa tttatccacc  41940
atcaaaaaaa gtttccagaa tgactgttta gcattttatt tttctcttaa acagcatcct  42000
taacaaagca aaaaaaccta ataagcatat gctaaatatt ctgataaggg ctattttggt  42060
tttgtgcaac agagactctt gcaagcttaa ctgagaagat attgttatag gagtacacaa  42120
ggaatctcat ggcaactaaa aatctagtga aagtagattt tctaggcctt ctctgtgctt  42180
ctgttttctt ctctcccagc cagcttcctc tattaaacct atttggacat ggctcctaat  42240
gcctgtccca gctcttggat ctgcaaagct tgtctattcc agcacctttg gcccattatg  42300
cttttattcc tgagtccaaa gtttggtcag ggagaaagaa cctgatgagc ccagcccttc  42360
ttttcctcaa actaggctac aaggcttaag tggctggtct gtgtgtggct taaatcattg  42420
tgggtagtgc tacagttggg attctgtgtt ataaaaatgg tttcttgagc tctaaggata  42480
gatttccccc aaaagggacc tgggaagtgt ctgtcagatc gcccctttg tccctttca  42540
tgcatgactc atatggggca ggtagctcac taatgtgctt tggttgctgc agatacaaag  42600
ggaaatactt tgaaggacac gggagagctc ttgagatcat ccagtgcttt ccctgtataa  42660
cagttcctct tccttgttgt cgtgttccag ggtcagagat tggtgttttg ccttctggag  42720
ctactgtcca ggcatctgga ggaaaagcag ctttcagagg gcaaaagctc ctcctcttac  42780
cacacttgga acacgggcac cgaagggcct ttcgtggaga gggtgactgc agtgtggaag  42840
agcatcttca gccttgacac ccctgagcag tatcaggaag cctttcagaa gctgcagaac  42900
atcaagtacc catctgctac aaataacaca cctgccaaac aggtaagcca tctgtaccag  42960
catttgacat taatcactca gtggtaagac ttccttaatc catgtctatt gtaacgggga  43020
aacaagcaga atactggact gtgtttcaga aaaggctaag gcatggccac gccacctgga  43080
aagatccctt tagactaatc aaagcccttt aactttaaag ttagtattag atcagtattc  43140
cctttttgt tttgtttttt ttagttgttt gaagctggag tgcagtggca tgatcttggc  43200
tcactgcagc cgccacctcc cagattcaag tgattctccc gcctcagact cctaagagct  43260
gtgattacag gcgtgcgcca ccacgcccag ccactatttc cttttctaaa aaagtaaaat  43320
```

```
aaaaagtcta gaaaatatag aaaagcagaa taataaccca tcaaccagaa ttaacagatg  43380
ttcacatttt gtcattttta ctttgtaggg ttttctggtt tcattttgta ttttgatttg  43440
aggactttat aaaataaaaa cagtagggca aagttgaagt ccttcttgtt cctttcctca  43500
gcccttcact ccttccctag ctcgccacag gcacctcctg tgtcagtgcc acatgtattg  43560
ttttgctgtt tgcttatttc agaggccatt gtttgtaaaa tctatccatg ttgataaaaa  43620
gagatcagtt gatttatttt aactgctatg tctgccttgt gaatatacct acttcttttt  43680
tttttttttt ttcctttctg gagactgggt ctcactgtta cccaggctgg tctcgaattc  43740
ctcaagtgat cctcccgcct cagcctccca aagtactggg attacaggca tgagccactg  43800
tgcctggcgt agttctttcc ctcatttcaa aatgagggaa cattatgata tttatgagga  43860
acaaggcttc tcaaatggta tatactttga aaaacagttg gacagtttct tttttttcttt  43920
tctttttcc ttttctttc tttcttttg aggcggaatt tcactcttgt tgctcaggct  43980
ggagtacagt ggcatgatat ctgctcactg caacctccgc ctcccaggtt caagcaattc  44040
tcctgcctca gccttccaag tagctgggat tacaggcatg tgccaccacg cccagctaat  44100
atttttactt tttttttttt tttagatgga gtctcactct gtcacccggg ctggagtaca  44160
gtggcatgat cttggctcac tgcaatctcc gcctcccagg ttcaagcaat tctcttgcct  44220
cagcctcccg ggtagctggg attacaggca cctgccacca tgcccggcta attttttgta  44280
tttttagtag agacaggggt ttcaccatgt tggccaggct ggtctcgaac tcctgacctc  44340
gtgatttgcc cacttcggcc tcccaaagtg ctgggattat aggcatgagc cactgcagcc  44400
agcctatttt tcagattttt agtagagaca gggtttcacc atgttggcca ggctggtctt  44460
gaacttctga cctcatgtga tccacctgcc tcggcctccc aaagtgctgg gattacaagt  44520
gtgagccatc acgcctggcc aggcagtttc ttataaagtt aaacatgcac atgccccatg  44580
tctcagcagt tctgctacct agatattcca ctaaaacaat gaaatcagat ggccacacaa  44640
agacttgtac acaaatgttt acagcagctt agtgcacagt agccaaaaac tagaaacaac  44700
ccaaatgtcc atcaactgat gaatggatat gcaaactgtg ttgtgtctat gcagtgaaat  44760
actatactgt ttaacaataa aaagggccag tcttggtggc tcacacctgt aatcccagca  44820
ctttgggagg ccaacgcggg tggatcgctt gagctcagga gtttgagacc agcctgggca  44880
acatggcgaa aacctgtctc tagtaaaaat acaaaaatta gccgggtgtg gtagcacaag  44940
cctgtaatcc caggtactag ggtggctaag gcaggagaat cattcaaatc tgggagacgg  45000
aggctgcagt gagccaagat ggaaccactg cactacagcc tgggtaagag aatgagaccc  45060
tgtctcaaaa aaagaaagta aaaaggaaca aattactgcc acacaaataa tatcggtgtt  45120
agccgggcgt ggtggcgggc tcctgtagtc ccagccactc tggaggctga ggcaagagaa  45180
tggtgtgaac ccaggaggcc aagcttacag tgagccgaga tcgtgccact gcactccagc  45240
ctgggcgaca gagcaagact ccatctcaaa aaaacaaaga agaagaagaa gaatatcggt  45300
gaatctcaaa agctttaaag acacaaaaga ctatatactc tgtggttcca tttatatgaa  45360
ttctagaaaa gaaaaaatta aagtgacaac cagttcagtg gttgccagtg gggtggggcc  45420
aggagatcgc ctgcagagga gccggagggc atatcttcag ttgatgaaaa tgttctgtct  45480
tgattttgct ggtagtgttg taactatata tgtttctcaa actacatact taaaattgag  45540
cacatttttc ttagttgtac tccaagcttt gttttgtttt gtttttggtg ggttttgatt  45600
tttttttttt gagacagcgt ctcactctgt cacccaggct caggtgtagt ggcttactgc  45660
aacctccgcc tctcgggttc aagcaattct tccgcctcac cctcccaagt agctgggatt  45720
```

```
acaggcgtgc accaccaagc ccggctaatt tttttttttt tttttttttt ttttagagac  45780
gggctttcac ctcgggtgat ccgcccgcct cagcctccca aagtgatggg gttataggtg  45840
tgagcaactg cacccagcct ttattttgtt tttaattaca gcttttagtt ccagaaactc  45900
actttttgtt tttgttgttt gtttgtttgt tttgagaggg agtctcactc tcatgctcag  45960
actggagtgc agtggcgcaa tctcagctca ccacaacctc caccttccgg gttcaagcaa  46020
ttcttctgtc tcagcctccc gagtagctgg gactacaggc acgcgccatc atgcctggct  46080
aatttttgtg tttttagtag aggcggggtt tcaccatgtt ggccaggctg gtcttgaact  46140
cctgaccttg tgatctgccc accttggcct cccaaagtgc tgggattaca ggcatgagcc  46200
accgcgcctg gcccactttt tgttttaatt aaatgcaaat gtaaaggtgt tttctcagtg  46260
tgaacagact ttaacaccgg gacgtgtgtg tgctgctgtg caactagaca tgagagtttc  46320
cgatgtggga agcaaaaatg ggtggcggag acaagaggaa ctttcaaagt gtgaattgtg  46380
tgtacttgtt tccaaatgcg gttcacagga acagtttggt ggcatcctct gcgcctaccg  46440
tgggaggatg tttaactcag actctggctt ctctctccag ctcctgcttc acatttgcca  46500
tgacttgacc ctggcagtgc tgagccaaca gatggcctcc tgggacgagg ctgtgcaggc  46560
gctccttcgg gcggtggtcc ggagctatga ctcagggagc ttcaccatca tgcaggaagt  46620
gtactcagcc tttctccctg atggtaagtg acttcctgct gcctgaggca caccctttaa  46680
tggacaacat caccaccatt agtggtgtgg cactgggagt acctagattc ttaaaagatg  46740
gagattggcc agctgtgtca ttttagtaga aagtttggat tctcttaccg aagcttttaa  46800
gaacaactat actgtttcct ttacctggcc ctaccctctt acagcctcct gtccactttc  46860
cacaaagttt aagggagaga gaaataggaa tgtagttaca tgttagtaag aacagaaaag  46920
aacagcaaaa aagatagaca ttccttgggc tgcatagtca gtcactgaac taaatcattg  46980
tgatttttca gagagacagt gtgatctgtt gtcgtggccc cagagccttc agtagtacaa  47040
atggaatact ctatcatgct ttgaatgact cctaggatgt agtaatgaga acactgtcgc  47100
aagccaggaa atgtttagcc tccagttggc tcttggtgga aaggcatgtg gcccggtgga  47160
tcacactgtt gtccttttc  ctggggtctg cttcttgggt gataagaaat agaacataag  47220
ggcaggaagc cacatttctg gcaactagag aaatgcatga cccagtatct ttttcctctt  47280
ttcctaggct gtgaccacct aagagacaag ttgggggacc atcaatcccc tgccacacca  47340
gctttcaaaa gtttggaggc cttttttctt tatgggcgtc tgtatgaatt ctggtggtct  47400
ctctccagac cttgcccaaa ttccagtgtc tgggtaaggg ctggtcacag aacactctct  47460
gttgagccaa gccagcagtt agacactgcc agcactgaag aaacggaccc tgaaacttct  47520
cagccagagc caaacaggcc ttcagaacta gacttgagac tcacagaaga aggtgagcga  47580
atgctgagta cttttaagga gctcttttca gaaaagcatg ccagtctcca aaactcacag  47640
agaactgttg ctgaagtcca agagaccttg gcagaaatga tccgacaaca ccaaaagagt  47700
caactctgta aatccacagc aaatggtcct gataagaatg aaccggaagt agaagcagag  47760
cagcccctct gcagttctca gagccagtgg taagtactga ggcaagtaca agacggaatg  47820
aaaaatgacc ctgctggcta ggaacagtgg ttcatgccta taatcccagc actttgggag  47880
gctgaagcag gaggatcact tggcccagga gttcaccacc agcccgggca aaaaagcgag  47940
accctgtctc tacaaaaaaa aaaaaaaaaa aaaaaagccc gggcacagtg gatcacgctt  48000
gtaatcccag cactttggga ggccgaggtg ggcagatcac ttgaagtaag gagtttgaga  48060
ccagcctggc caacatggtg aaaccccgtc tctaccaaaa attagctggg tatggtggca  48120
```

```
catgcctgta attccagcta cttgggggc tgaggccaga gaatcgtttg aacctgggca  48180
gcagaggttg cagtgagtca aaatcgcacc agtgcactcc agcctgggca acagagggag  48240
acttcatctc aaaaaataca aataaagtaa ccaggtgtgg tggcatgtac cctgtagcta  48300
cttaggaggc tgaggcagga ggatcacttg aggccaggag ctcaagttca gcctgggcta  48360
catattgaga ccctgtctct agaaaaatta attttttaa attagccagt agtggtggca  48420
tgcacttgta gtcccagcta ctcaggaggc tgaggtggga ggatcactta agcccaggag  48480
ttcgaggctg tagtgagata cgatcatgcc actcatacca gcctggttga cagaccctgt  48540
ctctacaaaa aaaaaaaaaa aaaattaaat tttaagaagc caggtgacaa aggaatttta  48600
tttataaaat gagataaaag taacccaggc aggggcatat gctctcaggg cctcctgagg  48660
gctgtgtcat aggcaaaagt ttaaattttt aaaaaaatatt aaaaataaaa ggtaaaagct  48720
acccaggcat aacaaaagat aatccaattc aaggatgggc aaaggacttg aatagacatt  48780
tctctaaaaa gccagtaagc acaggaaatg atgctcaaca tctcatcatt ggggaaatgc  48840
aaatcaaaac tacagtgaag cagcacttca tagccattag gctactatca gagaaacaga  48900
acaagtgttg aggaggatgc agagacattg gaacccttgt gcctgttggt gggaatgtaa  48960
aatgatgcag ccactgtgga aaacagtaca gcagcacttc ctccagaaat gtaaaataga  49020
atgaccatag gatccagcac ttccacatct gggtatacac ccaaaagaat tgaaagcagg  49080
gtctgaaata tgtgcacacc tgtgttcatg gcagcattat tcataatacc caaaacacgg  49140
gagcaaccta agtatccact gacagatgaa tggataagca aaatgtgcca tatccataca  49200
atggaatgtc attcagcctt acgaagggag gacatcatgc tgagtgaaat aagccagtca  49260
caaaaagaca tatactatat gactccactt atatgaacta ctcaaaatag ttaaatttat  49320
agagacagaa agtagaataa tgttgacagg ggctaaggga agcagaatga gaagttaatg  49380
tttaatgggt ataagatttc agttttacaa aatgacaaga gtttttggaa atgggtggtg  49440
gggatgtttt tcaccacatt atgaatttat ttaaaatcac tgaactatgt atttttaaat  49500
ggctaagatg gtaagcttta tgttatatac attttaccac agtaaaataa caatgggaga  49560
aaaatgttac ccagggcaag acatacaatt tacacctttt atttttttca ctagtaaaga  49620
agaaaaaaat gagccacttt ctctgcctga gttaaccaaa aggcttaccg aggcaaatca  49680
gagaatggca aaatttcctg agagcattaa ggtaagagtt aaagcagttc atttggtaaa  49740
gcatcacttt ttgtgttatc acttgactat accacattct tataaaggtc agctacctct  49800
ctgttcagtt tctaaaatct ctacccattc atatgtgctt aagaatttag aatccaggct  49860
gggcgtggtg gctcacgcct gtaatcccag cgctttggga ggctgaggct ggcggatcat  49920
gaggtcagga gatcaagacc atcctggcta acatggtgaa accccgtctc tactaaaaat  49980
acaaaatatt agccgggcgt gggggcaggt gcctgtagtc ccagttactc gggaggctga  50040
ggcaggagaa tagcatggag gcaggagaat ggcgtgaact caggaggcgg agcttgcagt  50100
gagccaagat cacgccactg cactccagcc tgggcaacag agcgagactc tgtctcaaaa  50160
aaaaaacaaa acaaaacaaa aaaaaagaat ttagaatcca attactttgg ttagctagaa  50220
tgttttgtga gactagaatt atcgatcaca caagtaattt tatacctcaa tcttcagaga  50280
aaccaaatag atttaatagg taagaagtaa aatttaaatt ggtgccatgt attagatagc  50340
ttacagatgg acaggtcttt ttggctgtgg gcccaaatat taatagaagc accattttta  50400
agggtggatt tgcatagggc tgtagaaaga gattgtgcca ttgagaagga catcgcagta  50460
gccatcctag ttttgagtgt catttctcct tggagtaact gttgaagaga aagacaggac  50520
```

```
attgccttag gagacagctg gctcagctgt gtccaagaag tgtctataga tgaacctgag  50580
tgactggtgc cttctgtgca ggtgtttgtg gctcttctgc aaatgcttcc ttattcatcc  50640
tcatgtcatc gtctttcagg cctggccctt cccagatgtg ctggagtgct gcctcgtcct  50700
gcttctcatc aggtcccact ttcctggctg tctggcccag gaaatgcagc agcaggccca  50760
agagctcctt cagaaatacg gcaacacgaa aacttacaga agacactgcc agaccttctg  50820
tatgtgaatt ttcacacacc ttgaagaaac tgccaaattg aaaatgtttg acatctttca  50880
cctctgcagt tatgcctcac cagacattca ctctggtccc tagatgtttt tgcagtaatc  50940
caaaagaata caaacaagga ttaagtttga atcaaccctg cctacccata gacaacggtg  51000
gatctgactt tagactcaat tgtggtctcc tactggaggg aagatcatga aaagcccaca  51060
gtagttattc agaactaaca cctgcagagt gttggtcatc tctacagcct taggcaggtt  51120
tcacccaaag aggagaaact tctgtcgtca cccaaagtgt tacatgctta aaacacaagc  51180
tacctttgta aatacttcat ctgatcagaa gtgtgtcatg cttgtttgag atggagttgc  51240
tgcattttag gactattgat accttttttt aattgttttt ataatattta atttgaaaga  51300
ggagaccctt ctctctctac tctttcatag actgaagttt gaatatgaaa taggccttaa  51360
ccatcatgtt gactctcctg tcagaatttt aggttggaaa tttggtttta ttctttcatg  51420
taattgctta tttgaacaga tcacttacta aagctttaga agaagtgatt caaatgtgtg  51480
ttttcccttc agttttataa caaatggatt gatggcagtc aaatagctca ggaataaatt  51540
actgtttcaa tggttcttaa actttcttgg atcataggat ccttttgaga atcagattaa  51600
agccaaagat actctttgga gaaaaatgca tattcctaat tttgcataga tgacctttgg  51660
attattggac tctgactatt gggaccctaa atactattta attataaatc ttttttttct  51720
cctccttggt tatttaaaca gttgaacagt gtcaggaaca gatgtttctg taatgtcaca  51780
gttgctagca tgggaaaatc agagtctggc atgggtgtag gaaggaacac tcctttcaga  51840
taattgaact gttttctcta ggattcattg tgaaggcttt tctgctcacg tttgtagttt  51900
atttttcaat taattcctag gattggagtt gttgggacag tgagaatgaa attcatttac  51960
aggaagtccc aggaaggaga aagtttgagg cagttttcaa agacgtgtat gtgcctagca  52020
ttagagttta ataaactcac aaagggaaat actgtagaat ttagatcctc acagttcttc  52080
atacagtgaa gtgaacttta ggaagacgat gctttgttac cagggatgga gaatctttct  52140
tgattgcaaa gacataaata ggcatggcta ggtagaaaac ctagcctagt tggtaggaca  52200
ccagttctac caactgctaa aatgaacttt acttacagag gtggaaaaaa tatatactcc  52260
cttccacttg agtaaagagt gatattgtta aactagaatt ctaaattcct ttgtgatctg  52320
tcagaagcat cacctgtggg tggaggagtc ctgcacactc ctcagttact gctttggtaa  52380
gaacaagatt atctatttga gtccaggcat ggtagctcat gcttgtaatc ccaacacttt  52440
gggaaaccaa ggcaagtgaa tcacttgagg acaggagttt gagaccagct gggcagtata  52500
tatggaggca gtatatattt gagaccaaca tttggcagta tatatggagg ggctgaattg  52560
cactcagttg cctggtgcta tggtgcacgc ctgtactctg gatactgtgg aggttgaggt  52620
gggaggattg cttgaggcca ggagttcagg gccagcctgt gcaacatagc aagctcccat  52680
ctctataagt aatgaataaa ctttttaaaa tgaattatgg ccaggcacag tggctcacac  52740
ctgtaatcct agcactttgg gaggccaagg caggcggatc acctgaggtc aggagttcga  52800
aaccagcctg gccaatatgg agaaaaccca tctctactaa aaatacaaaa attagctggg  52860
catggtggca catgtctgta atcccagtgt tggaaataag agctcagagt cacaaagaaa  52920
```

atgagcactc aaacaaaaga cttctcagca aggcaaattt acgtccgcag aagggtgctg 52980
ctgcctgcac cagtcacaat c 53001

<210> SEQ ID NO 17
<211> LENGTH: 492
<212> TYPE: DNA
<213> ORGANISM: Homo sapiens

<400> SEQUENCE: 17
gggtctccgc tcaacgatcc ttcctcaaag catggttgct gagtacccag agttgcgagg 60
agttttttaa ctgatttagc caggtggcaa tcatgagtga atggatgaag aaaggcccct 120
tagaatggca agattacatt tacaaagagg tccgagtgac agccagtgag aagaatgagt 180
ataaaggatg ggttttaact acagacccag tctctgccaa ggttctactg tcacccaggc 240
tggaatgcag tggcgagatc tcggctcttt gtaacctcca cctcgcaggt tcaagcgatt 300
ctcctgcctt agcctcccga gtagctggga ctacaggcat ttgccaccac gtctggctaa 360
tttttgtatt ttttgtggag acggggcttc gccatgttgc ccagtattgt ccttgtgaac 420
ttccttgaag atggcagcat gtctgtgacc ggaattatgg gacatgctgt gcagactgtt 480
gaaactatga at 492

<210> SEQ ID NO 18
<211> LENGTH: 972
<212> TYPE: DNA
<213> ORGANISM: Homo sapiens

<400> SEQUENCE: 18
agcggaagcg atccttcctc aaagcatggt tgctgagtac ccagagttgc gaggagtttt 60
ttaactgatt tagccaggtg gcaatcatga gtgaactgga tgaagaaagg ccccttagaa 120
tggcaagatt acatttacaa agaggtccga cgtgacagcc agtgagaaga atgagtataa 180
aggatgggtt ttaactacag acccagtctc tgccaatatt gtccttgtga acttccttga 240
agatggcagc atgtctgtga ccggaattat gggacatgct gtgcagactg ttgaaactat 300
gaatgaaggg gaccagtaga gtgagggaga agctgatgca ctttgttcac gtctggagac 360
tgcaacagca tacagcccag aggatctgga agagagaaag aacagcctaa agaaatggct 420
tgagaagaag ccacatcccc atcactgaac agggagacgc tccagggact ctctgtgtgg 480
ctggggtcct gactatagac ccaccatatg gtccagaaaa ttgctgcagc tctaatgcag 540
attattctgt cgcgtgttca ggatcttatt gaaggacatc ttacagcttc cccaatgaga 600
ggccaggaag tgtgaacata ctgatagaaa caagactata tgttatccct cataaaatgt 660
ttaaatgtaa atgtacatga ctgtggtgtg tgtatgtgtg tgtgtgtact aattcttgga 720
tgtgtcggta aaactcagag gagtgggtta taagtgctat ttccttgggg aaattaatga 780
acttagggca agtataagca tccccatggc ttaagattag gcgcagggac atcggaactc 840
gggttgggtc ttactttaac tttttaactt tttttttgag attggaagtc tcgctctgtt 900
gccagggttg aagtgccatg gggcaatctt caggtcgtgc accttccggc cccaggttc 960 aaccgaatcc cg 972

<210> SEQ ID NO 19
<211> LENGTH: 703
<212> TYPE: DNA
<213> ORGANISM: Homo sapiens

<400> SEQUENCE: 19

```
gggctcaacg atccttcctc aaagcatggt tgctgagtac ccagagttgc gaggagtttt      60

ttaactgatt tagccaggtg gcaatcatga gtgaatggat gaagaaaggc cccttagaat     120

ggcaagatta catttacaaa gaggtccgag tgacagccag tgagaagaat gagtataaag     180

gatgggtttt aactacagac ccagtctctg ccaatattgt ccttgtgaac ttccttgaag     240

atggcagcat gtctgtgacc ggaattatgg gacatgctgt gcagactgtt gaaactatga     300

atgaagggga ccatagagtg agggagaagc tgatgcattt gttcacgtct ggagactgca     360

aagcatacag cccagaggat ctggaagaga gaaagaacag cctaaagaaa tggcttgaga     420

agaaccacat ccccatcact gaacagggag acgctccaag gactctctgt gtggctgggg     480

tcctgactat agacccacca tatggtccag caaaattgca gcagctctaa tgagattatt     540

ctgtcgcgtg ttcaggatct tattgaagga catcttacag cttcccaatg agaggccagg     600

aagtgtgaac atactgatag aaaaagacta tattttatcc ctcataaaat gttttaaatg     660

taaaagaaaa aaaaaaaaaa aaaaaaaaaa aaaaaaaaaa aaa                       703
```

<210> SEQ ID NO 20
<211> LENGTH: 646
<212> TYPE: DNA
<213> ORGANISM: Homo sapiens

<400> SEQUENCE: 20

```
ttgctgagta cccagagttg cgaggagttt tttaactgat ttagccaggt ggcaatcatg      60

agtgaatgga tgaagaaagg ccccttagaa tggcaagatt acatttacaa agaggtccga     120

gtgacagcca gtgagaagaa tgagtataaa ggatgggttt taactacaga cccagtctct     180

gccaatattg tccttgtgaa cttccttgaa gatggcagca tgtctgtgac cggaattatg     240

ggacatgctg tgcagactgt tgaaactatg aatgaagggg accatagagt gagggagaag     300

ctgatgcatt tgttcacgtc tggagactgc aaagcataca gcccagagga tctggaagag     360

agaaagaaca gcctaaagaa atggcttgag aagaaccaca tccccatcac tgaacaggga     420

gacgctccaa ggactctctg tgtggctggg gtcctgacta tagacccacc atatgatcca     480

gaaaattgca gcagctctaa tgagattatt ctgtcgcgtg ttcaggatct tattgaagga     540

catcttacag cttcccaatg agaggccagg aagtgtgaac atactgatag aaaaagacta     600

tattttatcc ctcataaaat gttttaaatg taaaaaaaaa aaaaaa                    646
```

<210> SEQ ID NO 21
<211> LENGTH: 6001
<212> TYPE: DNA
<213> ORGANISM: Homo sapiens

<400> SEQUENCE: 21

```
atcgcaatac ctggagaaca aaggcattcc taattttgct ttaaagataa tagtattgat      60

gcttgaaaaa tatagtaatt aagaaaatta atcctttatc ataaaccctt gtagcagagc     120

gcatctcctc atacatagga ctattgtatc tagggtggac actttcctct tactttcggg     180

aacatcctac tctgtctatg gagcagctgt tctttcacca ctttactttc ttactaaact     240

tgcttttgct ttgcactgcg gactcgctct gaattctttc ttgcgcgaga tccaacaact     300

ctctcctggg gtctggatca ggaccccttt cctgtagcaa ccctatcgct cttctccacg     360

gcacgttcac ctcacattcc tagagcttta ggatttactc tgagggttca tgtgctttga     420

ttctaaggcg aaagtgcatt tccaagtcta ctatcattga ggacctggca cgagcttttt     480

cctctttatt tatttttatt tttaattttt ttgagacgga gtttcgctct tgttgcctag     540
```

```
gctggagtgc aatggtgcga tctcagcaca ctgcaacctc cgcctcccgg gttcaagcga    600
ttctcctgtc tcagcctcct gagtagctgg gattacaggc gcccgccact aggcccggct    660
aatttttggt atttttagta gagacggggt ttcaccatgt tggccaggct ggtctcgaac    720
tcctgaccgg tttcgaactc ctgatccacc cgcctcggta tcccaaagtg ctgggattac    780
aggcgtgagc caccgcgccc ggccgctttt tcctctttaa agaaaaaaag attatttgaa    840
ctgtccgtcg tggcaatgga gagggatagc cttagaggac atggcggttc attattatta    900
ttattattac agaacaatct tagactctgt ccgcaccctg cactctaggt cccgcgactc    960
tcagacctcc aagtaggact acaaaacaga ggtttctggg ggaaggaagt gacgatcggc   1020
gcaaagcatg ctggtctcag gcggtctccg ctcaacgatc cttcctcaaa gcatggttgc   1080
tgagtaccca gagttgcgag gagtttttta actggtattt ttctcgtttg tcagggttaa   1140
acgttaagta ccatttggtt tttagtacag tgttaggtat cgtgtggctg caggacagga   1200
ccagaaatct aagctctaga gctgtagccg ctggcccttc gtttgtgcat ccttcaaaca   1260
aattttaagg ggcagttgtc ataaatcggg ggagcctctc gatggcggga tccagcggag   1320
acacagagcc agagagcgcg tgggtggata tcaggagagt tttctggttc agttgaggag   1380
tggggtgaac tcctttgatc gatggaagga aaagcagagt tgaagggttt gagcatcatc   1440
tgcaggccag agtgaaagcg atttggaatg tggttgtgga tcggaataga cctgtgccag   1500
atgaatttcc tcagactgca cccgcggcaa atcggtgacc cctctgcttt aggccgaatt   1560
gtacatatta actattttcc ttttcctgat aaaaattctc aagcagcctt tacacgtgtt   1620
cttttcccca actatagtat cagttcctat cagtacatgc attaatactt aattgtatta   1680
agttacttat tacgaacttg aggcaaatca cagatgttct ctgtctctag gataggatgg   1740
agattaggga taagacattt gcttacgtgg aacatatatt aaccagcact ggtggttgtt   1800
tcagatttag ccaggtggca atcatgagtg aatggatgaa gaaaggcccc ttagaatggc   1860
aagattacat ttacaaagag gtccgagtga cagccagtga gaagaatgag tataaaggat   1920
gggttttaac tacagaccca gtctctgcca agtgagtatg catcctactt gcctgaaatc   1980
ttgacacccc tttgtgctgc ctgtatgtta tagacaaact aagaaagcag ataaatgaaa   2040
agctaattat taatattttc atataagaat tttttgtttg tttgagacag ggttctactg   2100
tcacccaggc tggaatgcag tggcgagatc tcggctcttt gtaacctcca cctcgcaggt   2160
tcaagcgatt ctcctgcctt agcctcccga gtagctggga ctacaggcat ttgccaccac   2220
gtctggctaa tttttgtatt ttttgtggag acggggcttc gccatgttgc ccaggttggt   2280
ctcaaactcc tgagctccaa ggatctgccc accttagcgt cacagagtgc tggcattaca   2340
ggctgagtca ctgtacccgg cctacatatg agaacttaac tgcctttgaa tctaaatgct   2400
gttctgacta tggattacct tatcagacca ggcaacttca tagaaattgg gcatagaaat   2460
tattcttact atatatatat atatatatat atatatatat atatattttt tttttttttt   2520
tttttttttt cgggggtggg atgaagtctc actctgttgc ccaggctgga gtggtgcagt   2580
tacaatcttg gctcactgca acttctgcct cccaggttca agtgattctc atgcctcagc   2640
ctccccagta gctggggtta cacacatgtg ccaacatgcc ccactaattt tttgtatttt   2700
tagtagagac ggggtttcgc tatgttggcc aggctggtct caaactcctg acctcaggtg   2760
atctgcccac cttggcctcc caaagtgcta ggatcatagg cttgagccac tgtccccagc   2820
ctataatttt gtttataaat acttcactat atctcttaaa agaaaaggac tttaaggccg   2880
ggcatggtgg ctcacgcctg taatcccagc actttgggag gccgaggcgg gtggatcacg   2940
```

-continued

```
aggtcaggag atcgagacca tcctggctaa catggtgaaa ccccgtctct actgaaaata   3000
caaaaaaaat tagccgggcg tggtagcagg cacctgtagt cccagctact caggaggctg   3060
gggcaggaga atggcgtgaa gctgggaggc agagcttgcc gtgagctgag atcgcgccac   3120
tgcactctag cctggacgac agagcaagac tccgtctcaa aaaaaaaaaa agaaaaagat   3180
aaggacttta aataaatgta accacaaaaa cttttttttt tgagatggag tctcgctgtg   3240
ttgcccaggc tggagtgcag tggcgtgatc tcagttcact gcaacctcca ccttcccagt   3300
tcaagtgatt ctcctgcctc aggctcctaa gtagctggga ttacaggcgt gtatttttag   3360
tagagatggg gtttcaccat gttagccagg acggtctcca tttcctgacc ttgcaatcca   3420
cccacctgac ctcccaaagt gttggggtta taggcgtgag ccacctcacc tgaccatttt   3480
tttttgaga tggagccttg ctctgttgcc caggctggag ttcaatggct cgatctcggc   3540
tcactgcaac ctctgcctcc cggattcaag tgattctcct gcctcagcct cctaagtagc   3600
tgggatcata gacatgtgct accacacccg gctaattttt gtatttttag tagagatggg   3660
gtttcaccat gttggccagg ctggccttga actccttacc tcaagtgatt tgcccgcctt   3720
gtcctcccaa agtgctggga ttacaggcgt gagccaccat gcccggccta gttattgttt   3780
ttttaactct aaaagttaag tctaccctgc cttcttcttt tttttttttt ttccacgaca   3840
gagtcttgct caggctggag tgcagtggca tgatctcggc tcactgcaac ctctgcctcc   3900
caggttcaag caattctctg cctctgcctc ccaagtagct gggattacag gtgactgcca   3960
ccacacccag ctaatatttg tatttttagt agggattggg tttcaccatc ttggccagag   4020
gttggtcttg aactcctgac ctcgtgatcc acccgcctcg gcctcccaaa gtgctgggat   4080
tacaggcgtg agccaccgcg cctggctacc ctgccttctt ttctaataca catttaaggc   4140
attcataact tgtttaatcc tttaactgta tcccacaatg attggctgta ggctgggcaa   4200
aaagtttacc tatttaggat ccttagtgaa tgtttgttga ataaatggaa gcattcattg   4260
gtgacaggat taatttcaaa cagagtagag tgtcatctat tattttagtg acctacttgg   4320
gttgatgatg cctctaaact tacttttcct ccaaagtatt gtccttgtga acttccttga   4380
agatggcagc atgtctgtga ccggaattat gggacatgct gtgcagactg ttgaaactat   4440
gaatgaaggg gaccatagag tgagggagaa gctgatgcat ttgttcacgt ctggagactg   4500
caaagcatac agcccagagg atctggaaga gagaaagaac agcctaaaga aatggcttga   4560
gaagaaccac atccccatca ctgaacaggg agacgctcca aggactctct gtgtggctgg   4620
ggtcctgact atagacccac catatggtcc agaaaattgc agcagctcta atgagattat   4680
tctgtcgcgt gttcaggatc ttattgaagg acatcttaca gcttcccaat gagaggccag   4740
gaagtgtgaa catactgata gaaaaagact atattttatc cctcataaaa tgttttaaat   4800
gtaaatgtac atgactgtgt gtgtgtatgt gtgtgtgtgt ataattcttt gttgttttgg   4860
taaaatcaga ggagtgggtt ataagtgcta atttccttgg gaaattaatg aactagggca   4920
agtatagcat cccatgcata aaattagcac agggacatca gaattgtatg ggtcttcttt   4980
tttctttttt tctttttttt ttgagatgga gtctcgctct gttgccaggt ttgagtgcag   5040
tggcgcaatc tcagctcagt gcaacctccg cctcccaggt tcaaccgatt cccctgcctc   5100
agcctctcga gtagctggga ctacaggtgc acgccaccac tcccagctaa tttttgtat    5160
tttagtagag atggggtttc acctgtatgg gtcttttctt gtgatggggt tacaccccca   5220
tttttgttag gcaagaaaag catttggaaa aaaatgtaac atgttagatt caatataaaa   5280
tattatggta agatcatggt cttgttaagt ctcttcacta actgtatgtg tctgttttta   5340
```

```
aaagatgtgt cttggtgggg cgcggtggct cacgcctgta atcccagcac tttgggaggc   5400

cgaggcaggt ggatcatgag gtcaggagat cgagaccatc ctggctaaca cggtgaaacc   5460

ccttctctac taaaaataca aaaaaaatta gccgggcgtg gtggcaggtg cctgtagtcc   5520

cagctactca ggaggctgag gcaggagaat ggcatgaacc cgggaggcag agcttgcagt   5580

gagccgagat cgcgccactg cactctagcc tgggtgacag agcgagactc cgtctcaaaa   5640

aaaaaaaaaa aaattattgg aacacagcat tacctattga attacagttt tctggttttt   5700

ttgtggagtt tttgttttgg tttttgagat ggagtttcac tcttgttccc caggctggag   5760

tgtaatagtg caatctcggc ttaccacaac ctctgcctcc caggttcaag caattctcct   5820

gcctcagcct cctgagtagc tggtattaca ggcatgcacc atcacgcccc actaattttg   5880

tattttttta gtagagacgg ggtttttcca tgttggtcag gctggtctca aactcccgac   5940

ctcaggtgat ccgcccgcct cggcctccca aagttctggg attacaggtg tgagccaccg   6000

t                                                                   6001


<210> SEQ ID NO 22
<211> LENGTH: 493
<212> TYPE: DNA
<213> ORGANISM: Homo sapiens

<400> SEQUENCE: 22

cggcttctct gttgacaact cagctggttc cacaccctgg caattgtgaa gagttggcca     60

aatgtttgtc cactgagctg atctcctctc tggagcaccg gggccaccag gagggaggtc    120

tgtgaaaccc ctgcccctgc cattgaccta agtgttgggc tcttgaatct aacagactag    180

tttttcaagt cgtgggggat gggcttgggc atttttccct gaaaccttcg gaaatccttg    240

ccttggagac tgaaaggata aaggcctctg gggccaggtc accagggaca atggataacg    300

cctgcctcta ccctcctggg cacaccctgt gtgatctttc ttaaaccagt ttcttatcag    360

gtcacacctt ggctccacag tctgcctttc tacatggggc acgggtgagg acctgagttt    420

gctccctctt cctccaccct ccagcttgca ccaaggaaat gatttttttt ttttgaaaca    480

gagtctcact ctg                                                       493


<210> SEQ ID NO 23
<211> LENGTH: 852
<212> TYPE: DNA
<213> ORGANISM: Homo sapiens

<400> SEQUENCE: 23

gcccaggctc cgcggcttgc ggcctgcccg ggcctctgca gcgggggcgc cggcggaagt     60

ggggacacca gtagccgcgg acctcgccaa gacaatgcaa actccagtga acattcccgt    120

gcctgtgctc cgtgctgccc cggggccctg atggcttcag ccgtggcttt gcccctgatg    180

gacgcagagc cccccttgagg ccagaggttc ctgaaatcca ggagtgtccc atagctcaag    240

aatccctgga atcccaggag cagcgggcac gagccgccct tcgggagcgt tacctccgca    300

gcctgctggc catggtgggt catcaggtga gcttcacgtt gcacgagggt gtgcgtgtgg    360

ccgcccactt tggagccacc gacctggatg tggccaactt ctacgtgtca cagctgcaga    420

ctcccatagg tgtgcaagca gaggcgctgc tccgatgtag tgacattatt tcatatacct    480

tcaagccata aagatattgt gttcactttt ctgcttgagg ctaaggcact gtatcccagg    540

cctcccaatg ttcccgagcc aggaactctg ggccccatgg agttatgagc tcccttggaa    600

ttttgagcca agctttaagc aagtctggac tcctgagacc tcctgggtct agtcagtaaa    660
```

```
attctgcaac tctaggaatt ctaagatccc attggaagga atgctctacc tcacagaact    720

ctgaacccta cagaacatat gggcctgcat gccatttcct gaaagaccgg gcatcggggt    780

gaggctgata aaggatacaa ctgcaacagg ggaaggttat acagaggttg aaaagtccag    840

caccctgaag aa                                                        852
```

<210> SEQ ID NO 24
<211> LENGTH: 851
<212> TYPE: DNA
<213> ORGANISM: Homo sapiens

<400> SEQUENCE: 24

```
ggttccctct ccccggcccc agctctggac gctcacccca gtgcaacgcc ctgagtgacg     60

gaaagagcca agacaatgca aactccagtg aacattcccg tgcctgtgct ccggctgccc    120

cggggccctg atggcttcag ccgtggcttt gcccctgatg gacgcagagc cccccttgagg   180

ccagaggttc ctgaaatcca ggagtgtccc atagctcaag aatccctgga atcccaggag    240

cagcgggcac gagccgccct tcgggagcgt tacctccgca gcctgctggc catggtgggt    300

catcaggtga gcttcacgtt gcacgagggt gtgcgtgtgg ccgcccactt tggagccacc    360

gacctggatg tggccaactt ctacgtgtca cagctgcaga ctcccatagg tgtgcaagca    420

gaggcgctgc tccgatgtag tgacattatt tcatatacct tcaagccata aagatattgt    480

gttcactttt ctgcttgagg ctaaggcact gtatcccagg cctcccaatg ttcccgagcc    540

aggaactctg ggccccatgg agttatgagc tcccttggaa ttttgagcca agctttaagc    600

aagtctggac tcctgagacc tcctgggtct agtcagtaaa attctgcaac tctaggaatt    660

ctaagatccc attgggaagg aatgctctac ctcacagaac tctgaaccct acagaaatat    720

gggccctgct gccatttcct gaagaccggg ggcatcgggg tgggggtgat aaaggataca    780

accctgcaca gggggaaagt tattaaaaga agctgcaaag tccagccacc cctgaaagat    840

actcccccg t                                                          851
```

<210> SEQ ID NO 25
<211> LENGTH: 1631
<212> TYPE: DNA
<213> ORGANISM: Homo sapiens

<400> SEQUENCE: 25

```
taggtggtgg ggggtcgcca gcaggttccc tctccccggc cccagctctg gacgctcacc     60

ccagtgcaac gccctgagtg acggaaagag gtctggcggc ttctctgttg acaactcagc    120

tggttccaca ccctggcaat tgtgaagagc tggccaaatg tttgtccact gagctgatct    180

cctctctgga gcaccggggc caccaggagg gagccaagac aatgcaaact ccagtgaaca    240

ttcccgtgcc tgtgctccgg ctgccccggg gccctgatgg cttcagccgt ggctttgccc    300

ctgatggacg cagagccccc ttgaggccag aggttcctga aatccaggag tgtcccatag    360

ctcaagaatc cctggaatcc caggagcagc gggcacgagc cgcccttcgg gagcgttacc    420

tccgcagcct gctggccatg gtgggtcatc aggtgagctt cacgttgcac gagggtgtgc    480

gtgtggccgc ccactttgga gccaccgacc tggatgtggc caacttctac gtgtcacagc    540

tgcagactcc cataggtgtg caagcagagg cgctgctccg atgtagtgac attatttcat    600

ataccttcaa gccataaaga tattgtgttc acttttctgc ttgaggctaa ggcactgtat    660

cccaggcctc ccaatgttcc cgagccagga actctgggcc ccatggagtt atgagctccc    720

ttggaatttt gagccaagct ttaagcaagt ctggactcct gagacctcct gggtctagtc    780
```

```
agtaaaactc tgcaactcta ggaattctaa gatcccattg gaaggaatgc tctacctcac    840

agaactctga accctacaga aatatgggcc tgctgccatt tcctgaagac cggggcatcg    900

aggtggggtg ataaaggata caacctgcac agggggaagt tattaaagag gctgcaaagt    960

ccagccaccc tgaagatact ccccagtgct cccctcctgc taaagaacca gttaccccgg   1020

gaaaattcga ctcctgtttt tctttaatta actataccga cggggatgga gtcatcttta   1080

ggggctggta gggtggttat ccaagggctg aatccagtgg agctgggcca agtacgacag   1140

gagtccagat aaaggtgtag ggctgcacgg gccgcaagtc tcctggaaag gctggagtga   1200

ccggcatgcc gggattggga gattaggatt tgatttcatt ttggggcggg cggtggctcg   1260

tgctgggtca cgtggtcgtg cccaagcgct cctcctgttg ccccacctgt ggttgctgtg   1320

gactgcacac gacagcagat tcgctgtccc ctcgttggag gcgaatggtc ggaccccgag   1380

tggcggcgcc cctgataaaa ggccgaggat tcgcgatcag ggtgcaactt cactccctcc   1440

tctcttctct ccagccttgc agcgtggccg ttcacatcac gcgcttcact aagcctccta   1500

tcactagtaa ccttccagcg cattgtttaa aaagaaagca gtttctgtcc ctttctgtag   1560

ttcctttaag ttcaggatgt aagcgaagcc ttccattaag taaaggtgtg tgtcgtttcg   1620

tctcagtcgc g                                                        1631
```

<210> SEQ ID NO 26
<211> LENGTH: 15001
<212> TYPE: DNA
<213> ORGANISM: Homo sapiens

<400> SEQUENCE: 26

```
cactccatga cctccatctg tccccagttc cctcttggat ctcactttct ccatctgtca     60

aaggaggtag ggcaggttgg aactagaggg ttatctgagg tggtttcttc ttcactgccg    120

cctcctctga tcaccctttt tttttttgta atttttaatt tttcaaaaaa aattattttt    180

aaatagagac agggactcgc tttgttgccc tggttggtct gaaactcttg gcttgaagcg    240

ctcctcctgc ttcagcatcc caaagtgctg agattacagg tgtgagacac tgcactcagc    300

ctcagaccac ccaattttaa gttccatggc aacccagcca ccccactatcc cattgccctt   360

attttactct tttttttttt tttttttttt gagatggagt ttcactcttg ttgcccaggc    420

tggagtgcag tggcacgacc tcagctcact gcaacctccg cctcccgggt tcaagtgatt    480

ctcctgcctg agcctccgga gtagctggga ttacagatgc ccggctaatt tttctatttt    540

tagtagagac agggtttcac catgttggcc aggctggtct cgaactcctg acctcaggtg    600

atccacccgc ctcagcctcc caaagtgctg gaattacagg cgtgagccac cgtgcccggc    660

ctattttatt ctttatacat cactttgatc aaaccctgaa ggatcttgtt tacatatttg    720

ctcattttac cctattctgt cccttctacc cccactagaa cgtaggttct aggaggcagg    780

atgggagtct gtcttgttca taaatacaac ccctactcgt tcatagttaa gtcaacaaat    840

atttattgcg cacctactat gtgtctgatg atattctttc aacagatatt tgcagagcac    900

caaattgtgt acctggcact aggccttggt gatctagtgg aaagcaaagg cccacaggat    960

ccctgcgtaa agaggacccc gcaaggagaa agtgaattct gactgggcct ggaataggga   1020

ggttcatatt ccccattcaa ggcctcagtt tccccctttg taaaatggga ctgcagggag   1080

agctggagga caaaatgacc gcctctgatc cagcccagct actttcttag tatgcggcat   1140

ctgaaaccat gatctccagg tttcctgtag aggagcgggg gttcccactg gaagcaaggg   1200

gttaggagtg ggtatgtgta gggggatggg gatgcaaaga ccgagctctg cccttaaccc   1260
```

-continued

```
agcagggagg aagtcttccc ctctctgaac ctcagtttct tcctgcctaa aatgggcatc   1320
ccagacgccc ccaactcgca ggcaggaaga tcggtcccaa gtgccccgca aagccgcggg   1380
ccaggtggcg acccgggctg tgctggcttc caagcctgcg agccagcccg cgaccacgtg   1440
gggcagtggc ggcggcgcgg gcggaaccca ggctccgcgg cttgcggcct gcccgggcct   1500
ctgcagcggg ggcgccggcg gaagtgggga caccagtagc cgcggacctc ggtgagtaca   1560
aggtggtggg gggtcgccag caggttccct ctccccggcc ccagctctgg acgctcaccc   1620
cagtgcaacg ccctgagtga cggaaagagg taggaccgcg cctgcagcgc cggctggagg   1680
gacgttctgg tccccagacg ctcctatcag ggactgtttg atcccgatcg ccggcagcgg   1740
gaatgcccca cgcgggtggg gtgaggagaa gggagaagga gaaaaacttc ccctccggaa   1800
aataataaat ggccacgata acagaagcat cggtggcagt catcccgctt tacctggagc   1860
ggaatcgctc gctcagtctg agcctggagg tgggaagaag gtccagtccg aacgcccagg   1920
gcggtgtggg gagtggacgc ctgggggccg ggaggaccta cttagtataa gaaaaggaga   1980
gcaatgggtg gtcagggcgg aattgaaagg aaactgaccg gccccagggg agaaggggag   2040
gggagagatt ctgtgcttgg ggttctgacc ctctcgggtg gccccattta gctaatttgc   2100
atcaagattc agcagccgat gatgtctgta tgtgtgtgtg tgtctgtgga cacgtcaaca   2160
ccttggttaa ttaattaggt ctggcggctt ctctgttgac aactcagctg gttccacacc   2220
ctggcaattg tgaagagttg gccaaatgtt tgtccactga gctgatctcc tctctggagc   2280
accggggcca ccaggaggga ggtctgtgaa acccctgccc ctgccattga cctaagtgtt   2340
gggctcttga atctaacaga ctagtttttc aagtcgtggg ggatgggctt gggcattttt   2400
ccctgaaacc ttcggaaatc cttgccttgg agactgaaag gataaaggcc tctggggcca   2460
ggtcaccagg gacaatggat aacgcctgcc tctaccctcc tgggcacacc ctgtgtgatc   2520
tttcttaaac cagtttctta tcaggtcaca ccttggctcc acagtctgcc tttctacatg   2580
gggcacgggt gaggaccaga gtttgctccc tcttcctcca ccctccagct tgcaccaagg   2640
aaatgatttt tttttttttt tttttgaaac agagtctcac tctgtggccc aggctggggt   2700
gcagaggcgt gatctccgct cactgcaacc tccgtctccc tggttcaagg gattctcctg   2760
cctcagcctc ctgcgtagct gggattacag atgcgtgcca ccacatccag ctaatttttt   2820
ttgtattttt agtagagata gggtttcacc atgttagcca ggctggtctt aaactcctga   2880
catcaggtga tctgcctccc tcagtctccc aaagtgctgg gattacaggt gtgaaccact   2940
gcacccagcc cgaggaaaga tttgacctgc cagcttcact ggccacttta caaaaatggg   3000
gattgcatca atatgaccaa atctcccttg tttttgtttt tttttttttt ttttcctgat   3060
ggagaaaaca aggccctata ctggccctcc cttaatttca ttttatccag ggatttaaca   3120
gaattctttg gccactctaa tcctatctaa gtcatttagt aagtactcac cctagagact   3180
aggggtttc tcttgaaact caagtgttaa tctaggctca ggaaagaccc tgggggctgg   3240
tgaggcctga ctaaattgga gtgacagtgg tcagagaaaa taaaaaatgc aagtagggcg   3300
tgttggcgtg ggcctgtaat cccagcttct cggaaggctg aggtgggagg atatcttgag   3360
tccaggagtt caagattagc gtgggcaata cagcgagacc tcacctcaaa gtaaataaat   3420
aagtaaatgt gctttttaaa aaattagaaa atgcaaggcc gggcacggtg gctcatgcct   3480
gtaatcccag cactttggga ggctgaagca ggcagatcag gagtttgaga ccagcctggc   3540
caacgtggcc aaaccgcgtc tctactaaaa atacaaaatt agccatgtgc agtggtgcgc   3600
gcctgtagtc ctagttactt gggaggctga ggcaggagaa ttgcttgaac ccgggaggcg   3660
```

```
gaggttgcag tgagttgaga tcatgccact gtactccagc ctgggcgaca agagtgagac   3720
tccgtcttaa aaaaaaaaaa aaaattagaa aatgcaacta tcccttaatt ccattcacgt   3780
ggtcttccct gtcaggaaaa aaaaaaaaaa ccttggagtc tcccttggct gctctttccc   3840
tcaaattata tatcccttat cctgtccatc accgagggct cttgaccttt cttttttgt    3900
ttgtttttgt tgttttgaga tggagtctca ctctgtcatc catgctggaa tgcaatggca   3960
cgatctccgc tcacttcaac ctccgcttcc cgggttcaag cgattcttct gcctcagcct   4020
cccgagtagc tgggattaca ggcacgcacc accacaccca gctaactttt gtatttttag   4080
tagagagagg tttcaccatg ttgaccaggc tggtctcatc ctgacctcag gcgatctacc   4140
cacctcagcc ttcaaaagtg ctgggattac aggcgtgacc tactgcgccc agcctcgacc   4200
tttcaaacat agcctaatct gaccacttct ccccattccc attgtcccca gcccatacta   4260
gacgccatct tcttccacct ggaccactac agtgacctcc tcattgcgtt cctagtgtct   4320
cccttcaatc tcgtttattg tccatgcagc aggcagagga tcctgaggac cttaagccag   4380
attctgccca tccttcactc agaactgtcc agtggcttca gtctcagagt agagacccaa   4440
attgtcatca cagcccacaa ggcactctct ctgtccctgc cccacctcc tccacactgg    4500
ccttgctacg ccccaaagcc accctttcca tgatctttgc attttgctct tccttctgac   4560
tggaatctcc acatggctcc attcctaatt tcattcaggt ctatgctcaa acgtaatctt   4620
atcataggga tctttcctgg gctcccttga aactaccctc tatcccccag gctgggtcag   4680
gtgtctcctc tggactcctt cattccagcc ctactcactt tgggtcatca ctgcctaagg   4740
acaggtctgt gtcccctatt ggactgtgag cccacaaagg cggaactggg ctctcagtcc   4800
tagacgtgtt tccaagaccg cccaatgtgg gtcatgcaca gagcaggcac tcagatgatg   4860
tgctaacaat gctagataat gtggatgagt gaattttttt tttttgaga caggtctca     4920
tactctgtca cccaggctgg agtacagtgg cacagttatg gctcactgca gcctccacct   4980
accaggctca agcgatcccc tcacctcggt ctccttagta gctgggactc tagtcgcaca   5040
ctacccatgc ccagctaatt tttttttttt tttgtagaga tggggttttg ctatattgct   5100
caggctggtc ttgaactcct acgctaaagc aattctccag cctcagtctc ccaaggtgct   5160
gggattatag ttgtgagcca ccgcacctgg ctagaaaact tttctttggt gcataaaaat   5220
gatataaaat tcaaatttca gtgtcccagt aagtaaggtt ttgttggaga acagccatgt   5280
tcatttgttt ccatattgtc tatggctgct gttgtgctac tgtggcagag ttgagcagtg   5340
acagtaaaat acttacagag aaggttcgca gacctctgct acgtattttg ccaagaagaa   5400
aaataaaata aagttaaaat tgaaaatatg ttgcccgctg ggcgcggtag ctcacgcctg   5460
taatcccggc actttgggaa gctgaactgg gggtgggtca cctgagacca ggagatgtag   5520
accagcctgg ccaacatggt gaaaccctgt ctctactaaa atacaaaaat tagccaggca   5580
tggtggcgcg cacctgtaat cccagctact caggaggctg aggcaggaga attgcttgaa   5640
cccaggaggc agaggttgca atgagccaag attgcaccac tgcactccag cctgggggat   5700
agagtgagac tccatcccca aaacaatttt gccaaggagg attctatttg ggccacctat   5760
gggcatgtga gatcagtaag atttggcagc taattatgca gagtgggtga tgaggtttag   5820
atgcctccca gggagagctc tttttcacat tttcttttcc aattcttctt cttttttttt   5880
ttttttttgt ttgagacagg gtctcactct tcccaggctg gagtgcagtg gtgcaatcac   5940
atctcactgc agcctcagcc tcctccggct cactagatct tcccacctca gcctcctgag   6000
tagctgggac tacaggagcg caccctttgc ccagctaatt tttctatttt tctggagacg   6060
```

```
agattttgct atgttgccca agctggtctc aaattcctgg gctcaagtga tccacctgcc   6120
tcagcctccc aaagttctgg aattacaggt gtgagccacc tcgtgcccag ctgcttcttg   6180
ctttctgaaa ttaaaattta ggccgggcac ggtggctcac gcctgtaata ctagcacttt   6240
gggaggccaa ggcgggtgga tcacctgagg taaggagttc aagaccagcc tggccaacat   6300
ggggaaaccc cgtctctact gaaaataaaa atatcagctg ggcgtggtcg cgggcacctg   6360
taatcccagc tacttgggag gctgagtgac gagaatcgct tgaacccggg aggcggacgt   6420
tgtagtgagc caagatcgcg ccactgcact cctgcctggg cgacaagagc gagactccat   6480
ctcacaaaaa aaaaaaaaaa aaaaagaaat taaaatttag tggctgggca tggtggctta   6540
gacctgtaat cccagcactt tgggaggctg aggcaagagg atcacttgag cccaggttgg   6600
agaccagcct gggcaatata gtgcgacttc atctctataa aataaaataa aattaattaa   6660
ttaaaaattt tatttattta tttatttatt ttgagacaga gtctcgctgt gttgtccagg   6720
ctggagtgca gtggcatgac ctcagctcac tgcagcctct ggctcacggg ttcaagcgat   6780
tcttatgcct cagcctcctg agtagttggg attacaggtg tgtgccacca tgcctggcta   6840
atttttgggg cgtttgtttg tttttgagat ggagtcccag tctgtcaccc agactggagt   6900
gcagtggcac aatatctcag ctcactgcaa cctctgcctc ccgggttcaa gagagtctcc   6960
tgcctcagcc tcctgagtag gcgggattac aggagcctgc caccatgccc agcccagcta   7020
attttattta tttatttatt ttttgagaca gagtttcact cttgttgcct aggctggagc   7080
gcaatggcgc agtctcggct caccacaacc tctgcctcct gagttcaagt gattctcctg   7140
cttcagcctt ccaagtagct gggattacag gcatgcacca ccactaatta cagaaatgca   7200
ccatcaggct aattttgtat ttttagtaga ggcagggtct ctccatgttg gtcaggctgg   7260
tctcgaactc ctgacctcag gtgatccgcc cacctcggcc tctcaaagtg ctggaattac   7320
aggcgtgagc cacagtgccc ggccaacacc cggctaattt ttgtatttct tagtacagac   7380
agggtttcac cgtgttgacc aggttggtct caaactcctg acctcaggtg atccgcctgc   7440
ctcggcctcc caaagttctg ggtttacagg cgggagccac tgtgcccagc ctatgttcat   7500
gtcttctata gccatcttta ttccttcctc cctctttgtg acctgtttgt ctgcatcagt   7560
gtttcatttg gggccatcag gagacgtttg gcaattcatg gagactttaa aaaaaaactg   7620
tattgagatg caattcacat tcaccaattc actgttcacc agtggtgaca tttttggctg   7680
tcacaacttg aagatgggat gctactggca tctattaata ggaggcagag gctaggatgc   7740
tgctcaaacc ctacacctat gcgttggaca gcccccacaa catagcagat aattatccag   7800
ccccaaatgt caatagtgtc cagactgagt agccctggtt cacatccttg gtctatctgc   7860
agggtcctgt cttgcaaggg gctcacagtt caggtgcaga gacaggaaga gcctaataag   7920
aaaaaggaca agttagtcca ggcacagtgg ctcacgcctg taatcccacc actttgggag   7980
gctgagatgg gggggatcac ttgcggtcag gagttcgaga ccagcctgac caacatggtg   8040
aaaccccgtc tctactaaaa atacaaaaag tagctgggca tggtggtgtg tgtctgtagt   8100
cgcagcttct cgggagactg aggcacaaga atctcttttt tttttttttt tttttttgag   8160
acggagtctc gctctgtcgc ccaggctgga gtgcagtggc gtggtctcgg ctcactgcaa   8220
gctccgcctc ccgggttcac gccattctcc tgcctcagcc tcccgagtag ctgggactac   8280
aggcgactgc caccacgccc ggctaatttt ttgtattttt aatagagatg gggtttcacc   8340
ttgttagcca ggatggtctc gatctcctga cctcgtgatc cgcctgcctt ggcctcccaa   8400
agtgctggta ttacaggcgt gagccaccac gcccggccac acaagaatct cttgaacctg   8460
```

-continued

```
ggaggcggag gttgcagtga gccgaggtgg caccactgca ctccggcctg ggtgacagag   8520
tgagactctg tctccaaaaa aggaaaaaaa agaaacagga caatttcaat cacctcccctt  8580
ctgtgcctgg ccccagggtc ttgggtaccc aacacttgtc actcagctca gttagtcctc   8640
actaggttta gagaggagag gaccaagcca cagggagtgg tgcagctgct aaaacctagg   8700
tcctcctctc tcaggtctgc acccacaagg ccagcatttc cctatacaca ttcaacatca   8760
tagcatagcg cttcatatgt cccagacatg tgccaaacat ggtaggttag ttaggtaatt   8820
tagtccccat gcccgccctg tgagttaggg ctctgtttta cagatgggga aacagaggca   8880
cagattagtc aagccattta ccccaggtca cacagcaata ctaacaataa gagcagttca   8940
ctattatgga gaacctagaa tgtgccaggc cctgtctggc aggagcctgt tgaatcctga   9000
taacagcata ggcagcaatt ggggctattt ttccatacaa tggaagagaa aactgtctct   9060
tactgatgtc acacagctaa accggcctgg gatctccact cttcattcat tttgtttttt   9120
gtttgtttgt ttttttcgag atgagtcttg ctctgtcgcc caggctggag tgcagtggcg   9180
agatctccgc ttactgcaac ccctgcctcc ctggtgcaag cgattctcct gcctcagcct   9240
catgagtagc tgggattaca ggcacgtgcc accatgccca gctaattttt gtattcttag   9300
tagagacggg gtttcaccat gttgatcagg ctggtcttga actcttgatc tcgtgatcca   9360
cctgctttgg cctcccaaag tgctgggatt acaggcgtga gccaccgcgc ccagccaatg   9420
tttgtttgtt tttgagatag agtattgctc tgttgcccag gctggagtac agtggcacaa   9480
tctctgctca ctgcaacctc tgcctcccag gttcaagtga ttctcatgcc tcaggctccc   9540
caagtagctg ggattacagg cacgcaccac cacgtccggc tgatttttgt attttagtac   9600
agacggggtt ttactatgtt ggccaggctg ctctcgaact cctgacctct agtgatcctc   9660
cagcctcagc ccctaaagtg ctaggattat aggcatgcgc cgccatgccc agctcattca   9720
tgaattctca ttggtctcta tggcaggcag tttctggggg ctggagatcc agcagtggga   9780
aaagcaaggt ggccaccttg aaactcacgg agggaaagga gatacaggca gatacaggga   9840
accgaaagtg caagagccca agaagggatt gccaggcatc gcgcctgagg atcagcgagg   9900
aggcctgtgt ggctggggtg gggagagcaa gcgtggtaca ccacgagggt gccggcagga   9960
tccagagcta agacagaagc cacaagaggg ctccgagcag aggagggata tgatctgact  10020
caggcattaa cagggtgttg gggtgcagac ggcggggggt gaaggtggaa gccagggacc  10080
cagtgaggag ttgactacag tactccaggc aggaagtgtc tgtggctgca gcaggatgct  10140
ggcagtggag gaggtgagaa gtgttaggtt gtgaataaat aaatatgtgt gtgtgtgtat  10200
atatagatat ataatttttt tttttttttt tttttgagac agagtcttgc tctgtcgccc  10260
aggctggagt actgtggcac aatctcggct cactgcaacc tctgcttccc aagttcaagt  10320
gactctcctg cctcggcctc ctgagtagct gggattacag gtgcccgcca cgatgcttgg  10380
ctaatttttg tatttttcgt agagacgggg tttcaccatg ttggccaggc tggtctcgaa  10440
ctcctgacct caagtgatct gcccacctcg gcctcccaaa gtgctgggat tacaggtgtg  10500
agccactgct cccagcctta tacaattttt ttctcagcct ttctttgtct tttatgactt  10560
taatattttt gaagagccca ggttagttgt gctgtttttg tttttgtttt ttctaagaca  10620
aagtctcact cttgcccagg cgtggagtgc agtggcgcga tcatagctca ctgcagcttc  10680
aaccttccag ggctccagtg attctcttac ctcagtcttc tgagtagctg ggacttccac  10740
gagtacattg tcaagcctgg ctaatgtttt ttatttttag tagagacgag gtcttaccat  10800
gttgcccagg ctgctcttga actcctgaac gcaagcaatc ctctcacctt ggcctcctga  10860
```

```
ggtgctggga ttataggcat gagccaccat gcctatccct gttgtccttg tttggcccag  10920
aggctggaag atcacttgag gccagaagtt caagaccagc ctcggcaaca tagtgagacc  10980
ctgtctcttt aaaatttaaa aaaaaaagaa aaggaatagc acagaagtgg tgccctgcct  11040
tcttagtgtc ccattcctgg agatgttggc tttgatcact aagttaaggg ggtgcatacc  11100
aggttcctcc agtataaatt tgtgtttgcc ctttacagtg aatgaatatc ttataagtct  11160
gttaagacta tgtagatacc ttatacttca tcaaactccc atccatgctt ttttttttt  11220
ttcttttttt tgacacagag tctcactctg tcgcccaggc tagagtgctg tggtgcgatc  11280
tctgctcact gcagcctccg ccttttgggt tcaaatgatt ctcctgcctt aacctcccga  11340
gtagctggga ctacaggcgc atgacaccac acccggctaa tttttgtatt tttggtagag  11400
gcggggtttc gccatgttga ccaggctggt ctcgaattcc tgacctcaag tgattcgccc  11460
accttggcct cccaaagtgt tgggattaca ggtgtgagcc accgcacccg gccctatcca  11520
cacatttttg catctattcc ttttatattt atttacttgc cagtctacag taaggattat  11580
attttccttc tcttccttat ttattcattt atttattatt ggtatggatt ctggatttct  11640
gttttatcca gtgggttata atctgtaact atcattattg tattgttcaa ataattccag  11700
atttggccac tgggagccct ttcaagctag ctcatgtgtg agtgggaatc tatctagaag  11760
atagaatttc ctgatggatt gggtgggttg tgtgtgagag aaagctgggg tttattcttt  11820
tttttagaga cagtgtctca ctctgtcacc caagctggag tgcagttgca caattacagc  11880
tcactgcagc ctccatctcc tgggctcaac taatccttct ccctcagcct cctgagtagc  11940
ccagctaatg taaaatatat atatatattt ttagaaatgg ggtctcgcta tattgcccag  12000
gctggtctca aactcccagc ttcaaagtga tcctcctgcc ttggcctccc aaagggctgg  12060
gattacaggc atgagccacc atgcctggcc aggttcatct tttggcaaat atttattgcc  12120
tataagttga gataaaaaca ttataaaagc agacaaaggt ccttgccttc acggggctca  12180
tgtttttgtg catgtgacac ttttgtttct gatccaagcc attgggggac gatggcacag  12240
attttaggag ggtggatcag tctggggcag gtgcagtgga gctgcctggt agaccagcct  12300
ctgcttccac tcctccctcc tccattagcc ccatgcttac catgtaatga cttcctgctc  12360
tttttcttca ctcaacagcc aagacaatgc aaactccagt gaacattccc gtgcctgtgc  12420
tccggctgcc ccggggccct gatggcttca gccgtggctt tgcccctgat ggacgcagag  12480
ccccccttgag gccagaggtt cctgaaatcc aggagtgtcc catagctcaa gaatccctgg  12540
aatcccagga gcagcgggca cgagccgccc ttcgggagcg ttacctccgc agcctgctgg  12600
ccatggtggg tcatcaggtg agcttcacgt tgcacgaggg tgtgcgtgtg gccgcccact  12660
ttggagccac cgacctggat gtggccaact tctacgtgtc acagctgcag actcccatag  12720
gtgtgcaagc agaggcgctg ctccgatgta gtgacattat ttcatatacc ttcaagccat  12780
aaagatattg tgttcacttt tctgcttgag gctaaggcac tgtatcccag gcctcccaat  12840
gttcccgagc caggaactct gggccccatg gagttatgag ctcccttgga attttgagcc  12900
aagctttaag caagtctgga ctcctgagac ctcctgggtc tagtcagtaa aattctgcaa  12960
ctctaggaat tctaagatcc cattggaagg aatgctctac ctcacagaac tctgaaccct  13020
acagaaatat gggcctgctg ccatttcctg aagaccgggg catcggggtg gggtgataaa  13080
ggatacaacc tgcacagggg gaagttatta aagaggctgc aaagtccagc caccctgaag  13140
atactcccca gtgctcccct cctgctaaag aaccagttac cccaggaaaa ttcgactcct  13200
gtttttcttt aattaactat accgacgggg atggagtcat ctttaggggc tggtagggtg  13260
```

gttatccaag ggctgaatcc agtggagctg ggccaagtac gacaggagtc cagataaagg 13320
tgtaggggct gcacggccgc aagtctcctg gaaaggctgg agtgaccggc atgccgggat 13380
tgggagatta ggatttgatt tcattttggg gcgggcggtg gctcgtgctg ggtcacgtgg 13440
tcgtgcccaa gcgctcctcc tgttgcccca cctgtggttg ctgtggactg cacacgacag 13500
cagattcgct gtcccctcgt tggaggcgaa tggtcggacc ccgagtggcg gcgcccctga 13560
taaaaggccg aggattcgcg atcagggtgc aacttcactc cctcctcttt tctctccagc 13620
cttgcagcgt ggccgttcac atcacgcgct tcactaagcc tcctatcact agtaaccttt 13680
cagcgcattg tttaaaaaga aagcagtttc tgtccctttc tgtagttcct ttaagttcag 13740
gatgtaagcg aagccttcca ttaagtaaag gtgagtgtcg tttcgtctca gtcgcgaaag 13800
tgcggcggcc gatgatgaac cgcgccagga gcagcctcag cggccatcag tccattcgca 13860
gcgccggctc cgccgaggcc cggacttagc tctcgagttg ccttggcgac gacgcagctc 13920
gctccgcccc agttcccttt tatggtttca gccccgcctc ctctagttag ccgggtgcgc 13980
ttcggcaagc gtggcgaaag tgcggcggcg aatgtcaagc gttgggtctg agcctagggg 14040
tgtggcttga gctcacgctg gttctttctt gcctcggtga tccaccagcc ttgtcaccca 14100
ggatttaggt tggcagattc gtctctcgcc tttggaattt ctaccttctc ctaggttttg 14160
ttttttaaaa tcaggcctat gataccgctc atgggctcat atttatttta gcattgtaat 14220
ttaagttgta ttttatgcaa ctctaccccg atacagagag ctgttgatgt aactgcagcg 14280
agcaaatgga ggactagaga ctagcgaagg ggccgagact tcgtctccag agtatccctg 14340
tcagcatcca tcaactgcac tcatatattg aatgcagctc ctatccgcct ttcttttcga 14400
cttcttcatg ccgttaccac tcttcatcag ttagtctagc ctcaatgttt tcatttattt 14460
cctttgtttt ttttgggggg gggggaacgg agtcttgctc tgtcgcccag gctggagtgc 14520
agtggcacga tctcggctca ctaaaagctc cgcctcccgg gttcacacca ttctcgtgcc 14580
tcaggctccc gagtagctgg gactacaggc gcccgccacc acgcccggct aatttttttgt 14640 atttttagta gagacggggt ttcaccgtgt tagccaggat ggtctcgatc tcctaacctc 14700
gtgatccgcc cgtgtcggcc ttccaaagtg ctgggattac aggcgtgagc caccgcgccc 14760
ggcccatttc tttcctttcg ttgagacagg gtctggctct gtctaccagg tcggagtgca 14820
ggggcgcgat catagctcag tgcagcctca acctaccggg ctcaagcgat cttcccacct 14880
cccaagtagc tggaactaca ggctcctgta accagaccct gctaattttt aaattttttg 14940
taaagacggg gccttgctat gttgcccagg ctggtctcga actcctggac tcaagcgatc 15000
t 15001

<210> SEQ ID NO 27
<211> LENGTH: 20
<212> TYPE: DNA
<213> ORGANISM: Artificial Sequence
<220> FEATURE:
<223> OTHER INFORMATION: Antisense Compound

<400> SEQUENCE: 27
ccctactcag taggcattgg 20

<210> SEQ ID NO 28
<211> LENGTH: 20
<212> TYPE: DNA
<213> ORGANISM: Artificial Sequence
<220> FEATURE:
<223> OTHER INFORMATION: Antisense Compound

<400> SEQUENCE: 28
gcccaagctg gcatccgtca 20

<210> SEQ ID NO 29
<211> LENGTH: 20
<212> TYPE: DNA
<213> ORGANISM: Artificial Sequence
<220> FEATURE:
<223> OTHER INFORMATION: Antisense Compound

<400> SEQUENCE: 29
cgtgtgtctg tgctagtccc 20

<210> SEQ ID NO 30
<211> LENGTH: 20
<212> TYPE: DNA
<213> ORGANISM: Artificial Sequence
<220> FEATURE:
<223> OTHER INFORMATION: Antisense Compound

<400> SEQUENCE: 30
ggcaacgtga acaggtccaa 20

<210> SEQ ID NO 31
<211> LENGTH: 20
<212> TYPE: DNA
<213> ORGANISM: Artificial Sequence
<220> FEATURE:
<223> OTHER INFORMATION: Antisense Compound

<400> SEQUENCE: 31
aggtagcttt gattatgtaa 20

<210> SEQ ID NO 32
<211> LENGTH: 18
<212> TYPE: DNA
<213> ORGANISM: Artificial Sequence
<220> FEATURE:
<223> OTHER INFORMATION: Antisense Compound

<400> SEQUENCE: 32
gcccattgct ggacatgc 18

<210> SEQ ID NO 33
<211> LENGTH: 20
<212> TYPE: DNA
<213> ORGANISM: Artificial Sequence
<220> FEATURE:
<223> OTHER INFORMATION: Antisense Compound

<400> SEQUENCE: 33
agcccattgc tggacatgca 20

<210> SEQ ID NO 34
<211> LENGTH: 20
<212> TYPE: DNA
<213> ORGANISM: Artificial Sequence
<220> FEATURE:
<223> OTHER INFORMATION: Antisense Compound

<400> SEQUENCE: 34
gcttgtgtgc tctgctgtct 20

<210> SEQ ID NO 35
<211> LENGTH: 20
<212> TYPE: DNA

<213> ORGANISM: Artificial Sequence
<220> FEATURE:
<223> OTHER INFORMATION: Antisense Compound

<400> SEQUENCE: 35
ttgtcccagt cccaggcctc 20

<210> SEQ ID NO 36
<211> LENGTH: 20
<212> TYPE: DNA
<213> ORGANISM: Artificial Sequence
<220> FEATURE:
<223> OTHER INFORMATION: Antisense Compound

<400> SEQUENCE: 36
ctctctgtag gcccgcttgg 20

<210> SEQ ID NO 37
<211> LENGTH: 20
<212> TYPE: DNA
<213> ORGANISM: Artificial Sequence
<220> FEATURE:
<223> OTHER INFORMATION: Antisense Compound

<400> SEQUENCE: 37
ctttccgttg gacccctggg 20

<210> SEQ ID NO 38
<211> LENGTH: 20
<212> TYPE: DNA
<213> ORGANISM: Artificial Sequence
<220> FEATURE:
<223> OTHER INFORMATION: Antisense Compound

<400> SEQUENCE: 38
gtgcgcgcga gcccgaaatc 20

<210> SEQ ID NO 39
<211> LENGTH: 20
<212> TYPE: DNA
<213> ORGANISM: Artificial Sequence
<220> FEATURE:
<223> OTHER INFORMATION: Antisense Compound

<400> SEQUENCE: 39
gctcagtgga catggatgag 20

<210> SEQ ID NO 40
<211> LENGTH: 20
<212> TYPE: DNA
<213> ORGANISM: Artificial Sequence
<220> FEATURE:
<223> OTHER INFORMATION: Antisense Compound

<400> SEQUENCE: 40
atccaagtgc tactgtagta 20

<210> SEQ ID NO 41
<211> LENGTH: 22
<212> TYPE: DNA
<213> ORGANISM: Artificial Sequence
<220> FEATURE:
<223> OTHER INFORMATION: Antisense Compound

<400> SEQUENCE: 41
ataccgcgat cagtgcatct tt 22

<210> SEQ ID NO 42
<211> LENGTH: 22
<212> TYPE: DNA
<213> ORGANISM: Artificial Sequence
<220> FEATURE:
<223> OTHER INFORMATION: Antisense Compound

<400> SEQUENCE: 42
agactagcgg tatctttatc cc 22

<210> SEQ ID NO 43
<211> LENGTH: 20
<212> TYPE: DNA
<213> ORGANISM: Artificial Sequence
<220> FEATURE:
<223> OTHER INFORMATION: Antisense Compound
<220> FEATURE:
<221> NAME/KEY: misc_feature
<222> LOCATION: 1-20
<223> OTHER INFORMATION: n is a, c, g, or t

<400> SEQUENCE: 43
nnnnnnnnnn nnnnnnnnnn 20

<210> SEQ ID NO 44
<211> LENGTH: 20
<212> TYPE: DNA
<213> ORGANISM: Artificial Sequence
<220> FEATURE:
<223> OTHER INFORMATION: Antisense Compound

<400> SEQUENCE: 44
ttctacctcg cgcgatttac 20

<210> SEQ ID NO 45
<211> LENGTH: 20
<212> TYPE: DNA
<213> ORGANISM: Artificial Sequence
<220> FEATURE:
<223> OTHER INFORMATION: Antisense Compound

<400> SEQUENCE: 45
tagtgcggac ctacccacga 20

<210> SEQ ID NO 46
<211> LENGTH: 20
<212> TYPE: DNA
<213> ORGANISM: Artificial Sequence
<220> FEATURE:
<223> OTHER INFORMATION: Antisense Compound

<400> SEQUENCE: 46
gccctccatg ctggcacagg 20

<210> SEQ ID NO 47
<211> LENGTH: 20
<212> TYPE: DNA
<213> ORGANISM: Artificial Sequence
<220> FEATURE:
<223> OTHER INFORMATION: Antisense Compound

<400> SEQUENCE: 47
agcaaaagat caatccgtta 20

<210> SEQ ID NO 48
<211> LENGTH: 20
<212> TYPE: DNA

<213> ORGANISM: Artificial Sequence
<220> FEATURE:
<223> OTHER INFORMATION: Antisense Compound

<400> SEQUENCE: 48
ggaccccgaa agaccaccag 20

<210> SEQ ID NO 49
<211> LENGTH: 20
<212> TYPE: DNA
<213> ORGANISM: Artificial Sequence
<220> FEATURE:
<223> OTHER INFORMATION: Antisense Compound

<400> SEQUENCE: 49
ctgctagcct ctggatttga 20

<210> SEQ ID NO 50
<211> LENGTH: 20
<212> TYPE: DNA
<213> ORGANISM: Artificial Sequence
<220> FEATURE:
<223> OTHER INFORMATION: Antisense Compound

<400> SEQUENCE: 50
ctgcctggat gggtgttttt 20

<210> SEQ ID NO 51
<211> LENGTH: 20
<212> TYPE: DNA
<213> ORGANISM: Artificial Sequence
<220> FEATURE:
<223> OTHER INFORMATION: Antisense Compound

<400> SEQUENCE: 51
tcccgcctgt gacatgcatt 20

<210> SEQ ID NO 52
<211> LENGTH: 20
<212> TYPE: DNA
<213> ORGANISM: Artificial Sequence
<220> FEATURE:
<223> OTHER INFORMATION: Antisense Compound

<400> SEQUENCE: 52
tacagaaggc tgggccttga 20

<210> SEQ ID NO 53
<211> LENGTH: 20
<212> TYPE: DNA
<213> ORGANISM: Artificial Sequence
<220> FEATURE:
<223> OTHER INFORMATION: Antisense Compound

<400> SEQUENCE: 53
atgcattctg cccccaagga 20

<210> SEQ ID NO 54
<211> LENGTH: 18
<212> TYPE: DNA
<213> ORGANISM: Artificial Sequence
<220> FEATURE:
<223> OTHER INFORMATION: Antisense Compound

<400> SEQUENCE: 54
ccaacctcaa atgtccca 18

<210> SEQ ID NO 55
<211> LENGTH: 20
<212> TYPE: DNA
<213> ORGANISM: Artificial Sequence
<220> FEATURE:
<223> OTHER INFORMATION: Antisense Compound

<400> SEQUENCE: 55
aggcatggtc tttgtcaata 20

<210> SEQ ID NO 56
<211> LENGTH: 18
<212> TYPE: DNA
<213> ORGANISM: Artificial Sequence
<220> FEATURE:
<223> OTHER INFORMATION: Antisense Compound

<400> SEQUENCE: 56
tgtgctattc tgtgaatt 18

<210> SEQ ID NO 57
<211> LENGTH: 21
<212> TYPE: DNA
<213> ORGANISM: Artificial Sequence
<220> FEATURE:
<223> OTHER INFORMATION: Forward Primer

<400> SEQUENCE: 57
caacggattt ggtcgtattg g 21

<210> SEQ ID NO 58
<211> LENGTH: 26
<212> TYPE: DNA
<213> ORGANISM: Artificial Sequence
<220> FEATURE:
<223> OTHER INFORMATION: Reverse Primer

<400> SEQUENCE: 58
ggcaacaata tccactttac cagagt 26

<210> SEQ ID NO 59
<211> LENGTH: 21
<212> TYPE: DNA
<213> ORGANISM: Artificial Sequence
<220> FEATURE:
<223> OTHER INFORMATION: Probe

<400> SEQUENCE: 59
cgcctggtca ccagggctgc t 21

<210> SEQ ID NO 60
<211> LENGTH: 19
<212> TYPE: DNA
<213> ORGANISM: Artificial Sequence
<220> FEATURE:
<223> OTHER INFORMATION: Forward Primer

<400> SEQUENCE: 60
gaaggtgaag gtcggagtc 19

<210> SEQ ID NO 61
<211> LENGTH: 20
<212> TYPE: DNA
<213> ORGANISM: Artificial Sequence
<220> FEATURE:
<223> OTHER INFORMATION: Reverse Primer

<400> SEQUENCE: 61
gaagatggtg atgggatttc 20

<210> SEQ ID NO 62
<211> LENGTH: 20
<212> TYPE: DNA
<213> ORGANISM: Artificial Sequence
<220> FEATURE:
<223> OTHER INFORMATION: Probe

<400> SEQUENCE: 62
caagcttccc gttctcagcc 20

<210> SEQ ID NO 63
<211> LENGTH: 20
<212> TYPE: DNA
<213> ORGANISM: Artificial Sequence
<220> FEATURE:
<223> OTHER INFORMATION: Probe

<400> SEQUENCE: 63
tggaatcata ttggaacatg 20

<210> SEQ ID NO 64
<211> LENGTH: 20
<212> TYPE: DNA
<213> ORGANISM: Artificial Sequence
<220> FEATURE:
<223> OTHER INFORMATION: Forward Primer

<400> SEQUENCE: 64
ggcaaattca acggcacagt 20

<210> SEQ ID NO 65
<211> LENGTH: 20
<212> TYPE: DNA
<213> ORGANISM: Artificial Sequence
<220> FEATURE:
<223> OTHER INFORMATION: Reverse Primer

<400> SEQUENCE: 65
gggtctcgct cctggaagat 20

<210> SEQ ID NO 66
<211> LENGTH: 27
<212> TYPE: DNA
<213> ORGANISM: Artificial Sequence
<220> FEATURE:
<223> OTHER INFORMATION: Probe

<400> SEQUENCE: 66
aaggccgaga atgggaagct tgtcatc 27

<210> SEQ ID NO 67
<211> LENGTH: 23
<212> TYPE: DNA
<213> ORGANISM: Artificial Sequence
<220> FEATURE:
<223> OTHER INFORMATION: Forward Primer

<400> SEQUENCE: 67
tgttctagag acagccgcat ctt 23

<210> SEQ ID NO 68
<211> LENGTH: 21
<212> TYPE: DNA

<213> ORGANISM: Artificial Sequence
<220> FEATURE:
<223> OTHER INFORMATION: Reverse Primer

<400> SEQUENCE: 68
caccgacctt caccatcttg t 21

<210> SEQ ID NO 69
<211> LENGTH: 24
<212> TYPE: DNA
<213> ORGANISM: Artificial Sequence
<220> FEATURE:
<223> OTHER INFORMATION: Probe

<400> SEQUENCE: 69
ttgtgcagtg ccagcctcgt ctca 24

<210> SEQ ID NO 70
<211> LENGTH: 24
<212> TYPE: DNA
<213> ORGANISM: Artificial Sequence
<220> FEATURE:
<223> OTHER INFORMATION: Forward Primer

<400> SEQUENCE: 70
caaattgacc caaagaagtt gaaa 24

<210> SEQ ID NO 71
<211> LENGTH: 22
<212> TYPE: DNA
<213> ORGANISM: Artificial Sequence
<220> FEATURE:
<223> OTHER INFORMATION: Reverse Primer

<400> SEQUENCE: 71
gttgctgttg ccattgaagt gt 22

<210> SEQ ID NO 72
<211> LENGTH: 24
<212> TYPE: DNA
<213> ORGANISM: Artificial Sequence
<220> FEATURE:
<223> OTHER INFORMATION: Probe

<400> SEQUENCE: 72
acccgcccct gaaggttatt cccc 24

<210> SEQ ID NO 73
<211> LENGTH: 20
<212> TYPE: DNA
<213> ORGANISM: Artificial Sequence
<220> FEATURE:
<223> OTHER INFORMATION: Forward Primer

<400> SEQUENCE: 73
gaagtgcagg gtcccaattc 20

<210> SEQ ID NO 74
<211> LENGTH: 22
<212> TYPE: DNA
<213> ORGANISM: Artificial Sequence
<220> FEATURE:
<223> OTHER INFORMATION: Reverse Primer

<400> SEQUENCE: 74
ttcatccaga cggtttcttt ga 22

<210> SEQ ID NO 75
<211> LENGTH: 22
<212> TYPE: DNA
<213> ORGANISM: Artificial Sequence
<220> FEATURE:
<223> OTHER INFORMATION: Probe

<400> SEQUENCE: 75
tctgccactt tcatggtgtc at 22

<210> SEQ ID NO 76
<211> LENGTH: 22
<212> TYPE: DNA
<213> ORGANISM: Artificial Sequence
<220> FEATURE:
<223> OTHER INFORMATION: Forward Primer

<400> SEQUENCE: 76
gcaaaagctc ctcctcttac ca 22

<210> SEQ ID NO 77
<211> LENGTH: 20
<212> TYPE: DNA
<213> ORGANISM: Artificial Sequence
<220> FEATURE:
<223> OTHER INFORMATION: Reverse Primer

<400> SEQUENCE: 77
gtcaccctct ccacgaaagg 20

<210> SEQ ID NO 78
<211> LENGTH: 22
<212> TYPE: DNA
<213> ORGANISM: Artificial Sequence
<220> FEATURE:
<223> OTHER INFORMATION: Probe

<400> SEQUENCE: 78
acttggaaca cgggcaccga ag 22

<210> SEQ ID NO 79
<211> LENGTH: 22
<212> TYPE: DNA
<213> ORGANISM: Artificial Sequence
<220> FEATURE:
<223> OTHER INFORMATION: Forward Primer

<400> SEQUENCE: 79
gagaagaacc acatccccat ca 22

<210> SEQ ID NO 80
<211> LENGTH: 19
<212> TYPE: DNA
<213> ORGANISM: Artificial Sequence
<220> FEATURE:
<223> OTHER INFORMATION: Reverse Primer

<400> SEQUENCE: 80
gaccccagcc acacagaga 19

<210> SEQ ID NO 81
<211> LENGTH: 23
<212> TYPE: DNA
<213> ORGANISM: Artificial Sequence
<220> FEATURE:
<223> OTHER INFORMATION: Probe

<400> SEQUENCE: 81
tgaacaggga gacgctccaa gga 23

<210> SEQ ID NO 82
<211> LENGTH: 27
<212> TYPE: DNA
<213> ORGANISM: Artificial Sequence
<220> FEATURE:
<223> OTHER INFORMATION: Forward Primer

<400> SEQUENCE: 82
ccttcaagcc ataaagatat tgtgttc 27

<210> SEQ ID NO 83
<211> LENGTH: 19
<212> TYPE: DNA
<213> ORGANISM: Artificial Sequence
<220> FEATURE:
<223> OTHER INFORMATION: Reverse Primer

<400> SEQUENCE: 83
ttgggaggcc tgggataca 19

<210> SEQ ID NO 84
<211> LENGTH: 23
<212> TYPE: DNA
<213> ORGANISM: Artificial Sequence
<220> FEATURE:
<223> OTHER INFORMATION: Probe

<400> SEQUENCE: 84
cttttctgct tgaggctaag gca 23

<210> SEQ ID NO 85
<211> LENGTH: 20
<212> TYPE: DNA
<213> ORGANISM: Artificial Sequence
<220> FEATURE:
<223> OTHER INFORMATION: Antisense Compound

<400> SEQUENCE: 85
ttactgttgc ttgtacataa 20

<210> SEQ ID NO 86
<211> LENGTH: 20
<212> TYPE: DNA
<213> ORGANISM: Artificial Sequence
<220> FEATURE:
<223> OTHER INFORMATION: Antisense Compound

<400> SEQUENCE: 86
gtcaaaatac cactaagagc 20

<210> SEQ ID NO 87
<211> LENGTH: 20
<212> TYPE: DNA
<213> ORGANISM: Artificial Sequence
<220> FEATURE:
<223> OTHER INFORMATION: Antisense Compound

<400> SEQUENCE: 87
tgcttcgatc cggcaatagc 20

<210> SEQ ID NO 88
<211> LENGTH: 20
<212> TYPE: DNA

<213> ORGANISM: Artificial Sequence
<220> FEATURE:
<223> OTHER INFORMATION: Antisense Compound

<400> SEQUENCE: 88
caataaaatt ttatatgtat 20

<210> SEQ ID NO 89
<211> LENGTH: 20
<212> TYPE: DNA
<213> ORGANISM: Artificial Sequence
<220> FEATURE:
<223> OTHER INFORMATION: Antisense Compound

<400> SEQUENCE: 89
taggagtcaa acaaaatttt 20

<210> SEQ ID NO 90
<211> LENGTH: 20
<212> TYPE: DNA
<213> ORGANISM: Artificial Sequence
<220> FEATURE:
<223> OTHER INFORMATION: Antisense Compound

<400> SEQUENCE: 90
gctaaggcca tccattgtct 20

<210> SEQ ID NO 91
<211> LENGTH: 20
<212> TYPE: DNA
<213> ORGANISM: Artificial Sequence
<220> FEATURE:
<223> OTHER INFORMATION: Antisense Compound

<400> SEQUENCE: 91
ttttaattct gatgctaagg 20

<210> SEQ ID NO 92
<211> LENGTH: 20
<212> TYPE: DNA
<213> ORGANISM: Artificial Sequence
<220> FEATURE:
<223> OTHER INFORMATION: Antisense Compound

<400> SEQUENCE: 92
gccatttaat ccagattatt 20

<210> SEQ ID NO 93
<211> LENGTH: 20
<212> TYPE: DNA
<213> ORGANISM: Artificial Sequence
<220> FEATURE:
<223> OTHER INFORMATION: Antisense Compound

<400> SEQUENCE: 93
cacattgcca tttaatccag 20

<210> SEQ ID NO 94
<211> LENGTH: 20
<212> TYPE: DNA
<213> ORGANISM: Artificial Sequence
<220> FEATURE:
<223> OTHER INFORMATION: Antisense Compound

<400> SEQUENCE: 94
ttgctgacta tgaacacatt 20

<210> SEQ ID NO 95
<211> LENGTH: 20
<212> TYPE: DNA
<213> ORGANISM: Artificial Sequence
<220> FEATURE:
<223> OTHER INFORMATION: Antisense Compound

<400> SEQUENCE: 95
aattttattg ctgactatga 20

<210> SEQ ID NO 96
<211> LENGTH: 20
<212> TYPE: DNA
<213> ORGANISM: Artificial Sequence
<220> FEATURE:
<223> OTHER INFORMATION: Antisense Compound

<400> SEQUENCE: 96
gccatcttcc ctgattcatt 20

<210> SEQ ID NO 97
<211> LENGTH: 20
<212> TYPE: DNA
<213> ORGANISM: Artificial Sequence
<220> FEATURE:
<223> OTHER INFORMATION: Antisense Compound

<400> SEQUENCE: 97
gaaaaccaat cattgtcaca 20

<210> SEQ ID NO 98
<211> LENGTH: 20
<212> TYPE: DNA
<213> ORGANISM: Artificial Sequence
<220> FEATURE:
<223> OTHER INFORMATION: Antisense Compound

<400> SEQUENCE: 98
cgcaggcgca ctaatagaca 20

<210> SEQ ID NO 99
<211> LENGTH: 20
<212> TYPE: DNA
<213> ORGANISM: Artificial Sequence
<220> FEATURE:
<223> OTHER INFORMATION: Antisense Compound

<400> SEQUENCE: 99
gtcacagcgc aggcgcacta 20

<210> SEQ ID NO 100
<211> LENGTH: 20
<212> TYPE: DNA
<213> ORGANISM: Artificial Sequence
<220> FEATURE:
<223> OTHER INFORMATION: Antisense Compound

<400> SEQUENCE: 100
ttctaggtca cagcgcaggc 20

<210> SEQ ID NO 101
<211> LENGTH: 20
<212> TYPE: DNA
<213> ORGANISM: Artificial Sequence
<220> FEATURE:
<223> OTHER INFORMATION: Antisense Compound

<400> SEQUENCE: 101
ggcgcatgcg cccattctag 20

<210> SEQ ID NO 102
<211> LENGTH: 20
<212> TYPE: DNA
<213> ORGANISM: Artificial Sequence
<220> FEATURE:
<223> OTHER INFORMATION: Antisense Compound

<400> SEQUENCE: 102
ttttcaaacc agccagttcc 20

<210> SEQ ID NO 103
<211> LENGTH: 20
<212> TYPE: DNA
<213> ORGANISM: Artificial Sequence
<220> FEATURE:
<223> OTHER INFORMATION: Antisense Compound

<400> SEQUENCE: 103
gtcaagtcgc aaggctctac 20

<210> SEQ ID NO 104
<211> LENGTH: 20
<212> TYPE: DNA
<213> ORGANISM: Artificial Sequence
<220> FEATURE:
<223> OTHER INFORMATION: Antisense Compound

<400> SEQUENCE: 104
gctaccacaa catctggaca 20

<210> SEQ ID NO 105
<211> LENGTH: 20
<212> TYPE: DNA
<213> ORGANISM: Artificial Sequence
<220> FEATURE:
<223> OTHER INFORMATION: Antisense Compound

<400> SEQUENCE: 105
tctttgggtc aatttgagct 20

<210> SEQ ID NO 106
<211> LENGTH: 20
<212> TYPE: DNA
<213> ORGANISM: Artificial Sequence
<220> FEATURE:
<223> OTHER INFORMATION: Antisense Compound

<400> SEQUENCE: 106
ttcaacttct ttgggtcaat 20

<210> SEQ ID NO 107
<211> LENGTH: 20
<212> TYPE: DNA
<213> ORGANISM: Artificial Sequence
<220> FEATURE:
<223> OTHER INFORMATION: Antisense Compound

<400> SEQUENCE: 107
cactttgctt ccttttcaac 20

<210> SEQ ID NO 108
<211> LENGTH: 20
<212> TYPE: DNA

<213> ORGANISM: Artificial Sequence
<220> FEATURE:
<223> OTHER INFORMATION: Antisense Compound

<400> SEQUENCE: 108
atcctgaaag agaaatattc 20

<210> SEQ ID NO 109
<211> LENGTH: 20
<212> TYPE: DNA
<213> ORGANISM: Artificial Sequence
<220> FEATURE:
<223> OTHER INFORMATION: Antisense Compound

<400> SEQUENCE: 109
gttgccattg aagtgttggg 20

<210> SEQ ID NO 110
<211> LENGTH: 20
<212> TYPE: DNA
<213> ORGANISM: Artificial Sequence
<220> FEATURE:
<223> OTHER INFORMATION: Antisense Compound

<400> SEQUENCE: 110
tgctgttgcc attgaagtgt 20

<210> SEQ ID NO 111
<211> LENGTH: 20
<212> TYPE: DNA
<213> ORGANISM: Artificial Sequence
<220> FEATURE:
<223> OTHER INFORMATION: Antisense Compound

<400> SEQUENCE: 111
gtgccacttg ttgctgttgc 20

<210> SEQ ID NO 112
<211> LENGTH: 20
<212> TYPE: DNA
<213> ORGANISM: Artificial Sequence
<220> FEATURE:
<223> OTHER INFORMATION: Antisense Compound

<400> SEQUENCE: 112
tcgaacagtt gaaaactgtg 20

<210> SEQ ID NO 113
<211> LENGTH: 20
<212> TYPE: DNA
<213> ORGANISM: Artificial Sequence
<220> FEATURE:
<223> OTHER INFORMATION: Antisense Compound

<400> SEQUENCE: 113
tgttcacatt ctgtcgaaca 20

<210> SEQ ID NO 114
<211> LENGTH: 20
<212> TYPE: DNA
<213> ORGANISM: Artificial Sequence
<220> FEATURE:
<223> OTHER INFORMATION: Antisense Compound

<400> SEQUENCE: 114
ataatctatt ccaggacttt 20

<210> SEQ ID NO 115
<211> LENGTH: 20
<212> TYPE: DNA
<213> ORGANISM: Artificial Sequence
<220> FEATURE:
<223> OTHER INFORMATION: Antisense Compound

<400> SEQUENCE: 115
gcctgattca ttctgctaac 20

<210> SEQ ID NO 116
<211> LENGTH: 20
<212> TYPE: DNA
<213> ORGANISM: Artificial Sequence
<220> FEATURE:
<223> OTHER INFORMATION: Antisense Compound

<400> SEQUENCE: 116
gttgcctgat tcattctgct 20

<210> SEQ ID NO 117
<211> LENGTH: 20
<212> TYPE: DNA
<213> ORGANISM: Artificial Sequence
<220> FEATURE:
<223> OTHER INFORMATION: Antisense Compound

<400> SEQUENCE: 117
caagacacta gttactgttg 20

<210> SEQ ID NO 118
<211> LENGTH: 20
<212> TYPE: DNA
<213> ORGANISM: Artificial Sequence
<220> FEATURE:
<223> OTHER INFORMATION: Antisense Compound

<400> SEQUENCE: 118
ttccaagaca ctagttactg 20

<210> SEQ ID NO 119
<211> LENGTH: 20
<212> TYPE: DNA
<213> ORGANISM: Artificial Sequence
<220> FEATURE:
<223> OTHER INFORMATION: Antisense Compound

<400> SEQUENCE: 119
agatattcca agacactagt 20

<210> SEQ ID NO 120
<211> LENGTH: 20
<212> TYPE: DNA
<213> ORGANISM: Artificial Sequence
<220> FEATURE:
<223> OTHER INFORMATION: Antisense Compound

<400> SEQUENCE: 120
caaaccaatt actcagatat 20

<210> SEQ ID NO 121
<211> LENGTH: 20
<212> TYPE: DNA
<213> ORGANISM: Artificial Sequence
<220> FEATURE:
<223> OTHER INFORMATION: Antisense Compound

<400> SEQUENCE: 121
gtctctttct ccaaaccaat 20

<210> SEQ ID NO 122
<211> LENGTH: 20
<212> TYPE: DNA
<213> ORGANISM: Artificial Sequence
<220> FEATURE:
<223> OTHER INFORMATION: Antisense Compound

<400> SEQUENCE: 122
gtaaagtctc tttctccaaa 20

<210> SEQ ID NO 123
<211> LENGTH: 20
<212> TYPE: DNA
<213> ORGANISM: Artificial Sequence
<220> FEATURE:
<223> OTHER INFORMATION: Antisense Compound

<400> SEQUENCE: 123
ctggagtaaa gtctctttct 20

<210> SEQ ID NO 124
<211> LENGTH: 20
<212> TYPE: DNA
<213> ORGANISM: Artificial Sequence
<220> FEATURE:
<223> OTHER INFORMATION: Antisense Compound

<400> SEQUENCE: 124
caattctgga gtaaagtctc 20

<210> SEQ ID NO 125
<211> LENGTH: 20
<212> TYPE: DNA
<213> ORGANISM: Artificial Sequence
<220> FEATURE:
<223> OTHER INFORMATION: Antisense Compound

<400> SEQUENCE: 125
cttcccaatt ctggagtaaa 20

<210> SEQ ID NO 126
<211> LENGTH: 20
<212> TYPE: DNA
<213> ORGANISM: Artificial Sequence
<220> FEATURE:
<223> OTHER INFORMATION: Antisense Compound

<400> SEQUENCE: 126
ccatcttccc aattctggag 20

<210> SEQ ID NO 127
<211> LENGTH: 20
<212> TYPE: DNA
<213> ORGANISM: Artificial Sequence
<220> FEATURE:
<223> OTHER INFORMATION: Antisense Compound

<400> SEQUENCE: 127
ttttcaagac aagccaataa 20

<210> SEQ ID NO 128
<211> LENGTH: 20
<212> TYPE: DNA

<213> ORGANISM: Artificial Sequence
<220> FEATURE:
<223> OTHER INFORMATION: Antisense Compound

<400> SEQUENCE: 128
ggcttttcaa gacaagccaa 20

<210> SEQ ID NO 129
<211> LENGTH: 20
<212> TYPE: DNA
<213> ORGANISM: Artificial Sequence
<220> FEATURE:
<223> OTHER INFORMATION: Antisense Compound

<400> SEQUENCE: 129
caaaggcttt tcaagacaag 20

<210> SEQ ID NO 130
<211> LENGTH: 20
<212> TYPE: DNA
<213> ORGANISM: Artificial Sequence
<220> FEATURE:
<223> OTHER INFORMATION: Antisense Compound

<400> SEQUENCE: 130
gtaacaaagg cttttcaaga 20

<210> SEQ ID NO 131
<211> LENGTH: 20
<212> TYPE: DNA
<213> ORGANISM: Artificial Sequence
<220> FEATURE:
<223> OTHER INFORMATION: Antisense Compound

<400> SEQUENCE: 131
agtgaatgag cctcaggtaa 20

<210> SEQ ID NO 132
<211> LENGTH: 20
<212> TYPE: DNA
<213> ORGANISM: Artificial Sequence
<220> FEATURE:
<223> OTHER INFORMATION: Antisense Compound

<400> SEQUENCE: 132
aaatacctgc taaccaagca 20

<210> SEQ ID NO 133
<211> LENGTH: 20
<212> TYPE: DNA
<213> ORGANISM: Artificial Sequence
<220> FEATURE:
<223> OTHER INFORMATION: Antisense Compound

<400> SEQUENCE: 133
tcaaaatacc tgctaaccaa 20

<210> SEQ ID NO 134
<211> LENGTH: 20
<212> TYPE: DNA
<213> ORGANISM: Artificial Sequence
<220> FEATURE:
<223> OTHER INFORMATION: Antisense Compound

<400> SEQUENCE: 134
ggctcatcag ctaaatcacg 20

<210> SEQ ID NO 135
<211> LENGTH: 20
<212> TYPE: DNA
<213> ORGANISM: Artificial Sequence
<220> FEATURE:
<223> OTHER INFORMATION: Antisense Compound

<400> SEQUENCE: 135
gatggctcat cagctaaatc 20

<210> SEQ ID NO 136
<211> LENGTH: 20
<212> TYPE: DNA
<213> ORGANISM: Artificial Sequence
<220> FEATURE:
<223> OTHER INFORMATION: Antisense Compound

<400> SEQUENCE: 136
atcaagatgg ctcatcagct 20

<210> SEQ ID NO 137
<211> LENGTH: 20
<212> TYPE: DNA
<213> ORGANISM: Artificial Sequence
<220> FEATURE:
<223> OTHER INFORMATION: Antisense Compound

<400> SEQUENCE: 137
tcagctacat caagatggct 20

<210> SEQ ID NO 138
<211> LENGTH: 20
<212> TYPE: DNA
<213> ORGANISM: Artificial Sequence
<220> FEATURE:
<223> OTHER INFORMATION: Antisense Compound

<400> SEQUENCE: 138
agaaatatct tctatccctg 20

<210> SEQ ID NO 139
<211> LENGTH: 20
<212> TYPE: DNA
<213> ORGANISM: Artificial Sequence
<220> FEATURE:
<223> OTHER INFORMATION: Antisense Compound

<400> SEQUENCE: 139
gttttcctca gagttaggct 20

<210> SEQ ID NO 140
<211> LENGTH: 20
<212> TYPE: DNA
<213> ORGANISM: Artificial Sequence
<220> FEATURE:
<223> OTHER INFORMATION: Antisense Compound

<400> SEQUENCE: 140
aagatgtgtt gaaatctgta 20

<210> SEQ ID NO 141
<211> LENGTH: 20
<212> TYPE: DNA
<213> ORGANISM: Artificial Sequence
<220> FEATURE:
<223> OTHER INFORMATION: Antisense Compound

<400> SEQUENCE: 141
tcacatagtg ttgaagatgt 20

<210> SEQ ID NO 142
<211> LENGTH: 20
<212> TYPE: DNA
<213> ORGANISM: Artificial Sequence
<220> FEATURE:
<223> OTHER INFORMATION: Antisense Compound

<400> SEQUENCE: 142
aacccttcac atagtgttga 20

<210> SEQ ID NO 143
<211> LENGTH: 20
<212> TYPE: DNA
<213> ORGANISM: Artificial Sequence
<220> FEATURE:
<223> OTHER INFORMATION: Antisense Compound

<400> SEQUENCE: 143
aagatgtgaa cccttcacat 20

<210> SEQ ID NO 144
<211> LENGTH: 20
<212> TYPE: DNA
<213> ORGANISM: Artificial Sequence
<220> FEATURE:
<223> OTHER INFORMATION: Antisense Compound

<400> SEQUENCE: 144
caggttaaga tgtgaaccct 20

<210> SEQ ID NO 145
<211> LENGTH: 20
<212> TYPE: DNA
<213> ORGANISM: Artificial Sequence
<220> FEATURE:
<223> OTHER INFORMATION: Antisense Compound

<400> SEQUENCE: 145
gtatcaatct gaattgcaca 20

<210> SEQ ID NO 146
<211> LENGTH: 20
<212> TYPE: DNA
<213> ORGANISM: Artificial Sequence
<220> FEATURE:
<223> OTHER INFORMATION: Antisense Compound

<400> SEQUENCE: 146
gtgggatttt ccattgatat 20

<210> SEQ ID NO 147
<211> LENGTH: 20
<212> TYPE: DNA
<213> ORGANISM: Artificial Sequence
<220> FEATURE:
<223> OTHER INFORMATION: Antisense Compound

<400> SEQUENCE: 147
actgagtggg attttccatt 20

<210> SEQ ID NO 148
<211> LENGTH: 20
<212> TYPE: DNA

<213> ORGANISM: Artificial Sequence
<220> FEATURE:
<223> OTHER INFORMATION: Antisense Compound

<400> SEQUENCE: 148
aaaaactgag tgggattttc 20

<210> SEQ ID NO 149
<211> LENGTH: 20
<212> TYPE: DNA
<213> ORGANISM: Artificial Sequence
<220> FEATURE:
<223> OTHER INFORMATION: Antisense Compound

<400> SEQUENCE: 149
gttcatcaaa aactgagtgg 20

<210> SEQ ID NO 150
<211> LENGTH: 20
<212> TYPE: DNA
<213> ORGANISM: Artificial Sequence
<220> FEATURE:
<223> OTHER INFORMATION: Antisense Compound

<400> SEQUENCE: 150
tgttcaaact gttcatcaaa 20

<210> SEQ ID NO 151
<211> LENGTH: 20
<212> TYPE: DNA
<213> ORGANISM: Artificial Sequence
<220> FEATURE:
<223> OTHER INFORMATION: Antisense Compound

<400> SEQUENCE: 151
gattacagaa aactgttcaa 20

<210> SEQ ID NO 152
<211> LENGTH: 20
<212> TYPE: DNA
<213> ORGANISM: Artificial Sequence
<220> FEATURE:
<223> OTHER INFORMATION: Antisense Compound

<400> SEQUENCE: 152
ctgcttgatt acagaaaact 20

<210> SEQ ID NO 153
<211> LENGTH: 20
<212> TYPE: DNA
<213> ORGANISM: Artificial Sequence
<220> FEATURE:
<223> OTHER INFORMATION: Antisense Compound

<400> SEQUENCE: 153
aatttctatg caagctgctt 20

<210> SEQ ID NO 154
<211> LENGTH: 20
<212> TYPE: DNA
<213> ORGANISM: Artificial Sequence
<220> FEATURE:
<223> OTHER INFORMATION: Antisense Compound

<400> SEQUENCE: 154
tgtaaaattt catcatacaa 20

<210> SEQ ID NO 155
<211> LENGTH: 20
<212> TYPE: DNA
<213> ORGANISM: Artificial Sequence
<220> FEATURE:
<223> OTHER INFORMATION: Antisense Compound

<400> SEQUENCE: 155
taagtaaccc atttaaagac 20

<210> SEQ ID NO 156
<211> LENGTH: 20
<212> TYPE: DNA
<213> ORGANISM: Artificial Sequence
<220> FEATURE:
<223> OTHER INFORMATION: Antisense Compound

<400> SEQUENCE: 156
atcctgaaag ctagagatca 20

<210> SEQ ID NO 157
<211> LENGTH: 20
<212> TYPE: DNA
<213> ORGANISM: Artificial Sequence
<220> FEATURE:
<223> OTHER INFORMATION: Antisense Compound

<400> SEQUENCE: 157
tgttcacatt ctaaaggaag 20

<210> SEQ ID NO 158
<211> LENGTH: 20
<212> TYPE: DNA
<213> ORGANISM: Artificial Sequence
<220> FEATURE:
<223> OTHER INFORMATION: Antisense Compound

<400> SEQUENCE: 158
ggaataaggt tatctacctt 20

<210> SEQ ID NO 159
<211> LENGTH: 20
<212> TYPE: DNA
<213> ORGANISM: Artificial Sequence
<220> FEATURE:
<223> OTHER INFORMATION: Antisense Compound

<400> SEQUENCE: 159
caaagaaagc taatttgttt 20

<210> SEQ ID NO 160
<211> LENGTH: 20
<212> TYPE: DNA
<213> ORGANISM: Artificial Sequence
<220> FEATURE:
<223> OTHER INFORMATION: Antisense Compound

<400> SEQUENCE: 160
tgcaacttac cactaagagc 20

<210> SEQ ID NO 161
<211> LENGTH: 20
<212> TYPE: DNA
<213> ORGANISM: Artificial Sequence
<220> FEATURE:
<223> OTHER INFORMATION: Antisense Compound

<400> SEQUENCE: 161
taatcactgt acagtcaaga 20

<210> SEQ ID NO 162
<211> LENGTH: 20
<212> TYPE: DNA
<213> ORGANISM: Artificial Sequence
<220> FEATURE:
<223> OTHER INFORMATION: Antisense Compound

<400> SEQUENCE: 162
ttaactatac ctgctaacca 20

<210> SEQ ID NO 163
<211> LENGTH: 20
<212> TYPE: DNA
<213> ORGANISM: Artificial Sequence
<220> FEATURE:
<223> OTHER INFORMATION: Antisense Compound

<400> SEQUENCE: 163
tgggcacaga gcaatcacac 20

<210> SEQ ID NO 164
<211> LENGTH: 20
<212> TYPE: DNA
<213> ORGANISM: Artificial Sequence
<220> FEATURE:
<223> OTHER INFORMATION: Antisense Compound

<400> SEQUENCE: 164
caatcacacg gccacaggat 20

<210> SEQ ID NO 165
<211> LENGTH: 20
<212> TYPE: DNA
<213> ORGANISM: Artificial Sequence
<220> FEATURE:
<223> OTHER INFORMATION: Antisense Compound

<400> SEQUENCE: 165
caatcacaca gccacaggat 20

<210> SEQ ID NO 166
<211> LENGTH: 20
<212> TYPE: DNA
<213> ORGANISM: Artificial Sequence
<220> FEATURE:
<223> OTHER INFORMATION: Antisense Compound

<400> SEQUENCE: 166
caagacggtg aatgagatcc 20

<210> SEQ ID NO 167
<211> LENGTH: 20
<212> TYPE: DNA
<213> ORGANISM: Artificial Sequence
<220> FEATURE:
<223> OTHER INFORMATION: Antisense Compound

<400> SEQUENCE: 167
cttaggcctg ctcacaacct 20

<210> SEQ ID NO 168
<211> LENGTH: 20
<212> TYPE: DNA

<213> ORGANISM: Artificial Sequence
<220> FEATURE:
<223> OTHER INFORMATION: Antisense Compound

<400> SEQUENCE: 168
ccgcgcttag gcctgctcac 20

<210> SEQ ID NO 169
<211> LENGTH: 20
<212> TYPE: DNA
<213> ORGANISM: Artificial Sequence
<220> FEATURE:
<223> OTHER INFORMATION: Antisense Compound

<400> SEQUENCE: 169
cacgatggga gacgcaggag 20

<210> SEQ ID NO 170
<211> LENGTH: 20
<212> TYPE: DNA
<213> ORGANISM: Artificial Sequence
<220> FEATURE:
<223> OTHER INFORMATION: Antisense Compound

<400> SEQUENCE: 170
ctcccctccg agaactcgaa 20

<210> SEQ ID NO 171
<211> LENGTH: 20
<212> TYPE: DNA
<213> ORGANISM: Artificial Sequence
<220> FEATURE:
<223> OTHER INFORMATION: Antisense Compound

<400> SEQUENCE: 171
tccttccagt caaaaacaag 20

<210> SEQ ID NO 172
<211> LENGTH: 20
<212> TYPE: DNA
<213> ORGANISM: Artificial Sequence
<220> FEATURE:
<223> OTHER INFORMATION: Antisense Compound

<400> SEQUENCE: 172
tttcagggaa acggtccacc 20

<210> SEQ ID NO 173
<211> LENGTH: 20
<212> TYPE: DNA
<213> ORGANISM: Artificial Sequence
<220> FEATURE:
<223> OTHER INFORMATION: Antisense Compound

<400> SEQUENCE: 173
cctaggtcca tggcggcgac 20

<210> SEQ ID NO 174
<211> LENGTH: 20
<212> TYPE: DNA
<213> ORGANISM: Artificial Sequence
<220> FEATURE:
<223> OTHER INFORMATION: Antisense Compound

<400> SEQUENCE: 174
caagggtcct aggtccatgg 20

<210> SEQ ID NO 175
<211> LENGTH: 20
<212> TYPE: DNA
<213> ORGANISM: Artificial Sequence
<220> FEATURE:
<223> OTHER INFORMATION: Antisense Compound

<400> SEQUENCE: 175
ttcaagggtc ctaggtccat 20

<210> SEQ ID NO 176
<211> LENGTH: 20
<212> TYPE: DNA
<213> ORGANISM: Artificial Sequence
<220> FEATURE:
<223> OTHER INFORMATION: Antisense Compound

<400> SEQUENCE: 176
catgcagaat agtcatttct 20

<210> SEQ ID NO 177
<211> LENGTH: 20
<212> TYPE: DNA
<213> ORGANISM: Artificial Sequence
<220> FEATURE:
<223> OTHER INFORMATION: Antisense Compound

<400> SEQUENCE: 177
gttaattctg ccagtgcctt 20

<210> SEQ ID NO 178
<211> LENGTH: 20
<212> TYPE: DNA
<213> ORGANISM: Artificial Sequence
<220> FEATURE:
<223> OTHER INFORMATION: Antisense Compound

<400> SEQUENCE: 178
tcttccaggc aaagggctgg 20

<210> SEQ ID NO 179
<211> LENGTH: 20
<212> TYPE: DNA
<213> ORGANISM: Artificial Sequence
<220> FEATURE:
<223> OTHER INFORMATION: Antisense Compound

<400> SEQUENCE: 179
gctttcttct tccaggcaaa 20

<210> SEQ ID NO 180
<211> LENGTH: 20
<212> TYPE: DNA
<213> ORGANISM: Artificial Sequence
<220> FEATURE:
<223> OTHER INFORMATION: Antisense Compound

<400> SEQUENCE: 180
tgccaccgtg tctctgtgtc 20

<210> SEQ ID NO 181
<211> LENGTH: 20
<212> TYPE: DNA
<213> ORGANISM: Artificial Sequence
<220> FEATURE:
<223> OTHER INFORMATION: Antisense Compound

<400> SEQUENCE: 181
tcttcggcag aagtgtcaac 20

<210> SEQ ID NO 182
<211> LENGTH: 20
<212> TYPE: DNA
<213> ORGANISM: Artificial Sequence
<220> FEATURE:
<223> OTHER INFORMATION: Antisense Compound

<400> SEQUENCE: 182
gatccgactc tggatctgtg 20

<210> SEQ ID NO 183
<211> LENGTH: 20
<212> TYPE: DNA
<213> ORGANISM: Artificial Sequence
<220> FEATURE:
<223> OTHER INFORMATION: Antisense Compound

<400> SEQUENCE: 183
cctctgtcag cgcaaacaca 20

<210> SEQ ID NO 184
<211> LENGTH: 20
<212> TYPE: DNA
<213> ORGANISM: Artificial Sequence
<220> FEATURE:
<223> OTHER INFORMATION: Antisense Compound

<400> SEQUENCE: 184
gagttccaca cagagatcac 20

<210> SEQ ID NO 185
<211> LENGTH: 20
<212> TYPE: DNA
<213> ORGANISM: Artificial Sequence
<220> FEATURE:
<223> OTHER INFORMATION: Antisense Compound

<400> SEQUENCE: 185
gtgtccgagt tccacacaga 20

<210> SEQ ID NO 186
<211> LENGTH: 20
<212> TYPE: DNA
<213> ORGANISM: Artificial Sequence
<220> FEATURE:
<223> OTHER INFORMATION: Antisense Compound

<400> SEQUENCE: 186
ttctgggtgt ccgagttcca 20

<210> SEQ ID NO 187
<211> LENGTH: 20
<212> TYPE: DNA
<213> ORGANISM: Artificial Sequence
<220> FEATURE:
<223> OTHER INFORMATION: Antisense Compound

<400> SEQUENCE: 187
cccgcagcag gtggtgcagg 20

<210> SEQ ID NO 188
<211> LENGTH: 20
<212> TYPE: DNA

<213> ORGANISM: Artificial Sequence
<220> FEATURE:
<223> OTHER INFORMATION: Antisense Compound

<400> SEQUENCE: 188
tctggctgaa ggaagtcaga 20

<210> SEQ ID NO 189
<211> LENGTH: 20
<212> TYPE: DNA
<213> ORGANISM: Artificial Sequence
<220> FEATURE:
<223> OTHER INFORMATION: Antisense Compound

<400> SEQUENCE: 189
aggaagtccc tgacacactc 20

<210> SEQ ID NO 190
<211> LENGTH: 20
<212> TYPE: DNA
<213> ORGANISM: Artificial Sequence
<220> FEATURE:
<223> OTHER INFORMATION: Antisense Compound

<400> SEQUENCE: 190
gttttcctca ggaagtccct 20

<210> SEQ ID NO 191
<211> LENGTH: 20
<212> TYPE: DNA
<213> ORGANISM: Artificial Sequence
<220> FEATURE:
<223> OTHER INFORMATION: Antisense Compound

<400> SEQUENCE: 191
aggccctgtt cttcagcacc 20

<210> SEQ ID NO 192
<211> LENGTH: 20
<212> TYPE: DNA
<213> ORGANISM: Artificial Sequence
<220> FEATURE:
<223> OTHER INFORMATION: Antisense Compound

<400> SEQUENCE: 192
gctgtgatat cctccaaggc 20

<210> SEQ ID NO 193
<211> LENGTH: 20
<212> TYPE: DNA
<213> ORGANISM: Artificial Sequence
<220> FEATURE:
<223> OTHER INFORMATION: Antisense Compound

<400> SEQUENCE: 193
cacacttcca tatggcggtc 20

<210> SEQ ID NO 194
<211> LENGTH: 20
<212> TYPE: DNA
<213> ORGANISM: Artificial Sequence
<220> FEATURE:
<223> OTHER INFORMATION: Antisense Compound

<400> SEQUENCE: 194
aaggcccact tcttctcaga 20

<210> SEQ ID NO 195
<211> LENGTH: 20
<212> TYPE: DNA
<213> ORGANISM: Artificial Sequence
<220> FEATURE:
<223> OTHER INFORMATION: Antisense Compound

<400> SEQUENCE: 195
tgttactccc caggcaggct 20

<210> SEQ ID NO 196
<211> LENGTH: 20
<212> TYPE: DNA
<213> ORGANISM: Artificial Sequence
<220> FEATURE:
<223> OTHER INFORMATION: Antisense Compound

<400> SEQUENCE: 196
agcctcaaca ccaagtctgg 20

<210> SEQ ID NO 197
<211> LENGTH: 20
<212> TYPE: DNA
<213> ORGANISM: Artificial Sequence
<220> FEATURE:
<223> OTHER INFORMATION: Antisense Compound

<400> SEQUENCE: 197
ctgcgtaaca ttccaggatc 20

<210> SEQ ID NO 198
<211> LENGTH: 20
<212> TYPE: DNA
<213> ORGANISM: Artificial Sequence
<220> FEATURE:
<223> OTHER INFORMATION: Antisense Compound

<400> SEQUENCE: 198
cataagccag caacttttca 20

<210> SEQ ID NO 199
<211> LENGTH: 20
<212> TYPE: DNA
<213> ORGANISM: Artificial Sequence
<220> FEATURE:
<223> OTHER INFORMATION: Antisense Compound

<400> SEQUENCE: 199
gtcttcctga aaaccctcca 20

<210> SEQ ID NO 200
<211> LENGTH: 20
<212> TYPE: DNA
<213> ORGANISM: Artificial Sequence
<220> FEATURE:
<223> OTHER INFORMATION: Antisense Compound

<400> SEQUENCE: 200
ttgaggtctt cctgaaaacc 20

<210> SEQ ID NO 201
<211> LENGTH: 20
<212> TYPE: DNA
<213> ORGANISM: Artificial Sequence
<220> FEATURE:
<223> OTHER INFORMATION: Antisense Compound

<400> SEQUENCE: 201
gggccacgga ggccacagct 20

<210> SEQ ID NO 202
<211> LENGTH: 20
<212> TYPE: DNA
<213> ORGANISM: Artificial Sequence
<220> FEATURE:
<223> OTHER INFORMATION: Antisense Compound

<400> SEQUENCE: 202
accgtgactt ccgggtgcac 20

<210> SEQ ID NO 203
<211> LENGTH: 20
<212> TYPE: DNA
<213> ORGANISM: Artificial Sequence
<220> FEATURE:
<223> OTHER INFORMATION: Antisense Compound

<400> SEQUENCE: 203
tgccgagatt gaccacagcc 20

<210> SEQ ID NO 204
<211> LENGTH: 20
<212> TYPE: DNA
<213> ORGANISM: Artificial Sequence
<220> FEATURE:
<223> OTHER INFORMATION: Antisense Compound

<400> SEQUENCE: 204
agggaaggca gtgagaatct 20

<210> SEQ ID NO 205
<211> LENGTH: 20
<212> TYPE: DNA
<213> ORGANISM: Artificial Sequence
<220> FEATURE:
<223> OTHER INFORMATION: Antisense Compound

<400> SEQUENCE: 205
cttccacaaa cctaagggca 20

<210> SEQ ID NO 206
<211> LENGTH: 20
<212> TYPE: DNA
<213> ORGANISM: Artificial Sequence
<220> FEATURE:
<223> OTHER INFORMATION: Antisense Compound

<400> SEQUENCE: 206
ggtgtagaga acttcatcca 20

<210> SEQ ID NO 207
<211> LENGTH: 20
<212> TYPE: DNA
<213> ORGANISM: Artificial Sequence
<220> FEATURE:
<223> OTHER INFORMATION: Antisense Compound

<400> SEQUENCE: 207
aggagctcta aaaattgctt 20

<210> SEQ ID NO 208
<211> LENGTH: 20
<212> TYPE: DNA

<213> ORGANISM: Artificial Sequence
<220> FEATURE:
<223> OTHER INFORMATION: Antisense Compound

<400> SEQUENCE: 208
agagcagcca ctggaatccc 20

<210> SEQ ID NO 209
<211> LENGTH: 20
<212> TYPE: DNA
<213> ORGANISM: Artificial Sequence
<220> FEATURE:
<223> OTHER INFORMATION: Antisense Compound

<400> SEQUENCE: 209
agaaaggcag gacaaattcc 20

<210> SEQ ID NO 210
<211> LENGTH: 20
<212> TYPE: DNA
<213> ORGANISM: Artificial Sequence
<220> FEATURE:
<223> OTHER INFORMATION: Antisense Compound

<400> SEQUENCE: 210
tcagactgag gtctacctct 20

<210> SEQ ID NO 211
<211> LENGTH: 20
<212> TYPE: DNA
<213> ORGANISM: Artificial Sequence
<220> FEATURE:
<223> OTHER INFORMATION: Antisense Compound

<400> SEQUENCE: 211
aaggtctcag cattggctga 20

<210> SEQ ID NO 212
<211> LENGTH: 20
<212> TYPE: DNA
<213> ORGANISM: Artificial Sequence
<220> FEATURE:
<223> OTHER INFORMATION: Antisense Compound

<400> SEQUENCE: 212
ggagccagga cagggacttg 20

<210> SEQ ID NO 213
<211> LENGTH: 20
<212> TYPE: DNA
<213> ORGANISM: Artificial Sequence
<220> FEATURE:
<223> OTHER INFORMATION: Antisense Compound

<400> SEQUENCE: 213
ttgcggtgga gccaggacag 20

<210> SEQ ID NO 214
<211> LENGTH: 20
<212> TYPE: DNA
<213> ORGANISM: Artificial Sequence
<220> FEATURE:
<223> OTHER INFORMATION: Antisense Compound

<400> SEQUENCE: 214
cctcaggccc acagtccagt 20

<210> SEQ ID NO 215
<211> LENGTH: 20
<212> TYPE: DNA
<213> ORGANISM: Artificial Sequence
<220> FEATURE:
<223> OTHER INFORMATION: Antisense Compound

<400> SEQUENCE: 215
agcagcactc catccaggcc 20

<210> SEQ ID NO 216
<211> LENGTH: 20
<212> TYPE: DNA
<213> ORGANISM: Artificial Sequence
<220> FEATURE:
<223> OTHER INFORMATION: Antisense Compound

<400> SEQUENCE: 216
acctcctcag gattgcccac 20

<210> SEQ ID NO 217
<211> LENGTH: 20
<212> TYPE: DNA
<213> ORGANISM: Artificial Sequence
<220> FEATURE:
<223> OTHER INFORMATION: Antisense Compound

<400> SEQUENCE: 217
aacagtctga cctcctcagg 20

<210> SEQ ID NO 218
<211> LENGTH: 20
<212> TYPE: DNA
<213> ORGANISM: Artificial Sequence
<220> FEATURE:
<223> OTHER INFORMATION: Antisense Compound

<400> SEQUENCE: 218
cgctgccact cctgagggct 20

<210> SEQ ID NO 219
<211> LENGTH: 20
<212> TYPE: DNA
<213> ORGANISM: Artificial Sequence
<220> FEATURE:
<223> OTHER INFORMATION: Antisense Compound

<400> SEQUENCE: 219
tggtcagctg gtgaaggcgc 20

<210> SEQ ID NO 220
<211> LENGTH: 20
<212> TYPE: DNA
<213> ORGANISM: Artificial Sequence
<220> FEATURE:
<223> OTHER INFORMATION: Antisense Compound

<400> SEQUENCE: 220
aaagggcttc aggttgagca 20

<210> SEQ ID NO 221
<211> LENGTH: 20
<212> TYPE: DNA
<213> ORGANISM: Artificial Sequence
<220> FEATURE:
<223> OTHER INFORMATION: Antisense Compound

<400> SEQUENCE: 221
tggctgcaga gaaactggaa 20

<210> SEQ ID NO 222
<211> LENGTH: 20
<212> TYPE: DNA
<213> ORGANISM: Artificial Sequence
<220> FEATURE:
<223> OTHER INFORMATION: Antisense Compound

<400> SEQUENCE: 222
caattacgac agctatggct 20

<210> SEQ ID NO 223
<211> LENGTH: 20
<212> TYPE: DNA
<213> ORGANISM: Artificial Sequence
<220> FEATURE:
<223> OTHER INFORMATION: Antisense Compound

<400> SEQUENCE: 223
gcaggtgagg gtttccaagg 20

<210> SEQ ID NO 224
<211> LENGTH: 20
<212> TYPE: DNA
<213> ORGANISM: Artificial Sequence
<220> FEATURE:
<223> OTHER INFORMATION: Antisense Compound

<400> SEQUENCE: 224
aggagctgac agaagggttg 20

<210> SEQ ID NO 225
<211> LENGTH: 20
<212> TYPE: DNA
<213> ORGANISM: Artificial Sequence
<220> FEATURE:
<223> OTHER INFORMATION: Antisense Compound

<400> SEQUENCE: 225
tctggagcaa ggagctgaca 20

<210> SEQ ID NO 226
<211> LENGTH: 20
<212> TYPE: DNA
<213> ORGANISM: Artificial Sequence
<220> FEATURE:
<223> OTHER INFORMATION: Antisense Compound

<400> SEQUENCE: 226
acgccaagtc agaagctgct 20

<210> SEQ ID NO 227
<211> LENGTH: 20
<212> TYPE: DNA
<213> ORGANISM: Artificial Sequence
<220> FEATURE:
<223> OTHER INFORMATION: Antisense Compound

<400> SEQUENCE: 227
gatcttctgc agacccgcca 20

<210> SEQ ID NO 228
<211> LENGTH: 20
<212> TYPE: DNA

<213> ORGANISM: Artificial Sequence
<220> FEATURE:
<223> OTHER INFORMATION: Antisense Compound

<400> SEQUENCE: 228 cagcttttc gctcccgcac 20

<210> SEQ ID NO 229
<211> LENGTH: 20
<212> TYPE: DNA
<213> ORGANISM: Artificial Sequence
<220> FEATURE:
<223> OTHER INFORMATION: Antisense Compound

<400> SEQUENCE: 229
acccctacag acctgccatg 20

<210> SEQ ID NO 230
<211> LENGTH: 20
<212> TYPE: DNA
<213> ORGANISM: Artificial Sequence
<220> FEATURE:
<223> OTHER INFORMATION: Antisense Compound

<400> SEQUENCE: 230
ctgctcgggt ctgaccccta 20

<210> SEQ ID NO 231
<211> LENGTH: 20
<212> TYPE: DNA
<213> ORGANISM: Artificial Sequence
<220> FEATURE:
<223> OTHER INFORMATION: Antisense Compound

<400> SEQUENCE: 231
tcacataact gtaaagtcca 20

<210> SEQ ID NO 232
<211> LENGTH: 20
<212> TYPE: DNA
<213> ORGANISM: Artificial Sequence
<220> FEATURE:
<223> OTHER INFORMATION: Antisense Compound

<400> SEQUENCE: 232
ccatgacttt ttgtggacag 20

<210> SEQ ID NO 233
<211> LENGTH: 20
<212> TYPE: DNA
<213> ORGANISM: Artificial Sequence
<220> FEATURE:
<223> OTHER INFORMATION: Antisense Compound

<400> SEQUENCE: 233
cggcacccac ctaggtccat 20

<210> SEQ ID NO 234
<211> LENGTH: 20
<212> TYPE: DNA
<213> ORGANISM: Artificial Sequence
<220> FEATURE:
<223> OTHER INFORMATION: Antisense Compound

<400> SEQUENCE: 234
gtgatacctc aggagcgcag 20

<210> SEQ ID NO 235
<211> LENGTH: 20
<212> TYPE: DNA
<213> ORGANISM: Artificial Sequence
<220> FEATURE:
<223> OTHER INFORMATION: Antisense Compound

<400> SEQUENCE: 235
ataaggacac tgaggcgcag 20

<210> SEQ ID NO 236
<211> LENGTH: 20
<212> TYPE: DNA
<213> ORGANISM: Artificial Sequence
<220> FEATURE:
<223> OTHER INFORMATION: Antisense Compound

<400> SEQUENCE: 236
ggccctagct ctgtgggaga 20

<210> SEQ ID NO 237
<211> LENGTH: 20
<212> TYPE: DNA
<213> ORGANISM: Artificial Sequence
<220> FEATURE:
<223> OTHER INFORMATION: Antisense Compound

<400> SEQUENCE: 237
ataaacttgc cttgggaaca 20

<210> SEQ ID NO 238
<211> LENGTH: 20
<212> TYPE: DNA
<213> ORGANISM: Artificial Sequence
<220> FEATURE:
<223> OTHER INFORMATION: Antisense Compound

<400> SEQUENCE: 238
aatcacacag ccacagggta 20

<210> SEQ ID NO 239
<211> LENGTH: 20
<212> TYPE: DNA
<213> ORGANISM: Artificial Sequence
<220> FEATURE:
<223> OTHER INFORMATION: Antisense Compound

<400> SEQUENCE: 239
ggcgagaccc tccagcaaag 20

<210> SEQ ID NO 240
<211> LENGTH: 20
<212> TYPE: DNA
<213> ORGANISM: Artificial Sequence
<220> FEATURE:
<223> OTHER INFORMATION: Antisense Compound

<400> SEQUENCE: 240
ttcaagggtc ctgcacacag 20

<210> SEQ ID NO 241
<211> LENGTH: 20
<212> TYPE: DNA
<213> ORGANISM: Artificial Sequence
<220> FEATURE:
<223> OTHER INFORMATION: Antisense Compound

<400> SEQUENCE: 241
cctccaaaac agctagatac 20

<210> SEQ ID NO 242
<211> LENGTH: 20
<212> TYPE: DNA
<213> ORGANISM: Artificial Sequence
<220> FEATURE:
<223> OTHER INFORMATION: Antisense Compound

<400> SEQUENCE: 242
agatcccatt gcaacagttc 20

<210> SEQ ID NO 243
<211> LENGTH: 20
<212> TYPE: DNA
<213> ORGANISM: Artificial Sequence
<220> FEATURE:
<223> OTHER INFORMATION: Antisense Compound

<400> SEQUENCE: 243
tctgatgagg cactgaagag 20

<210> SEQ ID NO 244
<211> LENGTH: 20
<212> TYPE: DNA
<213> ORGANISM: Artificial Sequence
<220> FEATURE:
<223> OTHER INFORMATION: Antisense Compound

<400> SEQUENCE: 244
tctatccatt gatgtagaaa 20

<210> SEQ ID NO 245
<211> LENGTH: 20
<212> TYPE: DNA
<213> ORGANISM: Artificial Sequence
<220> FEATURE:
<223> OTHER INFORMATION: Antisense Compound

<400> SEQUENCE: 245
gtatgcaaac ccaccaaggg 20

<210> SEQ ID NO 246
<211> LENGTH: 20
<212> TYPE: DNA
<213> ORGANISM: Artificial Sequence
<220> FEATURE:
<223> OTHER INFORMATION: Antisense Compound

<400> SEQUENCE: 246
gatatgtgct agaaatctgt 20

<210> SEQ ID NO 247
<211> LENGTH: 20
<212> TYPE: DNA
<213> ORGANISM: Artificial Sequence
<220> FEATURE:
<223> OTHER INFORMATION: Antisense Compound

<400> SEQUENCE: 247
gggaaggtct gtctccttct 20

<210> SEQ ID NO 248
<211> LENGTH: 20
<212> TYPE: DNA

<213> ORGANISM: Artificial Sequence
<220> FEATURE:
<223> OTHER INFORMATION: Antisense Compound

<400> SEQUENCE: 248
taagacaatc ccttctcctc 20

<210> SEQ ID NO 249
<211> LENGTH: 20
<212> TYPE: DNA
<213> ORGANISM: Artificial Sequence
<220> FEATURE:
<223> OTHER INFORMATION: Antisense Compound

<400> SEQUENCE: 249
tccactaagc ttccagggat 20

<210> SEQ ID NO 250
<211> LENGTH: 20
<212> TYPE: DNA
<213> ORGANISM: Artificial Sequence
<220> FEATURE:
<223> OTHER INFORMATION: Antisense Compound

<400> SEQUENCE: 250
tggagccaga ggccatcaga 20

<210> SEQ ID NO 251
<211> LENGTH: 20
<212> TYPE: DNA
<213> ORGANISM: Artificial Sequence
<220> FEATURE:
<223> OTHER INFORMATION: Antisense Compound

<400> SEQUENCE: 251
gcacgtaaat gactgcattg 20

<210> SEQ ID NO 252
<211> LENGTH: 20
<212> TYPE: DNA
<213> ORGANISM: Artificial Sequence
<220> FEATURE:
<223> OTHER INFORMATION: Antisense Compound

<400> SEQUENCE: 252
gggctgctct ctatgacagt 20

<210> SEQ ID NO 253
<211> LENGTH: 20
<212> TYPE: DNA
<213> ORGANISM: Artificial Sequence
<220> FEATURE:
<223> OTHER INFORMATION: Antisense Compound

<400> SEQUENCE: 253
atgtgggctc cacgccacac 20

<210> SEQ ID NO 254
<211> LENGTH: 20
<212> TYPE: DNA
<213> ORGANISM: Artificial Sequence
<220> FEATURE:
<223> OTHER INFORMATION: Antisense Compound

<400> SEQUENCE: 254
cccctgaata gatgcagtct 20

<210> SEQ ID NO 255
<211> LENGTH: 20
<212> TYPE: DNA
<213> ORGANISM: Artificial Sequence
<220> FEATURE:
<223> OTHER INFORMATION: Antisense Compound

<400> SEQUENCE: 255
tgaggaggcc gggaatgatc 20

<210> SEQ ID NO 256
<211> LENGTH: 20
<212> TYPE: DNA
<213> ORGANISM: Artificial Sequence
<220> FEATURE:
<223> OTHER INFORMATION: Antisense Compound

<400> SEQUENCE: 256
ttctcaaggt gggctttttc 20

<210> SEQ ID NO 257
<211> LENGTH: 20
<212> TYPE: DNA
<213> ORGANISM: Artificial Sequence
<220> FEATURE:
<223> OTHER INFORMATION: Antisense Compound

<400> SEQUENCE: 257
atcattctat acagggtagc 20

<210> SEQ ID NO 258
<211> LENGTH: 20
<212> TYPE: DNA
<213> ORGANISM: Artificial Sequence
<220> FEATURE:
<223> OTHER INFORMATION: Antisense Compound

<400> SEQUENCE: 258 tgacctttc cttcaatatc 20

<210> SEQ ID NO 259
<211> LENGTH: 20
<212> TYPE: DNA
<213> ORGANISM: Artificial Sequence
<220> FEATURE:
<223> OTHER INFORMATION: Antisense Compound

<400> SEQUENCE: 259
gaaataactc agggtggcca 20

<210> SEQ ID NO 260
<211> LENGTH: 20
<212> TYPE: DNA
<213> ORGANISM: Artificial Sequence
<220> FEATURE:
<223> OTHER INFORMATION: Antisense Compound

<400> SEQUENCE: 260
ggagaacacc tttgagatcc 20

<210> SEQ ID NO 261
<211> LENGTH: 20
<212> TYPE: DNA
<213> ORGANISM: Artificial Sequence
<220> FEATURE:
<223> OTHER INFORMATION: Antisense Compound

<400> SEQUENCE: 261
catagccaca aggttgtctg 20

<210> SEQ ID NO 262
<211> LENGTH: 20
<212> TYPE: DNA
<213> ORGANISM: Artificial Sequence
<220> FEATURE:
<223> OTHER INFORMATION: Antisense Compound

<400> SEQUENCE: 262
tggtagccag ctgctggtgc 20

<210> SEQ ID NO 263
<211> LENGTH: 20
<212> TYPE: DNA
<213> ORGANISM: Artificial Sequence
<220> FEATURE:
<223> OTHER INFORMATION: Antisense Compound

<400> SEQUENCE: 263
aagcagcctt gacatactga 20

<210> SEQ ID NO 264
<211> LENGTH: 20
<212> TYPE: DNA
<213> ORGANISM: Artificial Sequence
<220> FEATURE:
<223> OTHER INFORMATION: Antisense Compound

<400> SEQUENCE: 264
cagctccacc gcttcataca 20

<210> SEQ ID NO 265
<211> LENGTH: 20
<212> TYPE: DNA
<213> ORGANISM: Artificial Sequence
<220> FEATURE:
<223> OTHER INFORMATION: Antisense Compound

<400> SEQUENCE: 265
atcctctcct acgatggcag 20

<210> SEQ ID NO 266
<211> LENGTH: 20
<212> TYPE: DNA
<213> ORGANISM: Artificial Sequence
<220> FEATURE:
<223> OTHER INFORMATION: Antisense Compound

<400> SEQUENCE: 266
ctgagagcca gggaagcaga 20

<210> SEQ ID NO 267
<211> LENGTH: 20
<212> TYPE: DNA
<213> ORGANISM: Artificial Sequence
<220> FEATURE:
<223> OTHER INFORMATION: Antisense Compound

<400> SEQUENCE: 267
acccagttgt tggccagaag 20

<210> SEQ ID NO 268
<211> LENGTH: 20
<212> TYPE: DNA

<213> ORGANISM: Artificial Sequence
<220> FEATURE:
<223> OTHER INFORMATION: Antisense Compound

<400> SEQUENCE: 268
ctgaccctgt agactttcat 20

<210> SEQ ID NO 269
<211> LENGTH: 20
<212> TYPE: DNA
<213> ORGANISM: Artificial Sequence
<220> FEATURE:
<223> OTHER INFORMATION: Antisense Compound

<400> SEQUENCE: 269
gttctgcagc ttctgaaagg 20

<210> SEQ ID NO 270
<211> LENGTH: 20
<212> TYPE: DNA
<213> ORGANISM: Artificial Sequence
<220> FEATURE:
<223> OTHER INFORMATION: Antisense Compound

<400> SEQUENCE: 270
agtcatggca aatgtgaagc 20

<210> SEQ ID NO 271
<211> LENGTH: 20
<212> TYPE: DNA
<213> ORGANISM: Artificial Sequence
<220> FEATURE:
<223> OTHER INFORMATION: Antisense Compound

<400> SEQUENCE: 271
gaggccatct gttggctcag 20

<210> SEQ ID NO 272
<211> LENGTH: 20
<212> TYPE: DNA
<213> ORGANISM: Artificial Sequence
<220> FEATURE:
<223> OTHER INFORMATION: Antisense Compound

<400> SEQUENCE: 272
acacttcctg catgatggtg 20

<210> SEQ ID NO 273
<211> LENGTH: 20
<212> TYPE: DNA
<213> ORGANISM: Artificial Sequence
<220> FEATURE:
<223> OTHER INFORMATION: Antisense Compound

<400> SEQUENCE: 273
tggtcacagc catcagggag 20

<210> SEQ ID NO 274
<211> LENGTH: 20
<212> TYPE: DNA
<213> ORGANISM: Artificial Sequence
<220> FEATURE:
<223> OTHER INFORMATION: Antisense Compound

<400> SEQUENCE: 274
gcagtgtcta actgctggct 20

<210> SEQ ID NO 275
<211> LENGTH: 20
<212> TYPE: DNA
<213> ORGANISM: Artificial Sequence
<220> FEATURE:
<223> OTHER INFORMATION: Antisense Compound

<400> SEQUENCE: 275
tggctgagaa gtttcagggt 20

<210> SEQ ID NO 276
<211> LENGTH: 20
<212> TYPE: DNA
<213> ORGANISM: Artificial Sequence
<220> FEATURE:
<223> OTHER INFORMATION: Antisense Compound

<400> SEQUENCE: 276
tacactggct ctgagaactg 20

<210> SEQ ID NO 277
<211> LENGTH: 20
<212> TYPE: DNA
<213> ORGANISM: Artificial Sequence
<220> FEATURE:
<223> OTHER INFORMATION: Antisense Compound

<400> SEQUENCE: 277
attctctgat ttgcctcggt 20

<210> SEQ ID NO 278
<211> LENGTH: 20
<212> TYPE: DNA
<213> ORGANISM: Artificial Sequence
<220> FEATURE:
<223> OTHER INFORMATION: Antisense Compound

<400> SEQUENCE: 278
tgtgaaaatt cacatacaga 20

<210> SEQ ID NO 279
<211> LENGTH: 20
<212> TYPE: DNA
<213> ORGANISM: Artificial Sequence
<220> FEATURE:
<223> OTHER INFORMATION: Antisense Compound

<400> SEQUENCE: 279
gagtgaatgt ctggtgaggc 20

<210> SEQ ID NO 280
<211> LENGTH: 20
<212> TYPE: DNA
<213> ORGANISM: Artificial Sequence
<220> FEATURE:
<223> OTHER INFORMATION: Antisense Compound

<400> SEQUENCE: 280
aaacttaatc cttgtttgta 20

<210> SEQ ID NO 281
<211> LENGTH: 20
<212> TYPE: DNA
<213> ORGANISM: Artificial Sequence
<220> FEATURE:
<223> OTHER INFORMATION: Antisense Compound

<400> SEQUENCE: 281
gttgtctatg ggtaggcagg 20

<210> SEQ ID NO 282
<211> LENGTH: 20
<212> TYPE: DNA
<213> ORGANISM: Artificial Sequence
<220> FEATURE:
<223> OTHER INFORMATION: Antisense Compound

<400> SEQUENCE: 282
tttgggtgac gacagaagtt 20

<210> SEQ ID NO 283
<211> LENGTH: 20
<212> TYPE: DNA
<213> ORGANISM: Artificial Sequence
<220> FEATURE:
<223> OTHER INFORMATION: Antisense Compound

<400> SEQUENCE: 283
gaagtattta caaaggtagc 20

<210> SEQ ID NO 284
<211> LENGTH: 20
<212> TYPE: DNA
<213> ORGANISM: Artificial Sequence
<220> FEATURE:
<223> OTHER INFORMATION: Antisense Compound

<400> SEQUENCE: 284
tctcaaacaa gcatgacaca 20

<210> SEQ ID NO 285
<211> LENGTH: 20
<212> TYPE: DNA
<213> ORGANISM: Artificial Sequence
<220> FEATURE:
<223> OTHER INFORMATION: Antisense Compound

<400> SEQUENCE: 285
aaaggtatca atagtcctaa 20

<210> SEQ ID NO 286
<211> LENGTH: 20
<212> TYPE: DNA
<213> ORGANISM: Artificial Sequence
<220> FEATURE:
<223> OTHER INFORMATION: Antisense Compound

<400> SEQUENCE: 286
ggcctatttc atattcaaac 20

<210> SEQ ID NO 287
<211> LENGTH: 20
<212> TYPE: DNA
<213> ORGANISM: Artificial Sequence
<220> FEATURE:
<223> OTHER INFORMATION: Antisense Compound

<400> SEQUENCE: 287
ttcctgagct atttgactgc 20

<210> SEQ ID NO 288
<211> LENGTH: 20
<212> TYPE: DNA

<213> ORGANISM: Artificial Sequence
<220> FEATURE:
<223> OTHER INFORMATION: Antisense Compound

<400> SEQUENCE: 288
tgaaacagta atttattcct 20

<210> SEQ ID NO 289
<211> LENGTH: 20
<212> TYPE: DNA
<213> ORGANISM: Artificial Sequence
<220> FEATURE:
<223> OTHER INFORMATION: Antisense Compound

<400> SEQUENCE: 289
aataatccaa aggtcatcta 20

<210> SEQ ID NO 290
<211> LENGTH: 20
<212> TYPE: DNA
<213> ORGANISM: Artificial Sequence
<220> FEATURE:
<223> OTHER INFORMATION: Antisense Compound

<400> SEQUENCE: 290
ttaaatagta tttagggtcc 20

<210> SEQ ID NO 291
<211> LENGTH: 20
<212> TYPE: DNA
<213> ORGANISM: Artificial Sequence
<220> FEATURE:
<223> OTHER INFORMATION: Antisense Compound

<400> SEQUENCE: 291
gaagctgcca cagccgaccg 20

<210> SEQ ID NO 292
<211> LENGTH: 20
<212> TYPE: DNA
<213> ORGANISM: Artificial Sequence
<220> FEATURE:
<223> OTHER INFORMATION: Antisense Compound

<400> SEQUENCE: 292
ccgtcagaga caagagaagc 20

<210> SEQ ID NO 293
<211> LENGTH: 20
<212> TYPE: DNA
<213> ORGANISM: Artificial Sequence
<220> FEATURE:
<223> OTHER INFORMATION: Antisense Compound

<400> SEQUENCE: 293
tcctgcccca taactacaag 20

<210> SEQ ID NO 294
<211> LENGTH: 20
<212> TYPE: DNA
<213> ORGANISM: Artificial Sequence
<220> FEATURE:
<223> OTHER INFORMATION: Antisense Compound

<400> SEQUENCE: 294
cggacaagga agacggaggt 20

<210> SEQ ID NO 295
<211> LENGTH: 20
<212> TYPE: DNA
<213> ORGANISM: Artificial Sequence
<220> FEATURE:
<223> OTHER INFORMATION: Antisense Compound

<400> SEQUENCE: 295
gtgtcccacc aactctccta 20

<210> SEQ ID NO 296
<211> LENGTH: 20
<212> TYPE: DNA
<213> ORGANISM: Artificial Sequence
<220> FEATURE:
<223> OTHER INFORMATION: Antisense Compound

<400> SEQUENCE: 296
cagagaccct ttcggtgtgt 20

<210> SEQ ID NO 297
<211> LENGTH: 20
<212> TYPE: DNA
<213> ORGANISM: Artificial Sequence
<220> FEATURE:
<223> OTHER INFORMATION: Antisense Compound

<400> SEQUENCE: 297
atgttctgtc acaactgttt 20

<210> SEQ ID NO 298
<211> LENGTH: 20
<212> TYPE: DNA
<213> ORGANISM: Artificial Sequence
<220> FEATURE:
<223> OTHER INFORMATION: Antisense Compound

<400> SEQUENCE: 298
actattaagt cctttactcg 20

<210> SEQ ID NO 299
<211> LENGTH: 20
<212> TYPE: DNA
<213> ORGANISM: Artificial Sequence
<220> FEATURE:
<223> OTHER INFORMATION: Antisense Compound

<400> SEQUENCE: 299
ggctgtcatt tctgttaaac 20

<210> SEQ ID NO 300
<211> LENGTH: 20
<212> TYPE: DNA
<213> ORGANISM: Artificial Sequence
<220> FEATURE:
<223> OTHER INFORMATION: Antisense Compound

<400> SEQUENCE: 300
tgggttctat aaagaggtgc 20

<210> SEQ ID NO 301
<211> LENGTH: 20
<212> TYPE: DNA
<213> ORGANISM: Artificial Sequence
<220> FEATURE:
<223> OTHER INFORMATION: Antisense Compound

<400> SEQUENCE: 301
attatcacca ctatgccatc 20

<210> SEQ ID NO 302
<211> LENGTH: 20
<212> TYPE: DNA
<213> ORGANISM: Artificial Sequence
<220> FEATURE:
<223> OTHER INFORMATION: Antisense Compound

<400> SEQUENCE: 302
atcatcatgg cctcgaagcc 20

<210> SEQ ID NO 303
<211> LENGTH: 20
<212> TYPE: DNA
<213> ORGANISM: Artificial Sequence
<220> FEATURE:
<223> OTHER INFORMATION: Antisense Compound

<400> SEQUENCE: 303
ggacaccagg ctatggagtg 20

<210> SEQ ID NO 304
<211> LENGTH: 20
<212> TYPE: DNA
<213> ORGANISM: Artificial Sequence
<220> FEATURE:
<223> OTHER INFORMATION: Antisense Compound

<400> SEQUENCE: 304
aagtagcaac cttttgttac 20

<210> SEQ ID NO 305
<211> LENGTH: 20
<212> TYPE: DNA
<213> ORGANISM: Artificial Sequence
<220> FEATURE:
<223> OTHER INFORMATION: Antisense Compound

<400> SEQUENCE: 305
tgcttccagt ggctaagtag 20

<210> SEQ ID NO 306
<211> LENGTH: 20
<212> TYPE: DNA
<213> ORGANISM: Artificial Sequence
<220> FEATURE:
<223> OTHER INFORMATION: Antisense Compound

<400> SEQUENCE: 306
gattcgaatg gtttgatctt 20

<210> SEQ ID NO 307
<211> LENGTH: 20
<212> TYPE: DNA
<213> ORGANISM: Artificial Sequence
<220> FEATURE:
<223> OTHER INFORMATION: Antisense Compound

<400> SEQUENCE: 307
ccctcggcct ctagaacagc 20

<210> SEQ ID NO 308
<211> LENGTH: 20
<212> TYPE: DNA

<213> ORGANISM: Artificial Sequence
<220> FEATURE:
<223> OTHER INFORMATION: Antisense Compound

<400> SEQUENCE: 308
tttaacagtt gggtctatac 20

<210> SEQ ID NO 309
<211> LENGTH: 20
<212> TYPE: DNA
<213> ORGANISM: Artificial Sequence
<220> FEATURE:
<223> OTHER INFORMATION: Antisense Compound

<400> SEQUENCE: 309
ggttgattgc tgggccaatg 20

<210> SEQ ID NO 310
<211> LENGTH: 20
<212> TYPE: DNA
<213> ORGANISM: Artificial Sequence
<220> FEATURE:
<223> OTHER INFORMATION: Antisense Compound

<400> SEQUENCE: 310
ccttctcctc caagtgacat 20

<210> SEQ ID NO 311
<211> LENGTH: 20
<212> TYPE: DNA
<213> ORGANISM: Artificial Sequence
<220> FEATURE:
<223> OTHER INFORMATION: Antisense Compound

<400> SEQUENCE: 311
catcccacac ctgggctgta 20

<210> SEQ ID NO 312
<211> LENGTH: 20
<212> TYPE: DNA
<213> ORGANISM: Artificial Sequence
<220> FEATURE:
<223> OTHER INFORMATION: Antisense Compound

<400> SEQUENCE: 312
aagaactcac tttgattgaa 20

<210> SEQ ID NO 313
<211> LENGTH: 20
<212> TYPE: DNA
<213> ORGANISM: Artificial Sequence
<220> FEATURE:
<223> OTHER INFORMATION: Antisense Compound

<400> SEQUENCE: 313
cagccttata agaacattta 20

<210> SEQ ID NO 314
<211> LENGTH: 20
<212> TYPE: DNA
<213> ORGANISM: Artificial Sequence
<220> FEATURE:
<223> OTHER INFORMATION: Antisense Compound

<400> SEQUENCE: 314
ccaaagttac ctatgacagt 20

<210> SEQ ID NO 315
<211> LENGTH: 20
<212> TYPE: DNA
<213> ORGANISM: Artificial Sequence
<220> FEATURE:
<223> OTHER INFORMATION: Antisense Compound

<400> SEQUENCE: 315
ggttgccatg cctttctggt 20

<210> SEQ ID NO 316
<211> LENGTH: 20
<212> TYPE: DNA
<213> ORGANISM: Artificial Sequence
<220> FEATURE:
<223> OTHER INFORMATION: Antisense Compound

<400> SEQUENCE: 316
atttttgtac ctctggagtg 20

<210> SEQ ID NO 317
<211> LENGTH: 20
<212> TYPE: DNA
<213> ORGANISM: Artificial Sequence
<220> FEATURE:
<223> OTHER INFORMATION: Antisense Compound

<400> SEQUENCE: 317
agctgctgta aacatttgtg 20

<210> SEQ ID NO 318
<211> LENGTH: 20
<212> TYPE: DNA
<213> ORGANISM: Artificial Sequence
<220> FEATURE:
<223> OTHER INFORMATION: Antisense Compound

<400> SEQUENCE: 318
taactcttac cttaatgctc 20

<210> SEQ ID NO 319
<211> LENGTH: 20
<212> TYPE: DNA
<213> ORGANISM: Artificial Sequence
<220> FEATURE:
<223> OTHER INFORMATION: Antisense Compound

<400> SEQUENCE: 319
ggtactcagc aaccatgctt 20

<210> SEQ ID NO 320
<211> LENGTH: 20
<212> TYPE: DNA
<213> ORGANISM: Artificial Sequence
<220> FEATURE:
<223> OTHER INFORMATION: Antisense Compound

<400> SEQUENCE: 320
ctctgggtac tcagcaacca 20

<210> SEQ ID NO 321
<211> LENGTH: 20
<212> TYPE: DNA
<213> ORGANISM: Artificial Sequence
<220> FEATURE:
<223> OTHER INFORMATION: Antisense Compound

```
<400> SEQUENCE: 321

agaaccttgg cagagactgg                                                   20


<210> SEQ ID NO 322
<211> LENGTH: 20
<212> TYPE: DNA
<213> ORGANISM: Artificial Sequence
<220> FEATURE:
<223> OTHER INFORMATION: Antisense Compound

<400> SEQUENCE: 322

tttaccgaca catccaagaa                                                   20


<210> SEQ ID NO 323
<211> LENGTH: 20
<212> TYPE: DNA
<213> ORGANISM: Artificial Sequence
<220> FEATURE:
<223> OTHER INFORMATION: Antisense Compound

<400> SEQUENCE: 323

gccctaagtt cattaatttc                                                   20


<210> SEQ ID NO 324
<211> LENGTH: 20
<212> TYPE: DNA
<213> ORGANISM: Artificial Sequence
<220> FEATURE:
<223> OTHER INFORMATION: Antisense Compound

<400> SEQUENCE: 324

ctgcgcctaa tcttaagcca                                                   20


<210> SEQ ID NO 325
<211> LENGTH: 20
<212> TYPE: DNA
<213> ORGANISM: Artificial Sequence
<220> FEATURE:
<223> OTHER INFORMATION: Antisense Compound

<400> SEQUENCE: 325

acctgaagat tgccccatgg                                                   20


<210> SEQ ID NO 326
<211> LENGTH: 20
<212> TYPE: DNA
<213> ORGANISM: Artificial Sequence
<220> FEATURE:
<223> OTHER INFORMATION: Antisense Compound

<400> SEQUENCE: 326

ctcctcgcaa ctctgggtac                                                   20


<210> SEQ ID NO 327
<211> LENGTH: 20
<212> TYPE: DNA
<213> ORGANISM: Artificial Sequence
<220> FEATURE:
<223> OTHER INFORMATION: Antisense Compound

<400> SEQUENCE: 327

ctggctaaat cagttaaaaa                                                   20


<210> SEQ ID NO 328
<211> LENGTH: 20
<212> TYPE: DNA
```

<213> ORGANISM: Artificial Sequence
<220> FEATURE:
<223> OTHER INFORMATION: Antisense Compound

<400> SEQUENCE: 328
ttgccacctg gctaaatcag 20

<210> SEQ ID NO 329
<211> LENGTH: 20
<212> TYPE: DNA
<213> ORGANISM: Artificial Sequence
<220> FEATURE:
<223> OTHER INFORMATION: Antisense Compound

<400> SEQUENCE: 329
atgattgcca cctggctaaa 20

<210> SEQ ID NO 330
<211> LENGTH: 20
<212> TYPE: DNA
<213> ORGANISM: Artificial Sequence
<220> FEATURE:
<223> OTHER INFORMATION: Antisense Compound

<400> SEQUENCE: 330
ccattcactc atgattgcca 20

<210> SEQ ID NO 331
<211> LENGTH: 20
<212> TYPE: DNA
<213> ORGANISM: Artificial Sequence
<220> FEATURE:
<223> OTHER INFORMATION: Antisense Compound

<400> SEQUENCE: 331
ttcatccatt cactcatgat 20

<210> SEQ ID NO 332
<211> LENGTH: 20
<212> TYPE: DNA
<213> ORGANISM: Artificial Sequence
<220> FEATURE:
<223> OTHER INFORMATION: Antisense Compound

<400> SEQUENCE: 332
tgtaatcttg ccattctaag 20

<210> SEQ ID NO 333
<211> LENGTH: 20
<212> TYPE: DNA
<213> ORGANISM: Artificial Sequence
<220> FEATURE:
<223> OTHER INFORMATION: Antisense Compound

<400> SEQUENCE: 333
tgtaaatgta atcttgccat 20

<210> SEQ ID NO 334
<211> LENGTH: 20
<212> TYPE: DNA
<213> ORGANISM: Artificial Sequence
<220> FEATURE:
<223> OTHER INFORMATION: Antisense Compound

<400> SEQUENCE: 334
ctttgtaaat gtaatcttgc 20

<210> SEQ ID NO 335
<211> LENGTH: 20
<212> TYPE: DNA
<213> ORGANISM: Artificial Sequence
<220> FEATURE:
<223> OTHER INFORMATION: Antisense Compound

<400> SEQUENCE: 335
actcggacct ctttgtaaat 20

<210> SEQ ID NO 336
<211> LENGTH: 20
<212> TYPE: DNA
<213> ORGANISM: Artificial Sequence
<220> FEATURE:
<223> OTHER INFORMATION: Antisense Compound

<400> SEQUENCE: 336
ctggctgtca ctcggacctc 20

<210> SEQ ID NO 337
<211> LENGTH: 20
<212> TYPE: DNA
<213> ORGANISM: Artificial Sequence
<220> FEATURE:
<223> OTHER INFORMATION: Antisense Compound

<400> SEQUENCE: 337
ctcactggct gtcactcgga 20

<210> SEQ ID NO 338
<211> LENGTH: 20
<212> TYPE: DNA
<213> ORGANISM: Artificial Sequence
<220> FEATURE:
<223> OTHER INFORMATION: Antisense Compound

<400> SEQUENCE: 338
cttctcactg gctgtcactc 20

<210> SEQ ID NO 339
<211> LENGTH: 20
<212> TYPE: DNA
<213> ORGANISM: Artificial Sequence
<220> FEATURE:
<223> OTHER INFORMATION: Antisense Compound

<400> SEQUENCE: 339
ctcattcttc tcactggctg 20

<210> SEQ ID NO 340
<211> LENGTH: 20
<212> TYPE: DNA
<213> ORGANISM: Artificial Sequence
<220> FEATURE:
<223> OTHER INFORMATION: Antisense Compound

<400> SEQUENCE: 340
gtagttaaaa cccatccttt 20

<210> SEQ ID NO 341
<211> LENGTH: 20
<212> TYPE: DNA
<213> ORGANISM: Artificial Sequence
<220> FEATURE:
<223> OTHER INFORMATION: Antisense Compound

<400> SEQUENCE: 341
gtctgtagtt aaaacccatc 20

<210> SEQ ID NO 342
<211> LENGTH: 20
<212> TYPE: DNA
<213> ORGANISM: Artificial Sequence
<220> FEATURE:
<223> OTHER INFORMATION: Antisense Compound

<400> SEQUENCE: 342
ctgggtctgt agttaaaacc 20

<210> SEQ ID NO 343
<211> LENGTH: 20
<212> TYPE: DNA
<213> ORGANISM: Artificial Sequence
<220> FEATURE:
<223> OTHER INFORMATION: Antisense Compound

<400> SEQUENCE: 343
agactgggtc tgtagttaaa 20

<210> SEQ ID NO 344
<211> LENGTH: 20
<212> TYPE: DNA
<213> ORGANISM: Artificial Sequence
<220> FEATURE:
<223> OTHER INFORMATION: Antisense Compound

<400> SEQUENCE: 344
ttggcagaga ctgggtctgt 20

<210> SEQ ID NO 345
<211> LENGTH: 20
<212> TYPE: DNA
<213> ORGANISM: Artificial Sequence
<220> FEATURE:
<223> OTHER INFORMATION: Antisense Compound

<400> SEQUENCE: 345
aaggacaata ttggcagaga 20

<210> SEQ ID NO 346
<211> LENGTH: 20
<212> TYPE: DNA
<213> ORGANISM: Artificial Sequence
<220> FEATURE:
<223> OTHER INFORMATION: Antisense Compound

<400> SEQUENCE: 346
tcaaggaagt tcacaaggac 20

<210> SEQ ID NO 347
<211> LENGTH: 20
<212> TYPE: DNA
<213> ORGANISM: Artificial Sequence
<220> FEATURE:
<223> OTHER INFORMATION: Antisense Compound

<400> SEQUENCE: 347
gccatcttca aggaagttca 20

<210> SEQ ID NO 348
<211> LENGTH: 20
<212> TYPE: DNA

<213> ORGANISM: Artificial Sequence
<220> FEATURE:
<223> OTHER INFORMATION: Antisense Compound

<400> SEQUENCE: 348
ctgccatctt caaggaagtt 20

<210> SEQ ID NO 349
<211> LENGTH: 20
<212> TYPE: DNA
<213> ORGANISM: Artificial Sequence
<220> FEATURE:
<223> OTHER INFORMATION: Antisense Compound

<400> SEQUENCE: 349
gtcacagaca tgctgccatc 20

<210> SEQ ID NO 350
<211> LENGTH: 20
<212> TYPE: DNA
<213> ORGANISM: Artificial Sequence
<220> FEATURE:
<223> OTHER INFORMATION: Antisense Compound

<400> SEQUENCE: 350
ccggtcacag acatgctgcc 20

<210> SEQ ID NO 351
<211> LENGTH: 20
<212> TYPE: DNA
<213> ORGANISM: Artificial Sequence
<220> FEATURE:
<223> OTHER INFORMATION: Antisense Compound

<400> SEQUENCE: 351
acagcatgtc ccataattcc 20

<210> SEQ ID NO 352
<211> LENGTH: 20
<212> TYPE: DNA
<213> ORGANISM: Artificial Sequence
<220> FEATURE:
<223> OTHER INFORMATION: Antisense Compound

<400> SEQUENCE: 352
cagtctgcac agcatgtccc 20

<210> SEQ ID NO 353
<211> LENGTH: 20
<212> TYPE: DNA
<213> ORGANISM: Artificial Sequence
<220> FEATURE:
<223> OTHER INFORMATION: Antisense Compound

<400> SEQUENCE: 353
tcaacagtct gcacagcatg 20

<210> SEQ ID NO 354
<211> LENGTH: 20
<212> TYPE: DNA
<213> ORGANISM: Artificial Sequence
<220> FEATURE:
<223> OTHER INFORMATION: Antisense Compound

<400> SEQUENCE: 354
tcattcatag tttcaacagt 20

<210> SEQ ID NO 355
<211> LENGTH: 20
<212> TYPE: DNA
<213> ORGANISM: Artificial Sequence
<220> FEATURE:
<223> OTHER INFORMATION: Antisense Compound

<400> SEQUENCE: 355
tccccttcat tcatagtttc 20

<210> SEQ ID NO 356
<211> LENGTH: 20
<212> TYPE: DNA
<213> ORGANISM: Artificial Sequence
<220> FEATURE:
<223> OTHER INFORMATION: Antisense Compound

<400> SEQUENCE: 356
tatggtcccc ttcattcata 20

<210> SEQ ID NO 357
<211> LENGTH: 20
<212> TYPE: DNA
<213> ORGANISM: Artificial Sequence
<220> FEATURE:
<223> OTHER INFORMATION: Antisense Compound

<400> SEQUENCE: 357
tctatggtcc ccttcattca 20

<210> SEQ ID NO 358
<211> LENGTH: 20
<212> TYPE: DNA
<213> ORGANISM: Artificial Sequence
<220> FEATURE:
<223> OTHER INFORMATION: Antisense Compound

<400> SEQUENCE: 358
tgaacaaatg catcagcttc 20

<210> SEQ ID NO 359
<211> LENGTH: 20
<212> TYPE: DNA
<213> ORGANISM: Artificial Sequence
<220> FEATURE:
<223> OTHER INFORMATION: Antisense Compound

<400> SEQUENCE: 359
cagacgtgaa caaatgcatc 20

<210> SEQ ID NO 360
<211> LENGTH: 20
<212> TYPE: DNA
<213> ORGANISM: Artificial Sequence
<220> FEATURE:
<223> OTHER INFORMATION: Antisense Compound

<400> SEQUENCE: 360
ctttgcagtc tccagacgtg 20

<210> SEQ ID NO 361
<211> LENGTH: 20
<212> TYPE: DNA
<213> ORGANISM: Artificial Sequence
<220> FEATURE:
<223> OTHER INFORMATION: Antisense Compound

<400> SEQUENCE: 361
ctgggctgta tgctttgcag 20

<210> SEQ ID NO 362
<211> LENGTH: 20
<212> TYPE: DNA
<213> ORGANISM: Artificial Sequence
<220> FEATURE:
<223> OTHER INFORMATION: Antisense Compound

<400> SEQUENCE: 362
gatcctctgg gctgtatgct 20

<210> SEQ ID NO 363
<211> LENGTH: 20
<212> TYPE: DNA
<213> ORGANISM: Artificial Sequence
<220> FEATURE:
<223> OTHER INFORMATION: Antisense Compound

<400> SEQUENCE: 363
ccagatcctc tgggctgtat 20

<210> SEQ ID NO 364
<211> LENGTH: 20
<212> TYPE: DNA
<213> ORGANISM: Artificial Sequence
<220> FEATURE:
<223> OTHER INFORMATION: Antisense Compound

<400> SEQUENCE: 364
tttctctctt ccagatcctc 20

<210> SEQ ID NO 365
<211> LENGTH: 20
<212> TYPE: DNA
<213> ORGANISM: Artificial Sequence
<220> FEATURE:
<223> OTHER INFORMATION: Antisense Compound

<400> SEQUENCE: 365
caagccattt ctttaggctg 20

<210> SEQ ID NO 366
<211> LENGTH: 20
<212> TYPE: DNA
<213> ORGANISM: Artificial Sequence
<220> FEATURE:
<223> OTHER INFORMATION: Antisense Compound

<400> SEQUENCE: 366
tctcaagcca tttctttagg 20

<210> SEQ ID NO 367
<211> LENGTH: 20
<212> TYPE: DNA
<213> ORGANISM: Artificial Sequence
<220> FEATURE:
<223> OTHER INFORMATION: Antisense Compound

<400> SEQUENCE: 367
cttctcaagc catttcttta 20

<210> SEQ ID NO 368
<211> LENGTH: 20
<212> TYPE: DNA

<213> ORGANISM: Artificial Sequence
<220> FEATURE:
<223> OTHER INFORMATION: Antisense Compound

<400> SEQUENCE: 368
gttcttctca agccatttct 20

<210> SEQ ID NO 369
<211> LENGTH: 20
<212> TYPE: DNA
<213> ORGANISM: Artificial Sequence
<220> FEATURE:
<223> OTHER INFORMATION: Antisense Compound

<400> SEQUENCE: 369
tggttcttct caagccattt 20

<210> SEQ ID NO 370
<211> LENGTH: 20
<212> TYPE: DNA
<213> ORGANISM: Artificial Sequence
<220> FEATURE:
<223> OTHER INFORMATION: Antisense Compound

<400> SEQUENCE: 370
tgtggttctt ctcaagccat 20

<210> SEQ ID NO 371
<211> LENGTH: 20
<212> TYPE: DNA
<213> ORGANISM: Artificial Sequence
<220> FEATURE:
<223> OTHER INFORMATION: Antisense Compound

<400> SEQUENCE: 371
gggatgtggt tcttctcaag 20

<210> SEQ ID NO 372
<211> LENGTH: 20
<212> TYPE: DNA
<213> ORGANISM: Artificial Sequence
<220> FEATURE:
<223> OTHER INFORMATION: Antisense Compound

<400> SEQUENCE: 372
gtctccctgt tcagtgatgg 20

<210> SEQ ID NO 373
<211> LENGTH: 20
<212> TYPE: DNA
<213> ORGANISM: Artificial Sequence
<220> FEATURE:
<223> OTHER INFORMATION: Antisense Compound

<400> SEQUENCE: 373
acacagagag tccttggagc 20

<210> SEQ ID NO 374
<211> LENGTH: 20
<212> TYPE: DNA
<213> ORGANISM: Artificial Sequence
<220> FEATURE:
<223> OTHER INFORMATION: Antisense Compound

<400> SEQUENCE: 374
cagccacaca gagagtcctt 20

<210> SEQ ID NO 375
<211> LENGTH: 20
<212> TYPE: DNA
<213> ORGANISM: Artificial Sequence
<220> FEATURE:
<223> OTHER INFORMATION: Antisense Compound

<400> SEQUENCE: 375
accccagcca cacagagagt 20

<210> SEQ ID NO 376
<211> LENGTH: 20
<212> TYPE: DNA
<213> ORGANISM: Artificial Sequence
<220> FEATURE:
<223> OTHER INFORMATION: Antisense Compound

<400> SEQUENCE: 376
ggtctatagt caggacccca 20

<210> SEQ ID NO 377
<211> LENGTH: 20
<212> TYPE: DNA
<213> ORGANISM: Artificial Sequence
<220> FEATURE:
<223> OTHER INFORMATION: Antisense Compound

<400> SEQUENCE: 377
tatggtgggt ctatagtcag 20

<210> SEQ ID NO 378
<211> LENGTH: 20
<212> TYPE: DNA
<213> ORGANISM: Artificial Sequence
<220> FEATURE:
<223> OTHER INFORMATION: Antisense Compound

<400> SEQUENCE: 378
tcatatggtg ggtctatagt 20

<210> SEQ ID NO 379
<211> LENGTH: 20
<212> TYPE: DNA
<213> ORGANISM: Artificial Sequence
<220> FEATURE:
<223> OTHER INFORMATION: Antisense Compound

<400> SEQUENCE: 379
aattttctgg atcatatggt 20

<210> SEQ ID NO 380
<211> LENGTH: 20
<212> TYPE: DNA
<213> ORGANISM: Artificial Sequence
<220> FEATURE:
<223> OTHER INFORMATION: Antisense Compound

<400> SEQUENCE: 380
ctgcaatttt ctggatcata 20

<210> SEQ ID NO 381
<211> LENGTH: 20
<212> TYPE: DNA
<213> ORGANISM: Artificial Sequence
<220> FEATURE:
<223> OTHER INFORMATION: Antisense Compound

<400> SEQUENCE: 381
ttagagctgc tgcaattttc 20

<210> SEQ ID NO 382
<211> LENGTH: 20
<212> TYPE: DNA
<213> ORGANISM: Artificial Sequence
<220> FEATURE:
<223> OTHER INFORMATION: Antisense Compound

<400> SEQUENCE: 382
ctcattagag ctgctgcaat 20

<210> SEQ ID NO 383
<211> LENGTH: 20
<212> TYPE: DNA
<213> ORGANISM: Artificial Sequence
<220> FEATURE:
<223> OTHER INFORMATION: Antisense Compound

<400> SEQUENCE: 383
cgcgacagaa taatctcatt 20

<210> SEQ ID NO 384
<211> LENGTH: 20
<212> TYPE: DNA
<213> ORGANISM: Artificial Sequence
<220> FEATURE:
<223> OTHER INFORMATION: Antisense Compound

<400> SEQUENCE: 384
agatcctgaa cacgcgacag 20

<210> SEQ ID NO 385
<211> LENGTH: 20
<212> TYPE: DNA
<213> ORGANISM: Artificial Sequence
<220> FEATURE:
<223> OTHER INFORMATION: Antisense Compound

<400> SEQUENCE: 385
ctggcctctc attgggaagc 20

<210> SEQ ID NO 386
<211> LENGTH: 20
<212> TYPE: DNA
<213> ORGANISM: Artificial Sequence
<220> FEATURE:
<223> OTHER INFORMATION: Antisense Compound

<400> SEQUENCE: 386
gataaaatat agtctttttc 20

<210> SEQ ID NO 387
<211> LENGTH: 20
<212> TYPE: DNA
<213> ORGANISM: Artificial Sequence
<220> FEATURE:
<223> OTHER INFORMATION: Antisense Compound

<400> SEQUENCE: 387
tgagggataa aatatagtct 20

<210> SEQ ID NO 388
<211> LENGTH: 20
<212> TYPE: DNA

<213> ORGANISM: Artificial Sequence
<220> FEATURE:
<223> OTHER INFORMATION: Antisense Compound

<400> SEQUENCE: 388
acattttatg agggataaaa 20

<210> SEQ ID NO 389
<211> LENGTH: 20
<212> TYPE: DNA
<213> ORGANISM: Artificial Sequence
<220> FEATURE:
<223> OTHER INFORMATION: Antisense Compound

<400> SEQUENCE: 389
atttaaaaca ttttatgagg 20

<210> SEQ ID NO 390
<211> LENGTH: 20
<212> TYPE: DNA
<213> ORGANISM: Artificial Sequence
<220> FEATURE:
<223> OTHER INFORMATION: Antisense Compound

<400> SEQUENCE: 390
tctccgctgg atcccgccat 20

<210> SEQ ID NO 391
<211> LENGTH: 20
<212> TYPE: DNA
<213> ORGANISM: Artificial Sequence
<220> FEATURE:
<223> OTHER INFORMATION: Antisense Compound

<400> SEQUENCE: 391
acattccaaa tcgctttcac 20

<210> SEQ ID NO 392
<211> LENGTH: 20
<212> TYPE: DNA
<213> ORGANISM: Artificial Sequence
<220> FEATURE:
<223> OTHER INFORMATION: Antisense Compound

<400> SEQUENCE: 392
ctggctaaat ctgaaacaac 20

<210> SEQ ID NO 393
<211> LENGTH: 20
<212> TYPE: DNA
<213> ORGANISM: Artificial Sequence
<220> FEATURE:
<223> OTHER INFORMATION: Antisense Compound

<400> SEQUENCE: 393
gcatactcac ttggcagaga 20

<210> SEQ ID NO 394
<211> LENGTH: 20
<212> TYPE: DNA
<213> ORGANISM: Artificial Sequence
<220> FEATURE:
<223> OTHER INFORMATION: Antisense Compound

<400> SEQUENCE: 394
tcttttaaga gatatagtga 20

<210> SEQ ID NO 395
<211> LENGTH: 20
<212> TYPE: DNA
<213> ORGANISM: Artificial Sequence
<220> FEATURE:
<223> OTHER INFORMATION: Antisense Compound

<400> SEQUENCE: 395
aaagtaagtt tagaggcatc 20

<210> SEQ ID NO 396
<211> LENGTH: 20
<212> TYPE: DNA
<213> ORGANISM: Artificial Sequence
<220> FEATURE:
<223> OTHER INFORMATION: Antisense Compound

<400> SEQUENCE: 396
aaggacaata ctttggagga 20

<210> SEQ ID NO 397
<211> LENGTH: 20
<212> TYPE: DNA
<213> ORGANISM: Artificial Sequence
<220> FEATURE:
<223> OTHER INFORMATION: Antisense Compound

<400> SEQUENCE: 397
agagcccaac acttaggtca 20

<210> SEQ ID NO 398
<211> LENGTH: 20
<212> TYPE: DNA
<213> ORGANISM: Artificial Sequence
<220> FEATURE:
<223> OTHER INFORMATION: Antisense Compound

<400> SEQUENCE: 398
tagattcaag agcccaacac 20

<210> SEQ ID NO 399
<211> LENGTH: 20
<212> TYPE: DNA
<213> ORGANISM: Artificial Sequence
<220> FEATURE:
<223> OTHER INFORMATION: Antisense Compound

<400> SEQUENCE: 399
tccctggtga cctggcccca 20

<210> SEQ ID NO 400
<211> LENGTH: 20
<212> TYPE: DNA
<213> ORGANISM: Artificial Sequence
<220> FEATURE:
<223> OTHER INFORMATION: Antisense Compound

<400> SEQUENCE: 400
ttaagaaaga tcacacaggg 20

<210> SEQ ID NO 401
<211> LENGTH: 20
<212> TYPE: DNA
<213> ORGANISM: Artificial Sequence
<220> FEATURE:
<223> OTHER INFORMATION: Antisense Compound

<400> SEQUENCE: 401
ggtgtgacct gataagaaac 20

<210> SEQ ID NO 402
<211> LENGTH: 20
<212> TYPE: DNA
<213> ORGANISM: Artificial Sequence
<220> FEATURE:
<223> OTHER INFORMATION: Antisense Compound

<400> SEQUENCE: 402
gtgccccatg tagaaaggca 20

<210> SEQ ID NO 403
<211> LENGTH: 20
<212> TYPE: DNA
<213> ORGANISM: Artificial Sequence
<220> FEATURE:
<223> OTHER INFORMATION: Antisense Compound

<400> SEQUENCE: 403
agagggagca aactcaggtc 20

<210> SEQ ID NO 404
<211> LENGTH: 20
<212> TYPE: DNA
<213> ORGANISM: Artificial Sequence
<220> FEATURE:
<223> OTHER INFORMATION: Antisense Compound

<400> SEQUENCE: 404
ggaggaagag ggagcaaact 20

<210> SEQ ID NO 405
<211> LENGTH: 20
<212> TYPE: DNA
<213> ORGANISM: Artificial Sequence
<220> FEATURE:
<223> OTHER INFORMATION: Antisense Compound

<400> SEQUENCE: 405
cggctactgg tgtccccact 20

<210> SEQ ID NO 406
<211> LENGTH: 20
<212> TYPE: DNA
<213> ORGANISM: Artificial Sequence
<220> FEATURE:
<223> OTHER INFORMATION: Antisense Compound

<400> SEQUENCE: 406
gaggtccgcg gctactggtg 20

<210> SEQ ID NO 407
<211> LENGTH: 20
<212> TYPE: DNA
<213> ORGANISM: Artificial Sequence
<220> FEATURE:
<223> OTHER INFORMATION: Antisense Compound

<400> SEQUENCE: 407
attgtcttgg cgaggtccgc 20

<210> SEQ ID NO 408
<211> LENGTH: 20
<212> TYPE: DNA

<213> ORGANISM: Artificial Sequence
<220> FEATURE:
<223> OTHER INFORMATION: Antisense Compound

<400> SEQUENCE: 408
tgtcttggct ctttccgtca 20

<210> SEQ ID NO 409
<211> LENGTH: 20
<212> TYPE: DNA
<213> ORGANISM: Artificial Sequence
<220> FEATURE:
<223> OTHER INFORMATION: Antisense Compound

<400> SEQUENCE: 409
gccgccagac ctctttccgt 20

<210> SEQ ID NO 410
<211> LENGTH: 20
<212> TYPE: DNA
<213> ORGANISM: Artificial Sequence
<220> FEATURE:
<223> OTHER INFORMATION: Antisense Compound

<400> SEQUENCE: 410
tgtcaacaga gaagccgcca 20

<210> SEQ ID NO 411
<211> LENGTH: 20
<212> TYPE: DNA
<213> ORGANISM: Artificial Sequence
<220> FEATURE:
<223> OTHER INFORMATION: Antisense Compound

<400> SEQUENCE: 411
gagttgtcaa cagagaagcc 20

<210> SEQ ID NO 412
<211> LENGTH: 20
<212> TYPE: DNA
<213> ORGANISM: Artificial Sequence
<220> FEATURE:
<223> OTHER INFORMATION: Antisense Compound

<400> SEQUENCE: 412
aaccagctga gttgtcaaca 20

<210> SEQ ID NO 413
<211> LENGTH: 20
<212> TYPE: DNA
<213> ORGANISM: Artificial Sequence
<220> FEATURE:
<223> OTHER INFORMATION: Antisense Compound

<400> SEQUENCE: 413
ggtgtggaac cagctgagtt 20

<210> SEQ ID NO 414
<211> LENGTH: 20
<212> TYPE: DNA
<213> ORGANISM: Artificial Sequence
<220> FEATURE:
<223> OTHER INFORMATION: Antisense Compound

<400> SEQUENCE: 414
gagaggagat cagctcagtg 20

<210> SEQ ID NO 415
<211> LENGTH: 20
<212> TYPE: DNA
<213> ORGANISM: Artificial Sequence
<220> FEATURE:
<223> OTHER INFORMATION: Antisense Compound

<400> SEQUENCE: 415
ggtgctccag agaggagatc 20

<210> SEQ ID NO 416
<211> LENGTH: 20
<212> TYPE: DNA
<213> ORGANISM: Artificial Sequence
<220> FEATURE:
<223> OTHER INFORMATION: Antisense Compound

<400> SEQUENCE: 416
attgtcttgg ctccctcctg 20

<210> SEQ ID NO 417
<211> LENGTH: 20
<212> TYPE: DNA
<213> ORGANISM: Artificial Sequence
<220> FEATURE:
<223> OTHER INFORMATION: Antisense Compound

<400> SEQUENCE: 417
ggagtttgca ttgtcttggc 20

<210> SEQ ID NO 418
<211> LENGTH: 20
<212> TYPE: DNA
<213> ORGANISM: Artificial Sequence
<220> FEATURE:
<223> OTHER INFORMATION: Antisense Compound

<400> SEQUENCE: 418
gaatgttcac tggagtttgc 20

<210> SEQ ID NO 419
<211> LENGTH: 20
<212> TYPE: DNA
<213> ORGANISM: Artificial Sequence
<220> FEATURE:
<223> OTHER INFORMATION: Antisense Compound

<400> SEQUENCE: 419
ggcacgggaa tgttcactgg 20

<210> SEQ ID NO 420
<211> LENGTH: 20
<212> TYPE: DNA
<213> ORGANISM: Artificial Sequence
<220> FEATURE:
<223> OTHER INFORMATION: Antisense Compound

<400> SEQUENCE: 420
ctggatttca ggaacctctg 20

<210> SEQ ID NO 421
<211> LENGTH: 20
<212> TYPE: DNA
<213> ORGANISM: Artificial Sequence
<220> FEATURE:
<223> OTHER INFORMATION: Antisense Compound

<400> SEQUENCE: 421
atgggacact cctggatttc 20

<210> SEQ ID NO 422
<211> LENGTH: 20
<212> TYPE: DNA
<213> ORGANISM: Artificial Sequence
<220> FEATURE:
<223> OTHER INFORMATION: Antisense Compound

<400> SEQUENCE: 422
cttgagctat gggacactcc 20

<210> SEQ ID NO 423
<211> LENGTH: 20
<212> TYPE: DNA
<213> ORGANISM: Artificial Sequence
<220> FEATURE:
<223> OTHER INFORMATION: Antisense Compound

<400> SEQUENCE: 423
cccgctgctc ctgggattcc 20

<210> SEQ ID NO 424
<211> LENGTH: 20
<212> TYPE: DNA
<213> ORGANISM: Artificial Sequence
<220> FEATURE:
<223> OTHER INFORMATION: Antisense Compound

<400> SEQUENCE: 424
aagttggcca catccaggtc 20

<210> SEQ ID NO 425
<211> LENGTH: 20
<212> TYPE: DNA
<213> ORGANISM: Artificial Sequence
<220> FEATURE:
<223> OTHER INFORMATION: Antisense Compound

<400> SEQUENCE: 425
acgtagaagt tggccacatc 20

<210> SEQ ID NO 426
<211> LENGTH: 20
<212> TYPE: DNA
<213> ORGANISM: Artificial Sequence
<220> FEATURE:
<223> OTHER INFORMATION: Antisense Compound

<400> SEQUENCE: 426
tctgcagctg tgacacgtag 20

<210> SEQ ID NO 427
<211> LENGTH: 20
<212> TYPE: DNA
<213> ORGANISM: Artificial Sequence
<220> FEATURE:
<223> OTHER INFORMATION: Antisense Compound

<400> SEQUENCE: 427
cctatgggag tctgcagctg 20

<210> SEQ ID NO 428
<211> LENGTH: 20
<212> TYPE: DNA

<213> ORGANISM: Artificial Sequence
<220> FEATURE:
<223> OTHER INFORMATION: Antisense Compound

<400> SEQUENCE: 428
acacctatgg gagtctgcag 20

<210> SEQ ID NO 429
<211> LENGTH: 20
<212> TYPE: DNA
<213> ORGANISM: Artificial Sequence
<220> FEATURE:
<223> OTHER INFORMATION: Antisense Compound

<400> SEQUENCE: 429
ttgcacacct atgggagtct 20

<210> SEQ ID NO 430
<211> LENGTH: 20
<212> TYPE: DNA
<213> ORGANISM: Artificial Sequence
<220> FEATURE:
<223> OTHER INFORMATION: Antisense Compound

<400> SEQUENCE: 430
ctctgcttgc acacctatgg 20

<210> SEQ ID NO 431
<211> LENGTH: 20
<212> TYPE: DNA
<213> ORGANISM: Artificial Sequence
<220> FEATURE:
<223> OTHER INFORMATION: Antisense Compound

<400> SEQUENCE: 431
tgtcactaca tcggagcagc 20

<210> SEQ ID NO 432
<211> LENGTH: 20
<212> TYPE: DNA
<213> ORGANISM: Artificial Sequence
<220> FEATURE:
<223> OTHER INFORMATION: Antisense Compound

<400> SEQUENCE: 432
ggcttgaagg tatatgaaat 20

<210> SEQ ID NO 433
<211> LENGTH: 20
<212> TYPE: DNA
<213> ORGANISM: Artificial Sequence
<220> FEATURE:
<223> OTHER INFORMATION: Antisense Compound

<400> SEQUENCE: 433
acaatatctt tatggcttga 20

<210> SEQ ID NO 434
<211> LENGTH: 20
<212> TYPE: DNA
<213> ORGANISM: Artificial Sequence
<220> FEATURE:
<223> OTHER INFORMATION: Antisense Compound

<400> SEQUENCE: 434
gcccagagtt cctggctcgg 20

<210> SEQ ID NO 435
<211> LENGTH: 20
<212> TYPE: DNA
<213> ORGANISM: Artificial Sequence
<220> FEATURE:
<223> OTHER INFORMATION: Antisense Compound

<400> SEQUENCE: 435
gggagctcat aactccatgg 20

<210> SEQ ID NO 436
<211> LENGTH: 20
<212> TYPE: DNA
<213> ORGANISM: Artificial Sequence
<220> FEATURE:
<223> OTHER INFORMATION: Antisense Compound

<400> SEQUENCE: 436
ttaaagcttg gctcaaaatt 20

<210> SEQ ID NO 437
<211> LENGTH: 20
<212> TYPE: DNA
<213> ORGANISM: Artificial Sequence
<220> FEATURE:
<223> OTHER INFORMATION: Antisense Compound

<400> SEQUENCE: 437
aggagtccag acttgcttaa 20

<210> SEQ ID NO 438
<211> LENGTH: 20
<212> TYPE: DNA
<213> ORGANISM: Artificial Sequence
<220> FEATURE:
<223> OTHER INFORMATION: Antisense Compound

<400> SEQUENCE: 438
aggaggtctc aggagtccag 20

<210> SEQ ID NO 439
<211> LENGTH: 20
<212> TYPE: DNA
<213> ORGANISM: Artificial Sequence
<220> FEATURE:
<223> OTHER INFORMATION: Antisense Compound

<400> SEQUENCE: 439
cttagaattc ctagagttgc 20

<210> SEQ ID NO 440
<211> LENGTH: 20
<212> TYPE: DNA
<213> ORGANISM: Artificial Sequence
<220> FEATURE:
<223> OTHER INFORMATION: Antisense Compound

<400> SEQUENCE: 440
ttccttccaa tgggatctta 20

<210> SEQ ID NO 441
<211> LENGTH: 20
<212> TYPE: DNA
<213> ORGANISM: Artificial Sequence
<220> FEATURE:
<223> OTHER INFORMATION: Antisense Compound

<400> SEQUENCE: 441
tgtgaggtag agcattcctt 20

<210> SEQ ID NO 442
<211> LENGTH: 20
<212> TYPE: DNA
<213> ORGANISM: Artificial Sequence
<220> FEATURE:
<223> OTHER INFORMATION: Antisense Compound

<400> SEQUENCE: 442
tcagagttct gtgaggtaga 20

<210> SEQ ID NO 443
<211> LENGTH: 20
<212> TYPE: DNA
<213> ORGANISM: Artificial Sequence
<220> FEATURE:
<223> OTHER INFORMATION: Antisense Compound

<400> SEQUENCE: 443
ggcagcaggc ccatatttct 20

<210> SEQ ID NO 444
<211> LENGTH: 20
<212> TYPE: DNA
<213> ORGANISM: Artificial Sequence
<220> FEATURE:
<223> OTHER INFORMATION: Antisense Compound

<400> SEQUENCE: 444
acctcgatgc cccggtcttc 20

<210> SEQ ID NO 445
<211> LENGTH: 20
<212> TYPE: DNA
<213> ORGANISM: Artificial Sequence
<220> FEATURE:
<223> OTHER INFORMATION: Antisense Compound

<400> SEQUENCE: 445
aggttgtatc ctttatcacc 20

<210> SEQ ID NO 446
<211> LENGTH: 20
<212> TYPE: DNA
<213> ORGANISM: Artificial Sequence
<220> FEATURE:
<223> OTHER INFORMATION: Antisense Compound

<400> SEQUENCE: 446
actttgcagc ctctttaata 20

<210> SEQ ID NO 447
<211> LENGTH: 20
<212> TYPE: DNA
<213> ORGANISM: Artificial Sequence
<220> FEATURE:
<223> OTHER INFORMATION: Antisense Compound

<400> SEQUENCE: 447
aaacaggagt cgaattttcc 20

<210> SEQ ID NO 448
<211> LENGTH: 20
<212> TYPE: DNA

<213> ORGANISM: Artificial Sequence
<220> FEATURE:
<223> OTHER INFORMATION: Antisense Compound

<400> SEQUENCE: 448
aagatgactc catccccgtc 20

<210> SEQ ID NO 449
<211> LENGTH: 20
<212> TYPE: DNA
<213> ORGANISM: Artificial Sequence
<220> FEATURE:
<223> OTHER INFORMATION: Antisense Compound

<400> SEQUENCE: 449
accagcccct aaagatgact 20

<210> SEQ ID NO 450
<211> LENGTH: 20
<212> TYPE: DNA
<213> ORGANISM: Artificial Sequence
<220> FEATURE:
<223> OTHER INFORMATION: Antisense Compound

<400> SEQUENCE: 450
ggataaccac cctaccagcc 20

<210> SEQ ID NO 451
<211> LENGTH: 20
<212> TYPE: DNA
<213> ORGANISM: Artificial Sequence
<220> FEATURE:
<223> OTHER INFORMATION: Antisense Compound

<400> SEQUENCE: 451
acttggccca gctccactgg 20

<210> SEQ ID NO 452
<211> LENGTH: 20
<212> TYPE: DNA
<213> ORGANISM: Artificial Sequence
<220> FEATURE:
<223> OTHER INFORMATION: Antisense Compound

<400> SEQUENCE: 452
gacttgcggc cgtgcagccc 20

<210> SEQ ID NO 453
<211> LENGTH: 20
<212> TYPE: DNA
<213> ORGANISM: Artificial Sequence
<220> FEATURE:
<223> OTHER INFORMATION: Antisense Compound

<400> SEQUENCE: 453
ctttccagga gacttgcggc 20

<210> SEQ ID NO 454
<211> LENGTH: 20
<212> TYPE: DNA
<213> ORGANISM: Artificial Sequence
<220> FEATURE:
<223> OTHER INFORMATION: Antisense Compound

<400> SEQUENCE: 454
atgccggtca ctccagcctt 20

<210> SEQ ID NO 455
<211> LENGTH: 20
<212> TYPE: DNA
<213> ORGANISM: Artificial Sequence
<220> FEATURE:
<223> OTHER INFORMATION: Antisense Compound

<400> SEQUENCE: 455
tccacagcaa ccacaggtgg 20

<210> SEQ ID NO 456
<211> LENGTH: 20
<212> TYPE: DNA
<213> ORGANISM: Artificial Sequence
<220> FEATURE:
<223> OTHER INFORMATION: Antisense Compound

<400> SEQUENCE: 456
gggacagcga atctgctgtc 20

<210> SEQ ID NO 457
<211> LENGTH: 20
<212> TYPE: DNA
<213> ORGANISM: Artificial Sequence
<220> FEATURE:
<223> OTHER INFORMATION: Antisense Compound

<400> SEQUENCE: 457
caccctgatc gcgaatcctc 20

<210> SEQ ID NO 458
<211> LENGTH: 20
<212> TYPE: DNA
<213> ORGANISM: Artificial Sequence
<220> FEATURE:
<223> OTHER INFORMATION: Antisense Compound

<400> SEQUENCE: 458
gtgaagttgc accctgatcg 20

<210> SEQ ID NO 459
<211> LENGTH: 20
<212> TYPE: DNA
<213> ORGANISM: Artificial Sequence
<220> FEATURE:
<223> OTHER INFORMATION: Antisense Compound

<400> SEQUENCE: 459
tgcaaggctg gagagaagag 20

<210> SEQ ID NO 460
<211> LENGTH: 20
<212> TYPE: DNA
<213> ORGANISM: Artificial Sequence
<220> FEATURE:
<223> OTHER INFORMATION: Antisense Compound

<400> SEQUENCE: 460
aggcttagtg aagcgcgtga 20

<210> SEQ ID NO 461
<211> LENGTH: 20
<212> TYPE: DNA
<213> ORGANISM: Artificial Sequence
<220> FEATURE:
<223> OTHER INFORMATION: Antisense Compound

<400> SEQUENCE: 461
atgcgctgga aggttactag 20

<210> SEQ ID NO 462
<211> LENGTH: 20
<212> TYPE: DNA
<213> ORGANISM: Artificial Sequence
<220> FEATURE:
<223> OTHER INFORMATION: Antisense Compound

<400> SEQUENCE: 462
ctttttaaac aatgcgctgg 20

<210> SEQ ID NO 463
<211> LENGTH: 20
<212> TYPE: DNA
<213> ORGANISM: Artificial Sequence
<220> FEATURE:
<223> OTHER INFORMATION: Antisense Compound

<400> SEQUENCE: 463
aactgctttc tttttaaaca 20

<210> SEQ ID NO 464
<211> LENGTH: 20
<212> TYPE: DNA
<213> ORGANISM: Artificial Sequence
<220> FEATURE:
<223> OTHER INFORMATION: Antisense Compound

<400> SEQUENCE: 464
gaaggcttcg cttacatcct 20

<210> SEQ ID NO 465
<211> LENGTH: 20
<212> TYPE: DNA
<213> ORGANISM: Artificial Sequence
<220> FEATURE:
<223> OTHER INFORMATION: Antisense Compound

<400> SEQUENCE: 465
acacaccttt acttaatgga 20

<210> SEQ ID NO 466
<211> LENGTH: 20
<212> TYPE: DNA
<213> ORGANISM: Artificial Sequence
<220> FEATURE:
<223> OTHER INFORMATION: Antisense Compound

<400> SEQUENCE: 466
cgaaacgaca cacaccttta 20

<210> SEQ ID NO 467
<211> LENGTH: 20
<212> TYPE: DNA
<213> ORGANISM: Artificial Sequence
<220> FEATURE:
<223> OTHER INFORMATION: Antisense Compound

<400> SEQUENCE: 467
ttgtactcac cgaggtccgc 20

<210> SEQ ID NO 468
<211> LENGTH: 20
<212> TYPE: DNA

<213> ORGANISM: Artificial Sequence
<220> FEATURE:
<223> OTHER INFORMATION: Antisense Compound

<400> SEQUENCE: 468
gcggtcctac ctctttccgt 20

<210> SEQ ID NO 469
<211> LENGTH: 20
<212> TYPE: DNA
<213> ORGANISM: Artificial Sequence
<220> FEATURE:
<223> OTHER INFORMATION: Antisense Compound

<400> SEQUENCE: 469
tgcaggcgcg gtcctacctc 20

<210> SEQ ID NO 470
<211> LENGTH: 20
<212> TYPE: DNA
<213> ORGANISM: Artificial Sequence
<220> FEATURE:
<223> OTHER INFORMATION: Antisense Compound

<400> SEQUENCE: 470
gccgccagac ctaattaatt 20

<210> SEQ ID NO 471
<211> LENGTH: 20
<212> TYPE: DNA
<213> ORGANISM: Artificial Sequence
<220> FEATURE:
<223> OTHER INFORMATION: Antisense Compound

<400> SEQUENCE: 471
agacactagg aacgcaatga 20

<210> SEQ ID NO 472
<211> LENGTH: 20
<212> TYPE: DNA
<213> ORGANISM: Artificial Sequence
<220> FEATURE:
<223> OTHER INFORMATION: Antisense Compound

<400> SEQUENCE: 472
atgctatgat gttgaatgtg 20

<210> SEQ ID NO 473
<211> LENGTH: 20
<212> TYPE: DNA
<213> ORGANISM: Artificial Sequence
<220> FEATURE:
<223> OTHER INFORMATION: Antisense Compound

<400> SEQUENCE: 473
ctatgctgtt atcaggattc 20

<210> SEQ ID NO 474
<211> LENGTH: 20
<212> TYPE: DNA
<213> ORGANISM: Artificial Sequence
<220> FEATURE:
<223> OTHER INFORMATION: Antisense Compound

<400> SEQUENCE: 474
attgtcttgg ctgttgagtg 20

```
<210> SEQ ID NO 475
<211> LENGTH: 20
<212> TYPE: DNA
<213> ORGANISM: Artificial Sequence
<220> FEATURE:
<223> OTHER INFORMATION: Antisense Compound

<400> SEQUENCE: 475

tccgtcatcg ctcctcaggg                                              20
```